United States Patent
Graham et al.

(10) Patent No.: US 11,938,221 B2
(45) Date of Patent: Mar. 26, 2024

(54) MULTIVALENT NANOPARTICLE-BASED VACCINES

(71) Applicant: The United States of America, as represented by the Secretary, Department of Health and Human Services, Bethesda, MD (US)

(72) Inventors: Barney S. Graham, Rockville, MD (US); Masaru Kanekiyo, Chevy Chase, MD (US); Hadi M. Yassine, Boyds, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 8 days.

(21) Appl. No.: 17/519,142

(22) Filed: Nov. 4, 2021

(65) Prior Publication Data
US 2022/0054419 A1   Feb. 24, 2022

Related U.S. Application Data

(62) Division of application No. 15/540,898, filed as application No. PCT/US2015/068272 on Dec. 31, 2015, now Pat. No. 11,191,727.

(60) Provisional application No. 62/098,755, filed on Dec. 31, 2014.

(51) Int. Cl.
| | | |
|---|---|---|
| A61K 39/12 | (2006.01) | |
| A61K 9/16 | (2006.01) | |
| A61K 39/145 | (2006.01) | |
| C12N 7/00 | (2006.01) | |
| A61K 39/00 | (2006.01) | |

(52) U.S. Cl.
CPC .............. *A61K 9/167* (2013.01); *A61K 39/12* (2013.01); *A61K 39/145* (2013.01); *C12N 7/00* (2013.01); *A61K 2039/575* (2013.01); *A61K 2039/6031* (2013.01); *A61K 2039/6068* (2013.01); *A61K 2039/6075* (2013.01); *A61K 2039/70* (2013.01); *C12N 2760/16134* (2013.01); *C12N 2760/16171* (2013.01); *Y02A 50/30* (2018.01)

(58) Field of Classification Search
None
See application file for complete search history.

(56) References Cited

U.S. PATENT DOCUMENTS

| | | |
|---|---|---|
| 7,094,598 B2 | 8/2006 | Nabel et al. |
| 7,097,841 B2 | 8/2006 | Carter et al. |
| 7,608,268 B2 | 10/2009 | Carter et al. |
| 9,441,019 B2 | 9/2016 | Nabel et al. |
| 2002/0054882 A1 | 5/2002 | Okuno et al. |
| 2003/0211996 A1 | 11/2003 | Gowans et al. |
| 2005/0042229 A1 | 2/2005 | Yang et al. |
| 2005/0108791 A1 | 5/2005 | Edgerton |
| 2006/0251679 A1 | 11/2006 | Carter et al. |
| 2007/0082054 A1 | 4/2007 | Mooter et al. |
| 2007/0224205 A1 | 9/2007 | Powell et al. |
| 2008/0299151 A1 | 12/2008 | Fomsgaard |
| 2009/0233377 A1 | 9/2009 | Iwahori et al. |
| 2010/0137412 A1 | 6/2010 | Zhou et al. |
| 2010/0285982 A1 | 11/2010 | Golding et al. |
| 2010/0297174 A1 | 11/2010 | Garcia-Sastre et al. |
| 2011/0038025 A1 | 2/2011 | Naitou et al. |
| 2011/0059130 A1 | 3/2011 | Yusibov |
| 2011/0177122 A1 | 7/2011 | Nabel et al. |
| 2011/0212128 A1 | 9/2011 | Galarza et al. |
| 2016/0303224 A1 | 10/2016 | Kanekiyo et al. |
| 2017/0189518 A1 | 7/2017 | Nabel et al. |

FOREIGN PATENT DOCUMENTS

| | | |
|---|---|---|
| EP | 1504037 | 12/2009 |
| WO | WO 2003/094849 | 11/2003 |
| WO | WO 2009/109428 | 9/2009 |
| WO | WO 2010/036948 | 4/2010 |
| WO | WO 2010/117786 A1 | 10/2010 |
| WO | WO 2011/035422 | 3/2011 |
| WO | WO 2011/044152 | 4/2011 |
| WO | WO 2012/162428 | 11/2012 |
| WO | WO 2013/044203 A2 | 3/2013 |
| WO | WO 2015/054639 | 4/2015 |
| WO | WO 2015/183969 | 12/2015 |
| WO | WO 2016/021209 | 2/2016 |

OTHER PUBLICATIONS

A3KF33, UniProtKB A3KF33_I57A5, Sep. 21, 2011 [online]. [Retrieved on Feb. 26, 2013]. Retrieved from the internet <URL: http://www.uniprot.org/uniprot/A3KF33.txt?version=36>.

(Continued)

*Primary Examiner* — Benjamin P Blumel
(74) *Attorney, Agent, or Firm* — Klarquist Sparkman, LLP

(57) ABSTRACT

Novel, nanoparticle-based vaccines are provided that elicit an immune response to a broad range of infectious agents, such as influenza viruses. The nanoparticles comprise a heterogeneous population of fusion proteins, each comprising a monomeric subunit of a self-assembly protein, such as ferritin, joined to one or more immunogenic portions of a protein from an infectious agent, such as influenza virus. The fusion proteins self-assemble to form nanoparticles that display a heterogeneous population of immunogenic portions on their surface. When administered to an individual, such nanoparticles elicit an immune response to different strains, types, subtypes and species with in the same taxonomic family. Thus, such nanoparticles can be used to vaccinate an individual against infection by different Types, subtypes and/or strains of infectious agents. Also provided are specific fusion proteins, nucleic acid molecules encoding such fusion proteins and methods of using nanoparticles of the invention to vaccinate individuals.

8 Claims, 13 Drawing Sheets

Specification includes a Sequence Listing.

(56) References Cited

OTHER PUBLICATIONS

C0LT38, UniProtKB C0LT38_9INFB, Sep. 21, 2011 [online]. [Retrieved on Feb. 26, 2013]. Retrieved from the internet <URL: http://www.uniprot.org/uniprot/C0LT38.txt?version=18>.
GenBank Accession No. 3EGM_A submitted Sep. 11, 2008, 2 pages.
GenBank Accession No. AAP34324, submitted May 1, 2003, 2 pages.
Bachmann et al., "Neutralizing antiviral B cell responses," *Annu Rev Immunol.* 15: 235-270, 1997.
Bernacchioni et al. "Loop Electrostatics Modulates the Intersubunit Interactions in Ferritin," *ACS Chemical Biology* 9: 2517-2525, 2014.
Caton et al., "The antigenic structure of the influenza virus A/PR/8/34 hemagglutinin (H1 subtype)," *Cell* 31: 417-427, 1982.
Cohen et al., "Ferritin as an Endogenous MRI Reporter for Noninvasive Imaging Neoplasia of Gene Expression in C6 Glioma Tumors," *Neoplasia* 7.2: 109-117, Feb. 2005.
Corti et al., "Heterosubtypic neutralizing antibodies are produced by individuals immunized with a seasonal influenza vaccine," *J Clin Invest* 120: 1663-1673, 2010.
Corti et al., "A neutralizing antibody selected from plasma cells that binds to group 1 and group 2 influenza A hemagglutinins," *Science* 333: 850-856, 2011.
Dintzis et al., "Molecular determinants of immunogenicity: the immunon model of immune response," *Proc Natl Acad Sci USA* 73: 3671-3675, 1976.
Ekiert et al., "A highly conserved neutralizing epitope on group 2 influenza A viruses," *Science* 333: 843-850, 2011.
Ekiert et al., "Antibody recognition of a highly conserved influenza virus epitope," *Science* 324: 246-251, 2009.
Greenstone et al., "Chimeric papillomavirus virus-like particles elicit antitumor immunity against the E7 oncoprotein in an HPV16 tumor model," *Proc. Natl. Acad. Sci. USA* 95: 1800-1805, Feb. 1998.
Harrison, "The Structure and Function of Ferritin," *Biochemical Education* 14.4: 154-162, 1986.
Haynes, "Influenza virus-like particle vaccines," *Expert Rev Vaccines* 8: 435-445, 2009.
He et al., "Presenting native-like trimeric HIV-1 antigens with self-assembling nanoparticles," *Nature Communications* 7: 12041, Jun. 2016 (15 pages).
International Preliminary Report on Patentability for International Application No. PCT/US2015/068272, dated Jul. 13, 2017, 10 pages.
International Search Report and Written Opinion prepared by the European Patent Office dated Mar. 23, 2016, for International Application No. PCT/US2015/068272, 17 pages.
Joyce et al., "Vaccine-Induced Antibodies that Neutralize Group 1 and Group 2 Influenza A Viruses," *Cell* 166.3: 609-623, Jul. 2016.
Kanekiyo et al., "Rational Design of an Epstein-Barr Virus Vaccine Targeting the Receptor-Binding Site," *Cell* 162.5: 1090-1100, Aug. 2015.
Kanekiyo et al., "Self-assembling influenza nanoparticle vaccines elicit broadly neutralizing H1N1 antibodies," *Nature* 499.7456: 102-106, Jul. 4, 2013.
Kang et al., "Influenza vaccines based on virus-like particles," *Virus Research* 143.2: 140-146, Aug. 1, 2009.
Kashyap et al., "Combinatorial antibody libraries from survivors of the Turkish H5N1 avian influenza outbreak reveal virus neutralization strategies," *Proc Natl Acad Sci USA* 105: 5986-5991, 2008.
Kong et al., "Protective immunity to lethal challenge of the 1918 pandemic influenza virus by vaccination," *Proc Natl Acad Sci USA* 103: 15987-15991, 2006.
Kossovsky et al., "Nanocrystalline Epstein-Barr virus decoys," *Journal of Applied Biomaterials* 2.4: 251-259, Jan. 1991.

Krause et al., "A broadly neutralizing human monoclonal antibody that recognizes a conserved, novel epitope on the globular head of the influenza H1N1 virus hemagglutinin," *J Virol* 85: 10905-10908, 2011.
Lambert et al., "Influenza vaccines for the future," *N Engl J Med* 363: 2036-2044, 2010.
Lee et al., "Adaptations of nanoscale viruses and other protein cages for medical applications", *Nanomedicine* 2.3: 137-149, Sep. 1, 2006.
Lee et al. "Viruses and Virus-Like Protein Assemblies—Chemically Programmable Nanoscale Building Blocks," *Nano Res* 2: 349-364, 2009.
Li et al., "Ferritin nanoparticle technology: A new platform for antigen presentation and vaccine development," *Industrial Biotechnol* 2: 143-147, 2006.
Lopez-Sagaseta et al., "Self-assembling protein nanoparticles in the design of vaccines," *Computational and Structural Biotechnology Journal* 14: 58-68, 2016.
Meldrum et al., "Magnetoferritin: in vitro synthesis of a novel magnetic protein," *Science* 257: 522-523, 1992.
Nabel et al., "Induction of unnatural immunity: prospects for a broadly protective universal influenza vaccine," *Nat Med* 16: 1389-1391, 2010.
Ni et al., "Structural Insights into the Membrane Fusion Mechanism Mediated by Influenza Virus Hemagglutinin," *Biochemistry* 53: 846-854, 2014.
Official Action for Australia Patent Application No. 2015373928, dated Oct. 5, 2018, 29 pages.
Official Action for Canada Patent Application No. 2,974,346, dated May 30, 2019, 4 pages.
English Translation of Official Action for China Patent Application No. 201580076324.6, dated Mar. 26, 2020, 8 pages.
Official Action for European Patent Application No. 15825772.5, dated Jul. 2, 2018, 3 pages.
Official Action for European Patent Application No. 15825772.5, dated Apr. 9, 2019, 4 pages.
Official Action with English Translation for Japan Patent Application No. 2017- 534796, dated Jul. 10, 2018, 9 pages.
Official Action with English Translation for Japan Patent Application No. 2017/534796, dated May 21, 2019, 5 pages.
Okuno et al., "A common neutralizing epitope conserved between the hemagglutinins of influenza A virus H1 and H2 strains," *J Virol* 67: 2552-2558, 1993.
Pulford et al., "Expression of the Epstein-Barr Virus Envelope Fusion Glycoprotein GB85 Gene by a Recombinant Baculovirus," *Journal of General Virology* 75.11: 3241-3248, Nov. 1994.
Roldao et al., "Virus-like particles in vaccine development," *Expert Rev Vaccines* 9: 1149-1176, 2010.
Ruiss et al., "A Virus-Like Particle-Based Epstein-Barr Virus Vaccine," *J Virol* 85.24: 13105-13113, Dec. 2011.
Scorza et al., "Universal influenza vaccines: Shifting to better vaccines," *Vaccine* 34.26: 2926-2933, Mar. 2016.
Sheridan, "Flu vaccine makers upgrade technology—and pray for time," *Nat Biotechnol*, 27: 489-491, 2009.
Steel et al., "Influenza Virus Vaccine Based on the Conserved Hemagglutinin Stalk Domain," *mBio* 1.1: e00018-10, May 18, 2010 (9 pages).
Sui et al., "Structural and functional bases for broad-spectrum neutralization of avian and human influenza A viruses," *Nat Struct Mol Biol* 16: 265-273, 2009.
Treanor et al., "Safety and immunogenicity of a recombinant hemagglutinin vaccine for H5 influenza in humans," *Vaccine* 19: 1732-1737, 2001.
Treanor, "Safety and immunogenicity of a baculovirus-expressed hemagglutinin influenza vaccine: a randomized controlled trial," *JAMA* 297: 1577-1582, 2007.
Vallhov et al., "Exosomes Containing Glycoprotein 350 Released by EBV-Transformed B Cells Selectively Target B Cells through CD21 and Block EBV Infection in Vitro," *J Immunol.* 186.1: 73-82, Jan. 2011.
Wang et al., "Broadly protective monoclonal antibodies against H3 influenza viruses following sequential immunization with different hemagglutinins," *PLoS Pathog* 6.2: e1000796, 2010 (9 pages).

(56) References Cited

OTHER PUBLICATIONS

Wei et al., "Cross-neutralization of 1918 and 2009 influenza viruses: role of glycans in viral evolution and vaccine design," *Sci Transl Med* 2: 24ra21, 2010 (17 pages).
Wei et al., "Induction of broadly neutralizing H1N1 influenza antibodies by vaccination," *Science* 329: 1060-1064, 2010.
Wei et al., "Comparative efficacy of neutralizing antibodies elicited by recombinant hemagglutinin proteins from avian H5N1 influenza virus," *J Virol* 82: 6200-6208, 2008.
Whittle et al., "Broadly neutralizing human antibody that recognizes the receptor-binding pocket of influenza virus hemagglutinin," *Proc Natl Acad Sci USA* 108: 14216-14221, 2011.
WHO Reference on Animal Influenza Diagnosis and Surveillance, 2002, Department of Communicable Disease Surveillance and Response, World Health Organization).
Wu et al., "Mammalian expression of virus-like particles for advanced mimicry of authentic influenza virus," *PLoS One* 5: e9784, 2010 (17pages).
Xiong et al., "PCR-based accurate synthesis of long DNA sequences," *Nat Protoc* 1.2: 791-797, 2006.
Yamashita et al., "Ferritin in the field of nanodevices," *Biochim Biophys Acta* 1800: 846-857, 2010.
Yang et al., "Immunization by avian H5 influenza hemagglutinin mutants with altered receptor binding specificity," *Science* 317: 825-828, 2007.
Yassine et al., "Hemagglutinin-stem nanoparticles generate heterosubtypic influenza protection," *Nat Med.* 21.9: 1065-1070, Sep. 2015.
Zhang et al., "Self-Assembly in the Ferritin Nano-Cage Protein Super Family," *Int. J. Mol. Sci.* 12: 5406-5421, 2011.
Zhang et al. "Universal Influenza Vaccines, a Dream to Be Realized Soon," *Viruses* 6: 1974-1991, 2014.

SEQUENCE LISTING

```
<160> NUMBER OF SEQ ID NOS: 192

<210> SEQ ID NO 1
<211> LENGTH: 517
<212> TYPE: PRT
<213> ORGANISM: Influenza virus

<400> SEQUENCE: 1

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
```

```
            260                 265                 270
Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp
        515

<210> SEQ ID NO 2
<211> LENGTH: 518
<212> TYPE: PRT
<213> ORGANISM: Influenza virus

<400> SEQUENCE: 2

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110
```

```
Ile Asp Tyr Glu Glu Leu Arg Glu Gln Leu Ser Ser Val Ser Ser Phe
            115                 120                 125
Glu Arg Phe Glu Ile Phe Pro Lys Thr Ser Ser Trp Pro Asn His Asp
130                 135                 140
Ser Asn Lys Gly Val Thr Ala Ala Cys Pro His Ala Gly Ala Lys Ser
145                 150                 155                 160
Phe Tyr Lys Asn Leu Ile Trp Leu Val Lys Lys Gly Asn Ser Tyr Pro
                165                 170                 175
Lys Leu Ser Lys Ser Tyr Ile Asn Asp Lys Gly Lys Glu Val Leu Val
            180                 185                 190
Leu Trp Gly Ile His His Pro Ser Thr Ser Ala Asp Gln Gln Ser Leu
        195                 200                 205
Tyr Gln Asn Ala Asp Thr Tyr Val Phe Val Gly Ser Ser Arg Tyr Ser
    210                 215                 220
Lys Lys Phe Lys Pro Glu Ile Ala Ile Arg Pro Lys Val Arg Asp Gln
225                 230                 235                 240
Glu Gly Arg Met Asn Tyr Tyr Trp Thr Leu Val Glu Pro Gly Asp Lys
                245                 250                 255
Ile Thr Phe Glu Ala Thr Gly Asn Leu Val Val Pro Arg Tyr Ala Phe
            260                 265                 270
Ala Met Glu Arg Asn Ala Gly Ser Gly Ile Ile Ile Ser Asp Thr Pro
        275                 280                 285
Val His Asp Cys Asn Thr Thr Cys Gln Thr Pro Lys Gly Ala Ile Asn
    290                 295                 300
Thr Ser Leu Pro Phe Gln Asn Ile His Pro Ile Thr Ile Gly Lys Cys
305                 310                 315                 320
Pro Lys Tyr Val Lys Ser Thr Lys Leu Arg Leu Ala Thr Gly Leu Arg
                325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Val Asp Gly Trp Tyr Gly Tyr
        355                 360                 365
His His Gln Asn Glu Gln Gly Ser Gly Tyr Ala Ala Asp Leu Lys Ser
    370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
        435                 440                 445
Glu Arg Thr Leu Asp Tyr His Asp Ser Asn Val Lys Asn Leu Tyr Glu
    450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
                485                 490                 495
Lys Asn Gly Thr Tyr Asp Tyr Pro Lys Tyr Ser Glu Glu Ala Lys Leu
            500                 505                 510
Asn Arg Glu Glu Ile Asp
            515
```

```
<210> SEQ ID NO 3
<211> LENGTH: 514
<212> TYPE: PRT
<213> ORGANISM: Influenza virus

<400> SEQUENCE: 3

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Asp Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380
```

```
Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
            405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
            435                 440                 445

Asp Phe His Asp Ser Asn Val Lys Asn Leu Tyr Asp Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
            485                 490                 495

Tyr Asp Tyr Pro Lys Tyr Glu Glu Glu Ser Lys Leu Asn Arg Asn Glu
            500                 505                 510

Ile Lys

<210> SEQ ID NO 4
<211> LENGTH: 519
<212> TYPE: PRT
<213> ORGANISM: Influenza virus

<400> SEQUENCE: 4

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
            35                  40                  45

Gln Ile Glu Val Thr Asn Ala Thr Glu Leu Val Gln Ser Ser Ser Thr
50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Ile Thr Glu Gly Phe Thr Trp Thr
130                 135                 140

Gly Val Thr Gln Asn Gly Gly Ser Asn Ala Cys Lys Arg Gly Pro Gly
145                 150                 155                 160

Ser Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
            195                 200                 205

Ser Leu Tyr Val Gln Ala Ser Gly Arg Val Thr Val Ser Thr Arg Arg
210                 215                 220

Ser Gln Gln Thr Ile Ile Pro Asn Ile Gly Ser Arg Pro Trp Val Arg
225                 230                 235                 240
```

```
Gly Leu Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Arg Ser Asp Ala
        275                 280                 285

Pro Ile Asp Thr Cys Ile Ser Glu Cys Ile Thr Pro Asn Gly Ser Ile
    290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
    370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys
        515

<210> SEQ ID NO 5
<211> LENGTH: 519
<212> TYPE: PRT
<213> ORGANISM: Influenza virus

<400> SEQUENCE: 5

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95
```

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asn Glu Ser Phe Asn Trp Thr
130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
            195                 200                 205

Phe Pro Tyr Ala Gln Ala Ser Gly Arg Ile Thr Val Ser Thr Lys Arg
210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Ile Gly Gln Ala Ala Asp Leu Lys
370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys
        515

<210> SEQ ID NO 6
<211> LENGTH: 520
<212> TYPE: PRT
<213> ORGANISM: Influenza virus

<400> SEQUENCE: 6

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
                420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
                500                 505                 510

Arg Leu Lys Arg Glu Glu Ile Ser
        515                 520

<210> SEQ ID NO 7
<211> LENGTH: 534
<212> TYPE: PRT
<213> ORGANISM: Influenza virus

<400> SEQUENCE: 7

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
                100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
                180                 185                 190

Tyr Ile Cys Thr Glu Gly Glu Asp Gln Ile Thr Val Trp Gly Phe His
        195                 200                 205

Ser Asp Asp Lys Thr Gln Met Lys Asn Leu Tyr Gly Asp Ser Asn Pro

```
                210                 215                 220
Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr
        530

<210> SEQ ID NO 8
<211> LENGTH: 519
<212> TYPE: PRT
<213> ORGANISM: Influenza virus

<400> SEQUENCE: 8

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45
```

-continued

```
Gln Ile Glu Val Thr Asn Ala Thr Glu Leu Val Gln Ser Ser Thr
     50                  55                  60

Gly Glu Ile Cys Asp Ser Pro His Gln Ile Leu Asp Gly Lys Asn Cys
 65                  70                  75                  80

Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Glu Ser Phe Asn Trp Thr
130                 135                 140

Gly Val Thr Gln Asn Gly Thr Ser Ser Ala Cys Ile Arg Arg Ser Lys
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ser Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
```

```
            465                 470                 475                 480
        Gly Cys Phe Lys Ile Tyr His Lys Cys Asp Asn Ala Cys Ile Gly Ser
                        485                 490                 495
        Ile Arg Asn Gly Thr Tyr Asp His Asp Val Tyr Arg Asp Glu Ala Leu
                        500                 505                 510
        Asn Asn Arg Phe Gln Ile Lys
                        515
```

<210> SEQ ID NO 9
<211> LENGTH: 517
<212> TYPE: PRT
<213> ORGANISM: Influenza virus

<400> SEQUENCE: 9

```
        Met Lys Val Lys Leu Leu Val Leu Leu Cys Thr Phe Thr Ala Thr Tyr
        1               5                   10                  15

Ala Asp Thr Ile Cys Ile Gly Tyr His Ala Asn Asn Ser Thr Asp Thr
                        20                  25                  30

Val Asp Thr Val Leu Glu Lys Asn Val Thr Val Thr His Ser Val Asn
                        35                  40                  45

Leu Leu Glu Asn Ser His Asn Gly Lys Leu Cys Leu Leu Lys Gly Ile
                50                  55                  60

Ala Pro Leu Gln Leu Gly Asn Cys Ser Val Ala Gly Trp Ile Leu Gly
        65                  70                  75                  80

Asn Pro Glu Cys Glu Leu Leu Ile Ser Lys Glu Ser Trp Ser Tyr Ile
                        85                  90                  95

Val Glu Lys Pro Asn Pro Glu Asn Gly Thr Cys Tyr Pro Gly His Phe
                        100                 105                 110

Ala Asp Tyr Glu Glu Leu Arg Glu Gln Leu Ser Ser Val Ser Ser Phe
                        115                 120                 125

Glu Arg Phe Glu Ile Phe Pro Lys Glu Ser Ser Trp Pro Asn His Thr
                        130                 135                 140

Val Thr Gly Val Ser Ala Ser Cys Ser His Asn Gly Glu Ser Ser Phe
        145                 150                 155                 160

Tyr Arg Asn Leu Leu Trp Leu Thr Gly Lys Asn Gly Leu Tyr Pro Asn
                        165                 170                 175

Leu Ser Lys Ser Tyr Ala Asn Asn Lys Glu Lys Glu Val Leu Val Leu
                        180                 185                 190

Trp Gly Val His His Pro Pro Asn Ile Gly Ile Gln Lys Ala Leu Tyr
                        195                 200                 205

His Thr Glu Asn Ala Tyr Val Ser Val Val Ser Ser His Tyr Ser Arg
                        210                 215                 220

Lys Phe Thr Pro Glu Ile Ala Lys Arg Pro Lys Val Arg Asp Gln Glu
        225                 230                 235                 240

Gly Arg Ile Asn Tyr Tyr Trp Thr Leu Leu Glu Pro Gly Asp Thr Ile
                        245                 250                 255

Ile Phe Glu Ala Asn Gly Asn Leu Ile Ala Pro Arg Tyr Ala Phe Ala
                        260                 265                 270

Leu Ser Arg Gly Phe Gly Ser Gly Ile Ile Asn Ser Asn Ala Pro Met
                        275                 280                 285

Asp Lys Cys Asp Ala Lys Cys Gln Thr Pro Gln Gly Ala Ile Asn Ser
                        290                 295                 300

Ser Leu Pro Phe Gln Asn Val His Pro Val Thr Ile Gly Glu Cys Pro
        305                 310                 315                 320
```

```
Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp
        515

<210> SEQ ID NO 10
<211> LENGTH: 535
<212> TYPE: PRT
<213> ORGANISM: Influenza virus

<400> SEQUENCE: 10

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ile Thr Asn Gly Asn Gly Phe Phe Ala Thr Met Ala Trp Ala Val Pro
                165                 170                 175
```

Lys Asn Asp Lys Asn Lys Thr Ala Thr Asn Pro Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr
    530                 535

<210> SEQ ID NO 11
<211> LENGTH: 501
<212> TYPE: PRT
<213> ORGANISM: Influenza virus

<400> SEQUENCE: 11

Asp Thr Ile Cys Ile Gly Tyr His Ala Asn Asn Ser Thr Asp Thr Val

```
1               5                   10                  15
Asp Thr Leu Leu Glu Lys Asn Val Thr Val Thr His Ser Val Asn Leu
                20                  25                  30
Leu Glu Asp Ser His Asn Gly Lys Leu Cys Lys Leu Lys Gly Ile Ala
                35                  40                  45
Pro Leu Gln Leu Gly Lys Cys Asn Ile Ala Gly Trp Leu Leu Gly Asn
 50                  55                  60
Pro Glu Cys Asp Ser Leu Leu Pro Ala Lys Ser Trp Ser Tyr Ile Val
 65                  70                  75                  80
Glu Thr Pro Asn Ser Glu Asn Gly Ala Cys Tyr Pro Gly Asp Phe Ile
                85                  90                  95
Asp Tyr Glu Glu Leu Lys Glu Gln Leu Ser Ser Val Ser Ser Leu Glu
                100                 105                 110
Arg Phe Glu Ile Phe Pro Lys Glu Ser Ser Trp Pro Asn His Asn Thr
                115                 120                 125
Leu Lys Gly Val Thr Ala Ala Cys Ser His Arg Gly Lys Ser Ser Phe
                130                 135                 140
Tyr Arg Asn Leu Leu Trp Leu Thr Lys Thr Gly Asp Ser Tyr Pro Lys
145                 150                 155                 160
Leu Asn Asn Ser Tyr Val Asn Asn Lys Gly Lys Glu Val Leu Val Leu
                165                 170                 175
Trp Gly Val His His Pro Ser Ser Asn Glu Gln Gln Ser Leu Tyr
                180                 185                 190
His Asn Val Asn Ala Tyr Val Ser Val Val Ser Ser Asn Tyr Asn Arg
                195                 200                 205
Arg Phe Thr Pro Glu Ile Ala Ala Arg Pro Lys Val Arg Asp Gln Pro
                210                 215                 220
Gly Arg Met Asn Tyr Tyr Trp Thr Leu Leu Glu Pro Gly Asp Thr Ile
225                 230                 235                 240
Ile Phe Glu Ala Thr Gly Asn Leu Ile Ala Pro Trp Tyr Ala Phe Ala
                245                 250                 255
Leu Ser Arg Gly Phe Gly Ser Gly Ile Ile Thr Ser Asn Ala Ser Met
                260                 265                 270
His Glu Cys Asn Thr Lys Ser Gln Thr Pro Gln Gly Ala Ile Asn Ser
                275                 280                 285
Ser Leu Pro Phe Gln Asn Ile His Pro Val Pro Ile Gly Glu Cys Pro
                290                 295                 300
Lys Tyr Val Arg Ser Thr Lys Leu Arg Met Val Thr Gly Leu Arg Asn
305                 310                 315                 320
Ile Pro Ser Ile Gln Ser Arg Gly Leu Phe Gly Ala Ile Ala Gly Phe
                325                 330                 335
Ile Glu Gly Gly Trp Thr Gly Met Ile Asp Gly Trp Tyr Gly Tyr His
                340                 345                 350
His Gln Asn Glu Gln Gly Ser Gly Tyr Ala Ala Asp Gln Lys Ser Thr
                355                 360                 365
Gln Asn Ala Ile Asn Gly Ile Thr Asn Lys Val Asn Ser Ile Ile Glu
                370                 375                 380
Lys Met Asn Thr Gln Phe Thr Ala Val Ser Lys Glu Phe Asn Asn Leu
385                 390                 395                 400
Glu Lys Arg Met Glu Asn Leu Asn Lys Lys Val Asp Asp Gly Phe Leu
                405                 410                 415
Asp Ile Trp Thr Tyr Asn Ala Glu Leu Leu Val Leu Leu Glu Asn Glu
                420                 425                 430
```

Arg Thr Leu Asp Phe His Asp Ser Asn Val Lys Asn Leu Tyr Glu Lys
        435                 440                 445

Val Lys Ser Gln Leu Lys Asn Asn Ala Lys Glu Ile Gly Asn Gly Cys
        450                 455                 460

Phe Glu Phe Tyr His Lys Cys Asp Asn Glu Cys Met Glu Ser Val Arg
465                 470                 475                 480

Asn Gly Thr Tyr Asp Tyr Pro Lys Tyr Ser Glu Glu Ser Lys Leu Asn
                485                 490                 495

Arg Glu Lys Ile Asp
            500

<210> SEQ ID NO 12
<211> LENGTH: 501
<212> TYPE: PRT
<213> ORGANISM: Influenza virus

<400> SEQUENCE: 12

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Ser Ile Ala Gly Trp Ile Leu Gly Asn
    50                  55                  60

Pro Glu Cys Glu Ser Leu Phe Ser Lys Lys Ser Trp Ser Tyr Ile Ala
65                  70                  75                  80

Glu Thr Pro Asn Ser Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Arg Ser Trp Pro Lys His Asn Val
        115                 120                 125

Thr Arg Gly Val Thr Ala Ser Cys Ser His Lys Gly Lys Ser Ser Phe
    130                 135                 140

Tyr Arg Asn Leu Leu Trp Leu Thr Glu Lys Asn Gly Ser Tyr Pro Asn
145                 150                 155                 160

Leu Ser Lys Ser Tyr Val Asn Asn Lys Glu Lys Val Leu Val Leu
                165                 170                 175

Trp Gly Val His His Pro Ser Asn Ile Glu Asp Gln Lys Thr Ile Tyr
            180                 185                 190

Arg Lys Glu Asn Ala Tyr Val Ser Val Ser Ser Asn Tyr Asn Arg
        195                 200                 205

Arg Phe Thr Pro Glu Ile Ala Glu Arg Pro Lys Val Arg Gly Gln Ala
    210                 215                 220

Gly Arg Ile Asn Tyr Tyr Trp Thr Leu Leu Glu Pro Gly Asp Thr Ile
225                 230                 235                 240

Ile Phe Glu Ala Asn Gly Asn Leu Ile Ala Pro Trp His Ala Phe Ala
                245                 250                 255

Leu Ser Arg Gly Phe Gly Ser Gly Ile Ile Thr Ser Asn Ala Ser Met
            260                 265                 270

Asp Glu Cys Asp Thr Lys Cys Gln Thr Pro Gln Gly Ala Ile Asn Ser
        275                 280                 285

Ser Leu Pro Phe Gln Asn Ile His Pro Val Thr Ile Gly Glu Cys Pro

```
                    290                 295                 300
Lys Tyr Val Arg Ser Thr Lys Leu Arg Met Val Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Ile Asp Gly Trp Tyr Gly Tyr His
                340                 345                 350

His Gln Asn Glu Gln Gly Ser Gly Tyr Ala Ala Asp Gln Lys Ser Thr
                355                 360                 365

Gln Asn Ala Ile Asn Gly Ile Thr Asn Lys Val Asn Ser Val Ile Glu
                370                 375                 380

Lys Met Asn Thr Gln Phe Thr Ala Val Gly Lys Glu Phe Asn Lys Leu
385                 390                 395                 400

Glu Lys Arg Met Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
                420                 425                 430

Arg Thr Leu Asp Phe His Asp Ser Asn Val Lys Asn Leu Tyr Glu Lys
                435                 440                 445

Val Lys Ser Gln Leu Lys Asn Asn Ala Lys Glu Ile Gly Asn Gly Cys
                450                 455                 460

Phe Glu Phe Tyr His Lys Cys Asn Asn Glu Cys Met Glu Ser Val Lys
465                 470                 475                 480

Asn Gly Thr Tyr Asp Tyr Pro Lys Tyr Ser Glu Glu Ser Lys Leu Asn
                485                 490                 495

Arg Glu Lys Ile Asp
                500

<210> SEQ ID NO 13
<211> LENGTH: 501
<212> TYPE: PRT
<213> ORGANISM: Influenza virus

<400> SEQUENCE: 13

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Ser His Asn Gly Lys Leu Cys Arg Leu Lys Gly Ile Ala
                35                  40                  45

Pro Leu Gln Leu Gly Asn Cys Ser Val Ala Gly Trp Ile Leu Gly Asn
                50                  55                  60

Pro Lys Cys Glu Ser Leu Phe Ser Lys Glu Ser Trp Ser Tyr Ile Ala
65                  70                  75                  80

Glu Thr Pro Asn Pro Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
                100                 105                 110

Arg Phe Glu Ile Phe Pro Lys Glu Ser Ser Trp Pro Asn His Thr Val
                115                 120                 125

Thr Lys Gly Val Thr Thr Ser Cys Ser His Asn Gly Lys Ser Ser Phe
                130                 135                 140

Tyr Arg Asn Leu Leu Trp Leu Thr Glu Lys Asn Gly Leu Tyr Pro Asn
145                 150                 155                 160
```

Leu Ser Lys Ser Tyr Val Asn Asn Lys Glu Lys Val Leu Val Leu
            165                 170                 175

Trp Gly Val His His Pro Ser Asn Ile Arg Asp Gln Arg Ala Ile Tyr
        180                 185                 190

His Thr Glu Asn Ala Tyr Val Ser Val Ser Ser His Tyr Ser Arg
            195                 200                 205

Arg Phe Thr Pro Glu Ile Ala Lys Arg Pro Lys Val Arg Gly Gln Glu
        210                 215                 220

Gly Arg Ile Asn Tyr Tyr Trp Thr Leu Leu Glu Pro Gly Asp Thr Ile
225                 230                 235                 240

Ile Phe Glu Ala Asn Gly Asn Leu Ile Ala Pro Trp Tyr Ala Phe Ala
            245                 250                 255

Leu Ser Arg Gly Phe Gly Ser Gly Ile Ile Thr Ser Asn Ala Ser Met
            260                 265                 270

Asp Glu Cys Asp Ala Lys Cys Gln Thr Pro Gln Gly Ala Ile Asn Ser
            275                 280                 285

Ser Leu Pro Phe Gln Asn Val His Pro Val Thr Ile Gly Glu Cys Pro
            290                 295                 300

Lys Tyr Val Arg Ser Thr Lys Leu Arg Met Val Thr Gly Leu Arg Asn
305                 310                 315                 320

Ile Pro Ser Ile Gln Ser Arg Gly Leu Phe Gly Ala Ile Ala Gly Phe
            325                 330                 335

Ile Glu Gly Gly Trp Thr Gly Met Ile Asp Gly Trp Tyr Gly Tyr His
            340                 345                 350

His Gln Asn Glu Gln Gly Ser Gly Tyr Ala Ala Asp Gln Lys Ser Thr
            355                 360                 365

Gln Asn Ala Ile Asn Gly Ile Thr Asn Lys Val Asn Ser Val Ile Glu
    370                 375                 380

Lys Met Asn Thr Gln Phe Thr Ala Val Gly Lys Glu Phe Asn Lys Leu
385                 390                 395                 400

Glu Arg Arg Met Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Gly
            420                 425                 430

Arg Thr Leu Asp Phe His Asp Ser Asn Val Lys Asn Leu Tyr Glu Lys
        435                 440                 445

Val Lys Ser Gln Leu Lys Asn Asn Ala Lys Glu Ile Gly Asn Gly Cys
    450                 455                 460

Phe Glu Phe Tyr His Lys Cys Asn Asn Glu Cys Met Glu Ser Val Lys
465                 470                 475                 480

Asn Gly Thr Tyr Asp Tyr Pro Lys Tyr Ser Glu Glu Ser Lys Leu Asn
                485                 490                 495

Arg Gly Lys Ile Asp
            500

<210> SEQ ID NO 14
<211> LENGTH: 501
<212> TYPE: PRT
<213> ORGANISM: Influenza virus

<400> SEQUENCE: 14

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

```
Leu Glu Asp Ser His Asn Gly Lys Leu Cys Arg Leu Lys Gly Ile Ala
         35                  40                  45
Pro Leu Gln Leu Gly Asn Cys Ser Ile Ala Gly Trp Ile Leu Gly Asn
 50                  55                  60
Pro Glu Cys Glu Ser Leu Phe Ser Lys Ser Trp Ser Tyr Ile Ala
 65                  70                  75                  80
Glu Thr Pro Asn Ser Glu Asn Gly Thr Cys Tyr Pro Gly Tyr Phe Ala
                 85                  90                  95
Asp Tyr Glu Glu Leu Arg Glu Gln Leu Ser Ser Val Ser Ser Phe Glu
                100                 105                 110
Arg Phe Glu Ile Phe Pro Lys Glu Ser Ser Trp Pro Asn His Thr Val
                115                 120                 125
Thr Lys Gly Val Thr Ala Ser Cys Ser His Lys Gly Arg Ser Ser Phe
        130                 135                 140
Tyr Arg Asn Leu Leu Trp Leu Thr Lys Lys Asn Gly Ser Tyr Pro Asn
145                 150                 155                 160
Leu Ser Lys Ser Tyr Val Asn Asn Lys Glu Lys Glu Val Leu Val Leu
                165                 170                 175
Trp Gly Val His His Pro Ser Asn Ile Gly Asp Gln Arg Ala Ile Tyr
                180                 185                 190
His Thr Glu Asn Ala Tyr Val Ser Val Val Ser Ser His Tyr Asn Arg
            195                 200                 205
Arg Phe Thr Pro Glu Ile Ala Lys Arg Pro Lys Val Arg Asp Gln Glu
210                 215                 220
Gly Arg Ile Asn Tyr Tyr Trp Thr Leu Leu Glu Pro Gly Asp Thr Ile
225                 230                 235                 240
Ile Phe Glu Ala Asn Gly Asn Leu Ile Ala Pro Trp Tyr Ala Phe Ala
                245                 250                 255
Leu Ser Arg Gly Phe Gly Ser Gly Ile Ile Thr Ser Asn Ala Ser Met
                260                 265                 270
Asp Glu Cys Asp Ala Lys Cys Gln Thr Pro Gln Gly Ala Ile Asn Ser
            275                 280                 285
Ser Leu Pro Phe Gln Asn Val His Pro Val Thr Ile Gly Glu Cys Pro
        290                 295                 300
Lys Tyr Val Arg Ser Thr Lys Leu Arg Met Val Thr Gly Leu Arg Asn
305                 310                 315                 320
Ile Pro Ser Ile Gln Ser Arg Gly Leu Phe Gly Ala Ile Ala Gly Phe
                325                 330                 335
Ile Glu Gly Gly Trp Thr Gly Met Ile Asp Gly Trp Tyr Gly Tyr His
                340                 345                 350
His Gln Asn Glu Gln Gly Ser Gly Tyr Ala Ala Asp Gln Lys Ser Thr
            355                 360                 365
Gln Asn Ala Ile Asn Gly Ile Thr Asn Lys Val Asn Ser Val Ile Glu
        370                 375                 380
Lys Met Asn Thr Gln Phe Thr Ala Val Gly Lys Glu Phe Asn Lys Leu
385                 390                 395                 400
Glu Arg Arg Met Glu Asn Leu Asn Lys Lys Val Asp Asp Gly Phe Leu
                405                 410                 415
Asp Ile Trp Thr Tyr Asn Ala Glu Leu Leu Val Leu Leu Glu Asn Glu
                420                 425                 430
Arg Thr Leu Asp Phe His Asp Ser Asn Val Lys Asn Leu Tyr Glu Lys
            435                 440                 445
```

```
Val Lys Ser Gln Leu Lys Asn Asn Ala Lys Glu Ile Gly Asn Gly Cys
    450                 455                 460

Phe Glu Phe Tyr His Lys Cys Asn Asn Glu Cys Met Glu Ser Val Lys
465                 470                 475                 480

Asn Gly Thr Tyr Asp Tyr Pro Lys Tyr Ser Glu Glu Ser Lys Leu Asn
                485                 490                 495

Arg Glu Lys Ile Asp
                500

<210> SEQ ID NO 15
<211> LENGTH: 501
<212> TYPE: PRT
<213> ORGANISM: Influenza virus

<400> SEQUENCE: 15

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
                20                  25                  30

Leu Glu Asp Asn His Asn Gly Lys Leu Cys Lys Leu Lys Gly Ile Ala
            35                  40                  45

Pro Leu Gln Leu Gly Lys Cys Ser Ile Ala Gly Trp Ile Leu Gly Asn
50                  55                  60

Pro Glu Cys Glu Ser Leu Phe Ser Lys Lys Ser Trp Ser Tyr Ile Ala
65                  70                  75                  80

Glu Thr Pro Asn Ser Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
                100                 105                 110

Arg Phe Glu Ile Phe Pro Lys Glu Ser Ser Trp Pro Lys His Asn Val
            115                 120                 125

Thr Lys Gly Val Thr Ala Ser Cys Ser His Lys Gly Lys Ser Ser Phe
130                 135                 140

Tyr Arg Asn Leu Leu Trp Leu Thr Glu Lys Asn Gly Ser Tyr Pro Asn
145                 150                 155                 160

Leu Ser Lys Ser Tyr Val Asn Asn Lys Glu Lys Glu Val Leu Val Leu
                165                 170                 175

Trp Gly Val His His Pro Ser Asn Ile Glu Asp Gln Lys Thr Ile Tyr
            180                 185                 190

Arg Lys Glu Asn Ala Tyr Val Ser Val Ser Ser His Tyr Asn Arg
            195                 200                 205

Arg Phe Thr Pro Glu Ile Ala Lys Arg Pro Lys Val Arg Asn Gln Glu
210                 215                 220

Gly Arg Ile Asn Tyr Tyr Trp Thr Leu Leu Glu Pro Gly Asp Thr Ile
225                 230                 235                 240

Ile Phe Glu Ala Asn Gly Asn Leu Ile Ala Pro Trp Tyr Ala Phe Ala
                245                 250                 255

Leu Ser Arg Gly Phe Gly Ser Gly Ile Ile Thr Ser Asn Ala Ser Met
            260                 265                 270

Asp Glu Cys Asp Ala Lys Cys Gln Thr Pro Gln Gly Ala Ile Asn Ser
            275                 280                 285

Ser Leu Pro Phe Gln Asn Val His Pro Val Thr Ile Gly Glu Cys Pro
290                 295                 300

Lys Tyr Val Arg Ser Thr Lys Leu Arg Met Val Thr Gly Leu Arg Asn
305                 310                 315                 320
```

```
Ile Pro Ser Ile Gln Ser Arg Gly Leu Phe Gly Ala Ile Ala Gly Phe
                325                 330                 335

Ile Glu Gly Gly Trp Thr Gly Met Ile Asp Gly Trp Tyr Gly Tyr His
            340                 345                 350

His Gln Asn Glu Gln Gly Ser Gly Tyr Ala Ala Asp Gln Lys Ser Thr
            355                 360                 365

Gln Asn Ala Ile Asn Gly Ile Thr Asn Lys Val Asn Ser Ile Ile Glu
    370                 375                 380

Lys Met Asn Thr Gln Phe Thr Ala Val Gly Lys Glu Phe Asn Lys Leu
385                 390                 395                 400

Glu Lys Arg Met Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Phe His Asp Ser Asn Val Lys Asn Leu Tyr Glu Lys
            435                 440                 445

Val Lys Ser Gln Leu Lys Asn Asn Ala Lys Glu Ile Gly Asn Gly Cys
    450                 455                 460

Phe Glu Phe Tyr His Lys Cys Asn Asn Glu Cys Met Glu Ser Val Lys
465                 470                 475                 480

Asn Gly Thr Tyr Asp Tyr Pro Lys Tyr Ser Glu Glu Ser Lys Leu Asn
                485                 490                 495

Arg Glu Lys Ile Asp
                500

<210> SEQ ID NO 16
<211> LENGTH: 501
<212> TYPE: PRT
<213> ORGANISM: Influenza virus

<400> SEQUENCE: 16

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Ile Leu Gly Asn
    50                  55                  60

Pro Glu Cys Glu Ser Leu Leu Ser Asn Arg Ser Trp Ser Tyr Ile Ala
65                  70                  75                  80

Glu Thr Pro Asn Ser Glu Asn Gly Ile Cys Tyr Pro Gly Asp Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Lys His Asn Ile
        115                 120                 125

Thr Arg Gly Val Thr Val Ala Cys Ser His Ala Lys Lys Ser Ser Phe
    130                 135                 140

Tyr Lys Asn Leu Leu Trp Leu Thr Glu Ala Asn Gly Leu Tyr Pro Ser
145                 150                 155                 160

Leu Ser Lys Ser Tyr Val Asn Asp Arg Glu Lys Glu Val Leu Val Leu
                165                 170                 175

Trp Gly Val His His Pro Ser Asn Ile Glu Asp Gln Arg Thr Leu Tyr
```

180                 185                 190
Arg Lys Glu Asn Ala Tyr Val Ser Val Ser Ser Asn Tyr Asn Arg
            195                 200                 205

Arg Phe Thr Pro Glu Ile Ala Glu Arg Pro Lys Val Arg Gly Gln Pro
210                 215                 220

Gly Arg Met Asn Tyr Tyr Trp Thr Leu Leu Glu Pro Gly Asp Lys Ile
225                 230                 235                 240

Ile Phe Glu Ala Asn Gly Asn Leu Ile Ala Pro Trp Tyr Ala Phe Ala
            245                 250                 255

Leu Ser Arg Gly Pro Gly Ser Gly Ile Ile Thr Ser Asn Ala Ser Met
            260                 265                 270

Asp Glu Cys Asp Thr Lys Cys Gln Thr Pro Gln Gly Ala Ile Asn Ser
            275                 280                 285

Ser Leu Pro Phe Gln Asn Ile His Pro Val Thr Ile Gly Glu Cys Pro
            290                 295                 300

Lys Tyr Val Arg Ser Thr Lys Leu Arg Met Val Thr Gly Leu Arg Asn
305                 310                 315                 320

Ile Pro Ser Ile Gln Ser Arg Gly Leu Phe Gly Ala Ile Ala Gly Phe
            325                 330                 335

Ile Glu Gly Gly Trp Thr Gly Met Val Asp Gly Trp Tyr Gly Tyr His
            340                 345                 350

His Gln Asn Glu Gln Gly Ser Gly Tyr Ala Ala Asp Gln Lys Ser Thr
            355                 360                 365

Gln Asn Ala Ile Asn Gly Ile Thr Asn Lys Val Asn Ser Val Ile Glu
            370                 375                 380

Lys Met Asn Thr Gln Phe Thr Ala Val Gly Lys Glu Phe Asn Lys Leu
385                 390                 395                 400

Glu Lys Arg Met Glu Asn Leu Asn Lys Lys Val Asp Asp Gly Phe Leu
            405                 410                 415

Asp Ile Trp Thr Tyr Asn Ala Glu Leu Leu Val Leu Leu Glu Asn Glu
            420                 425                 430

Arg Thr Leu Asp Phe His Asp Ser Asn Val Lys Asn Leu Tyr Glu Lys
            435                 440                 445

Val Lys Asn Gln Leu Arg Asn Asn Ala Lys Glu Ile Gly Asn Gly Cys
            450                 455                 460

Phe Glu Phe Tyr His Lys Cys Asp Asn Glu Cys Met Glu Ser Val Lys
465                 470                 475                 480

Asn Gly Thr Tyr Asp Tyr Pro Lys Tyr Ser Glu Glu Ser Lys Leu Asn
            485                 490                 495

Arg Ala Lys Ile Asp
            500

<210> SEQ ID NO 17
<211> LENGTH: 500
<212> TYPE: PRT
<213> ORGANISM: Influenza virus

<400> SEQUENCE: 17

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
            35                  40                  45

-continued

Pro Leu Gln Leu Gly Lys Cys Asn Ile Ala Gly Trp Ile Leu Gly Asn
 50                 55                  60

Pro Glu Cys Glu Ser Leu Leu Ser Glu Arg Ser Trp Ser Tyr Ile Val
 65              70                  75                  80

Glu Thr Pro Asn Ser Glu Asn Gly Thr Cys Tyr Pro Gly Asp Phe Ile
                 85                  90                  95

Asp Tyr Glu Glu Leu Arg Glu Gln Leu Ser Ser Val Ser Ser Phe Glu
            100                 105                 110

Arg Phe Glu Ile Phe Ser Lys Glu Ser Ser Trp Pro Lys His Thr Thr
            115                 120                 125

Gly Gly Val Thr Ala Ala Cys Ser His Ala Gly Lys Ser Ser Phe Tyr
130                 135                 140

Arg Asn Leu Leu Trp Leu Thr Glu Lys Asp Gly Ser Tyr Pro Asn Leu
145             150                 155                 160

Asn Asn Ser Tyr Val Asn Lys Lys Gly Lys Glu Val Leu Val Leu Trp
                165                 170                 175

Gly Val His His Pro Ser Asn Ile Lys Asp Gln Gln Thr Leu Tyr Gln
            180                 185                 190

Lys Glu Asn Ala Tyr Val Ser Val Val Ser Ser Asn Tyr Asn Arg Arg
            195                 200                 205

Phe Thr Pro Glu Ile Ala Glu Arg Pro Lys Val Arg Gly Gln Ala Gly
            210                 215                 220

Arg Ile Asn Tyr Tyr Trp Thr Leu Leu Lys Pro Gly Asp Thr Ile Met
225                 230                 235                 240

Phe Glu Ala Asn Gly Asn Leu Ile Ala Pro Trp Tyr Ala Phe Ala Leu
                245                 250                 255

Ser Arg Gly Phe Gly Ser Gly Ile Ile Thr Ser Asn Ala Ser Met His
            260                 265                 270

Glu Cys Asp Thr Lys Cys Gln Thr Pro Gln Gly Ala Ile Asn Ser Ser
            275                 280                 285

Leu Pro Phe Gln Asn Ile His Pro Val Thr Ile Gly Glu Cys Pro Lys
            290                 295                 300

Tyr Val Arg Ser Thr Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Ile Asp Gly Trp Tyr Gly Tyr His His
            340                 345                 350

Gln Asn Glu Gln Gly Ser Gly Tyr Ala Ala Asp Gln Lys Ser Thr Gln
            355                 360                 365

Asn Ala Ile Asn Gly Ile Thr Asn Lys Val Asn Ser Val Ile Glu Lys
370                 375                 380

Met Asn Thr Gln Phe Thr Ala Val Gly Lys Glu Phe Asn Asn Leu Glu
385                 390                 395                 400

Lys Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
            435                 440                 445

Lys Asn Gln Leu Arg Asn Asn Ala Lys Glu Ile Gly Asn Gly Cys Phe
450                 455                 460

Glu Phe Tyr His Lys Cys Asn Asn Glu Cys Met Glu Ser Val Lys Asn

```
                    465                 470                 475                 480
Gly Thr Tyr Asp Tyr Pro Lys Tyr Ser Glu Glu Ser Lys Leu Asn Arg
                485                 490                 495
Glu Lys Ile Asp
            500

<210> SEQ ID NO 18
<211> LENGTH: 501
<212> TYPE: PRT
<213> ORGANISM: Influenza virus

<400> SEQUENCE: 18

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Ser Ile Ala Gly Trp Ile Leu Gly Asn
    50                  55                  60

Pro Glu Cys Glu Ser Leu Phe Ser Lys Lys Ser Trp Ser Tyr Ile Ala
65                  70                  75                  80

Glu Thr Pro Asn Ser Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Arg Ser Trp Pro Lys His Asn Val
        115                 120                 125

Thr Arg Gly Val Thr Ala Ser Cys Ser His Lys Gly Lys Ser Ser Phe
    130                 135                 140

Tyr Arg Asn Leu Leu Trp Leu Thr Glu Lys Asn Gly Ser Tyr Pro Asn
145                 150                 155                 160

Leu Ser Lys Ser Tyr Val Asn Asn Lys Glu Lys Glu Val Leu Val Leu
                165                 170                 175

Trp Gly Val His His Pro Ser Asn Ile Glu Asp Gln Lys Thr Ile Tyr
            180                 185                 190

Arg Lys Glu Asn Ala Tyr Val Ser Val Ser Ser Asn Tyr Asn Arg
        195                 200                 205

Arg Phe Thr Pro Glu Ile Ala Glu Arg Pro Lys Val Arg Gly Gln Ala
    210                 215                 220

Gly Arg Ile Asn Tyr Tyr Trp Thr Leu Leu Glu Pro Gly Asp Thr Ile
225                 230                 235                 240

Ile Phe Glu Ala Asn Gly Asn Leu Ile Ala Pro Trp Tyr Ala Phe Ala
                245                 250                 255

Leu Ser Arg Gly Phe Gly Ser Gly Ile Ile Thr Ser Asn Ala Ser Met
            260                 265                 270

Asp Glu Cys Asp Thr Lys Cys Gln Thr Pro Gln Gly Ala Ile Asn Ser
        275                 280                 285

Ser Leu Pro Phe Gln Asn Val His Pro Val Thr Ile Gly Glu Cys Pro
    290                 295                 300

Lys Tyr Val Arg Ser Thr Lys Leu Arg Met Val Thr Gly Leu Arg Asn
305                 310                 315                 320

Ile Pro Ser Ile Gln Ser Arg Gly Leu Phe Gly Ala Ile Ala Gly Phe
                325                 330                 335
```

```
Ile Glu Gly Gly Trp Thr Gly Met Ile Asp Gly Trp Tyr Gly Tyr His
            340                 345                 350

His Gln Asn Glu Gln Gly Ser Gly Tyr Ala Ala Asp Gln Lys Ser Thr
            355                 360                 365

Gln Asn Ala Ile Asn Gly Ile Thr Asn Lys Val Asn Ser Val Ile Glu
370                 375                 380

Lys Met Asn Thr Gln Phe Thr Ala Val Gly Lys Glu Phe Asn Lys Leu
385                 390                 395                 400

Glu Lys Arg Met Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Phe His Asp Ser Asn Val Lys Asn Leu Tyr Glu Lys
            435                 440                 445

Val Lys Ser Gln Leu Lys Asn Asn Ala Lys Glu Ile Gly Asn Gly Cys
            450                 455                 460

Phe Glu Phe Tyr His Lys Cys Asn Asn Glu Cys Met Glu Ser Val Lys
465                 470                 475                 480

Asn Gly Thr Tyr Asp Tyr Pro Lys Tyr Ser Glu Glu Ser Lys Leu Asn
                485                 490                 495

Arg Glu Lys Ile Asp
            500

<210> SEQ ID NO 19
<211> LENGTH: 501
<212> TYPE: PRT
<213> ORGANISM: Influenza virus

<400> SEQUENCE: 19

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Asn Ile Ala Gly Trp Ile Leu Gly Asn
    50                  55                  60

Pro Glu Cys Glu Ser Leu Leu Ser Lys Arg Ser Trp Ser Tyr Ile Ala
65                  70                  75                  80

Glu Thr Pro Asn Ser Glu Asn Gly Ala Cys Tyr Pro Gly Asp Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Arg Ser Trp Pro Lys His Asn Ile
        115                 120                 125

Thr Arg Gly Val Thr Ala Ala Cys Ser His Ala Gly Lys Ser Ser Phe
    130                 135                 140

Tyr Lys Asn Leu Leu Trp Leu Thr Glu Thr Asp Gly Ser Tyr Pro Lys
145                 150                 155                 160

Leu Ser Lys Ser Tyr Val Asn Asn Lys Glu Lys Glu Val Leu Val Leu
                165                 170                 175

Trp Gly Val His His Pro Ser Asn Ile Glu Asp Gln Lys Thr Leu Tyr
            180                 185                 190

Arg Lys Glu Asn Ala Tyr Val Ser Val Val Ser Ser Asn Tyr Asn Arg
        195                 200                 205
```

```
Arg Phe Thr Pro Glu Ile Ala Glu Arg Pro Lys Val Arg Gly Gln Ala
            210                 215                 220

Gly Arg Ile Asn Tyr Tyr Trp Thr Leu Leu Glu Pro Gly Asp Thr Ile
225                 230                 235                 240

Ile Phe Glu Ala Asn Gly Asn Leu Ile Ala Pro Trp Tyr Ala Phe Ala
                245                 250                 255

Leu Ser Arg Asp Phe Gly Ser Gly Ile Ile Thr Ser Asn Ala Ser Met
            260                 265                 270

Asp Glu Cys Asp Thr Lys Cys Gln Thr Pro Gln Gly Ala Ile Asn Ser
        275                 280                 285

Ser Leu Pro Phe Gln Asn Ile His Pro Val Thr Ile Gly Glu Cys Pro
290                 295                 300

Lys Tyr Val Lys Ser Thr Lys Leu Arg Met Val Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Ile Asp Gly Trp Tyr Gly Tyr His
            340                 345                 350

His Gln Asn Glu Gln Gly Ser Gly Tyr Ala Ala Asp Gln Lys Ser Thr
        355                 360                 365

Gln Asn Ala Ile Asn Trp Ile Thr Asn Lys Val Asn Ser Val Ile Glu
370                 375                 380

Lys Met Asn Thr Gln Phe Thr Ala Val Gly Lys Glu Phe Asn Lys Leu
385                 390                 395                 400

Glu Lys Arg Met Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Phe His Asp Ser Asn Val Lys Asn Leu Tyr Glu Lys
        435                 440                 445

Val Lys Asn Gln Leu Arg Asn Asn Ala Lys Glu Ile Gly Asn Gly Cys
450                 455                 460

Phe Glu Phe Tyr His Lys Cys Asn Asn Glu Cys Met Glu Ser Val Lys
465                 470                 475                 480

Asn Gly Thr Tyr Asp Tyr Pro Lys Tyr Ser Glu Glu Ser Lys Leu Asn
                485                 490                 495

Arg Glu Lys Ile Asp
            500

<210> SEQ ID NO 20
<211> LENGTH: 500
<212> TYPE: PRT
<213> ORGANISM: Influenza virus

<400> SEQUENCE: 20

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asn Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
50                  55                  60

Pro Glu Cys Glu Leu Leu Ile Ser Lys Glu Ser Trp Ser Tyr Ile Val
```

```
                65                  70                  75                  80
        Glu Lys Pro Asn Pro Glu Asn Gly Thr Cys Tyr Pro Gly His Phe Ala
                            85                  90                  95

Asp Tyr Glu Glu Leu Arg Glu Gln Leu Ser Ser Val Ser Ser Phe Glu
                           100                 105                 110

Arg Phe Glu Ile Phe Pro Lys Glu Ser Ser Trp Pro Asn His Thr Val
                           115                 120                 125

Thr Gly Val Ser Ala Ser Cys Ser His Asn Gly Glu Ser Ser Phe Tyr
                           130                 135                 140

Arg Asn Leu Leu Trp Leu Thr Gly Lys Asn Gly Leu Tyr Pro Asn Leu
        145                 150                 155                 160

Ser Lys Ser Tyr Ala Asn Asn Lys Glu Lys Glu Val Leu Val Leu Trp
                           165                 170                 175

Gly Val His His Pro Pro Asn Ile Gly Asn Gln Lys Ala Leu Tyr His
                           180                 185                 190

Thr Glu Asn Ala Tyr Val Ser Val Val Ser Ser His Tyr Ser Arg Lys
                           195                 200                 205

Phe Thr Pro Glu Ile Ala Lys Arg Pro Lys Val Arg Asp Gln Glu Gly
                           210                 215                 220

Arg Ile Asn Tyr Tyr Trp Thr Leu Leu Glu Pro Gly Asp Thr Ile Ile
        225                 230                 235                 240

Phe Glu Ala Asn Gly Asn Leu Ile Ala Pro Arg Tyr Ala Phe Ala Leu
                           245                 250                 255

Ser Arg Gly Phe Gly Ser Gly Ile Ile Asn Ser Asn Ala Pro Met Asp
                           260                 265                 270

Lys Cys Asp Ala Lys Cys Gln Thr Pro Gln Gly Ala Ile Asn Ser Ser
                           275                 280                 285

Leu Pro Phe Gln Asn Val His Pro Val Thr Ile Gly Glu Cys Pro Lys
                           290                 295                 300

Tyr Val Arg Ser Ala Lys Leu Arg Met Val Thr Gly Leu Arg Asn Ile
        305                 310                 315                 320

Pro Ser Ile Gln Ser Arg Gly Leu Phe Gly Ala Ile Ala Gly Phe Ile
                           325                 330                 335

Glu Gly Gly Trp Thr Gly Met Val Asp Gly Trp Tyr Gly Tyr His His
                           340                 345                 350

Gln Asn Glu Gln Gly Ser Gly Tyr Ala Ala Asp Gln Lys Ser Thr Gln
                           355                 360                 365

Asn Ala Ile Asn Gly Ile Thr Asn Lys Val Asn Ser Val Ile Glu Lys
                           370                 375                 380

Met Asn Thr Gln Phe Thr Ala Val Gly Lys Glu Phe Asn Lys Leu Glu
        385                 390                 395                 400

Arg Arg Met Glu Asn Leu Asn Lys Lys Val Asp Asp Gly Phe Ile Asp
                           405                 410                 415

Ile Trp Thr Tyr Asn Ala Glu Leu Leu Val Leu Leu Glu Asn Glu Arg
                           420                 425                 430

Thr Leu Asp Phe His Asp Ser Asn Val Lys Asn Leu Tyr Glu Lys Val
                           435                 440                 445

Lys Ser Gln Leu Lys Asn Asn Ala Lys Glu Ile Gly Asn Gly Cys Phe
                           450                 455                 460

Glu Phe Tyr His Lys Cys Asn Asp Glu Cys Met Glu Ser Val Lys Asn
        465                 470                 475                 480

Gly Thr Tyr Asp Tyr Pro Lys Tyr Ser Glu Glu Ser Lys Leu Asn Arg
                           485                 490                 495
```

Glu Lys Ile Asp
            500

<210> SEQ ID NO 21
<211> LENGTH: 501
<212> TYPE: PRT
<213> ORGANISM: Influenza virus

<400> SEQUENCE: 21

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Arg Leu Lys Gly Ile Ala
        35                  40                  45

Pro Leu Gln Leu Gly Lys Cys Ser Ile Ala Gly Trp Ile Leu Gly Asn
50                  55                  60

Pro Glu Cys Glu Ser Leu Phe Ser Lys Lys Ser Trp Ser Tyr Ile Ala
65                  70                  75                  80

Glu Thr Pro Asn Ser Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Lys His Asn Val
        115                 120                 125

Thr Arg Gly Val Thr Ala Ser Cys Ser His Lys Gly Lys Cys Ser Phe
130                 135                 140

Tyr Arg Asn Leu Leu Trp Leu Thr Glu Lys Asn Gly Ser Tyr Pro Asn
145                 150                 155                 160

Leu Ser Lys Ser Tyr Val Asn Asn Lys Glu Lys Glu Val Leu Val Leu
                165                 170                 175

Trp Gly Val His His Pro Ser Asn Ile Glu Asp Gln Lys Thr Ile Tyr
            180                 185                 190

Arg Lys Glu Asn Ala Tyr Val Ser Val Val Ser Ser His Tyr Asn Arg
        195                 200                 205

Arg Phe Thr Pro Glu Ile Ala Lys Arg Pro Lys Val Arg Asp Gln Glu
210                 215                 220

Gly Arg Ile Asn Tyr Tyr Trp Thr Leu Leu Glu Pro Gly Asp Thr Ile
225                 230                 235                 240

Ile Phe Glu Ala Asn Gly Asn Leu Ile Ala Pro Trp Tyr Ala Phe Ala
                245                 250                 255

Leu Ser Arg Gly Phe Gly Ser Gly Ile Ile Thr Ser Asn Ala Ser Met
            260                 265                 270

Asp Glu Cys Asp Ala Lys Cys Gln Thr Pro Gln Gly Ala Ile Asn Ser
        275                 280                 285

Ser Leu Pro Phe Gln Asn Val His Pro Val Thr Ile Gly Glu Cys Pro
290                 295                 300

Lys Tyr Val Arg Ser Thr Lys Leu Arg Met Val Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Ile Asp Gly Trp Tyr Gly Tyr His
            340                 345                 350

His Gln Asn Glu Gln Gly Ser Gly Tyr Ala Ala Asp Gln Lys Ser Thr

-continued

```
                355                 360                 365
Gln Asn Ala Ile Asn Gly Ile Thr Asn Lys Val Asn Ser Val Ile Glu
    370                 375                 380
Lys Met Asn Thr Gln Phe Thr Ala Val Gly Lys Glu Phe Asn Lys Leu
385                 390                 395                 400
Glu Lys Arg Met Glu Asn Leu Asn Lys Lys Val Asp Asp Gly Phe Leu
                405                 410                 415
Asp Ile Trp Thr Tyr Asn Ala Glu Leu Leu Val Leu Leu Glu Asn Glu
            420                 425                 430
Arg Thr Leu Asp Phe His Asp Ser Asn Val Lys Asn Leu Tyr Glu Lys
        435                 440                 445
Val Lys Ser Gln Leu Lys Asn Asn Ala Lys Glu Ile Gly Asn Gly Cys
    450                 455                 460
Phe Glu Phe Tyr His Lys Cys Asn Asn Glu Cys Met Glu Ser Val Lys
465                 470                 475                 480
Asn Gly Thr Tyr Asp Tyr Pro Lys Tyr Ser Glu Glu Ser Lys Leu Asn
                485                 490                 495
Arg Glu Lys Ile Asp
            500

<210> SEQ ID NO 22
<211> LENGTH: 501
<212> TYPE: PRT
<213> ORGANISM: Influenza virus

<400> SEQUENCE: 22

Asp Thr Ile Cys Ile Gly Tyr His Ala Asn Asn Ser Thr Asp Thr Val
1               5                   10                  15
Asp Thr Val Leu Glu Lys Asn Val Thr Val Thr His Ser Val Asn Leu
            20                  25                  30
Leu Glu Asp Ser His Asn Gly Lys Leu Cys Arg Leu Lys Gly Ile Ala
        35                  40                  45
Pro Leu Gln Leu Gly Lys Cys Asn Ile Ala Gly Trp Ile Leu Gly Asn
    50                  55                  60
Pro Glu Cys Glu Ser Leu Phe Ser Lys Lys Ser Trp Ser Tyr Ile Ala
65                  70                  75                  80
Glu Thr Pro Asn Ser Glu Asn Gly Thr Cys Tyr Pro Gly Tyr Phe Ala
                85                  90                  95
Asp Tyr Glu Glu Leu Arg Glu Gln Leu Ser Ser Val Ser Ser Phe Glu
                100                 105                 110
Arg Phe Glu Ile Phe Pro Lys Glu Arg Ser Trp Pro Lys His Asn Ile
            115                 120                 125
Thr Arg Gly Val Thr Ala Ala Cys Ser His Lys Gly Lys Ser Ser Phe
        130                 135                 140
Tyr Arg Asn Leu Leu Trp Leu Thr Glu Lys Asn Gly Ser Tyr Pro Asn
145                 150                 155                 160
Leu Asn Lys Ser Tyr Val Asn Asn Lys Glu Lys Glu Val Leu Val Leu
                165                 170                 175
Trp Gly Val His His Pro Ser Asn Ile Glu Asp Gln Lys Thr Leu Tyr
                180                 185                 190
Arg Lys Glu Asn Ala Tyr Val Ser Val Val Ser Ser Asn Tyr Asn Arg
            195                 200                 205
Arg Phe Thr Pro Glu Ile Ala Glu Arg Pro Lys Val Arg Gly Gln Ala
        210                 215                 220
```

-continued

```
Gly Arg Ile Asn Tyr Tyr Trp Thr Leu Leu Glu Pro Gly Asp Thr Ile
225                 230                 235                 240

Ile Phe Glu Ala Asn Gly Asn Leu Ile Ala Pro Trp His Ala Phe Ala
                245                 250                 255

Leu Ser Arg Gly Phe Gly Ser Gly Ile Ile Thr Ser Asn Ala Ser Met
            260                 265                 270

Asp Glu Cys Asp Thr Lys Cys Gln Thr Pro Gln Gly Ala Ile Asn Ser
        275                 280                 285

Ser Leu Pro Phe Gln Asn Ile His Pro Val Thr Ile Gly Glu Cys Pro
    290                 295                 300

Lys Tyr Val Arg Ser Thr Lys Leu Arg Met Val Thr Gly Leu Arg Asn
305                 310                 315                 320

Ile Pro Ser Ile Gln Ser Arg Gly Leu Phe Gly Ala Ile Ala Gly Phe
                325                 330                 335

Ile Glu Gly Gly Trp Thr Gly Met Ile Asp Gly Trp Tyr Gly Tyr His
            340                 345                 350

His Gln Asn Glu Gln Gly Ser Gly Tyr Ala Ala Asp Gln Lys Ser Thr
        355                 360                 365

Gln Asn Ala Ile Asn Gly Ile Thr Asn Lys Val Asn Ser Val Ile Glu
    370                 375                 380

Lys Met Asn Thr Gln Phe Thr Ala Val Gly Lys Glu Phe Asn Lys Leu
385                 390                 395                 400

Glu Lys Arg Met Glu Asn Leu Asn Lys Lys Val Asp Asp Gly Phe Leu
                405                 410                 415

Asp Ile Trp Thr Tyr Asn Ala Glu Leu Leu Val Leu Leu Glu Asn Glu
            420                 425                 430

Arg Thr Leu Asp Phe His Asp Ser Asn Val Lys Asn Leu Tyr Glu Lys
        435                 440                 445

Val Lys Ser Gln Leu Lys Asn Asn Ala Lys Glu Ile Gly Asn Gly Cys
    450                 455                 460

Phe Glu Phe Tyr His Lys Cys Asn Asn Glu Cys Met Glu Ser Val Lys
465                 470                 475                 480

Asn Gly Thr Tyr Asp Tyr Pro Lys Tyr Ser Glu Glu Ser Lys Leu Asn
                485                 490                 495

Arg Glu Lys Ile Asp
            500

<210> SEQ ID NO 23
<211> LENGTH: 504
<212> TYPE: PRT
<213> ORGANISM: Influenza virus

<400> SEQUENCE: 23

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Arg Thr His Asn Gly Lys Leu Cys Asp Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Ser Pro Ala Asn Asp Leu Cys Tyr Pro Gly Asn Phe Asn
                85                  90                  95
```

-continued

```
Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asn His Asp Ala Ser
        115                 120                 125

Ser Gly Val Ser Ser Ala Cys Pro Tyr Leu Gly Arg Ser Ser Phe Phe
    130                 135                 140

Arg Asn Val Val Trp Leu Ile Lys Lys Asn Ser Ala Tyr Pro Thr Ile
145                 150                 155                 160

Lys Arg Ser Tyr Asn Asn Thr Asn Gln Glu Asp Leu Leu Val Leu Trp
                165                 170                 175

Gly Val His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Glu Ile Ala Thr Arg Pro Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Thr
305                 310                 315                 320

Pro Gln Arg Glu Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Cys Tyr Ser Ala Asp Lys
        355                 360                 365

Glu Ser Thr Gln Lys Ala Ile Asp Gly Val Thr Asn Lys Val Asn Ser
    370                 375                 380

Ile Ile Asn Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Val Lys Asn Gly Thr Tyr Asp Tyr Pro Gln Tyr Ser Glu Glu Ala
                485                 490                 495

Arg Leu Asn Arg Glu Glu Ile Ser
        500
```

<210> SEQ ID NO 24
<211> LENGTH: 503
<212> TYPE: PRT
<213> ORGANISM: Influenza virus

<400> SEQUENCE: 24

```
Asp His Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asn Gly Val Lys
        35                  40                  45

Pro Leu Ile Leu Lys Asp Cys Ser Val Ala Gly Trp Leu Leu Gly Asn
50                  55                  60

Pro Met Cys Asp Glu Phe Ile Asn Val Pro Glu Trp Ser Tyr Ile Val
65                  70                  75                  80

Glu Lys Ala Asn Pro Ala Asn Asp Leu Cys Tyr Pro Gly Asn Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Asp Ser Trp Ser Asp His Glu Ala Ser
        115                 120                 125

Leu Gly Val Ser Ser Ala Cys Pro Tyr Gln Gly Asn Ser Ser Phe Phe
130                 135                 140

Arg Asn Val Val Trp Leu Ile Lys Lys Gly Asn Ala Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Glu Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
210                 215                 220

Arg Ile Asp Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Val Glu Tyr Gly
            260                 265                 270

Asn Cys Asn Thr Arg Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Lys Leu Val Leu Ala Thr Gly Leu Arg Asn Ser
305                 310                 315                 320

Pro Gln Arg Glu Arg Arg Arg Lys Arg Gly Leu Phe Gly Ala Ile Ala
                325                 330                 335

Gly Phe Ile Glu Gly Gly Trp Gln Gly Met Val Asp Gly Trp Tyr Gly
            340                 345                 350

Tyr His His Ser Asn Glu Gln Gly Ser Gly Tyr Ala Ala Asp Lys Glu
        355                 360                 365

Ser Thr Gln Lys Ala Ile Asp Gly Val Thr Asn Lys Val Asn Ser Ile
370                 375                 380
```

```
Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
                405                 410                 415

Phe Leu Asp Val Trp Thr Tyr Asn Ala Glu Leu Leu Val Leu Met Glu
            420                 425                 430

Asn Glu Arg Thr Leu Asp Phe His Asp Ser Asn Val Lys Asn Leu Tyr
        435                 440                 445

Asp Lys Val Arg Leu Gln Leu Arg Asp Asn Ala Lys Glu Leu Gly Asn
    450                 455                 460

Gly Cys Phe Glu Phe Tyr His Lys Cys Asp Asn Glu Cys Met Glu Ser
465                 470                 475                 480

Val Arg Asn Gly Thr Tyr Asp Tyr Pro Gln Tyr Ser Glu Glu Ala Arg
                485                 490                 495

Leu Lys Arg Glu Glu Ile Ser
            500

<210> SEQ ID NO 25
<211> LENGTH: 503
<212> TYPE: PRT
<213> ORGANISM: Influenza virus

<400> SEQUENCE: 25

Asp Gln Ile Cys Val Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asn Leu Asp Gly Val Lys
        35                  40                  45

Pro Leu Ile Leu Lys Asp Cys Ser Val Ala Gly Trp Leu Leu Gly Asn
    50                  55                  60

Pro Met Cys Asp Glu Phe Leu Asn Val Ser Glu Trp Ser Tyr Ile Val
65                  70                  75                  80

Glu Lys Ala Ser Pro Ala Asn Gly Leu Cys Tyr Pro Gly Asp Phe Asn
                85                  90                  95

Asp Tyr Glu Glu Leu Lys His Leu Leu Ser Arg Ile Asn His Phe Glu
            100                 105                 110

Lys Ile Lys Ile Ile Pro Lys Ser Ser Trp Ser Asn His Glu Ala Ser
        115                 120                 125

Gly Val Ser Ser Ala Cys Ser Tyr Leu Gly Lys Pro Ser Phe Phe Arg
    130                 135                 140

Asn Leu Val Trp Leu Ile Lys Lys Asn Asn Thr Tyr Pro Pro Ile Lys
145                 150                 155                 160

Val Asn Tyr Thr Asn Thr Asn Gln Glu Asp Leu Leu Val Leu Trp Gly
                165                 170                 175

Ile His His Pro Asn Asp Glu Thr Glu Gln Val Lys Ile Tyr Gln Asn
            180                 185                 190

Pro Thr Thr Tyr Ile Ser Val Gly Thr Ser Thr Leu Asn Gln Arg Leu
        195                 200                 205

Val Pro Lys Ile Ala Thr Arg Ser Lys Val Asn Gly Gln Ser Gly Arg
    210                 215                 220

Met Glu Phe Phe Trp Thr Ile Leu Lys Pro Asn Asp Ala Ile Asn Phe
225                 230                 235                 240

Asp Ser Asn Gly Asn Phe Ile Ala Pro Glu Tyr Ala Tyr Lys Ile Val
```

```
                    245                 250                 255
Lys Lys Gly Asp Ser Ala Ile Met Lys Ser Glu Leu Glu Tyr Gly Asn
            260                 265                 270

Cys Asn Thr Lys Cys Gln Thr Pro Met Gly Ala Ile Asn Ser Ser Met
        275                 280                 285

Pro Phe His Asn Ile His Pro Leu Thr Ile Gly Glu Cys Pro Lys Tyr
    290                 295                 300

Val Lys Ser Asn Arg Leu Val Leu Ala Thr Gly Leu Arg Asn Ala Pro
305                 310                 315                 320

Gln Arg Glu Gly Gly Arg Arg Lys Arg Gly Leu Phe Gly Ala Ile Ala
                325                 330                 335

Gly Phe Ile Glu Gly Gly Trp Gln Gly Met Val Asp Gly Trp Tyr Gly
            340                 345                 350

Tyr His His Ser Asn Glu Gln Gly Ser Gly Tyr Ala Ala Asp Lys Glu
        355                 360                 365

Ser Thr Gln Lys Ala Ile Asp Gly Ile Thr Asn Lys Val Asn Ser Ile
    370                 375                 380

Ile Asp Lys Met Asn Thr Gln Phe Glu Ala Val Gly Arg Glu Phe Asn
385                 390                 395                 400

Asn Leu Glu Arg Arg Ile Glu Asn Leu Asn Lys Lys Met Glu Asp Gly
                405                 410                 415

Phe Leu Asp Val Trp Thr Tyr Asn Ala Glu Leu Leu Val Leu Met Glu
            420                 425                 430

Asn Glu Arg Thr Leu Asp Phe His Asp Ser Asn Val Lys Asn Leu Tyr
        435                 440                 445

Glu Lys Val Arg Leu Gln Leu Arg Asp Asn Ala Lys Glu Leu Gly Asn
    450                 455                 460

Gly Cys Phe Glu Phe Tyr His Lys Cys Asp Asn Glu Cys Met Glu Ser
465                 470                 475                 480

Val Lys Asn Gly Thr Tyr Asp Tyr Pro Gln Tyr Ser Glu Glu Ala Arg
                485                 490                 495

Leu Asn Arg Glu Glu Ile Ser
            500

<210> SEQ ID NO 26
<211> LENGTH: 504
<212> TYPE: PRT
<213> ORGANISM: Influenza virus

<400> SEQUENCE: 26

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Ser Pro Ala Asn Asp Leu Cys Tyr Pro Gly Asp Phe Asn
                85                  90                  95

Asp Tyr Glu Glu Leu Lys His Leu Leu Ser Arg Ile Asn His Phe Glu
            100                 105                 110
```

Lys Ile Gln Ile Ile Pro Lys Ser Ser Trp Ser Asn His Glu Ala Ser
            115                 120                 125

Ser Gly Val Ser Ser Ala Cys Pro Tyr Leu Gly Lys Ser Ser Phe Phe
130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Asn Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Lys Ile Ala Thr Arg Ser Lys Val Asn Gly Gln Ser Gly
210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
290                 295                 300

Tyr Val Lys Ser Asn Arg Leu Val Leu Ala Thr Gly Leu Arg Asn Thr
305                 310                 315                 320

Pro Gln Arg Glu Arg Arg Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Val Lys Asn Gly Thr Tyr Asp Tyr Pro Gln Tyr Ser Glu Glu Ala
                485                 490                 495

Arg Leu Asn Arg Glu Glu Ile Ser
            500

<210> SEQ ID NO 27
<211> LENGTH: 504
<212> TYPE: PRT

<213> ORGANISM: Influenza virus

<400> SEQUENCE: 27

Asp Gln Ile Cys Ile Gly Tyr His Ala Asn Asn Ser Thr Glu Gln Val
1 5 10 15

Asp Thr Ile Met Glu Lys Asn Val Ala Val Thr His Ala Gln Asp Ile
20 25 30

Leu Glu Lys Thr His Asn Gly Lys Leu Cys Asp Leu Asp Gly Val Lys
35 40 45

Pro Leu Ile Leu Arg Asp Cys Ser Val Ala Gly Trp Leu Leu Gly Asn
50 55 60

Pro Met Cys Asp Glu Phe Ile Asn Val Pro Glu Trp Ser Tyr Ile Val
65 70 75 80

Glu Lys Ala Ser Pro Ala Asn Gly Leu Cys Tyr Pro Gly Asp Phe Asn
85 90 95

Asp Tyr Glu Glu Leu Lys His Leu Leu Ser Arg Ile Asn His Phe Glu
100 105 110

Lys Ile Gln Ile Ile Pro Lys Ser Ser Trp Ser Asn His Glu Ala Ser
115 120 125

Ser Gly Val Ser Ser Ala Cys Pro Tyr Gln Gly Lys Ser Ser Phe Phe
130 135 140

Arg Asn Val Val Trp Leu Ile Lys Lys Asn Ser Thr Tyr Pro Thr Ile
145 150 155 160

Lys Arg Ser Tyr Asn Asn Thr Asn Gln Glu Asp Leu Leu Val Leu Trp
165 170 175

Gly Ile His His Pro Asn Asp Ala Ala Glu Gln Thr Arg Leu Tyr Gln
180 185 190

Asn Pro Thr Thr Tyr Ile Ser Val Gly Thr Ser Thr Leu Asn Gln Arg
195 200 205

Leu Val Pro Lys Ile Ala Thr Arg Ser Lys Val Asn Gly Gln Ser Gly
210 215 220

Arg Met Glu Phe Phe Trp Thr Ile Leu Lys Pro Asn Asp Ala Ile Asn
225 230 235 240

Phe Glu Ser Asn Gly Asn Phe Ile Ala Pro Glu Tyr Ala Tyr Lys Ile
245 250 255

Val Lys Lys Gly Asp Ser Ala Ile Met Lys Ser Glu Leu Glu Tyr Gly
260 265 270

Asn Cys Asn Thr Lys Cys Gln Thr Pro Met Gly Ala Ile Asn Ser Ser
275 280 285

Met Pro Phe His Asn Ile His Pro Leu Thr Ile Gly Glu Cys Pro Lys
290 295 300

Tyr Val Lys Ser Asn Arg Leu Val Leu Ala Thr Gly Leu Arg Asn Ser
305 310 315 320

Pro Gln Arg Glu Arg Arg Arg Lys Lys Arg Gly Leu Phe Gly Ala Ile
325 330 335

Ala Gly Phe Ile Glu Gly Gly Trp Gln Gly Met Val Asp Gly Trp Tyr
340 345 350

Gly Tyr His His Ser Asn Glu Gln Gly Ser Gly Tyr Ala Ala Asp Lys
355 360 365

Glu Ser Thr Gln Lys Ala Ile Asp Gly Val Thr Asn Lys Val Asn Ser
370 375 380

Ile Ile Asp Lys Met Asn Thr Gln Phe Glu Ala Val Gly Arg Glu Phe
385 390 395 400

-continued

Asn Asn Leu Glu Arg Arg Ile Glu Asn Leu Asn Lys Lys Met Glu Asp
            405                 410                 415

Gly Phe Leu Asp Val Trp Thr Tyr Asn Ala Glu Leu Leu Val Leu Met
        420                 425                 430

Glu Asn Glu Arg Thr Leu Asp Phe His Asp Ser Asn Val Lys Asn Leu
            435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ala
            485                 490                 495

Arg Leu Lys Arg Glu Glu Ile Ser
            500

<210> SEQ ID NO 28
<211> LENGTH: 503
<212> TYPE: PRT
<213> ORGANISM: Influenza virus

<400> SEQUENCE: 28

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Asn Ser Ser Ile
        35                  40                  45

Gly Glu Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Ile Arg Arg Ser Asn
    130                 135                 140

Asn Ser Phe Phe Ser Arg Leu Asn Trp Leu Thr Gln Leu Asn Phe Lys
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Val Thr Asp Lys Asp Gln Ile
            180                 185                 190

Phe Leu Tyr Ala Gln Ser Ser Gly Arg Ile Thr Val Ser Thr Lys Arg
        195                 200                 205

Ser Gln Gln Ala Val Ile Pro Asn Ile Gly Tyr Arg Pro Arg Ile Arg
    210                 215                 220

Asn Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

```
Pro Ile Gly Lys Cys Asn Ser Glu Cys Ile Thr Pro Asn Gly Ser Ile
            275                 280                 285

Pro Asn Asp Lys Pro Phe Gln Asn Val Asn Arg Ile Thr Tyr Gly Ala
290                 295                 300

Cys Pro Arg Tyr Val Lys Gln Ser Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Arg Gly Gln Ala Ala Asp Leu Lys
            355                 360                 365

Ser Thr Gln Ala Ala Ile Asp Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Lys Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys
            500

<210> SEQ ID NO 29
<211> LENGTH: 532
<212> TYPE: PRT
<213> ORGANISM: Influenza virus

<400> SEQUENCE: 29

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser Tyr Phe Ala Asn Leu Lys Gly Thr Lys
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Arg Pro Val Thr Ser Gly Cys Phe Pro
                85                  90                  95

Ile Met His Asp Arg Thr Lys Ile Arg Gln Leu Ala Asn Leu Leu Arg
            100                 105                 110

Gly Tyr Glu Asn Ile Arg Leu Ser Thr Gln Asn Val Ile Asp Ala Glu
        115                 120                 125

Lys Ala Pro Gly Gly Pro Tyr Arg Leu Gly Thr Ser Gly Ser Cys Pro
```

```
            130                 135                 140
Asn Ala Thr Ser Lys Ser Gly Phe Phe Ala Thr Met Ala Trp Ala Val
145                 150                 155                 160

Pro Lys Asp Asn Asn Lys Asn Ala Thr Asn Pro Leu Thr Val Glu Val
                165                 170                 175

Pro Tyr Ile Cys Ala Glu Gly Glu Asp Gln Ile Thr Val Trp Gly Phe
                180                 185                 190

His Ser Asp Asp Lys Thr Gln Met Lys Asn Leu Tyr Gly Asp Ser Asn
                195                 200                 205

Pro Gln Lys Phe Thr Ser Ser Ala Asn Gly Val Thr Thr His Tyr Val
        210                 215                 220

Ser Gln Ile Gly Gly Phe Pro Asp Gln Thr Glu Asp Gly Gly Leu Pro
225                 230                 235                 240

Gln Ser Gly Arg Ile Val Val Asp Tyr Met Met Gln Lys Pro Gly Lys
                245                 250                 255

Thr Gly Thr Ile Val Tyr Gln Arg Gly Val Leu Leu Pro Gln Lys Val
                260                 265                 270

Trp Cys Ala Ser Gly Arg Ser Lys Val Ile Lys Gly Ser Leu Pro Leu
            275                 280                 285

Ile Gly Glu Ala Asp Cys Leu His Glu Lys Tyr Gly Gly Leu Asn Lys
        290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg Gly Phe Phe Gly Ala Ile
                340                 345                 350

Ala Gly Phe Leu Glu Gly Gly Trp Glu Gly Met Ile Ala Gly Trp His
            355                 360                 365

Gly Tyr Thr Ser His Gly Ala His Gly Val Ala Val Ala Ala Asp Leu
        370                 375                 380

Lys Ser Thr Gln Glu Ala Ile Asn Lys Ile Thr Lys Asn Leu Asn Ser
385                 390                 395                 400

Leu Ser Glu Leu Glu Val Lys Asn Leu Gln Arg Leu Ser Gly Ala Met
                405                 410                 415

Asp Glu Leu His Asn Glu Ile Leu Glu Leu Asp Glu Lys Val Asp Asp
                420                 425                 430

Leu Arg Ala Asp Thr Ile Ser Ser Gln Ile Glu Leu Ala Val Leu Leu
            435                 440                 445

Ser Asn Glu Gly Ile Ile Asn Ser Glu Asp Glu His Leu Leu Ala Leu
        450                 455                 460

Glu Arg Lys Leu Lys Lys Met Leu Gly Pro Ser Ala Val Asp Ile Gly
465                 470                 475                 480

Asn Gly Cys Phe Glu Thr Lys His Lys Cys Asn Gln Thr Cys Leu Asp
                485                 490                 495

Arg Ile Ala Ala Gly Thr Phe Asn Ala Gly Glu Phe Ser Leu Pro Thr
                500                 505                 510

Phe Asp Ser Leu Asn Ile Thr Ala Ala Ser Leu Asn Asp Asp Gly Leu
            515                 520                 525

Asp Asn His Thr
        530

<210> SEQ ID NO 30
```

-continued

<211> LENGTH: 533
<212> TYPE: PRT
<213> ORGANISM: Influenza virus

<400> SEQUENCE: 30

```
Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Lys Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu His Ile Arg Leu Ser Thr His Asn Val Ile Asn Ala Glu
        115                 120                 125

Asn Ala Pro Gly Gly Pro Tyr Lys Ile Gly Thr Ser Gly Ser Cys Pro
    130                 135                 140

Asn Ile Thr Asn Gly Asn Gly Phe Phe Ala Thr Met Ala Trp Ala Val
145                 150                 155                 160

Pro Lys Asn Asp Lys Asn Lys Thr Ala Thr Asn Pro Leu Thr Ile Glu
                165                 170                 175

Val Pro Tyr Ile Cys Thr Glu Gly Glu Asp Gln Ile Thr Val Trp Gly
            180                 185                 190

Phe His Ser Asp Asn Glu Thr Gln Met Ala Lys Leu Tyr Gly Asp Ser
        195                 200                 205

Lys Pro Gln Lys Phe Thr Ser Ser Ala Asn Gly Val Thr Thr His Tyr
    210                 215                 220

Val Ser Gln Ile Gly Gly Phe Pro Asn Gln Thr Glu Asp Gly Gly Leu
225                 230                 235                 240

Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
        275                 280                 285

Leu Ile Gly Glu Ala Asp Cys Leu His Glu Lys Tyr Gly Gly Leu Asn
    290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg Gly Phe Phe Gly Ala
            340                 345                 350

Ile Ala Gly Phe Leu Glu Gly Gly Trp Glu Gly Met Ile Ala Gly Trp
        355                 360                 365

His Gly Tyr Thr Ser His Gly Ala His Gly Val Ala Val Ala Ala Asp
    370                 375                 380

Leu Lys Ser Thr Gln Glu Ala Ile Asn Lys Ile Thr Lys Asn Leu Asn
```

```
385                 390                 395                 400
Ser Leu Ser Glu Leu Glu Val Lys Asn Leu Gln Arg Leu Ser Gly Ala
                405                 410                 415

Met Asp Glu Leu His Asn Glu Ile Leu Glu Leu Asp Glu Lys Val Asp
                420                 425                 430

Asp Leu Arg Ala Asp Thr Ile Ser Ser Gln Ile Glu Leu Ala Val Leu
            435                 440                 445

Leu Ser Asn Glu Gly Ile Ile Asn Ser Glu Asp Glu His Leu Leu Ala
        450                 455                 460

Leu Glu Arg Lys Leu Lys Lys Met Leu Gly Pro Ser Ala Val Glu Ile
465                 470                 475                 480

Gly Asn Gly Cys Phe Glu Thr Lys His Lys Cys Asn Gln Thr Cys Leu
                485                 490                 495

Asp Arg Ile Ala Ala Gly Thr Phe Asp Ala Gly Glu Phe Ser Leu Pro
            500                 505                 510

Thr Phe Asp Ser Leu Asn Ile Thr Ala Ala Ser Leu Asn Asp Asp Gly
        515                 520                 525

Leu Asp Asn His Thr
    530

<210> SEQ ID NO 31
<211> LENGTH: 503
<212> TYPE: PRT
<213> ORGANISM: Influenza virus

<400> SEQUENCE: 31

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
                20                  25                  30

Arg Ile Glu Val Thr Asn Ala Thr Glu Leu Val Gln Asn Ser Ser Ile
            35                  40                  45

Gly Glu Ile Cys Asp Ser Pro His Gln Ile Leu Asp Gly Glu Asn Cys
        50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Asn
        115                 120                 125

Gly Val Thr Gln Asn Gly Thr Ser Ser Ala Cys Ile Arg Arg Ser Asn
    130                 135                 140

Asn Ser Phe Phe Ser Arg Leu Asn Trp Leu Thr His Leu Asn Phe Lys
145                 150                 155                 160

Tyr Pro Ala Leu Asn Val Thr Met Pro Asn Asn Glu Gln Phe Asp Lys
                165                 170                 175

Leu Tyr Ile Trp Gly Val His His Pro Val Thr Asp Lys Asp Gln Ile
            180                 185                 190

Phe Leu Tyr Ala Gln Pro Ser Gly Arg Ile Thr Val Ser Thr Lys Arg
        195                 200                 205

Ser Gln Gln Ala Val Ile Pro Asn Ile Gly Phe Arg Pro Arg Ile Arg
    210                 215                 220
```

```
Asn Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
            245                 250                 255

Tyr Phe Lys Ile Arg Ser Gly Lys Ser Ser Ile Met Arg Ser Asp Ala
        260                 265                 270

Pro Ile Gly Lys Cys Lys Ser Glu Cys Ile Thr Pro Asn Gly Ser Ile
    275                 280                 285

Pro Asn Asp Lys Pro Phe Gln Asn Val Asn Arg Ile Thr Tyr Gly Ala
290                 295                 300

Cys Pro Arg Tyr Val Lys Gln Ser Thr Leu Lys Leu Ala Thr Gly Met
305                 310                 315                 320

Arg Asn Val Pro Glu Lys Gln Thr Arg Gly Ile Phe Gly Ala Ile Ala
            325                 330                 335

Gly Phe Ile Glu Asn Gly Trp Glu Gly Met Val Asp Gly Trp Tyr Gly
        340                 345                 350

Phe Arg His Gln Asn Ser Glu Gly Arg Gly Gln Ala Ala Asp Leu Lys
    355                 360                 365

Ser Thr Gln Ala Ala Ile Asp Gln Ile Asn Gly Lys Leu Asn Arg Leu
370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
            405                 410                 415

Lys Ile Asp Leu Trp Ser Tyr Asn Ala Glu Leu Leu Val Ala Leu Glu
        420                 425                 430

Asn Gln His Thr Ile Asp Leu Thr Asp Ser Glu Met Asn Lys Leu Phe
    435                 440                 445

Glu Lys Thr Lys Lys Gln Leu Arg Glu Asn Ala Glu Asp Met Gly Asn
450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
            485                 490                 495

Asn Asn Arg Phe Gln Ile Lys
            500

<210> SEQ ID NO 32
<211> LENGTH: 213
<212> TYPE: PRT
<213> ORGANISM: Influenza virus

<400> SEQUENCE: 32

Ile Ala Pro Leu Gln Leu Gly Asn Cys Ser Val Ala Gly Trp Ile Leu
1               5                   10                  15

Gly Asn Pro Glu Cys Glu Leu Leu Ile Ser Lys Glu Ser Trp Ser Tyr
            20                  25                  30

Ile Val Glu Thr Pro Asn Pro Glu Asn Gly Thr Cys Tyr Pro Gly Tyr
        35                  40                  45

Phe Ala Asp Tyr Glu Glu Leu Arg Glu Gln Leu Ser Ser Val Ser Ser
    50                  55                  60

Phe Glu Arg Phe Glu Ile Phe Pro Lys Glu Ser Ser Trp Pro Asn His
65                  70                  75                  80

Thr Val Thr Gly Val Ser Ala Ser Cys Ser His Asn Gly Lys Ser Ser
            85                  90                  95
```

Phe Tyr Arg Asn Leu Leu Trp Leu Thr Gly Lys Asn Gly Leu Tyr Pro
            100                 105                 110

Asn Leu Ser Lys Ser Tyr Val Asn Asn Lys Glu Lys Glu Val Leu Val
            115                 120                 125

Leu Trp Gly Val His His Pro Pro Asn Ile Gly Asn Gln Arg Ala Leu
130                 135                 140

Tyr His Thr Glu Asn Ala Tyr Val Ser Val Val Ser Ser His Tyr Ser
145                 150                 155                 160

Arg Arg Phe Thr Pro Glu Ile Ala Lys Arg Pro Lys Val Arg Asp Gln
                165                 170                 175

Glu Gly Arg Ile Asn Tyr Tyr Trp Thr Leu Leu Glu Pro Gly Asp Thr
            180                 185                 190

Ile Ile Phe Glu Ala Asn Gly Asn Leu Ile Ala Pro Trp Tyr Ala Phe
        195                 200                 205

Ala Leu Ser Arg Gly
        210

<210> SEQ ID NO 33
<211> LENGTH: 213
<212> TYPE: PRT
<213> ORGANISM: Influenza virus

<400> SEQUENCE: 33

Ile Ala Pro Leu Gln Leu Gly Asn Cys Ser Val Ala Gly Trp Ile Leu
1               5                   10                  15

Gly Asn Pro Glu Cys Glu Leu Leu Ile Ser Lys Glu Ser Trp Ser Tyr
            20                  25                  30

Ile Val Glu Thr Pro Asn Pro Glu Asn Gly Thr Cys Phe Pro Gly Tyr
        35                  40                  45

Phe Ala Asp Tyr Glu Glu Leu Arg Glu Gln Leu Ser Ser Val Ser Ser
    50                  55                  60

Phe Glu Arg Phe Glu Ile Phe Pro Lys Glu Ser Ser Trp Pro Asn His
65                  70                  75                  80

Thr Val Thr Gly Val Ser Ala Ser Cys Ser His Asn Gly Lys Ser Ser
                85                  90                  95

Phe Tyr Arg Asn Leu Leu Trp Leu Thr Gly Lys Asn Gly Leu Tyr Pro
            100                 105                 110

Asn Leu Ser Lys Ser Tyr Val Asn Asn Lys Glu Lys Glu Val Leu Val
            115                 120                 125

Leu Trp Gly Val His His Pro Pro Asn Ile Gly Asn Gln Arg Ala Leu
130                 135                 140

Tyr His Thr Glu Asn Ala Tyr Val Ser Val Val Ser Ser His Tyr Ser
145                 150                 155                 160

Arg Arg Phe Thr Pro Glu Ile Ala Lys Arg Pro Lys Val Arg Asp Gln
                165                 170                 175

Glu Gly Arg Ile Asn Tyr Tyr Trp Thr Leu Leu Glu Pro Gly Asp Thr
            180                 185                 190

Ile Ile Phe Glu Ala Asn Gly Asn Leu Ile Ala Pro Trp Tyr Ala Phe
        195                 200                 205

Ala Leu Ser Arg Gly
        210

<210> SEQ ID NO 34
<211> LENGTH: 214
<212> TYPE: PRT

<213> ORGANISM: Influenza virus

<400> SEQUENCE: 34

Val Ala Pro Leu His Leu Gly Lys Cys Asn Ile Ala Gly Trp Ile

```
Leu Tyr Gln Asn Ala Asp Thr Tyr Val Phe Val Gly Ser Ser Arg Tyr
145                 150                 155                 160

Ser Lys Lys Phe Lys Pro Glu Ile Ala Ile Arg Pro Lys Val Arg Asp
                165                 170                 175

Gln Glu Gly Arg Met Asn Tyr Tyr Trp Thr Leu Val Glu Pro Gly Asp
            180                 185                 190

Lys Ile Thr Phe Glu Ala Thr Gly Asn Leu Val Val Pro Arg Tyr Ala
        195                 200                 205

Phe Ala Met Glu Arg Asn
    210

<210> SEQ ID NO 36
<211> LENGTH: 213
<212> TYPE: PRT
<213> ORGANISM: Influenza virus

<400> SEQUENCE: 36

Ile Pro Pro Leu Glu Leu Gly Asp Cys Ser Ile Ala Gly Trp Leu Leu
1               5                   10                  15

Gly Asn Pro Glu Cys Asp Arg Leu Leu Ser Val Pro Glu Trp Ser Tyr
            20                  25                  30

Ile Met Glu Lys Glu Asn Pro Arg Asp Gly Leu Cys Tyr Pro Gly Ser
        35                  40                  45

Phe Asn Asp Tyr Glu Glu Leu Lys His Leu Leu Ser Ser Val Lys His
    50                  55                  60

Phe Glu Lys Val Lys Ile Leu Pro Lys Asp Arg Trp Thr Gln His Thr
65                  70                  75                  80

Thr Thr Gly Gly Ser Arg Ala Cys Ala Val Ser Gly Asn Pro Ser Phe
                85                  90                  95

Phe Arg Asn Met Val Trp Leu Thr Lys Lys Gly Ser Asn Tyr Pro Val
            100                 105                 110

Ala Lys Gly Ser Tyr Asn Asn Thr Ser Gly Glu Gln Met Leu Ile Ile
        115                 120                 125

Trp Gly Val His His Pro Asn Asp Glu Thr Glu Gln Arg Thr Leu Tyr
    130                 135                 140

Gln Asn Val Gly Thr Tyr Val Ser Val Gly Thr Ser Thr Leu Asn Lys
145                 150                 155                 160

Arg Ser Thr Pro Asp Ile Ala Thr Arg Pro Lys Val Asn Gly Gln Gly
                165                 170                 175

Gly Arg Met Glu Phe Ser Trp Thr Leu Leu Asp Met Trp Asp Thr Ile
            180                 185                 190

Asn Phe Glu Ser Thr Gly Asn Leu Ile Ala Pro Glu Tyr Gly Phe Lys
        195                 200                 205

Ile Ser Lys Arg Gly
    210

<210> SEQ ID NO 37
<211> LENGTH: 209
<212> TYPE: PRT
<213> ORGANISM: Influenza virus

<400> SEQUENCE: 37

His Arg Ile Leu Asp Gly Ile Asp Cys Thr Leu Ile Asp Ala Leu Leu
1               5                   10                  15

Gly Asp Pro His Cys Asp Val Phe Gln Asn Glu Thr Trp Asp Leu Phe
```

```
            20                  25                  30
Val Glu Arg Ser Lys Ala Phe Ser Asn Cys Tyr Pro Tyr Asp Val Pro
             35                  40                  45

Asp Tyr Ala Ser Leu Arg Ser Leu Val Ala Ser Ser Gly Thr Leu Glu
         50                  55                  60

Phe Ile Thr Glu Gly Phe Thr Trp Thr Gly Val Thr Gln Asn Gly Gly
 65                  70                  75                  80

Ser Asn Ala Cys Lys Arg Gly Pro Gly Ser Gly Phe Phe Ser Arg Leu
                 85                  90                  95

Asn Trp Leu Thr Lys Ser Gly Ser Thr Tyr Pro Val Leu Asn Val Thr
            100                 105                 110

Met Pro Asn Asn Asp Asn Phe Asp Lys Leu Tyr Ile Trp Gly Val His
            115                 120                 125

His Pro Ser Thr Asn Gln Glu Gln Thr Ser Leu Tyr Val Gln Ala Ser
        130                 135                 140

Gly Arg Val Thr Val Ser Thr Arg Arg Ser Gln Gln Thr Ile Ile Pro
145                 150                 155                 160

Asn Ile Glu Ser Arg Pro Trp Val Arg Gly Leu Ser Ser Arg Ile Ser
                165                 170                 175

Ile Tyr Trp Thr Ile Val Lys Pro Gly Asp Val Leu Val Ile Asn Ser
            180                 185                 190

Asn Gly Asn Leu Ile Ala Pro Arg Gly Tyr Phe Lys Met Arg Thr Gly
            195                 200                 205

Lys

<210> SEQ ID NO 38
<211> LENGTH: 209
<212> TYPE: PRT
<213> ORGANISM: Influenza virus

<400> SEQUENCE: 38

His Gln Ile Leu Asp Gly Glu Asn Cys Thr Leu Ile Asp Ala Leu Leu
 1               5                  10                  15

Gly Asp Pro Gln Cys Asp Gly Phe Gln Asn Lys Lys Trp Asp Leu Phe
             20                  25                  30

Val Glu Arg Ser Lys Ala Tyr Ser Asn Cys Tyr Pro Tyr Asp Val Pro
             35                  40                  45

Asp Tyr Ala Ser Leu Arg Ser Leu Val Ala Ser Ser Gly Thr Leu Glu
         50                  55                  60

Phe Asn Asn Glu Ser Phe Asn Trp Thr Gly Val Thr Gln Asn Gly Thr
 65                  70                  75                  80

Ser Ser Ala Cys Ile Arg Arg Ser Asn Asn Ser Phe Phe Ser Arg Leu
                 85                  90                  95

Asn Trp Leu Thr His Leu Lys Phe Lys Tyr Pro Ala Leu Asn Val Thr
            100                 105                 110

Met Pro Asn Asn Glu Lys Phe Asp Lys Leu Tyr Ile Trp Gly Val His
            115                 120                 125

His Pro Gly Thr Asp Asn Asp Gln Ile Phe Pro Tyr Ala Gln Ala Ser
        130                 135                 140

Gly Arg Ile Thr Val Ser Thr Lys Arg Ser Gln Gln Thr Val Ile Pro
145                 150                 155                 160

Asn Ile Gly Ser Arg Pro Arg Val Arg Asn Ile Pro Ser Arg Ile Ser
                165                 170                 175

Ile Tyr Trp Thr Ile Val Lys Pro Gly Asp Ile Leu Leu Ile Asn Ser
```

```
                180                 185                 190
Thr Gly Asn Leu Ile Ala Pro Arg Gly Tyr Phe Lys Ile Arg Ser Gly
            195                 200                 205
Lys

<210> SEQ ID NO 39
<211> LENGTH: 232
<212> TYPE: PRT
<213> ORGANISM: Influenza virus

<400> SEQUENCE: 39

Arg Thr Arg Gly Lys Leu Cys Pro Asp Cys Leu Asn Cys Thr Asp Leu
1               5                   10                  15

Asp Val Ala Leu Gly Arg Pro Met Cys Val Gly Thr Thr Pro Ser Ala
            20                  25                  30

Lys Ala Ser Ile Leu His Glu Val Lys Pro Val Thr Ser Gly Cys Phe
        35                  40                  45

Pro Ile Met His Asp Arg Thr Lys Ile Arg Gln Leu Pro Asn Leu Leu
    50                  55                  60

Arg Gly Tyr Glu Asn Ile Arg Leu Ser Thr Gln Asn Val Ile Asp Ala
65                  70                  75                  80

Glu Lys Ala Pro Gly Gly Pro Tyr Arg Leu Gly Thr Ser Gly Ser Cys
                85                  90                  95

Pro Asn Ala Thr Ser Lys Ser Gly Phe Phe Ala Thr Met Ala Trp Ala
            100                 105                 110

Val Pro Lys Asp Asn Asn Lys Asn Ala Thr Asn Pro Leu Thr Val Glu
        115                 120                 125

Val Pro Tyr Ile Cys Thr Glu Gly Glu Asp Gln Ile Thr Val Trp Gly
    130                 135                 140

Phe His Ser Asp Asp Lys Thr Gln Met Lys Asn Leu Tyr Gly Asp Ser
145                 150                 155                 160

Asn Pro Gln Lys Phe Thr Ser Ser Ala Asn Gly Val Thr Thr His Tyr
                165                 170                 175

Val Ser Gln Ile Gly Ser Phe Pro Asp Gln Thr Glu Asp Gly Gly Leu
            180                 185                 190

Pro Gln Ser Gly Arg Ile Val Val Asp Tyr Met Met Gln Lys Pro Gly
        195                 200                 205

Lys Thr Gly Thr Ile Val Tyr Gln Arg Gly Val Leu Leu Pro Gln Lys
    210                 215                 220

Val Trp Cys Ala Ser Gly Arg Ser
225                 230

<210> SEQ ID NO 40
<211> LENGTH: 209
<212> TYPE: PRT
<213> ORGANISM: Influenza virus

<400> SEQUENCE: 40

His Gln Ile Leu Asp Gly Lys Asn Cys Thr Leu Ile Asp Ala Leu Leu
1               5                   10                  15

Gly Asp Pro Gln Cys Asp Gly Phe Gln Asn Lys Lys Trp Asp Leu Phe
            20                  25                  30

Val Glu Arg Ser Lys Ala Tyr Ser Asn Cys Tyr Pro Tyr Asp Val Pro
        35                  40                  45

Asp Tyr Ala Ser Leu Arg Ser Leu Val Ala Ser Ser Gly Thr Leu Glu
    50                  55                  60
```

```
Phe Asn Asn Glu Ser Phe Asn Trp Thr Gly Val Thr Gln Asn Gly Thr
 65                  70                  75                  80

Ser Ser Ala Cys Ile Arg Arg Ser Lys Asn Ser Phe Phe Ser Arg Leu
                 85                  90                  95

Asn Trp Leu Thr His Leu Asn Phe Lys Tyr Pro Ala Leu Asn Val Thr
            100                 105                 110

Met Pro Asn Asn Glu Gln Phe Asp Lys Leu Tyr Ile Trp Gly Val His
        115                 120                 125

His Pro Gly Thr Asp Lys Asp Gln Ile Phe Leu Tyr Ala Gln Ala Ser
    130                 135                 140

Gly Arg Ile Thr Val Ser Thr Lys Arg Ser Gln Gln Thr Val Ser Pro
145                 150                 155                 160

Asn Ile Gly Ser Arg Pro Arg Val Arg Asn Ile Pro Ser Arg Ile Ser
                165                 170                 175

Ile Tyr Trp Thr Ile Val Lys Pro Gly Asp Ile Leu Leu Ile Asn Ser
            180                 185                 190

Thr Gly Asn Leu Ile Ala Pro Arg Gly Tyr Phe Lys Ile Arg Ser Gly
        195                 200                 205

Lys

<210> SEQ ID NO 41
<211> LENGTH: 214
<212> TYPE: PRT
<213> ORGANISM: Influenza virus

<400> SEQUENCE: 41

Ile Ala Pro Leu Gln Leu Gly Lys Cys Asn Ile Ala Gly Trp Leu Leu
  1               5                  10                  15

Gly Asn Pro Glu Cys Asp Ser Leu Leu Pro Ala Lys Ser Trp Ser Tyr
                 20                  25                  30

Ile Val Glu Thr Pro Asn Ser Glu Asn Gly Ala Cys Phe Pro Gly Asp
             35                  40                  45

Phe Ile Asp Tyr Glu Glu Leu Lys Glu Gln Leu Ser Ser Val Ser Ser
 50                  55                  60

Leu Glu Arg Phe Glu Ile Phe Pro Lys Glu Ser Ser Trp Pro Asn His
 65                  70                  75                  80

Asn Thr Leu Lys Gly Val Thr Ala Ala Cys Ser His Arg Gly Lys Ser
                 85                  90                  95

Ser Phe Tyr Arg Asn Leu Leu Trp Leu Thr Lys Thr Gly Asp Ser Tyr
            100                 105                 110

Pro Lys Leu Asn Asn Ser Tyr Val Asn Asn Lys Gly Lys Glu Val Leu
        115                 120                 125

Val Leu Trp Gly Val His His Pro Ser Ser Ser Asn Glu Gln Gln Ser
    130                 135                 140

Leu Tyr His Asn Val Asn Ala Tyr Val Ser Val Val Ser Ser Asn Tyr
145                 150                 155                 160

Asn Arg Arg Phe Thr Pro Glu Ile Ala Ala Arg Pro Lys Val Arg Asp
                165                 170                 175

Gln Pro Gly Arg Met Asn Tyr Tyr Trp Thr Leu Leu Glu Pro Gly Asp
            180                 185                 190

Thr Ile Ile Phe Glu Ala Thr Gly Asn Leu Ile Ala Pro Trp Tyr Ala
        195                 200                 205

Phe Ala Leu Ser Arg Gly
        210
```

<210> SEQ ID NO 42
<211> LENGTH: 214
<212> TYPE: PRT
<213> ORGANISM: Influenza virus

<400> SEQUENCE: 42

Ile Ala Pro Leu Gln Leu Gly Lys Cys Ser Ile Ala Gly Trp Ile Leu
1               5                   10                  15

Gly Asn Pro Glu Cys Glu Ser Leu Phe Ser Lys Lys Ser Trp Ser Tyr
            20                  25                  30

Ile Ala Glu Thr Pro Asn Ser Glu Asn Gly Thr Cys Phe Pro Gly Tyr
        35                  40                  45

Phe Ala Asp Tyr Glu Glu Leu Arg Glu Gln Leu Ser Ser Val Ser Ser
    50                  55                  60

Phe Glu Arg Phe Glu Ile Phe Pro Lys Glu Arg Ser Trp Pro Lys His
65                  70                  75                  80

Asn Val Thr Arg Gly Val Thr Ala Ser Cys Ser His Lys Gly Lys Ser
                85                  90                  95

Ser Phe Tyr Arg Asn Leu Leu Trp Leu Thr Glu Lys Asn Gly Ser Tyr
            100                 105                 110

Pro Asn Leu Ser Lys Ser Tyr Val Asn Asn Lys Glu Lys Glu Val Leu
        115                 120                 125

Val Leu Trp Gly Val His His Pro Ser Asn Ile Glu Asp Gln Lys Thr
    130                 135                 140

Ile Tyr Arg Lys Glu Asn Ala Tyr Val Ser Val Ser Ser Asn Tyr
145                 150                 155                 160

Asn Arg Arg Phe Thr Pro Glu Ile Ala Glu Arg Pro Lys Val Arg Gly
                165                 170                 175

Gln Ala Gly Arg Ile Asn Tyr Tyr Trp Thr Leu Leu Glu Pro Gly Asp
            180                 185                 190

Thr Ile Ile Phe Glu Ala Asn Gly Asn Leu Ile Ala Pro Trp His Ala
        195                 200                 205

Phe Ala Leu Ser Arg Gly
    210

<210> SEQ ID NO 43
<211> LENGTH: 214
<212> TYPE: PRT
<213> ORGANISM: Influenza virus

<400> SEQUENCE: 43

Ile Ala Pro Leu Gln Leu Gly Asn Cys Ser Val Ala Gly Trp Ile Leu
1               5                   10                  15

Gly Asn Pro Lys Cys Glu Ser Leu Phe Ser Lys Glu Ser Trp Ser Tyr
            20                  25                  30

Ile Ala Glu Thr Pro Asn Pro Glu Asn Gly Thr Cys Phe Pro Gly Tyr
        35                  40                  45

Phe Ala Asp Tyr Glu Glu Leu Arg Glu Gln Leu Ser Ser Val Ser Ser
    50                  55                  60

Phe Glu Arg Phe Glu Ile Phe Pro Lys Glu Ser Ser Trp Pro Asn His
65                  70                  75                  80

Thr Val Thr Lys Gly Val Thr Thr Ser Cys Ser His Asn Gly Lys Ser
                85                  90                  95

Ser Phe Tyr Arg Asn Leu Leu Trp Leu Thr Glu Lys Asn Gly Leu Tyr
            100                 105                 110

-continued

Pro Asn Leu Ser Lys Ser Tyr Val Asn Asn Lys Glu Lys Glu Val Leu
        115                 120                 125

Val Leu Trp Gly Val His His Pro Ser Asn Ile Arg Asp Gln Arg Ala
    130                 135                 140

Ile Tyr His Thr Glu Asn Ala Tyr Val Ser Val Ser Ser His Tyr
145                 150                 155                 160

Ser Arg Arg Phe Thr Pro Glu Ile Ala Lys Arg Pro Lys Val Arg Gly
                165                 170                 175

Gln Glu Gly Arg Ile Asn Tyr Tyr Trp Thr Leu Leu Glu Pro Gly Asp
            180                 185                 190

Thr Ile Ile Phe Glu Ala Asn Gly Asn Leu Ile Ala Pro Trp Tyr Ala
        195                 200                 205

Phe Ala Leu Ser Arg Gly
    210

<210> SEQ ID NO 44
<211> LENGTH: 214
<212> TYPE: PRT
<213> ORGANISM: Influenza virus

<400> SEQUENCE: 44

Ile Ala Pro Leu Gln Leu Gly Asn Cys Ser Ile Ala Gly Trp Ile Leu
1               5                   10                  15

Gly Asn Pro Glu Cys Glu Ser Leu Phe Ser Lys Lys Ser Trp Ser Tyr
            20                  25                  30

Ile Ala Glu Thr Pro Asn Ser Glu Asn Gly Thr Cys Phe Pro Gly Tyr
        35                  40                  45

Phe Ala Asp Tyr Glu Glu Leu Arg Glu Gln Leu Ser Ser Val Ser Ser
    50                  55                  60

Phe Glu Arg Phe Glu Ile Phe Pro Lys Glu Ser Ser Trp Pro Asn His
65                  70                  75                  80

Thr Val Thr Lys Gly Val Thr Ala Ser Cys Ser His Lys Gly Arg Ser
                85                  90                  95

Ser Phe Tyr Arg Asn Leu Leu Trp Leu Thr Lys Lys Asn Gly Ser Tyr
            100                 105                 110

Pro Asn Leu Ser Lys Ser Tyr Val Asn Asn Lys Glu Lys Glu Val Leu
        115                 120                 125

Val Leu Trp Gly Val His His Pro Ser Asn Ile Gly Asp Gln Arg Ala
    130                 135                 140

Ile Tyr His Thr Glu Asn Ala Tyr Val Ser Val Ser Ser His Tyr
145                 150                 155                 160

Asn Arg Arg Phe Thr Pro Glu Ile Ala Lys Arg Pro Lys Val Arg Asp
                165                 170                 175

Gln Glu Gly Arg Ile Asn Tyr Tyr Trp Thr Leu Leu Glu Pro Gly Asp
            180                 185                 190

Thr Ile Ile Phe Glu Ala Asn Gly Asn Leu Ile Ala Pro Trp Tyr Ala
        195                 200                 205

Phe Ala Leu Ser Arg Gly
    210

<210> SEQ ID NO 45
<211> LENGTH: 214
<212> TYPE: PRT
<213> ORGANISM: Influenza virus

<400> SEQUENCE: 45

Ile Ala Pro Leu Gln Leu Gly Lys Cys Ser Ile Ala Gly Trp Ile Leu
1               5                   10                  15

Gly Asn Pro Glu Cys Glu Ser Leu Phe Ser Lys Ser Trp Ser Tyr
            20                  25                  30

Ile Ala Glu Thr Pro Asn Ser Glu Asn Gly Thr Cys Phe Pro Gly Tyr
            35                  40                  45

Phe Ala Asp Tyr Glu Glu Leu Arg Glu Gln Leu Ser Ser Val Ser Ser
50                  55                  60

Phe Glu Arg Phe Glu Ile Phe Pro Lys Glu Ser Ser Trp Pro Lys His
65                  70                  75                  80

Asn Val Thr Lys Gly Val Thr Ala Ser Cys Ser His Lys Gly Lys Ser
                85                  90                  95

Ser Phe Tyr Arg Asn Leu Leu Trp Leu Thr Glu Lys Asn Gly Ser Tyr
            100                 105                 110

Pro Asn Leu Ser Lys Ser Tyr Val Asn Asn Lys Glu Lys Glu Val Leu
            115                 120                 125

Val Leu Trp Gly Val His His Pro Ser Asn Ile Glu Asp Gln Lys Thr
130                 135                 140

Ile Tyr Arg Lys Glu Asn Ala Tyr Val Ser Val Val Ser Ser His Tyr
145                 150                 155                 160

Asn Arg Arg Phe Thr Pro Glu Ile Ala Lys Arg Pro Lys Val Arg Asn
                165                 170                 175

Gln Glu Gly Arg Ile Asn Tyr Tyr Trp Thr Leu Leu Glu Pro Gly Asp
            180                 185                 190

Thr Ile Ile Phe Glu Ala Asn Gly Asn Leu Ile Ala Pro Trp Tyr Ala
            195                 200                 205

Phe Ala Leu Ser Arg Gly
            210

<210> SEQ ID NO 46
<211> LENGTH: 214
<212> TYPE: PRT
<213> ORGANISM: Influenza virus

<400> SEQUENCE: 46

Ile Ala Pro Leu Gln Leu Gly Lys Cys Asn Ile Ala Gly Trp Ile Leu
1               5                   10                  15

Gly Asn Pro Glu Cys Glu Ser Leu Leu Ser Asn Arg Ser Trp Ser Tyr
            20                  25                  30

Ile Ala Glu Thr Pro Asn Ser Glu Asn Gly Ile Cys Phe Pro Gly Asp
            35                  40                  45

Phe Ala Asp Tyr Glu Glu Leu Arg Glu Gln Leu Ser Ser Val Ser Ser
50                  55                  60

Phe Glu Arg Phe Glu Ile Phe Pro Lys Glu Ser Ser Trp Pro Lys His
65                  70                  75                  80

Asn Ile Thr Arg Gly Val Thr Val Ala Cys Ser His Ala Lys Lys Ser
                85                  90                  95

Ser Phe Tyr Lys Asn Leu Leu Trp Leu Thr Glu Ala Asn Gly Leu Tyr
            100                 105                 110

Pro Ser Leu Ser Lys Ser Tyr Val Asn Asp Arg Glu Lys Glu Val Leu
            115                 120                 125

Val Leu Trp Gly Val His His Pro Ser Asn Ile Glu Asp Gln Arg Thr
130                 135                 140

Leu Tyr Arg Lys Glu Asn Ala Tyr Val Ser Val Val Ser Ser Asn Tyr

```
            145                 150                 155                 160
Asn Arg Arg Phe Thr Pro Glu Ile Ala Glu Arg Pro Lys Val Arg Gly
                165                 170                 175

Gln Pro Gly Arg Met Asn Tyr Tyr Trp Thr Leu Leu Glu Pro Gly Asp
            180                 185                 190

Lys Ile Ile Phe Glu Ala Asn Gly Asn Leu Ile Ala Pro Trp Tyr Ala
            195                 200                 205

Phe Ala Leu Ser Arg Gly
            210

<210> SEQ ID NO 47
<211> LENGTH: 213
<212> TYPE: PRT
<213> ORGANISM: Influenza virus

<400> SEQUENCE: 47

Ile Ala Pro Leu Gln Leu Gly Lys Cys Asn Ile Ala Gly Trp Ile Leu
1               5                   10                  15

Gly Asn Pro Glu Cys Glu Ser Leu Leu Ser Glu Arg Ser Trp Ser Tyr
                20                  25                  30

Ile Val Glu Thr Pro Asn Ser Glu Asn Gly Thr Cys Phe Pro Gly Asp
            35                  40                  45

Phe Ile Asp Tyr Glu Glu Leu Arg Glu Gln Leu Ser Ser Val Ser Ser
50                  55                  60

Phe Glu Arg Phe Glu Ile Phe Ser Lys Glu Ser Ser Trp Pro Lys His
65                  70                  75                  80

Thr Thr Gly Gly Val Thr Ala Ala Cys Ser His Ala Gly Lys Ser Ser
                85                  90                  95

Phe Tyr Arg Asn Leu Leu Trp Leu Thr Glu Lys Asp Gly Ser Tyr Pro
            100                 105                 110

Asn Leu Asn Asn Ser Tyr Val Asn Lys Lys Gly Lys Glu Val Leu Val
            115                 120                 125

Leu Trp Gly Val His His Pro Ser Asn Ile Lys Asp Gln Gln Thr Leu
130                 135                 140

Tyr Gln Lys Glu Asn Ala Tyr Val Ser Val Val Ser Ser Asn Tyr Asn
145                 150                 155                 160

Arg Arg Phe Thr Pro Glu Ile Ala Glu Arg Pro Lys Val Arg Gly Gln
                165                 170                 175

Ala Gly Arg Ile Asn Tyr Tyr Trp Thr Leu Leu Lys Pro Gly Asp Thr
            180                 185                 190

Ile Met Phe Glu Ala Asn Gly Asn Leu Ile Ala Pro Trp Tyr Ala Phe
            195                 200                 205

Ala Leu Ser Arg Gly
            210

<210> SEQ ID NO 48
<211> LENGTH: 214
<212> TYPE: PRT
<213> ORGANISM: Influenza virus

<400> SEQUENCE: 48

Ile Ala Pro Leu Gln Leu Gly Lys Cys Ser Ile Ala Gly Trp Ile Leu
1               5                   10                  15

Gly Asn Pro Glu Cys Glu Ser Leu Phe Ser Lys Lys Ser Trp Ser Tyr
                20                  25                  30

Ile Ala Glu Thr Pro Asn Ser Glu Asn Gly Thr Cys Phe Pro Gly Tyr
```

```
                35                  40                  45
Phe Ala Asp Tyr Glu Glu Leu Arg Glu Gln Leu Ser Ser Val Ser Ser
 50                  55                  60
Phe Glu Arg Phe Glu Ile Phe Pro Lys Glu Arg Ser Trp Pro Lys His
65                  70                  75                  80
Asn Val Thr Arg Gly Val Thr Ala Ser Cys Ser His Lys Gly Lys Ser
                85                  90                  95
Ser Phe Tyr Arg Asn Leu Leu Trp Leu Thr Glu Lys Asn Gly Ser Tyr
                100                 105                 110
Pro Asn Leu Ser Lys Ser Tyr Val Asn Asn Lys Glu Lys Glu Val Leu
            115                 120                 125
Val Leu Trp Gly Val His His Pro Ser Asn Ile Glu Asp Gln Lys Thr
        130                 135                 140
Ile Tyr Arg Lys Glu Asn Ala Tyr Val Ser Val Val Ser Ser Asn Tyr
145                 150                 155                 160
Asn Arg Arg Phe Thr Pro Glu Ile Ala Glu Arg Pro Lys Val Arg Gly
                165                 170                 175
Gln Ala Gly Arg Ile Asn Tyr Tyr Trp Thr Leu Leu Glu Pro Gly Asp
            180                 185                 190
Thr Ile Ile Phe Glu Ala Asn Gly Asn Leu Ile Ala Pro Trp Tyr Ala
        195                 200                 205
Phe Ala Leu Ser Arg Gly
    210

<210> SEQ ID NO 49
<211> LENGTH: 214
<212> TYPE: PRT
<213> ORGANISM: Influenza virus

<400> SEQUENCE: 49

Ile Ala Pro Leu Gln Leu Gly Lys Cys Asn Ile Ala Gly Trp Ile Leu
1               5                   10                  15
Gly Asn Pro Glu Cys Glu Ser Leu Leu Ser Lys Arg Ser Trp Ser Tyr
                20                  25                  30
Ile Ala Glu Thr Pro Asn Ser Glu Asn Gly Ala Cys Phe Pro Gly Asp
            35                  40                  45
Phe Ala Asp Tyr Glu Glu Leu Arg Glu Gln Leu Ser Ser Val Ser Ser
 50                  55                  60
Phe Glu Arg Phe Glu Ile Phe Pro Lys Glu Arg Ser Trp Pro Lys His
65                  70                  75                  80
Asn Ile Thr Arg Gly Val Thr Ala Ala Cys Ser His Ala Gly Lys Ser
                85                  90                  95
Ser Phe Tyr Lys Asn Leu Leu Trp Leu Thr Glu Thr Asp Gly Ser Tyr
                100                 105                 110
Pro Lys Leu Ser Lys Ser Tyr Val Asn Asn Lys Glu Lys Glu Val Leu
            115                 120                 125
Val Leu Trp Gly Val His His Pro Ser Asn Ile Glu Asp Gln Lys Thr
        130                 135                 140
Leu Tyr Arg Lys Glu Asn Ala Tyr Val Ser Val Val Ser Ser Asn Tyr
145                 150                 155                 160
Asn Arg Arg Phe Thr Pro Glu Ile Ala Glu Arg Pro Lys Val Arg Gly
                165                 170                 175
Gln Ala Gly Arg Ile Asn Tyr Tyr Trp Thr Leu Leu Glu Pro Gly Asp
            180                 185                 190
```

```
Thr Ile Ile Phe Glu Ala Asn Gly Asn Leu Ile Ala Pro Trp Tyr Ala
        195                 200                 205

Phe Ala Leu Ser Arg Asp
    210
```

<210> SEQ ID NO 50
<211> LENGTH: 213
<212> TYPE: PRT
<213> ORGANISM: Influenza virus

<400> SEQUENCE: 50

```
Ile Ala Pro Leu Gln Leu Gly Asn Cys Ser Val Ala Gly Trp Ile Leu
1               5                   10                  15

Gly Asn Pro Glu Cys Glu Leu Leu Ile Ser Lys Glu Ser Trp Ser Tyr
            20                  25                  30

Ile Val Glu Lys Pro Asn Pro Glu Asn Gly Thr Cys Phe Pro Gly His
        35                  40                  45

Phe Ala Asp Tyr Glu Glu Leu Arg Glu Gln Leu Ser Ser Val Ser Ser
    50                  55                  60

Phe Glu Arg Phe Glu Ile Phe Pro Lys Glu Ser Ser Trp Pro Asn His
65                  70                  75                  80

Thr Val Thr Gly Val Ser Ala Ser Cys Ser His Asn Gly Glu Ser Ser
                85                  90                  95

Phe Tyr Arg Asn Leu Leu Trp Leu Thr Gly Lys Asn Gly Leu Tyr Pro
            100                 105                 110

Asn Leu Ser Lys Ser Tyr Ala Asn Asn Lys Glu Lys Glu Val Leu Val
        115                 120                 125

Leu Trp Gly Val His His Pro Pro Asn Ile Gly Ile Gln Lys Ala Leu
    130                 135                 140

Tyr His Thr Glu Asn Ala Tyr Val Ser Val Val Ser Ser His Tyr Ser
145                 150                 155                 160

Arg Lys Phe Thr Pro Glu Ile Ala Lys Arg Pro Lys Val Arg Asp Gln
                165                 170                 175

Glu Gly Arg Ile Asn Tyr Tyr Trp Thr Leu Leu Glu Pro Gly Asp Thr
            180                 185                 190

Ile Ile Phe Glu Ala Asn Gly Asn Leu Ile Ala Pro Arg Tyr Ala Phe
        195                 200                 205

Ala Leu Ser Arg Gly
    210
```

<210> SEQ ID NO 51
<211> LENGTH: 214
<212> TYPE: PRT
<213> ORGANISM: Influenza virus

<400> SEQUENCE: 51

```
Ile Ala Pro Leu Gln Leu Gly Lys Cys Ser Ile Ala Gly Trp Ile Leu
1               5                   10                  15

Gly Asn Pro Glu Cys Glu Ser Leu Phe Ser Lys Lys Ser Trp Ser Tyr
            20                  25                  30

Ile Ala Glu Thr Pro Asn Ser Glu Asn Gly Thr Cys Phe Pro Gly Tyr
        35                  40                  45

Phe Ala Asp Tyr Glu Glu Leu Arg Glu Gln Leu Ser Ser Val Ser Ser
    50                  55                  60

Phe Glu Arg Phe Glu Ile Phe Pro Lys Glu Ser Ser Trp Pro Lys His
65                  70                  75                  80
```

```
Asn Val Thr Arg Gly Val Thr Ala Ser Cys Ser His Lys Gly Lys Cys
                85                  90                  95

Ser Phe Tyr Arg Asn Leu Leu Trp Leu Thr Glu Lys Asn Gly Ser Tyr
            100                 105                 110

Pro Asn Leu Ser Lys Ser Tyr Val Asn Asn Lys Glu Lys Glu Val Leu
        115                 120                 125

Val Leu Trp Gly Val His His Pro Ser Asn Ile Glu Asp Gln Lys Thr
130                 135                 140

Ile Tyr Arg Lys Glu Asn Ala Tyr Val Ser Val Ser Ser His Tyr
145                 150                 155                 160

Asn Arg Arg Phe Thr Pro Glu Ile Ala Lys Arg Pro Lys Val Arg Asp
                165                 170                 175

Gln Glu Gly Arg Ile Asn Tyr Tyr Trp Thr Leu Leu Glu Pro Gly Asp
            180                 185                 190

Thr Ile Ile Phe Glu Ala Asn Gly Asn Leu Ile Ala Pro Trp Tyr Ala
        195                 200                 205

Phe Ala Leu Ser Arg Gly
    210

<210> SEQ ID NO 52
<211> LENGTH: 214
<212> TYPE: PRT
<213> ORGANISM: Influenza virus

<400> SEQUENCE: 52

Ile Ala Pro Leu Gln Leu Gly Lys Cys Asn Ile Ala Gly Trp Ile Leu
1               5                   10                  15

Gly Asn Pro Glu Cys Glu Ser Leu Phe Ser Lys Lys Ser Trp Ser Tyr
            20                  25                  30

Ile Ala Glu Thr Pro Asn Ser Glu Asn Gly Thr Cys Phe Pro Gly Tyr
        35                  40                  45

Phe Ala Asp Tyr Glu Glu Leu Arg Glu Gln Leu Ser Ser Val Ser Ser
    50                  55                  60

Phe Glu Arg Phe Glu Ile Phe Pro Lys Glu Arg Ser Trp Pro Lys His
65                  70                  75                  80

Asn Ile Thr Arg Gly Val Thr Ala Ala Cys Ser His Lys Gly Lys Ser
                85                  90                  95

Ser Phe Tyr Arg Asn Leu Leu Trp Leu Thr Glu Lys Asn Gly Ser Tyr
            100                 105                 110

Pro Asn Leu Asn Lys Ser Tyr Val Asn Asn Lys Glu Lys Glu Val Leu
        115                 120                 125

Val Leu Trp Gly Val His His Pro Ser Asn Ile Glu Asp Gln Lys Thr
130                 135                 140

Leu Tyr Arg Lys Glu Asn Ala Tyr Val Ser Val Ser Ser Asn Tyr
145                 150                 155                 160

Asn Arg Arg Phe Thr Pro Glu Ile Ala Glu Arg Pro Lys Val Arg Gly
                165                 170                 175

Gln Ala Gly Arg Ile Asn Tyr Tyr Trp Thr Leu Leu Glu Pro Gly Asp
            180                 185                 190

Thr Ile Ile Phe Glu Ala Asn Gly Asn Leu Ile Ala Pro Trp His Ala
        195                 200                 205

Phe Ala Leu Ser Arg Gly
    210

<210> SEQ ID NO 53
```

<211> LENGTH: 213
<212> TYPE: PRT
<213> ORGANISM: Influenza virus

<400> SEQUENCE: 53

```
Val Lys Pro Leu Ile Leu Arg Asp Cys Ser Val Ala Gly Trp Leu Leu
1               5                   10                  15

Gly Asn Pro Met Cys Asp Glu Phe Ile Asn Val Pro Glu Trp Ser Tyr
            20                  25                  30

Ile Val Glu Lys Ala Asn Pro Thr Asn Asp Leu Cys Phe Pro Gly Ser
        35                  40                  45

Phe Asn Asp Tyr Glu Glu Leu Lys His Leu Leu Ser Arg Ile Asn His
    50                  55                  60

Phe Glu Lys Ile Gln Ile Ile Pro Lys Ser Ser Trp Ser Asp His Glu
65                  70                  75                  80

Ala Ser Ser Gly Val Ser Ser Ala Cys Pro Tyr Leu Gly Ser Pro Ser
                85                  90                  95

Phe Phe Arg Asn Val Val Trp Leu Ile Lys Lys Asn Ser Thr Tyr Pro
            100                 105                 110

Thr Ile Lys Lys Ser Tyr Asn Asn Thr Asn Gln Glu Asp Leu Leu Val
        115                 120                 125

Leu Trp Gly Ile His His Pro Asn Asp Ala Ala Glu Gln Thr Arg Leu
    130                 135                 140

Tyr Gln Asn Pro Thr Thr Tyr Ile Ser Ile Gly Thr Ser Thr Leu Asn
145                 150                 155                 160

Gln Arg Leu Val Pro Lys Ile Ala Thr Arg Ser Lys Val Asn Gly Gln
                165                 170                 175

Ser Gly Arg Met Glu Phe Phe Trp Thr Ile Leu Lys Pro Asn Asp Ala
            180                 185                 190

Ile Asn Phe Glu Ser Asn Gly Asn Phe Ile Ala Pro Glu Tyr Ala Tyr
        195                 200                 205

Lys Ile Val Lys Lys
    210
```

<210> SEQ ID NO 54
<211> LENGTH: 213
<212> TYPE: PRT
<213> ORGANISM: Influenza virus

<400> SEQUENCE: 54

```
Val Lys Pro Leu Ile Leu Arg Asp Cys Ser Val Ala Gly Trp Leu Leu
1               5                   10                  15

Gly Asn Pro Met Cys Asp Glu Phe Ile Asn Val Pro Glu Trp Ser Tyr
            20                  25                  30

Ile Val Glu Lys Ala Ser Pro Ala Asn Asp Leu Cys Phe Pro Gly Asn
        35                  40                  45

Phe Asn Asp Tyr Glu Glu Leu Lys His Leu Leu Ser Arg Ile Asn His
    50                  55                  60

Phe Glu Lys Ile Gln Ile Ile Pro Lys Ser Ser Trp Ser Asn His Asp
65                  70                  75                  80

Ala Ser Ser Gly Val Ser Ser Ala Cys Pro Tyr Leu Gly Arg Ser Ser
                85                  90                  95

Phe Phe Arg Asn Val Val Trp Leu Ile Lys Lys Asn Ser Ala Tyr Pro
            100                 105                 110

Thr Ile Lys Arg Ser Tyr Asn Asn Thr Asn Gln Glu Asp Leu Leu Val
        115                 120                 125
```

-continued

Leu Trp Gly Val His His Pro Asn Asp Ala Glu Gln Thr Lys Leu
       130                 135                 140

Tyr Gln Asn Pro Thr Thr Tyr Ile Ser Val Gly Thr Ser Thr Leu Asn
145                 150                 155                 160

Gln Arg Leu Val Pro Glu Ile Ala Thr Arg Pro Lys Val Asn Gly Gln
                165                 170                 175

Ser Gly Arg Met Glu Phe Phe Trp Thr Ile Leu Lys Pro Asn Asp Ala
            180                 185                 190

Ile Asn Phe Glu Ser Asn Gly Asn Phe Ile Ala Pro Glu Tyr Ala Tyr
        195                 200                 205

Lys Ile Val Lys Lys
    210

<210> SEQ ID NO 55
<211> LENGTH: 213
<212> TYPE: PRT
<213> ORGANISM: Influenza virus

<400> SEQUENCE: 55

Val Lys Pro Leu Ile Leu Lys Asp Cys Ser Val Ala Gly Trp Leu Leu
1               5                   10                  15

Gly Asn Pro Met Cys Asp Glu Phe Ile Asn Val Pro Glu Trp Ser Tyr
            20                  25                  30

Ile Val Glu Lys Ala Asn Pro Ala Asn Asp Leu Cys Phe Pro Gly Asn
        35                  40                  45

Phe Asn Asp Tyr Glu Glu Leu Lys His Leu Leu Ser Arg Ile Asn His
50                  55                  60

Phe Glu Lys Ile Gln Ile Ile Pro Lys Asp Ser Trp Ser Asp His Glu
65                  70                  75                  80

Ala Ser Leu Gly Val Ser Ser Ala Cys Pro Tyr Gln Gly Asn Ser Ser
                85                  90                  95

Phe Phe Arg Asn Val Val Trp Leu Ile Lys Lys Gly Asn Ala Tyr Pro
            100                 105                 110

Thr Ile Lys Lys Ser Tyr Asn Asn Thr Asn Gln Glu Asp Leu Leu Val
        115                 120                 125

Leu Trp Gly Ile His His Pro Asn Asp Glu Ala Glu Gln Thr Arg Leu
130                 135                 140

Tyr Gln Asn Pro Thr Thr Tyr Ile Ser Ile Gly Thr Ser Thr Leu Asn
145                 150                 155                 160

Gln Arg Leu Val Pro Lys Ile Ala Thr Arg Ser Lys Val Asn Gly Gln
                165                 170                 175

Ser Gly Arg Ile Asp Phe Phe Trp Thr Ile Leu Lys Pro Asn Asp Ala
            180                 185                 190

Ile Asn Phe Glu Ser Asn Gly Asn Phe Ile Ala Pro Glu Tyr Ala Tyr
        195                 200                 205

Lys Ile Val Lys Lys
    210

<210> SEQ ID NO 56
<211> LENGTH: 212
<212> TYPE: PRT
<213> ORGANISM: Influenza virus

<400> SEQUENCE: 56

Val Lys Pro Leu Ile Leu Lys Asp Cys Ser Val Ala Gly Trp Leu Leu
1               5                   10                  15

-continued

```
Gly Asn Pro Met Cys Asp Glu Phe Leu Asn Val Ser Glu Trp Ser Tyr
            20                  25                  30

Ile Val Glu Lys Ala Ser Pro Ala Asn Gly Leu Cys Phe Pro Gly Asp
        35                  40                  45

Phe Asn Asp Tyr Glu Glu Leu Lys His Leu Leu Ser Arg Ile Asn His
 50                  55                  60

Phe Glu Lys Ile Lys Ile Ile Pro Lys Ser Ser Trp Ser Asn His Glu
65                  70                  75                  80

Ala Ser Gly Val Ser Ser Ala Cys Ser Tyr Leu Gly Lys Pro Ser Phe
                85                  90                  95

Phe Arg Asn Leu Val Trp Leu Ile Lys Lys Asn Asn Thr Tyr Pro Pro
            100                 105                 110

Ile Lys Val Asn Tyr Thr Asn Thr Asn Gln Glu Asp Leu Leu Val Leu
        115                 120                 125

Trp Gly Ile His His Pro Asn Asp Glu Thr Glu Gln Val Lys Ile Tyr
130                 135                 140

Gln Asn Pro Thr Thr Tyr Ile Ser Val Gly Thr Ser Thr Leu Asn Gln
145                 150                 155                 160

Arg Leu Val Pro Lys Ile Ala Thr Arg Ser Lys Val Asn Gly Gln Ser
                165                 170                 175

Gly Arg Met Glu Phe Phe Trp Thr Ile Leu Lys Pro Asn Asp Ala Ile
            180                 185                 190

Asn Phe Asp Ser Asn Gly Asn Phe Ile Ala Pro Glu Tyr Ala Tyr Lys
        195                 200                 205

Ile Val Lys Lys
    210

<210> SEQ ID NO 57
<211> LENGTH: 213
<212> TYPE: PRT
<213> ORGANISM: Influenza virus

<400> SEQUENCE: 57

Val Lys Pro Leu Ile Leu Arg Asp Cys Ser Val Ala Gly Trp Leu Leu
1               5                   10                  15

Gly Asn Pro Met Cys Asp Glu Phe Ile Asn Val Pro Glu Trp Ser Tyr
            20                  25                  30

Ile Val Glu Lys Ala Ser Pro Ala Asn Asp Leu Cys Phe Pro Gly Asp
        35                  40                  45

Phe Asn Asp Tyr Glu Glu Leu Lys His Leu Leu Ser Arg Ile Asn His
 50                  55                  60

Phe Glu Lys Ile Gln Ile Ile Pro Lys Ser Ser Trp Ser Asn His Glu
65                  70                  75                  80

Ala Ser Ser Gly Val Ser Ser Ala Cys Pro Tyr Leu Gly Lys Ser Ser
                85                  90                  95

Phe Phe Arg Asn Val Val Trp Leu Ile Lys Lys Asn Ser Thr Tyr Pro
            100                 105                 110

Thr Ile Lys Arg Ser Tyr Asn Asn Thr Asn Gln Glu Asp Leu Leu Val
        115                 120                 125

Leu Trp Gly Ile His His Pro Asn Asp Ala Ala Glu Gln Thr Lys Leu
    130                 135                 140

Tyr Gln Asn Pro Thr Thr Tyr Ile Ser Val Gly Thr Ser Thr Leu Asn
145                 150                 155                 160

Gln Arg Leu Val Pro Lys Ile Ala Thr Arg Ser Lys Val Asn Gly Gln
```

```
                165                 170                 175
Ser Gly Arg Met Glu Phe Phe Trp Thr Ile Leu Lys Pro Asn Asp Ala
            180                 185                 190

Ile Asn Phe Glu Ser Asn Gly Asn Phe Ile Ala Pro Glu Tyr Ala Tyr
        195                 200                 205

Lys Ile Val Lys Lys
    210

<210> SEQ ID NO 58
<211> LENGTH: 213
<212> TYPE: PRT
<213> ORGANISM: Influenza virus

<400> SEQUENCE: 58

Val Lys Pro Leu Ile Leu Arg Asp Cys Ser Val Ala Gly Trp Leu Leu
1               5                   10                  15

Gly Asn Pro Met Cys Asp Glu Phe Ile Asn Val Pro Glu Trp Ser Tyr
            20                  25                  30

Ile Val Glu Lys Ala Ser Pro Ala Asn Gly Leu Cys Phe Pro Gly Asp
        35                  40                  45

Phe Asn Asp Tyr Glu Glu Leu Lys His Leu Leu Ser Arg Ile Asn His
    50                  55                  60

Phe Glu Lys Ile Gln Ile Ile Pro Lys Ser Ser Trp Ser Asn His Glu
65                  70                  75                  80

Ala Ser Ser Gly Val Ser Ser Ala Cys Pro Tyr Gln Gly Lys Ser Ser
                85                  90                  95

Phe Phe Arg Asn Val Val Trp Leu Ile Lys Lys Asn Ser Thr Tyr Pro
            100                 105                 110

Thr Ile Lys Arg Ser Tyr Asn Asn Thr Asn Gln Glu Asp Leu Leu Val
        115                 120                 125

Leu Trp Gly Ile His His Pro Asn Asp Ala Ala Glu Gln Thr Arg Leu
    130                 135                 140

Tyr Gln Asn Pro Thr Thr Tyr Ile Ser Val Gly Thr Ser Thr Leu Asn
145                 150                 155                 160

Gln Arg Leu Val Pro Lys Ile Ala Thr Arg Ser Lys Val Asn Gly Gln
                165                 170                 175

Ser Gly Arg Met Glu Phe Phe Trp Thr Ile Leu Lys Pro Asn Asp Ala
            180                 185                 190

Ile Asn Phe Glu Ser Asn Gly Asn Phe Ile Ala Pro Glu Tyr Ala Tyr
        195                 200                 205

Lys Ile Val Lys Lys
    210

<210> SEQ ID NO 59
<211> LENGTH: 208
<212> TYPE: PRT
<213> ORGANISM: Influenza virus

<400> SEQUENCE: 59

His Gln Ile Leu Asp Gly Glu Asn Cys Thr Leu Ile Asp Ala Leu Leu
1               5                   10                  15

Gly Asp Pro Gln Cys Asp Gly Phe Gln Asn Lys Lys Trp Asp Leu Phe
            20                  25                  30

Val Glu Arg Ser Lys Ala Tyr Ser Asn Cys Phe Pro Tyr Asp Val Pro
        35                  40                  45

Asp Tyr Ala Ser Leu Arg Ser Leu Val Ala Ser Ser Gly Thr Leu Glu
```

```
                  50                  55                  60

Phe Asn Glu Ser Phe Asn Trp Thr Gly Val Thr Gln Asn Gly Thr
 65                  70                  75                  80

Ser Ser Ala Cys Ile Arg Arg Ser Asn Asn Ser Phe Phe Ser Arg Leu
                 85                  90                  95

Asn Trp Leu Thr Gln Leu Asn Phe Lys Tyr Pro Ala Leu Asn Val Thr
                100                 105                 110

Met Pro Asn Asn Glu Gln Phe Asp Lys Leu Tyr Ile Trp Gly Val His
            115                 120                 125

His Pro Val Thr Asp Lys Asp Gln Ile Phe Leu Tyr Ala Gln Ser Ser
        130                 135                 140

Gly Arg Ile Thr Val Ser Thr Lys Arg Ser Gln Gln Ala Val Ile Pro
145                 150                 155                 160

Asn Ile Gly Tyr Arg Pro Arg Ile Arg Asn Ile Pro Ser Arg Ile Ser
                165                 170                 175

Ile Tyr Trp Thr Ile Val Lys Pro Gly Asp Ile Leu Leu Ile Asn Ser
            180                 185                 190

Thr Gly Asn Leu Ile Ala Pro Arg Gly Tyr Phe Lys Ile Arg Ser Gly
        195                 200                 205

<210> SEQ ID NO 60
<211> LENGTH: 231
<212> TYPE: PRT
<213> ORGANISM: Influenza virus

<400> SEQUENCE: 60

Lys Thr Arg Gly Lys Leu Cys Pro Asp Cys Leu Asn Cys Thr Asp Leu
  1               5                  10                  15

Asp Val Ala Leu Gly Arg Pro Met Cys Val Gly Thr Thr Pro Ser Ala
                 20                  25                  30

Lys Ala Ser Ile Leu His Glu Val Arg Pro Val Thr Ser Gly Cys Phe
             35                  40                  45

Pro Ile Met His Asp Arg Thr Lys Ile Arg Gln Leu Ala Asn Leu Leu
 50                  55                  60

Arg Gly Tyr Glu Asn Ile Arg Leu Ser Thr Gln Asn Val Ile Asp Ala
 65                  70                  75                  80

Glu Lys Ala Pro Gly Gly Pro Tyr Arg Leu Gly Thr Ser Gly Ser Cys
                 85                  90                  95

Pro Asn Ala Thr Ser Lys Ser Gly Phe Phe Ala Thr Met Ala Trp Ala
            100                 105                 110

Val Pro Lys Asp Asn Asn Lys Asn Ala Thr Asn Pro Leu Thr Val Glu
        115                 120                 125

Val Pro Tyr Ile Cys Ala Glu Gly Glu Asp Gln Ile Thr Val Trp Gly
    130                 135                 140

Phe His Ser Asp Asp Lys Thr Gln Met Lys Asn Leu Tyr Gly Asp Ser
145                 150                 155                 160

Asn Pro Gln Lys Phe Thr Ser Ser Ala Asn Gly Val Thr Thr His Tyr
                165                 170                 175

Val Ser Gln Ile Gly Gly Phe Pro Asp Gln Thr Glu Asp Gly Gly Leu
            180                 185                 190

Pro Gln Ser Gly Arg Ile Val Val Asp Tyr Met Met Gln Lys Pro Gly
        195                 200                 205

Lys Thr Gly Thr Ile Val Tyr Gln Arg Gly Val Leu Leu Pro Gln Lys
    210                 215                 220
```

Val Trp Cys Ala Ser Gly Arg
225                 230

<210> SEQ ID NO 61
<211> LENGTH: 232
<212> TYPE: PRT
<213> ORGANISM: Influenza virus

<400> SEQUENCE: 61

Glu Thr Arg Gly Lys Leu Cys Pro Lys Cys Leu Asn Cys Thr Asp Leu
1               5                   10                  15

Asp Val Ala Leu Gly Arg Pro Lys Cys Thr Gly Lys Ile Pro Ser Ala
            20                  25                  30

Arg Val Ser Ile Leu His Glu Val Arg Pro Val Thr Ser Gly Cys Phe
        35                  40                  45

Pro Ile Met His Asp Arg Thr Lys Ile Arg Gln Leu Pro Asn Leu Leu
    50                  55                  60

Arg Gly Tyr Glu His Ile Arg Leu Ser Thr His Asn Val Ile Asn Ala
65                  70                  75                  80

Glu Asn Ala Pro Gly Gly Pro Tyr Lys Ile Gly Thr Ser Gly Ser Cys
                85                  90                  95

Pro Asn Ile Thr Asn Gly Asn Gly Phe Phe Ala Thr Met Ala Trp Ala
            100                 105                 110

Val Pro Lys Asn Asp Lys Asn Lys Thr Ala Thr Asn Pro Leu Thr Ile
        115                 120                 125

Glu Val Pro Tyr Ile Cys Thr Glu Gly Glu Asp Gln Ile Thr Val Trp
    130                 135                 140

Gly Phe His Ser Asp Asn Glu Thr Gln Met Ala Lys Leu Tyr Gly Asp
145                 150                 155                 160

Ser Lys Pro Gln Lys Phe Thr Ser Ser Ala Asn Gly Val Thr Thr His
                165                 170                 175

Tyr Val Ser Gln Ile Gly Gly Phe Pro Asn Gln Thr Glu Asp Gly Gly
            180                 185                 190

Leu Pro Gln Ser Gly Arg Ile Val Val Asp Tyr Met Val Gln Lys Ser
        195                 200                 205

Gly Lys Thr Gly Thr Ile Thr Tyr Gln Arg Gly Ile Leu Leu Pro Gln
    210                 215                 220

Lys Val Trp Cys Ala Ser Gly Arg
225                 230

<210> SEQ ID NO 62
<211> LENGTH: 208
<212> TYPE: PRT
<213> ORGANISM: Influenza virus

<400> SEQUENCE: 62

Gln Ile Leu Asp Gly Glu Asn Cys Thr Leu Ile Asp Ala Leu Leu Gly
1               5                   10                  15

Asp Pro Gln Cys Asp Gly Phe Gln Asn Lys Lys Trp Asp Leu Phe Val
            20                  25                  30

Glu Arg Ser Lys Ala Tyr Ser Asn Cys Tyr Pro Tyr Asp Val Pro Asp
        35                  40                  45

Tyr Ala Ser Leu Arg Ser Leu Val Ala Ser Ser Gly Thr Leu Glu Phe
    50                  55                  60

Asn Asn Glu Ser Phe Asn Trp Asn Gly Val Thr Gln Asn Gly Thr Ser
65                  70                  75                  80

Ser Ala Cys Ile Arg Arg Ser Asn Asn Ser Phe Phe Ser Arg Leu Asn
                85                  90                  95

Trp Leu Thr His Leu Asn Phe Lys Tyr Pro Ala Leu Asn Val Thr Met
            100                 105                 110

Pro Asn Asn Glu Gln Phe Asp Lys Leu Tyr Ile Trp Gly Val His His
            115                 120                 125

Pro Val Thr Asp Lys Asp Gln Ile Phe Leu Tyr Ala Gln Pro Ser Gly
        130                 135                 140

Arg Ile Thr Val Ser Thr Lys Arg Ser Gln Gln Ala Val Ile Pro Asn
145                 150                 155                 160

Ile Gly Phe Arg Pro Arg Ile Arg Asn Ile Pro Ser Arg Ile Ser Ile
                165                 170                 175

Tyr Trp Thr Ile Val Lys Pro Gly Asp Ile Leu Leu Ile Asn Ser Thr
            180                 185                 190

Gly Asn Leu Ile Ala Pro Arg Gly Tyr Phe Lys Ile Arg Ser Gly Lys
            195                 200                 205

<210> SEQ ID NO 63
<211> LENGTH: 504
<212> TYPE: DNA
<213> ORGANISM: Helicobacter pylori

<400> SEQUENCE: 63

| | | | | |
|---|---|---|---|---|
| atgttatcaa aagacatcat taagttgcta aacgaacaag tgaataagga aatgaactct | 60 |
| tccaacttgt atatgagcat gagttcatgg tgctatatccc atagcttaga tggcgcgggg | 120 |
| ctttctcttgt ttgaccatgc ggctgaagaa tacgagcatg ctaaaaagct tattatcttc | 180 |
| ttgaatgaaa acaatgtgcc tgtgcaattg accagcatca gcgcgcctga gcataagttt | 240 |
| gaaggtttga ctcaaatttt ccaaaaagcc tatgaacatg agcaaacacat cagcgagtct | 300 |
| attaacaata tcgtagatca cgccataaaa agcaaagatc atgcgacttt caatttcttg | 360 |
| caatggtatg tggctgaaca gcatgaagaa gaagtgcttt tcaaggatat tttggataaa | 420 |
| attgagttga ttggtaatga aaaccatggc ttgtatttag ccgatcagta tgtcaaaggg | 480 |
| atcgctaaaa gcaggaaatc ttaa | 504 |

<210> SEQ ID NO 64
<211> LENGTH: 167
<212> TYPE: PRT
<213> ORGANISM: Helicobacter pylori

<400> SEQUENCE: 64

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ala Gly Leu Phe Leu Phe Asp His Ala Ala
        35                  40                  45

Glu Glu Tyr Glu His Ala Lys Lys Leu Ile Ile Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
                85                  90                  95

Ile Ser Glu Ser Ile Asn Asn Ile Val Asp His Ala Ile Lys Ser Lys
            100                 105                 110

```
Asp His Ala Thr Phe Asn Phe Leu Gln Trp Tyr Val Ala Glu Gln His
            115                 120                 125

Glu Glu Glu Val Leu Phe Lys Asp Ile Leu Asp Lys Val Glu Leu Ile
130                 135                 140

Gly Asn Glu Asn His Gly Leu Tyr Leu Ala Asp Gln Tyr Val Lys Gly
145                 150                 155                 160

Ile Ala Lys Ser Arg Lys Ser
                165

<210> SEQ ID NO 65
<211> LENGTH: 504
<212> TYPE: DNA
<213> ORGANISM: Helicobacter pylori

<400> SEQUENCE: 65
ttaagatttc ctgcttttag cgatcccttt gacatactga tcggctaaat acaagccatg      60
gttttcatta ccaatcaact caatttatc caaaatatcc ttgaaaagca cttcttcttc     120
atgctgttca gccacatacc attgcaagaa attgaaagtc gcatgatctt gctttttat     180 ggcgtgatct acgatattgt taatagactc gctgatgtgt tgctcatgtt cataggcttt     240
ttggaaaatt tgagtcaaac cttcaaactt atgctcaggc gcgctgatgc tggtcaattg     300
cacaggcaca ttgttttcat tcaagaagat aataagcttt ttagcatgct cgtattcttc     360
agccgcatgg tcaaacaaga aaagccccgc gccatctaag ctatgggtat agcaccatga     420
actcatgctc atatacaagt tggaagagtt catttcctta ttcacttgtt cgtttagcaa     480
cttaatgatg tcttttgata acat                                            504

<210> SEQ ID NO 66

<400> SEQUENCE: 66

000

<210> SEQ ID NO 67
<211> LENGTH: 165
<212> TYPE: PRT
<213> ORGANISM: Escherichia coli

<400> SEQUENCE: 67

Met Leu Lys Pro Glu Met Ile Glu Lys Leu Asn Glu Gln Met Asn Leu
1               5                   10                  15

Glu Leu Tyr Ser Ser Leu Leu Tyr Gln Gln Met Ser Ala Trp Cys Ser
            20                  25                  30

Tyr His Thr Phe Glu Gly Ala Ala Ala Phe Leu Arg Arg His Ala Gln
        35                  40                  45

Glu Glu Met Thr His Met Gln Arg Leu Phe Asp Tyr Leu Thr Asp Thr
    50                  55                  60

Gly Asn Leu Pro Arg Ile Asn Thr Val Glu Ser Pro Phe Ala Glu Tyr
65                  70                  75                  80

Ser Ser Leu Asp Glu Leu Phe Gln Glu Thr Tyr Lys His Glu Gln Leu
                85                  90                  95

Ile Thr Gln Lys Ile Asn Glu Leu Ala His Ala Ala Met Thr Asn Gln
            100                 105                 110

Asp Tyr Pro Thr Phe Asn Phe Leu Gln Trp Tyr Val Ser Glu Gln His
        115                 120                 125

Glu Glu Glu Lys Leu Phe Lys Ser Ile Ile Asp Lys Leu Ser Leu Ala
    130                 135                 140
```

```
Gly Lys Ser Gly Glu Gly Leu Tyr Phe Ile Asp Lys Glu Leu Ser Thr
145                 150                 155                 160

Leu Asp Ala Gln Asn
                165
```

<210> SEQ ID NO 68

<400> SEQUENCE: 68

000

<210> SEQ ID NO 69

<400> SEQUENCE: 69

000

<210> SEQ ID NO 70
<211> LENGTH: 173
<212> TYPE: PRT
<213> ORGANISM: Rana catesbeiana

<400> SEQUENCE: 70

```
Met Glu Ser Gln Val Arg Gln Asn Phe His Gln Asp Cys Glu Ala Gly
1               5                   10                  15

Leu Asn Arg Thr Val Asn Leu Lys Phe His Ser Ser Tyr Val Tyr Leu
                20                  25                  30

Ser Met Ala Ser Tyr Phe Asn Arg Asp Asp Val Ala Leu Ser Asn Phe
            35                  40                  45

Ala Lys Phe Phe Arg Glu Arg Ser Glu Glu Lys Glu His Ala Glu
    50                  55                  60

Lys Leu Ile Glu Tyr Gln Asn Gln Arg Gly Gly Arg Val Phe Leu Gln
65                  70                  75                  80

Ser Val Glu Lys Pro Glu Arg Asp Asp Trp Ala Asn Gly Leu Glu Ala
                85                  90                  95

Leu Gln Thr Ala Leu Lys Leu Gln Lys Ser Val Asn Gln Ala Leu Leu
                100                 105                 110

Asp Leu His Ala Val Ala Ala Asp Lys Ser Asp Pro His Met Thr Asp
            115                 120                 125

Phe Leu Glu Ser Pro Tyr Leu Ser Glu Ser Val Glu Thr Ile Lys Lys
        130                 135                 140

Leu Gly Asp His Ile Thr Ser Leu Lys Lys Leu Trp Ser Ser His Pro
145                 150                 155                 160

Gly Met Ala Glu Tyr Leu Phe Asn Lys His Thr Leu Gly
                165                 170
```

<210> SEQ ID NO 71

<400> SEQUENCE: 71

000

<210> SEQ ID NO 72
<211> LENGTH: 531
<212> TYPE: DNA
<213> ORGANISM: Artificial Sequence
<220> FEATURE:
<223> OTHER INFORMATION: Synthetic

<400> SEQUENCE: 72

```
tccggagaga gccaggtgag gcagcagttc agcaaggaca tcgagaagct gctgaacgag      60
caggtgaaca aggagatgca gagcagcaac ctgtacatga gcatgagcag ctggtgctac     120
acccacagcc tggacggcgc cggcctgttc ctgttcgacc acgccgccga ggagtacgag     180
cacgccaaga agctgatcat cttcctgaac gagaacaacg tgcccgtgca gctgaccagc     240
atcagcgccc ccgagcacaa gttcgagggc ctgacccaga tcttccagaa ggcctacgag     300
cacgagcagc acatcagcga gagcatcaac aacatcgtgg accacgccat caagagcaag     360
gaccacgcca ccttcaactt cctgcagtgg tacgtggccg agcagcacga ggaggaggtg     420
ctgttcaagg acatcctgga caagatcgag ctgatcggca acgagaacca cggcctgtac     480
ctggccgacc agtacgtgaa gggcatcgcc aagagcagga gagcggatc c               531
```

<210> SEQ ID NO 73
<211> LENGTH: 177
<212> TYPE: PRT
<213> ORGANISM: Artificial Sequence
<220> FEATURE:
<223> OTHER INFORMATION: Synthetic

<400> SEQUENCE: 73

```
Ser Gly Glu Ser Gln Val Arg Gln Gln Phe Ser Lys Asp Ile Glu Lys
1               5                   10                  15

Leu Leu Asn Glu Gln Val Asn Lys Glu Met Gln Ser Ser Asn Leu Tyr
            20                  25                  30

Met Ser Met Ser Ser Trp Cys Tyr Thr His Ser Leu Asp Gly Ala Gly
        35                  40                  45

Leu Phe Leu Phe Asp His Ala Ala Glu Glu Tyr Glu His Ala Lys Lys
    50                  55                  60

Leu Ile Ile Phe Leu Asn Glu Asn Asn Val Pro Val Gln Leu Thr Ser
65                  70                  75                  80

Ile Ser Ala Pro Glu His Lys Phe Glu Gly Leu Thr Gln Ile Phe Gln
                85                  90                  95

Lys Ala Tyr Glu His Glu Gln His Ile Ser Glu Ser Ile Asn Asn Ile
            100                 105                 110

Val Asp His Ala Ile Lys Ser Lys Asp His Ala Thr Phe Asn Phe Leu
        115                 120                 125

Gln Trp Tyr Val Ala Glu Gln His Glu Glu Val Leu Phe Lys Asp
    130                 135                 140

Ile Leu Asp Lys Ile Glu Leu Ile Gly Asn Glu Asn His Gly Leu Tyr
145                 150                 155                 160

Leu Ala Asp Gln Tyr Val Lys Gly Ile Ala Lys Ser Arg Lys Ser Gly
                165                 170                 175

Ser
```

<210> SEQ ID NO 74
<211> LENGTH: 531
<212> TYPE: DNA
<213> ORGANISM: Artificial Sequence
<220> FEATURE:
<223> OTHER INFORMATION: Synthetic

<400> SEQUENCE: 74

```
ggatccgctc ttcctgctct tggcgatgcc cttcacgtac tggtcggcca ggtacaggcc      60
gtggttctcg ttgccgatca gctcgatctt gtccaggatg tccttgaaca gcacctcctc     120
ctcgtgctgc tcggccacgt accactgcag gaagttgaag gtggcgtggt ccttgctctt     180
```

```
gatggcgtgg tccacgatgt tgttgatgct ctcgctgatg tgctgctcgt gctcgtaggc    240
cttctggaag atctgggtca ggccctcgaa cttgtgctcg ggggcgctga tgctggtcag    300
ctgcacgggc acgttgttct cgttcaggaa gatgatcagc ttcttggcgt gctcgtactc    360
ctcggcggcg tggtcgaaca ggaacaggcc ggcgccgtcc aggctgtggg tgtagcacca    420
gctgctcatg ctcatgtaca ggttgctgct ctgcatctcc ttgttcacct gctcgttcag    480
cagcttctcg atgtccttgc tgaactgctg cctcacctgg ctctctccgg a             531
```

<210> SEQ ID NO 75
<211> LENGTH: 516
<212> TYPE: DNA
<213> ORGANISM: Artificial Sequence
<220> FEATURE:
<223> OTHER INFORMATION: Synthetic

<400> SEQUENCE: 75

```
tccggagaga gccaggtgag gcagaacttc aagcccgaga tggaggagaa gctgaacgag     60
cagatgaacc tggagctgta cagcagcctg ctgtaccagc agatgagcgc ctggtgcagc    120
taccacacct cgagggcgc cgccgccttc ctgaggaggc acgcccagga ggagatgacc    180
cacatgcaga ggctgttcga ctacctgacc gacaccggca acctgcccag gatcaacacc    240
gtggagagcc ccttcgccga gtacagcagc ctggacgagc tgttccagga gacctacaag    300
cacgagcagc tgatcaccca gaagatcaac gagctggccc acgccgccat gaccaaccag    360
gactacccca ccttcaactt cctgcagtgg tacgtgagcg agcagcacga ggaggagaag    420
ctgttcaaga gcatcatcga caagctgagc ctggccggca gagcggcga gggcctgtac    480 ttcatcgaca aggagctgag caccctggac ggatcc                              516
```

<210> SEQ ID NO 76
<211> LENGTH: 172
<212> TYPE: PRT
<213> ORGANISM: Artificial Sequence
<220> FEATURE:
<223> OTHER INFORMATION: Synthetic

<400> SEQUENCE: 76

```
Ser Gly Glu Ser Gln Val Arg Gln Asn Phe Lys Pro Glu Met Glu Glu
  1               5                  10                  15

Lys Leu Asn Glu Gln Met Asn Leu Glu Leu Tyr Ser Ser Leu Leu Tyr
             20                  25                  30

Gln Gln Met Ser Ala Trp Cys Ser Tyr His Thr Phe Glu Gly Ala Ala
         35                  40                  45

Ala Phe Leu Arg Arg His Ala Gln Glu Glu Met Thr His Met Gln Arg
     50                  55                  60

Leu Phe Asp Tyr Leu Thr Asp Thr Gly Asn Leu Pro Arg Ile Asn Thr
 65                  70                  75                  80

Val Glu Ser Pro Phe Ala Glu Tyr Ser Ser Leu Asp Glu Leu Phe Gln
                 85                  90                  95

Glu Thr Tyr Lys His Glu Gln Leu Ile Thr Gln Lys Ile Asn Glu Leu
            100                 105                 110

Ala His Ala Ala Met Thr Asn Gln Asp Tyr Pro Thr Phe Asn Phe Leu
        115                 120                 125

Gln Trp Tyr Val Ser Glu Gln His Glu Glu Glu Lys Leu Phe Lys Ser
    130                 135                 140

Ile Ile Asp Lys Leu Ser Leu Ala Gly Lys Ser Gly Glu Gly Leu Tyr
145                 150                 155                 160
```

Phe Ile Asp Lys Glu Leu Ser Thr Leu Asp Gly Ser
            165                 170

<210> SEQ ID NO 77
<211> LENGTH: 516
<212> TYPE: DNA
<213> ORGANISM: Artificial Sequence
<220> FEATURE:
<223> OTHER INFORMATION: Synthetic

<400> SEQUENCE: 77
ggatccgtcc agggtgctca gctccttgtc gatgaagtac aggccctcgc cgctcttgcc      60
ggccaggctc agcttgtcga tgatgctctt gaacagcttc tcctcctcgt gctgctcgct     120
cacgtaccac tgcaggaagt tgaaggtggg gtagtcctgg ttggtcatgg cggcgtgggc     180
cagctcgttg atcttctggg tgatcagctg ctcgtgcttg taggtctcct ggaacagctc     240
gtccaggctg ctgtactcgg cgaaggggct ctccacggtg ttgatcctgg gcaggttgcc     300
ggtgtcggtc aggtagtcga acagcctctg catgtgggtc atctcctcct gggcgtgcct     360
cctcaggaag gcggcggcgc cctcgaaggt gtggtagctg caccaggcgc tcatctgctg     420
gtacagcagg ctgctgtaca gctccaggtt catctgctcg ttcagcttct cctccatctc     480
gggcttgaag ttctgcctca cctggctctc tccgga                               516

<210> SEQ ID NO 78
<211> LENGTH: 792
<212> TYPE: DNA
<213> ORGANISM: Thermotoga maritima

<400> SEQUENCE: 78
atggagttcc tgaagaggag cttcgcccct ctgaccgaga agcagtggca ggagatcgac      60
aacagggcca gggagatctt caagacccag ctgtacggca ggaagttcgt ggacgtggag     120 ggccccctacg ctgggagta cgccgcccac cccctgggcg aggtggaggt gctgagcgac     180
gagaacgagg tggtgaagtg gggcctgagg aagagcctgc ccctgatcga gctgagggcc     240
accttcaccc tggaccctgtg ggagctggac aacctggaga gggcaagcc caacgtggac     300 ctgagcagcc tggaggagac cgtgaggaag gtggccgagt cgaggacga ggtgatcttc     360 agggggctgcg agaagagcgg cgtgaagggc ctgctgagct cgaggagag gaagatcgag     420 tgcggcagca ccccccaagga cctgctggag gccatcgtga gggccctgag catcttcagc     480
aaggacggca tcgagggccc ctacacccctg gtgatcaaca ccgacaggtg gatcaacttc     540
ctgaaggagg aggccggcca ctaccccctg gagaagaggg tggaggagtg cctgaggggc     600
ggcaagatca tcaccacccc caggatcgag gacgccctgg tggtgagcga gggggcggc     660 gacttcaagc tgatcctggg ccaggacctg agcatcggct acgaggacag ggagaaggac     720
gccgtgaggc tgttcatcac cgagaccttc accttccagg tggtgaaccc cgaggccctg     780
atcctgctga ag                                                         792

<210> SEQ ID NO 79
<211> LENGTH: 264
<212> TYPE: PRT
<213> ORGANISM: Thermotoga maritima

<400> SEQUENCE: 79

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys
            260

<210> SEQ ID NO 80
<211> LENGTH: 792
<212> TYPE: DNA
<213> ORGANISM: Thermotoga maritima

<400> SEQUENCE: 80
cttcagcagg atcagggcct cggggttcac cacctggaag gtgaaggtct cggtgatgaa      60
cagcctcacg gcgtccttct ccctgtcctc gtagccgatg ctcaggtcct ggcccaggat     120
cagcttgaag tcgccgcccc tctcgctcac caccagggcg tcctcgatcc tgggggtggt     180
gatgatcttg ccgcccctca ggcactcctc caccctcttc tccaggggagt agtggccggc     240
ctcctcctcc aggaagttga tccacctgtc ggtgttgatc accagggtgt aggggccctc     300
gatgccgtcc ttgctgaaga tgctcagggc cctcacgatg gcctccagca ggtccttggg     360
ggtgctgccg cactcgatct tcctctcctc gaagctcagc aggcccttca gcgcctctt      420
ctcgcagccc tgaagatca cctcgtcctc gaactcggcc accttcctca cggtctcctc     480
caggctgctc aggtccacgt tgggcttgcc cctctccagg ttgtccagct cccacaggtc     540
cagggtgaag gtggccctca gctcgatcag gggcaggctc ttcctcaggc cccacttcac     600
cacctcgttc tcgtcgctca gcacctccac ctcgcccagg gggtgggcgg cgtactccca     660
gccgtagggg ccctccacgt ccacgaactt cctgccgtac agctgggtct tgaagatctc     720

```
cctggccctg ttgtcgatct cctgccactg cttctcggtc agaggggcga agctcctctt    780
caggaactcc at                                                         792
```

<210> SEQ ID NO 81

<400> SEQUENCE: 81

000

<210> SEQ ID NO 82
<211> LENGTH: 192
<212> TYPE: PRT
<213> ORGANISM: Artificial Sequence
<220> FEATURE:
<223> OTHER INFORMATION: Synthetic

<400> SEQUENCE: 82

```
Met Ser Gln Ala Ile Gly Ile Leu Glu Leu Thr Ser Ile Ala Ala Gly
1               5                   10                  15

Met Glu Leu Gly Asp Ala Met Leu Lys Ser Ala Asn Val Asp Leu Leu
            20                  25                  30

Val Ser Lys Thr Ile Ser Pro Gly Lys Phe Leu Leu Met Leu Gly Gly
        35                  40                  45

Asp Ile Gly Ala Ile Gln Gln Ala Ile Glu Thr Gly Thr Ser Gln Ala
    50                  55                  60

Gly Glu Leu Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Arg Ala Val Lys Gly Ser Asn Val Thr Leu Val Arg Val His Met
        115                 120                 125

Ala Phe Gly Ile Gly Gly Lys Cys Tyr Met Val Val Ala Gly Asp Val
    130                 135                 140

Ser Asp Val Ala Leu Ala Val Thr Val Ala Ser Ser Ser Ala Gly Ala
145                 150                 155                 160

Tyr Gly Leu Leu Val Tyr Ala Ser Leu Ile Pro Arg Pro His Glu Ala
                165                 170                 175

Met Trp Arg Gln Met Val Glu Gly Leu Glu His His His His His His
            180                 185                 190
```

<210> SEQ ID NO 83

<400> SEQUENCE: 83

000

<210> SEQ ID NO 84

<400> SEQUENCE: 84

000

<210> SEQ ID NO 85
<211> LENGTH: 318
<212> TYPE: PRT
<213> ORGANISM: Acidianus ambivalens
<220> FEATURE:
<221> NAME/KEY: misc_feature
<222> LOCATION: (31)..(31)
<223> OTHER INFORMATION: Xaa can be any naturally occurring amino acid

<400> SEQUENCE: 85

Met Pro Lys Pro Tyr Val Ala Ile Asn Met Ala Glu Leu Lys Asn Glu
1               5                   10                  15

Pro Lys Thr Phe Glu Met Phe Ala Ser Val Gly Pro Lys Val Xaa Met
            20                  25                  30

Val Thr Ala Arg His Pro Gly Phe Val Gly Phe Gln Asn His Ile Gln
        35                  40                  45

Ile Gly Ile Leu Pro Phe Gly Asn Arg Tyr Gly Gly Ala Lys Met Asp
    50                  55                  60

Met Thr Lys Glu Ser Ser Thr Val Arg Val Leu Gln Tyr Thr Phe Trp
65                  70                  75                  80

Lys Asp Trp Lys Asp His Glu Glu Met His Arg Gln Asn Trp Ser Tyr
                85                  90                  95

Leu Phe Arg Leu Cys Tyr Ser Cys Ala Ser Gln Met Ile Trp Gly Pro
            100                 105                 110

Trp Glu Pro Ile Tyr Glu Ile Ile Tyr Ala Asn Met Pro Ile Asn Thr
        115                 120                 125

Glu Met Thr Asp Phe Thr Ala Val Val Gly Lys Lys Phe Ala Glu Gly
130                 135                 140

Lys Pro Leu Asp Ile Pro Val Ile Ser Gln Pro Tyr Gly Lys Arg Val
145                 150                 155                 160

Val Ala Phe Ala Glu His Ser Val Ile Pro Gly Lys Glu Lys Gln Phe
                165                 170                 175

Glu Asp Ala Ile Val Arg Thr Leu Glu Met Leu Lys Lys Ala Pro Gly
            180                 185                 190

Phe Leu Gly Ala Met Val Leu Lys Glu Ile Gly Val Ser Gly Ile Gly
        195                 200                 205

Ser Met Gln Phe Gly Ala Lys Gly Phe His Val Leu Glu Asn Pro
210                 215                 220

Gly Ser Leu Glu Pro Asp Pro Asn Asn Val Met Tyr Ser Val Pro Glu
225                 230                 235                 240

Ala Lys Asn Thr Pro Gln Gln Tyr Ile Val His Val Glu Trp Ala Asn
                245                 250                 255

Thr Asp Ala Leu Met Phe Gly Met Gly Arg Val Leu Tyr Pro Glu
            260                 265                 270

Leu Arg Gln Val His Asp Glu Val Leu Asp Thr Leu Val Tyr Gly Pro
        275                 280                 285

Tyr Ile Arg Ile Leu Asn Pro Met Met Glu Gly Thr Phe Trp Arg Glu
290                 295                 300

Tyr Leu Asn Glu Gln Ala Trp Arg His Pro Gln Phe Gly Gly
305                 310                 315

<210> SEQ ID NO 86

<400> SEQUENCE: 86

000

<210> SEQ ID NO 87

<400> SEQUENCE: 87

000

<210> SEQ ID NO 88
<211> LENGTH: 154
<212> TYPE: PRT
<213> ORGANISM: Aquifex aeolicus

<400> SEQUENCE: 88

```
Met Gln Ile Tyr Glu Gly Lys Leu Thr Ala Glu Gly Leu Arg Phe Gly
1               5                   10                  15
Ile Val Ala Ser Arg Phe Asn His Ala Leu Val Asp Arg Leu Val Glu
            20                  25                  30
Gly Ala Ile Asp Cys Ile Val Arg His Gly Gly Arg Glu Glu Asp Ile
        35                  40                  45
Thr Leu Val Arg Val Pro Gly Ser Trp Glu Ile Pro Val Ala Ala Gly
    50                  55                  60
Glu Leu Ala Arg Lys Glu Asp Ile Asp Ala Val Ile Ala Ile Gly Val
65                  70                  75                  80
Leu Ile Arg Gly Ala Thr Pro His Phe Asp Tyr Ile Ala Ser Glu Val
                85                  90                  95
Ser Lys Gly Leu Ala Asn Leu Ser Leu Glu Leu Arg Lys Pro Ile Thr
            100                 105                 110
Phe Gly Val Ile Thr Ala Asp Thr Leu Glu Gln Ala Ile Glu Arg Ala
        115                 120                 125
Gly Thr Lys His Gly Asn Lys Gly Trp Glu Ala Ala Leu Ser Ala Ile
    130                 135                 140
Glu Met Ala Asn Leu Phe Lys Ser Leu Arg
145                 150
```

<210> SEQ ID NO 89

<400> SEQUENCE: 89

000

<210> SEQ ID NO 90

<400> SEQUENCE: 90

000

<210> SEQ ID NO 91
<211> LENGTH: 242
<212> TYPE: PRT
<213> ORGANISM: Bacillus stearothermophilus

<400> SEQUENCE: 91

```
Ala Ala Ala Lys Pro Ala Thr Thr Glu Gly Glu Phe Pro Glu Thr Arg
1               5                   10                  15
Glu Lys Met Ser Gly Ile Arg Arg Ala Ile Ala Lys Ala Met Val His
            20                  25                  30
Ser Lys His Thr Ala Pro His Val Thr Leu Met Asp Glu Ala Asp Val
        35                  40                  45
Thr Lys Leu Val Ala His Arg Lys Lys Phe Lys Ala Ile Ala Ala Glu
    50                  55                  60
Lys Gly Ile Lys Leu Thr Phe Leu Pro Tyr Val Val Lys Ala Leu Val
65                  70                  75                  80
Ser Ala Leu Arg Glu Tyr Pro Val Leu Asn Thr Ser Ile Asp Asp Glu
                85                  90                  95
Thr Glu Glu Ile Ile Gln Lys His Tyr Tyr Asn Ile Gly Ile Ala Ala
```

```
                 100                 105                 110
Asp Thr Asp Arg Gly Leu Leu Val Pro Val Ile Lys His Ala Asp Arg
            115                 120                 125

Lys Pro Ile Phe Ala Leu Ala Gln Glu Ile Asn Glu Leu Ala Glu Lys
        130                 135                 140

Ala Arg Asp Gly Lys Leu Thr Pro Gly Glu Met Lys Gly Ala Ser Cys
145                 150                 155                 160

Thr Ile Thr Asn Ile Gly Ser Ala Gly Gly Gln Trp Phe Thr Pro Val
                165                 170                 175

Ile Asn His Pro Glu Val Ala Ile Leu Gly Ile Gly Arg Ile Ala Glu
            180                 185                 190

Lys Pro Ile Val Arg Asp Gly Glu Ile Val Ala Ala Pro Met Leu Ala
        195                 200                 205

Leu Ser Leu Ser Phe Asp His Arg Met Ile Asp Gly Ala Thr Ala Gln
    210                 215                 220

Lys Ala Leu Asn His Ile Lys Arg Leu Leu Ser Asp Pro Glu Leu Leu
225                 230                 235                 240

Leu Met

<210> SEQ ID NO 92

<400> SEQUENCE: 92

000

<210> SEQ ID NO 93
<211> LENGTH: 3747
<212> TYPE: DNA
<213> ORGANISM: Chikungunya virus

<400> SEQUENCE: 93
atggagttca tcccgacgca aactttctat aacagaaggt accaaccccg accctgggcc      60
ccacgcccta caattcaagt aattagacct agaccacgtc cacagaggca ggctgggcaa     120
ctcgcccagc tgatctccgc agtcaacaaa ttgaccatgc gcgcggtacc tcaacgaaag     180
cctcgcagaa atcggaaaaa caagaagcaa aggcagaaga agcaggcgcc gcaaaacgac     240
ccaaagcaaa agaagcaacc accacaaaag aagccggctc aaaagaagaa gaaaccaggc     300
cgtagggaga gaatgtgcat gaaaattgaa atgattgcat cttcgaagt caagcatgaa     360 ggcaaagtga tgggctacgc atgcctggtg ggggataaag taatgaaacc agcacatgtg     420
aagggaacta tcgacaatgc cgatctggct aaactggcct ttaagcggtc gtctaaatac     480
gatcttgaat gtgcacagat accggtgcac atgaagtctg atgcctcgaa gtttacccac     540
gagaaacccg aggggtacta taactggcat cacggagcag tgcagtattc aggaggccgg     600
ttcactatcc cgacgggtgc aggcaagccg ggagacagcg gcagaccgat cttcgacaac     660
aaaggacggg tggtggccat cgtcctagga ggggccaacg aaggtgcccg cacggccctc     720
tccgtggtga cgtggaacaa agacatcgtc acaaaaatta cccctgaggg agccgaagag     780
tggagcctcg ccctcccggt cttgtgcctt ttggcaaaca ctacattccc ctgctctcag     840
ccgccttgca caccctgctg ctacgaaaag gaaccggaaa gcaccttgcg catgcttgag     900
gacaacgtga tgagacccgg atactaccag ctactaaaag catcgctgac ttgctctccc     960
caccgccaaa gacgcagtac taaggacaat tttaatgtct ataaagccac aagaccatat    1020
ctagctcatt gtcctgactg cggagaaggg cattcgtgcc acagcccat cgcattggag    1080
```

```
cgcatcagaa atgaagcaac ggacggaacg ctgaaaatcc aggtctcttt gcagatcggg    1140
ataaagacag atgacagcca cgattggacc aagctgcgct atatggatag ccatacgcca    1200
gcggacgcgg agcgagccgg attgcttgta aggacttcag caccgtgcac gatcaccggg    1260
accatgggac actttattct cgcccgatgc ccgaaaggag agacgctgac agtgggattt    1320
acggacagca gaaagatcag ccacacatgc acacacccgt tccatcatga accacctgtg    1380
ataggtaggg agaggttcca ctctcgacca caacatggta aagagttacc ttgcagcacg    1440
tacgtgcaga gcaccgctgc cactgctgag gagatagagg tgcatatgcc cccagatact    1500
cctgaccgca cgctgatgac gcagcagtct ggcaacgtga agatcacagt taatgggcag    1560
acggtgcggt acaagtgcaa ctgcggtggc tcaaacgagg gactgacaac cacagacaaa    1620
gtgatcaata actgcaaaat tgatcagtgc catgctgcag tcactaatca aagaattgg     1680 caatacaact cccctttagt cccgcgcaac gctgaactcg ggaccgtaa aggaaagatc     1740 cacatcccat tcccattggc aaacgtgact tgcagagtgc caaaagcaag aaaccctaca    1800
gtaacttacg gaaaaaacca agtcaccatg ctgctgtatc ctgaccatcc gacactcttg    1860
tcttaccgta acatgggaca ggaaccaaat taccacgagg agtgggtgac acacaagaag    1920
gaggttacct tgaccgtgcc tactgagggt ctggaggtca cttggggcaa caacgaacca    1980
tacaagtact ggccgcagat gtctacgaac ggtactgctc atggtcaccc acatgagata    2040
atcttgtact attatgagct gtaccccact atgactgtag tcattgtgtc ggtggcctcg    2100
ttcgtgcttc tgtcgatggt gggcacagca gtgggaatgt gtgtgtgcgc acggcgcaga    2160
tgcattacac catatgaatt aacaccagga gccactgttc ccttcctgct cagcctgcta    2220
tgctgcgtca gaacgaccaa ggcggccaca tattacgagg ctgcggcata tctatggaac    2280
gaacagcagc ccctgttctg gttgcaggct cttatcccgc tggccgcctt gatcgtcctg    2340
tgcaactgtc tgaaactctt gccatgctgc tgtaagaccc tggctttttt agccgtaatg    2400
agcatcggtg cccacactgt gagcgcgtac gaacacgtaa cagtgatccc gaacacggtg    2460
ggagtaccgt ataagactct tgtcaacaga ccgggttaca gccccatggt gttggagatg    2520
gagctacaat cagtcacctt ggaaccaaca ctgtcacttg actacatcac gtgcgagtac    2580
aaaactgtca tcccctcccc gtacgtgaag tgctgtggta cagcagagtg caaggacaag    2640
agcctaccag actacagctg caaggtcttt actggagtct acccatttat gtggggcggc    2700
gcctactgct ttgcgacgc cgaaaatacg caattgagcg aggcacatgt agagaaatct    2760
gaatcttgca aaacagagtt tgcatcggcc tacagagccc acaccgcatc ggcgtcggcg    2820
aagctccgcg tcctttacca aggaaacaac attaccgtag ctgcctacgc taacggtgac    2880
catgccgtca cagtaaagga cgccaagttt gtcgtgggcc caatgtcctc cgcctggaca    2940
ccttttgaca caaaatcgt ggtgtacaaa ggcgacgtct acaacatgga ctacccacct    3000
tttggcgcag gaagaccagg acaatttggt gacattcaaa gtcgtacacc ggaaagtaaa    3060
gacgtttatg ccaacactca gttggtacta cagaggccag cagcaggcac ggtacatgta    3120
ccatactctc aggcaccatc tggcttcaag tattggctga aggaacgagg agcatcgcta    3180
cagcacacgg caccgttcgg ttgccagatt gcgacaaacc cggtaagagc tgtaaattgc    3240
gctgtgggga acataccaat ttccatcgac ataccggatg cggcctttac tagggttgtc    3300
gatgcaccct ctgtaacgga catgtcatgc gaagtaccag cctgcactca ctcctccgac    3360
tttgggggcg tcgccatcat caaatacaca gctagcaaga aggtaaatg tgcagtacat    3420 tcgatgacca acgccgttac cattcgagaa gccgacgtag aagtagaggg gaactcccag    3480
```

-continued

```
ctgcaaatat ccttctcaac agccctggca agcgccgagt ttcgcgtgca agtgtgctcc    3540
acacaagtac actgcgcagc cgcatgccac cctccaaagg accacatagt caattaccca    3600
gcatcacaca ccaccttgg ggtccaggat atatccacaa cggcaatgtc ttgggtgcag     3660
aagattacgg gaggagtagg attaattgtt gctgttgctg ccttaatttt aattgtggtg    3720
ctatgcgtgt cgtttagcag gcactaa                                        3747
```

<210> SEQ ID NO 94
<211> LENGTH: 1248
<212> TYPE: PRT
<213> ORGANISM: Chikungunya virus

<400> SEQUENCE: 94

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
50                  55                  60

Arg Lys Asn Lys Lys Gln Arg Gln Lys Gln Ala Pro Gln Asn Asp
65                  70                  75                  80

Pro Lys Gln Lys Lys Gln Pro Pro Gln Lys Pro Ala Gln Lys Lys
            85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
            115                 120                 125

Leu Val Gly Asp Lys Val Met Lys Pro Ala His Val Lys Gly Thr Ile
        130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Ser Pro
305                 310                 315                 320
```

```
His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Ile Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Ser His Thr Pro
385                 390                 395                 400

Ala Asp Ala Glu Arg Ala Gly Leu Leu Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
        435                 440                 445

Thr Cys Thr His Pro Phe His His Glu Pro Pro Val Ile Gly Arg Glu
    450                 455                 460

Arg Phe His Ser Arg Pro Gln His Gly Lys Glu Leu Pro Cys Ser Thr
465                 470                 475                 480

Tyr Val Gln Ser Thr Ala Ala Thr Ala Glu Glu Ile Glu Val His Met
                485                 490                 495

Pro Pro Asp Thr Pro Asp Arg Thr Leu Met Thr Gln Gln Ser Gly Asn
            500                 505                 510

Val Lys Ile Thr Val Asn Gly Gln Thr Val Arg Tyr Lys Cys Asn Cys
        515                 520                 525

Gly Gly Ser Asn Glu Gly Leu Thr Thr Thr Asp Lys Val Ile Asn Asn
    530                 535                 540

Cys Lys Ile Asp Gln Cys His Ala Ala Val Thr Asn His Lys Asn Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
        595                 600                 605

Thr Met Leu Leu Tyr Pro Asp His Pro Thr Leu Leu Ser Tyr Arg Asn
    610                 615                 620

Met Gly Gln Glu Pro Asn Tyr His Glu Glu Trp Val Thr His Lys Lys
625                 630                 635                 640

Glu Val Thr Leu Thr Val Pro Thr Glu Gly Leu Glu Val Thr Trp Gly
                645                 650                 655

Asn Asn Glu Pro Tyr Lys Tyr Trp Pro Gln Met Ser Thr Asn Gly Thr
            660                 665                 670

Ala His Gly His Pro His Glu Ile Ile Leu Tyr Tyr Tyr Glu Leu Tyr
        675                 680                 685

Pro Thr Met Thr Val Val Ile Val Ser Val Ala Ser Phe Val Leu Leu
    690                 695                 700

Ser Met Val Gly Thr Ala Val Gly Met Cys Val Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Leu Cys Cys Val Arg Thr Thr Lys Ala Ala Thr Tyr Tyr
```

```
                740             745             750
Glu Ala Ala Ala Tyr Leu Trp Asn Glu Gln Gln Pro Leu Phe Trp Leu
        755             760             765

Gln Ala Leu Ile Pro Leu Ala Ala Leu Ile Val Leu Cys Asn Cys Leu
        770             775             780

Lys Leu Leu Pro Cys Cys Cys Lys Thr Leu Ala Phe Leu Ala Val Met
785             790             795             800

Ser Ile Gly Ala His Thr Val Ser Ala Tyr Glu His Val Thr Val Ile
            805             810             815

Pro Asn Thr Val Gly Val Pro Tyr Lys Thr Leu Val Asn Arg Pro Gly
        820             825             830

Tyr Ser Pro Met Val Leu Glu Met Glu Leu Gln Ser Val Thr Leu Glu
        835             840             845

Pro Thr Leu Ser Leu Asp Tyr Ile Thr Cys Glu Tyr Lys Thr Val Ile
        850             855             860

Pro Ser Pro Tyr Val Lys Cys Cys Gly Thr Ala Glu Cys Lys Asp Lys
865             870             875             880

Ser Leu Pro Asp Tyr Ser Cys Lys Val Phe Thr Gly Val Tyr Pro Phe
            885             890             895

Met Trp Gly Gly Ala Tyr Cys Phe Cys Asp Ala Glu Asn Thr Gln Leu
            900             905             910

Ser Glu Ala His Val Glu Lys Ser Glu Ser Cys Lys Thr Glu Phe Ala
        915             920             925

Ser Ala Tyr Arg Ala His Thr Ala Ser Ala Ser Ala Lys Leu Arg Val
        930             935             940

Leu Tyr Gln Gly Asn Asn Ile Thr Val Ala Ala Tyr Ala Asn Gly Asp
945             950             955             960

His Ala Val Thr Val Lys Asp Ala Lys Phe Val Val Gly Pro Met Ser
            965             970             975

Ser Ala Trp Thr Pro Phe Asp Asn Lys Ile Val Val Tyr Lys Gly Asp
            980             985             990

Val Tyr Asn Met Asp Tyr Pro Pro Phe Gly Ala Gly Arg Pro Gly Gln
        995             1000            1005

Phe Gly Asp Ile Gln Ser Arg Thr Pro Glu Ser Lys Asp Val Tyr
    1010            1015            1020

Ala Asn Thr Gln Leu Val Leu Gln Arg Pro Ala Ala Gly Thr Val
    1025            1030            1035

His Val Pro Tyr Ser Gln Ala Pro Ser Gly Phe Lys Tyr Trp Leu
    1040            1045            1050

Lys Glu Arg Gly Ala Ser Leu Gln His Thr Ala Pro Phe Gly Cys
    1055            1060            1065

Gln Ile Ala Thr Asn Pro Val Arg Ala Val Asn Cys Ala Val Gly
    1070            1075            1080

Asn Ile Pro Ile Ser Ile Asp Ile Pro Asp Ala Ala Phe Thr Arg
    1085            1090            1095

Val Val Asp Ala Pro Ser Val Thr Asp Met Ser Cys Glu Val Pro
    1100            1105            1110

Ala Cys Thr His Ser Ser Asp Phe Gly Gly Val Ala Ile Ile Lys
    1115            1120            1125

Tyr Thr Ala Ser Lys Lys Gly Lys Cys Ala Val His Ser Met Thr
    1130            1135            1140

Asn Ala Val Thr Ile Arg Glu Ala Asp Val Glu Val Glu Gly Asn
    1145            1150            1155
```

| | | | | | | | | | | |
|---|---|---|---|---|---|---|---|---|---|---|
|Ser|Gln|Leu|Gln|Ile|Ser|Phe|Ser|Thr|Ala|Leu|Ala|Ser|Ala|Glu|
| |1160| | | |1165| | | |1170| |

Phe Arg Val Gln Val Cys Ser Thr Gln Val His Cys Ala Ala Ala
    1175            1180            1185

Cys His Pro Pro Lys Asp His Ile Val Asn Tyr Pro Ala Ser His
    1190            1195            1200

Thr Thr Leu Gly Val Gln Asp Ile Ser Thr Thr Ala Met Ser Trp
    1205            1210            1215

Val Gln Lys Ile Thr Gly Gly Val Gly Leu Ile Val Ala Val Ala
    1220            1225            1230

Ala Leu Ile Leu Ile Val Val Leu Cys Val Ser Phe Ser Arg His
    1235            1240            1245

<210> SEQ ID NO 95
<211> LENGTH: 3747
<212> TYPE: DNA
<213> ORGANISM: Chikungunya virus

<400> SEQUENCE: 95

```
ttagtgcctg ctaaacgaca cgcatagcac cacaattaaa attaaggcag caacagcaac    60
aattaatcct actcctcccg taatcttctg cacccaagac attgccgttg tggatatatc   120
ctggacccca agggtggtgt gtgatgctgg gtaattgact atgtggtcct ttggagggtg   180
gcatgcggct gcgcagtgta cttgtgtgga gcacacttgc acgcgaaact cggcgcttgc   240
cagggctgtt gagaaggata tttgcagctg ggagttcccc tctacttcta cgtcggcttc   300
tcgaatggta acggcgttgg tcatcgaatg tactgcacat ttaccttttct tgctagctgt   360
gtatttgatg atggcgacgc ccccaaagtc ggaggagtga gtgcaggctg gtacttcgca   420
tgacatgtcc gttacagagg gtgcatcgac aaccctagta aaggccgcat ccggtatgtc   480
gatggaaatt ggtatgttcc ccacagcgca atttacagct cttaccgggt tgtcgcaat   540
ctggcaaccg aacggtgccg tgtgctgtag cgatgctcct cgttccttca gccaatactt   600
gaagccagat ggtgcctgag agtatggtac atgtaccgtg cctgctgctg gcctctgtag   660
taccaactga gtgttggcat aaacgtcttt actttccggt gtacgacttt gaatgtcacc   720
aaattgtcct ggtcttcctg cgccaaaagg tgggtagtcc atgttgtaga cgtcgccttt   780
gtacaccacg attttgttgt caaaaggtgt ccaggcggag acattgggc ccacgacaaa   840
cttggcgtcc tttactgtga cggcatggtc accgttagcg taggcagcta cggtaatgtt   900
gtttccttgg taaaggacgc ggagcttcgc cgacgccgat gcggtgtggg ctctgtaggc   960
cgatgcaaac tctgttttgc aagattcaga tttctctaca tgtgcctcgc tcaattgcgt  1020
attttcggcg tcgcaaaagc agtaggcgcc gccccacata aatgggtaga ctccagtaaa  1080
gaccttgcag ctgtagtctg gtaggctctt gtccttgcac tctgctgtac cacagcactt  1140
cacgtacggg gagggatga cagttttgta ctcgcacgtg atgtagtcaa gtgacagtgt  1200
tggttccaag gtgactgatt gtagctccat ctccaacacc atgggctgt aacccggtct  1260
gttgacaaga gtcttatacg gtactcccac cgtgttcggg atcactgtta cgtgttcgta  1320
cgcgctcaca gtgtgggcac cgatgctcat tacggctaaa aaagccaggg tcttacagca  1380
gcatggcaag agtttcagac agttgcacag gacgatcaag gcggccagcg ggataagagc  1440
ctgcaaccag aacaggggct gctgttcgtt ccatagatat gccgcagcct cgtaatatgt  1500
ggccgccttg gtcgttctga cgcagcatag caggctgagc aggaagggaa cagtggctcc  1560
```

```
tggtgttaat tcatatggtg taatgcatct gcgccgtgcg cacacacaca ttcccactgc    1620
tgtgcccacc atcgacagaa gcacgaacga ggccaccgac acaatgacta cagtcatagt    1680
ggggtacagc tcataatagt acaagattat ctcatgtggg tgaccatgag cagtaccgtt    1740
cgtagacatc tgcggccagt acttgtatgg ttcgttgttg ccccaagtga cctccagacc    1800
ctcagtaggc acggtcaagg taacctcctt cttgtgtgtc acccactcct cgtggtaatt    1860
tggttcctgt cccatgttac ggtaagacaa gagtgtcgga tggtcaggat acagcagcat    1920
ggtgacttgg ttttttccgt aagttactgt agggtttctt gcttttggca ctctgcaagt    1980
cacgtttgcc aatgggaatg ggatgtggat cttttccttta cggtccccga gttcagcgtt    2040
gcgcgggact aaaggggagt tgtattgcca attcttgtga ttagtgactg cagcatggca    2100
ctgatcaatt ttgcagttat tgatcacttt gtctgtggtt gtcagtccct cgtttgagcc    2160
accgcagttg cacttgtacc gcaccgtctg cccattaact gtgatcttca cgttgccaga    2220
ctgctgcgtc atcagcgtgc ggtcaggagt atctgggggc atatgcacct ctatctcctc    2280
agcagtggca gcggtgctct gcacgtacgt gctgcaaggt aactctttac catgttgtgg    2340
tcgagagtgg aacctctccc tacctatcac aggtggttca tgatggaacg ggtgtgtgca    2400
tgtgtggctg atctttctgc tgtccgtaaa tcccactgtc agcgtctctc ctttcgggca    2460
tcgggcgaga ataaagtgtc ccatggtccc ggtgatcgtg cacggtgctg aagtccttac    2520
aagcaatccg gctcgctccg cgtccgctgg cgtatggcta tccatatagc gcagcttggt    2580
ccaatcgtgg ctgtcatctg tctttatccc gatctgcaaa gagacctgga ttttcagcgt    2640
tccgtccgtt gcttcatttc tgatgcgctc caatgcgata gggctgtggc acgaatgccc    2700
ttctccgcag tcaggacaat gagctagata tggtcttgtg gctttataga cattaaaatt    2760
gtccttagta ctgcgtcttt ggcggtgggg agagcaagtc agcgatgctt ttagtagctg    2820
gtagtatccg ggtctcatca cgttgtcctc aagcatgcgc aaggtgcttt ccggttcctt    2880
ttcgtagcag cagggtgtgc aaggcggctg agagcagggg aatgtagtgt ttgccaacag    2940
gcacaagacc gggagggcga ggctccactc ttcggctccc tcagggtaa tttttgtgac     3000
gatgtctttg ttccacgtca ccacggagag ggccgtgcgg gcaccttcgt tggcccctcc    3060
taggacgatg gccaccaccc gtcctttgtt gtcgaagatc ggtctgccgc tgtctcccgg    3120
cttgcctgca cccgtcggga tagtgaaccg gcctcctgaa tactgcactg ctccgtgatg    3180
ccagttatag taccctcgg gtttctcgtg ggtaaacttc gaggcatcag acttcatgtg     3240
caccggtatc tgtgcacatt caagatcgta tttagacgac cgcttaaagg ccagtttagc    3300
cagatcggca ttgtcgatag ttcccttcac atgtgctggt ttcattactt tatcccccac    3360
caggcatgcg tagcccatca ctttgccttc atgcttgact tcgaagatgc aatcattttc    3420
aattttcatg cacattctct ccctacggcc tggtttcttc ttcttttgag ccggcttctt    3480
ttgtggtggt tgcttctttt gctttgggtc gttttgcggc gcctgcttct tctgcctttg    3540
cttcttgttt ttccgattc tgcgaggctt ctgttgaggt accgcgcgca tggtcaattt     3600
gttgactgcg gagatcagct gggcgagttg cccagcctgc ctctgtggac gtggtctagg    3660
tctaattact tgaattgtag ggcgtggggc ccagggtcgg ggttggtacc ttctgttata    3720
gaaagtttgc gtcgggatga actccat                                         3747
```

<210> SEQ ID NO 96
<211> LENGTH: 1266
<212> TYPE: DNA
<213> ORGANISM: Artificial Sequence

```
<220> FEATURE:
<223> OTHER INFORMATION: Synthetic

<400> SEQUENCE: 96
atggacagca agggcagcag ccagaagggc agcagactgc tgctgctgct ggtggtgagc      60
aacctgctgc tgcctcaggg cgtgctagcc attgccctc tgcagctggg caattgttct     120
gtggccggat ggattctggg caaccccgag tgtgagctgc tgatttctaa ggagagctgg     180
agctacatcg tggagacccc caatcctgag aatggcacct gctaccctgg ctacttcgcc     240
gattacgagg agctgcgcga gcagctgtct agcgtgtcca gcttcgagag attcgagatc     300
ttccccaagg agtccagctg gcctaatcac acagtgacag gcgtgtctgc cagctgtagc     360
cacaacggca aaagcagctt ctaccggaac ctgctgtggc tgacaggcaa gaatggcctg     420
taccccaacc tgagcaagag ctacgtgaac aacaaggaaa aggaagtgct ggtgctgtgg     480
ggagtgcacc accctcccaa catcggaaat cagcgggccc tgtaccacac agagaacgcc     540
tatgtgagcg tggtgtccag ccactacagc agaagattca cccccgagat cgccaagaga     600
cccaaagtga gagaccagga gggccggatc aattactact ggaccctgct ggagcctggc     660
gataccatca tcttcgaggc aacggcaat ctgatcgccc cttggtatgc ctttgccctg      720
agcagaggcg cctccggaga gagccaggtg aggcagcagt tcagcaagga catcgagaag     780
ctgctgaacg agcaggtgaa caaggagatg cagagcagca acctgtacat gagcatgagc     840
agctggtgct acacccacag cctggacggc gccggctgt tcctgttcga ccacgccgcc      900
gaggagtacg agcacgccaa gaagctgatc atcttcctga cgagaacaa cgtgcccgtg      960
cagctgacca gcatcagcgc ccccgagcac aagttcgagg gcctgaccca gatcttccag    1020
aaggcctacg agcacgagca gcacatcagc gagagcatca acaacatcgt ggaccacgcc    1080
atcaagagca aggaccacgc caccttcaac ttcctgcagt ggtacgtggc cgagcagcac    1140
gaggaggagg tgctgttcaa ggacatcctg gacaagatcg agctgatcgg caacgagaac    1200
cacggcctgt acctggccga ccagtacgtg aagggcatcg ccaagagcag gaagagcgga    1260
tcctag                                                                1266

<210> SEQ ID NO 97
<211> LENGTH: 421
<212> TYPE: PRT
<213> ORGANISM: Artificial Sequence
<220> FEATURE:
<223> OTHER INFORMATION: Synthetic

<400> SEQUENCE: 97

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ile Ala
            20                  25                  30

Pro Leu Gln Leu Gly Asn Cys Ser Val Ala Gly Trp Ile Leu Gly Asn
        35                  40                  45

Pro Glu Cys Glu Leu Leu Ile Ser Lys Glu Ser Trp Ser Tyr Ile Val
    50                  55                  60

Glu Thr Pro Asn Pro Glu Asn Gly Thr Cys Tyr Pro Gly Tyr Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Ser Ser Trp Pro Asn His Thr Val
            100                 105                 110
```

Thr Gly Val Ser Ala Ser Cys Ser His Asn Gly Lys Ser Ser Phe Tyr
        115                 120                 125

Arg Asn Leu Leu Trp Leu Thr Gly Lys Asn Gly Leu Tyr Pro Asn Leu
        130                 135                 140

Ser Lys Ser Tyr Val Asn Asn Lys Glu Lys Glu Val Leu Val Leu Trp
145                 150                 155                 160

Gly Val His His Pro Pro Asn Ile Gly Asn Gln Arg Ala Leu Tyr His
                165                 170                 175

Thr Glu Asn Ala Tyr Val Ser Val Val Ser Ser His Tyr Ser Arg Arg
        180                 185                 190

Phe Thr Pro Glu Ile Ala Lys Arg Pro Lys Val Arg Asp Gln Glu Gly
        195                 200                 205

Arg Ile Asn Tyr Tyr Trp Thr Leu Leu Glu Pro Gly Asp Thr Ile Ile
        210                 215                 220

Phe Glu Ala Asn Gly Asn Leu Ile Ala Pro Trp Tyr Ala Phe Ala Leu
225                 230                 235                 240

Ser Arg Gly Ala Ser Gly Glu Ser Gln Val Arg Gln Gln Phe Ser Lys
                245                 250                 255

Asp Ile Glu Lys Leu Leu Asn Glu Gln Val Asn Lys Glu Met Gln Ser
        260                 265                 270

Ser Asn Leu Tyr Met Ser Met Ser Ser Trp Cys Tyr Thr His Ser Leu
        275                 280                 285

Asp Gly Ala Gly Leu Phe Leu Phe Asp His Ala Ala Glu Glu Tyr Glu
        290                 295                 300

His Ala Lys Lys Leu Ile Ile Phe Leu Asn Glu Asn Asn Val Pro Val
305                 310                 315                 320

Gln Leu Thr Ser Ile Ser Ala Pro Glu His Lys Phe Glu Gly Leu Thr
        325                 330                 335

Gln Ile Phe Gln Lys Ala Tyr Glu His Glu Gln His Ile Ser Glu Ser
        340                 345                 350

Ile Asn Asn Ile Val Asp His Ala Ile Lys Ser Lys Asp His Ala Thr
        355                 360                 365

Phe Asn Phe Leu Gln Trp Tyr Val Ala Glu Gln His Glu Glu Glu Val
        370                 375                 380

Leu Phe Lys Asp Ile Leu Asp Lys Ile Glu Leu Ile Gly Asn Glu Asn
385                 390                 395                 400

His Gly Leu Tyr Leu Ala Asp Gln Tyr Val Lys Gly Ile Ala Lys Ser
                405                 410                 415

Arg Lys Ser Gly Ser
        420

<210> SEQ ID NO 98
<211> LENGTH: 1266
<212> TYPE: DNA
<213> ORGANISM: Artificial Sequence
<220> FEATURE:
<223> OTHER INFORMATION: Synthetic

<400> SEQUENCE: 98
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240

```
ggccttctgg aagatctggg tcaggccctc gaacttgtgc tcggggcgc tgatgctggt      300 cagctgcacg ggcacgttgt tctcgttcag gaagatgatc agcttcttgg cgtgctcgta      360
ctcctcggcg gcgtggtcga acaggaacag gccggcgccg tccaggctgt gggtgtagca      420
ccagctgctc atgctcatgt acaggttgct gctctgcatc tccttgttca cctgctcgtt      480
cagcagcttc tcgatgtcct tgctgaactg ctgcctcacc tggctctctc cggaggcgcc      540
tctgctcagg gcaaaggcat accaagggc gatcagattg ccgttggcct cgaagatgat      600
ggtatcgcca ggctccagca gggtccagta gtaattgatc cggccctcct ggtctctcac      660
tttgggtctc ttggcgatct cggggtgaa tcttctgctg tagtggctgg acaccacgct      720
cacataggcg ttctctgtgt ggtacagggc ccgctgattt ccgatgttgg gagggtggtg      780
cactccccac agcaccagca cttccttttc cttgttgttc acgtagctct tgctcaggtt      840
ggggtacagg ccattcttgc ctgtcagcca cagcaggttc cggtagaagc tgcttttgcc      900
gttgtggcta cagctggcag acacgcctgt cactgtgtga ttaggccagc tggactcctt      960
ggggaagatc tcgaatctct cgaagctgga cacgctagac agctgctcgc gcagctcctc     1020
gtaatcggcg aagtagccag ggtagcaggt gccattctca ggattggggg tctccacgat     1080
gtagctccag ctctccttag aaatcagcag ctcacactcg gggttgccca gaatccatcc     1140
ggccacagaa caattgccca gctgcagagg ggcaatggct agcacgccct gaggcagcag     1200
caggttgctc accaccagca gcagcagcag tctgctgccc ttctggctgc tgcccttgct     1260
gtccat                                                                1266

<210> SEQ ID NO 99
<211> LENGTH: 1266
<212> TYPE: DNA
<213> ORGANISM: Artificial Sequence
<220> FEATURE:
<223> OTHER INFORMATION: Synthetic

<400> SEQUENCE: 99
atggacagca agggcagcag ccagaagggc agcagactgc tgctgctgct ggtggtgagc       60
aacctgctgc tgcctcaggg cgtgctagcc attgcccctc tgcagctggg caattgttct      120
gtggccggat ggattctggg caaccccgag tgtgagctgc tgatttctaa ggagagctgg      180
agctacatcg tggagacccc caatcctgag aatggcacct gcttccctgg ctacttcgcc      240
gattacgagg agctgcgcga gcagctgtct agcgtgtcca gcttcgagag attcgagatc      300
ttccccaagg agtccagctg gcctaatcac acagtgacag gcgtgtctgc cagctgtagc      360
cacaacggca aaagcagctt ctaccggaac ctgctgtggc tgacaggcaa gaatggcctg      420
taccccaacc tgagcaagag ctacgtgaac aacaaggaaa aggaagtgct ggtgctgtgg      480
ggagtgcacc accctcccaa catcggaaat cagcgggccc tgtaccacac agagaacgcc      540
tatgtgagcg tggtgtccag ccactacagc agaagattca ccccgagat cgccaagaga      600 cccaaagtga gagaccagga gggccggatc aattactact ggaccctgct ggagcctggc      660
gataccatca tcttcgaggc caacggcaat ctgatcgccc cttggtatgc ctttgccctg      720
agcagaggcg cctccggaga gagccaggtg aggcagcagt tcagcaagga catcgagaag      780
ctgctgaacg agcaggtgaa caaggagatg cagagcagca acctgtacat gagcatgagc      840
agctggtgct acacccacag cctggacggc cggcctgt tcctgttcga ccacgccgcc      900
gaggagtacg agcacgccaa gaagctgatc atcttcctga acgagaacaa cgtgcccgtg      960
cagctgacca gcatcagcgc ccccgagcac aagttcgagg gcctgaccca gatcttccag     1020
```

```
aaggcctacg agcacgagca gcacatcagc gagagcatca acaacatcgt ggaccacgcc   1080
atcaagagca aggaccacgc caccttcaac ttcctgcagt ggtacgtggc cgagcagcac   1140
gaggaggagg tgctgttcaa ggacatcctg gacaagatcg agctgatcgg caacgagaac   1200
cacggcctgt acctggccga ccagtacgtg aagggcatcg ccaagagcag gaagagcgga   1260
tcctag                                                              1266
```

<210> SEQ ID NO 100
<211> LENGTH: 421
<212> TYPE: PRT
<213> ORGANISM: Artificial Sequence
<220> FEATURE:
<223> OTHER INFORMATION: Synthetic

<400> SEQUENCE: 100

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Ile Ala
            20                  25                  30

Pro Leu Gln Leu Gly Asn Cys Ser Val Ala Gly Trp Ile Leu Gly Asn
        35                  40                  45

Pro Glu Cys Glu Leu Leu Ile Ser Lys Glu Ser Trp Ser Tyr Ile Val
    50                  55                  60

Glu Thr Pro Asn Pro Glu Asn Gly Thr Cys Phe Pro Gly Tyr Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Ser Ser Trp Pro Asn His Thr Val
            100                 105                 110

Thr Gly Val Ser Ala Ser Cys Ser His Asn Gly Lys Ser Ser Phe Tyr
        115                 120                 125

Arg Asn Leu Leu Trp Leu Thr Gly Lys Asn Gly Leu Tyr Pro Asn Leu
    130                 135                 140

Ser Lys Ser Tyr Val Asn Asn Lys Glu Lys Glu Val Leu Val Leu Trp
145                 150                 155                 160

Gly Val His His Pro Pro Asn Ile Gly Asn Gln Arg Ala Leu Tyr His
                165                 170                 175

Thr Glu Asn Ala Tyr Val Ser Val Val Ser Ser His Tyr Ser Arg Arg
            180                 185                 190

Phe Thr Pro Glu Ile Ala Lys Arg Pro Lys Val Arg Asp Gln Glu Gly
        195                 200                 205

Arg Ile Asn Tyr Tyr Trp Thr Leu Leu Glu Pro Gly Asp Thr Ile Ile
    210                 215                 220

Phe Glu Ala Asn Gly Asn Leu Ile Ala Pro Trp Tyr Ala Phe Ala Leu
225                 230                 235                 240

Ser Arg Gly Ala Ser Gly Glu Ser Gln Val Arg Gln Phe Ser Lys
                245                 250                 255

Asp Ile Glu Lys Leu Leu Asn Glu Gln Val Asn Lys Glu Met Gln Ser
            260                 265                 270

Ser Asn Leu Tyr Met Ser Met Ser Ser Trp Cys Tyr Thr His Ser Leu
        275                 280                 285

Asp Gly Ala Gly Leu Phe Leu Phe Asp His Ala Ala Glu Glu Tyr Glu
    290                 295                 300

His Ala Lys Lys Leu Ile Ile Phe Leu Asn Glu Asn Asn Val Pro Val
```

```
                305                 310                 315                 320
Gln Leu Thr Ser Ile Ser Ala Pro Glu His Lys Phe Glu Gly Leu Thr
                    325                 330                 335

Gln Ile Phe Gln Lys Ala Tyr Glu His Gln His Ile Ser Glu Ser
                340                 345                 350

Ile Asn Asn Ile Val Asp His Ala Ile Lys Ser Lys Asp His Ala Thr
                    355                 360                 365

Phe Asn Phe Leu Gln Trp Tyr Val Ala Glu Gln His Glu Glu Val
            370                 375                 380

Leu Phe Lys Asp Ile Leu Asp Lys Ile Glu Leu Ile Gly Asn Glu Asn
385                 390                 395                 400

His Gly Leu Tyr Leu Ala Asp Gln Tyr Val Lys Gly Ile Ala Lys Ser
                    405                 410                 415

Arg Lys Ser Gly Ser
            420

<210> SEQ ID NO 101
<211> LENGTH: 1266
<212> TYPE: DNA
<213> ORGANISM: Artificial Sequence
<220> FEATURE:
<223> OTHER INFORMATION: Synthetic

<400> SEQUENCE: 101
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt     300 cagctgcacg gcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaggcgcc     540
tctgctcagg gcaaaggcat accaagggc gatcagattg ccgttggcct cgaagatgat     600
ggtatcgcca ggctccagca gggtccagta gtaattgatc cggccctcct ggtctctcac     660
tttgggtctc ttggcgatct cggggggtgaa tcttctgctg tagtggctgg acaccacgct     720
cacataggcg ttctctgtgt ggtacagggc ccgctgattt ccgatgttgg gagggtggtg     780
cactccccac agcaccagca cttcctttc cttgttgttc acgtagctct tgctcaggtt     840
ggggtacagg ccattcttgc ctgtcagcca cagcaggttc cggtagaagc tgcttttgcc     900
gttgtggcta cagctggcag acacgcctgt cactgtgtga ttaggccagc tggactcctt     960
ggggaagatc tcgaatctct cgaagctgga cacgctagac agctgctcgc gcagctcctc    1020
gtaatcggcg aagtagccag ggaagcaggt gccattctca ggattggggg tctccacgat    1080
gtagctccag ctctccttag aaatcagcag ctcacactcg gggttgccca gaatccatcc    1140
ggccacagaa caattgccca gctgcagagg ggcaatggct agcacgccct gaggcagcag    1200
caggttgctc accaccagca gcagcagcag tctgctgccc ttctggctgc tgcccttgct    1260
gtccat                                                               1266

<210> SEQ ID NO 102
```

<211> LENGTH: 1269
<212> TYPE: DNA
<213> ORGANISM: Artificial Sequence
<220> FEATURE:
<223> OTHER INFORMATION: Synthetic

<400> SEQUENCE: 102

```
atggacagca agggcagcag ccagaagggc agcagactgc tgctgctgct ggtggtgagc      60
aacctgctgc tgcctcaggg cgtgctagcc gtggcccccc tgcacctggg caagtgcaac     120
atcgccggct ggattctggg caaccccgag tgcgagagcc tgagcaccgc cagcagctgg     180
agctacatcg tggagacccc cagcagcgac aacggcacct gctacccgg cgacttcatc      240
gactacgagg agctgcggga gcagctgagc agcgtgagca gcttcgagcg gttcgagatc     300
ttccccaaga ccagcagctg gcccaaccac gacagcaaca agggcgtgac cgccgcctgc     360
ccccacgccg gcgccaagag cttctacaag aacctgatct ggctggtgaa gaagggcaac     420
agctacccca gctgagcaa gagctacatc aacgacaagg gcaaggaggt gctggtgctg     480
tggggcatcc accaccccag caccagcgcc gaccagcaga gcctgtacca gaacgccgac     540
acctacgtgt tcgtgggcag cagccggtac agcaagaagt tcaagcccga gatcgccatc     600
cggcccaagg tgcgggacca ggagggccgg atgaactact actggaccct ggtggagccc     660
ggcgacaaga tcaccttcga ggccaccggc aacctggtgg tgccccggta cgccttcgcc     720
atggagcgga cgcctccgg agagagccag gtgaggcag agttcagcaa ggacatcgag      780
aagctgctga cgagcaggt gaacaaggag atgcagagca gcaacctgta catgagcatg     840
agcagctggt gctacaccca cagcctggac ggcgccggcc tgttcctgtt cgaccacgcc     900
gccgaggagt acgagcacgc caagaagctg atcatcttcc tgaacgagaa caacgtgccc     960
gtgcagctga ccagcatcag cgcccccgag cacaagttcg agggcctgac ccagatcttc    1020
cagaaggcct acgagcacga gcagcacatc agcgagagca tcaacaacat cgtggaccac    1080
gccatcaaga gcaaggacca cgccaccttc aacttcctgc agtggtacgt ggccgagcag    1140
cacgaggagg aggtgctgtt caaggacatc ctggacaaga tcgagctgat cggcaacgag    1200
aaccacggcc tgtacctggc cgaccagtac gtgaagggca tcgccaagag caggaagagc    1260
ggatcctag                                                            1269
```

<210> SEQ ID NO 103
<211> LENGTH: 422
<212> TYPE: PRT
<213> ORGANISM: Artificial Sequence
<220> FEATURE:
<223> OTHER INFORMATION: Synthetic

<400> SEQUENCE: 103

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Val Ala
            20                  25                  30

Pro Leu His Leu Gly Lys Cys Asn Ile Ala Gly Trp Ile Leu Gly Asn
        35                  40                  45

Pro Glu Cys Glu Ser Leu Ser Thr Ala Ser Ser Trp Ser Tyr Ile Val
    50                  55                  60

Glu Thr Pro Ser Ser Asp Asn Gly Thr Cys Tyr Pro Gly Asp Phe Ile
65                  70                  75                  80

Asp Tyr Glu Glu Leu Arg Glu Gln Leu Ser Ser Val Ser Ser Phe Glu
                85                  90                  95
```

Arg Phe Glu Ile Phe Pro Lys Thr Ser Ser Trp Pro Asn His Asp Ser
                    100                 105                 110

Asn Lys Gly Val Thr Ala Ala Cys Pro His Ala Gly Ala Lys Ser Phe
                115                 120                 125

Tyr Lys Asn Leu Ile Trp Leu Val Lys Gly Asn Ser Tyr Pro Lys
130                 135                 140

Leu Ser Lys Ser Tyr Ile Asn Asp Lys Gly Lys Glu Val Leu Val Leu
145                 150                 155                 160

Trp Gly Ile His His Pro Ser Thr Ser Ala Asp Gln Gln Ser Leu Tyr
                    165                 170                 175

Gln Asn Ala Asp Thr Tyr Val Phe Val Gly Ser Ser Arg Tyr Ser Lys
                180                 185                 190

Lys Phe Lys Pro Glu Ile Ala Ile Arg Pro Lys Val Arg Asp Gln Glu
                195                 200                 205

Gly Arg Met Asn Tyr Tyr Trp Thr Leu Val Glu Pro Gly Asp Lys Ile
                210                 215                 220

Thr Phe Glu Ala Thr Gly Asn Leu Val Val Pro Arg Tyr Ala Phe Ala
225                 230                 235                 240

Met Glu Arg Asn Ala Ser Gly Glu Ser Gln Val Arg Gln Gln Phe Ser
                245                 250                 255

Lys Asp Ile Glu Lys Leu Leu Asn Glu Gln Val Asn Lys Glu Met Gln
                260                 265                 270

Ser Ser Asn Leu Tyr Met Ser Met Ser Ser Trp Cys Tyr Thr His Ser
                275                 280                 285

Leu Asp Gly Ala Gly Leu Phe Leu Phe Asp His Ala Ala Glu Glu Tyr
290                 295                 300

Glu His Ala Lys Lys Leu Ile Ile Phe Leu Asn Glu Asn Asn Val Pro
305                 310                 315                 320

Val Gln Leu Thr Ser Ile Ser Ala Pro Glu His Lys Phe Glu Gly Leu
                325                 330                 335

Thr Gln Ile Phe Gln Lys Ala Tyr Glu His Glu Gln His Ile Ser Glu
                340                 345                 350

Ser Ile Asn Asn Ile Val Asp His Ala Ile Lys Ser Lys Asp His Ala
                355                 360                 365

Thr Phe Asn Phe Leu Gln Trp Tyr Val Ala Glu Gln His Glu Glu Glu
                370                 375                 380

Val Leu Phe Lys Asp Ile Leu Asp Lys Ile Glu Leu Ile Gly Asn Glu
385                 390                 395                 400

Asn His Gly Leu Tyr Leu Ala Asp Gln Tyr Val Lys Gly Ile Ala Lys
                    405                 410                 415

Ser Arg Lys Ser Gly Ser
                420

<210> SEQ ID NO 104
<211> LENGTH: 1269
<212> TYPE: DNA
<213> ORGANISM: Artificial Sequence
<220> FEATURE:
<223> OTHER INFORMATION: Synthetic

<400> SEQUENCE: 104
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180

```
cttgatggcg tggtccacga tgttgttgat gctctcgctg atgtgctgct cgtgctcgta    240
ggccttctgg aagatctggg tcaggccctc gaacttgtgc tcggggggcgc tgatgctggt    300 cagctgcacg ggcacgttgt tctcgttcag gaagatgatc agcttcttgg cgtgctcgta    360
ctcctcggcg gcgtggtcga acaggaacag gccggcgccg tccaggctgt gggtgtagca    420
ccagctgctc atgctcatgt acaggttgct gctctgcatc tccttgttca cctgctcgtt    480
cagcagcttc tcgatgtcct tgctgaactg ctgcctcacc tggctctctc cggaggcgtt    540
ccgctccatg gcgaaggcgt accggggcac caccaggttg ccggtggcct cgaaggtgat    600
cttgtcgccg ggctccacca gggtccagta gtagttcatc cggccctcct ggtcccgcac    660
cttgggccgg atggcgatct cgggcttgaa cttcttgctg taccggctgc tgcccacgaa    720
cacgtaggtg tcggcgttct ggtacaggct ctgctggtcg gcgctggtgc tggggtggtg    780
gatgccccac agcaccagca cctccttgcc cttgtcgttg atgtagctct tgctcagctt    840
ggggtagctg ttgcccttct tcaccagcca gatcaggttc ttgtagaagc tcttggcgcc    900
ggcgtggggg caggcggcgg tcacgccctt gttgctgtcg tggttgggcc agctgctggt    960
cttggggaag atctcgaacc gctcgaagct gctcacgctg ctcagctgct cccgcagctc   1020
ctcgtagtcg atgaagtcgc cggggtagca ggtgccgttg tcgctgctgg gggtctccac   1080
gatgtagctc cagctgctgg cggtgctcag gctctcgcac tcggggttgc ccagaatcca   1140
gccggcgatg ttgcacttgc ccaggtgcag ggggccacg gctagcacgc cctgaggcag     1200
cagcaggttg ctcaccacca gcagcagcag cagtctgctg cccttctggc tgctgccctt   1260
gctgtccat                                                            1269

<210> SEQ ID NO 105
<211> LENGTH: 1269
<212> TYPE: DNA
<213> ORGANISM: Artificial Sequence
<220> FEATURE:
<223> OTHER INFORMATION: Synthetic

<400> SEQUENCE: 105
atggacagca agggcagcag ccagaagggc agcagactgc tgctgctgct ggtggtgagc      60
aacctgctgc tgcctcaggg cgtgctagcc gtggcccccc tgcacctggg caagtgcaac    120
atcgccggct ggattctggg caaccccgag tgcgagagcc tgagcaccgc cagcagctgg    180
agctacatcg tggagacccc cagcagcgac aacggcacct gcttccccgg cgacttcatc    240
gactacgagg agctgcggga gcagctgagc agcgtgagca gttcgagcg gttcgagatc    300 ttccccaaga ccagcagctg gcccaaccac gacagcaaca agggcgtgac cgccgcctgc    360
ccccacgccg cgccaagag cttctacaag aacctgatct ggctggtgaa gaagggcaac    420 agctaccccca gctgagcaa gagctacatc aacgacaagg gcaaggaggt gctggtgctg    480
tggggcatcc accacccag caccagcgcc gaccagcaga gcctgtacca gaacgccgac    540
acctacgtgt tcgtgggcag cagccggtac agcaagaagt tcaagcccga tcgccatc     600 cggcccaagg tgcgggacca ggagggccgg atgaactact actggaccct ggtggagccc    660
ggcgacaaga tcaccttcga ggccaccggc aacctggtgg tgccccggta cgccttcgcc    720
atggagcgga acgcctccgg agagagccag gtgaggcagc agttcagcaa ggacatcgag    780
aagctgctga acgagcaggt gaacaaggag atgcagagca gcaacctgta catgagcatg    840
agcagctggt gctacacccca gcctggac ggcgccggcc tgttcctgtt cgaccacgcc    900
```

```
gccgaggagt acgagcacgc caagaagctg atcatcttcc tgaacgagaa caacgtgccc   960
gtgcagctga ccagcatcag cgcccccgag cacaagttcg agggcctgac ccagatcttc  1020
cagaaggcct acgagcacga gcagcacatc agcgagagca tcaacaacat cgtggaccac  1080
gccatcaaga gcaaggacca cgccaccttc aacttcctgc agtggtacgt ggccgagcag  1140
cacgaggagg aggtgctgtt caaggacatc ctggacaaga tcgagctgat cggcaacgag  1200
aaccacggcc tgtacctggc cgaccagtac gtgaagggca tcgccaagag caggaagagc  1260
ggatcctag                                                         1269

<210> SEQ ID NO 106
<211> LENGTH: 422
<212> TYPE: PRT
<213> ORGANISM: Artificial Sequence
<220> FEATURE:
<223> OTHER INFORMATION: Synthetic

<400> SEQUENCE: 106

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Val Ala
            20                  25                  30

Pro Leu His Leu Gly Lys Cys Asn Ile Ala Gly Trp Ile Leu Gly Asn
        35                  40                  45

Pro Glu Cys Glu Ser Leu Ser Thr Ala Ser Ser Trp Ser Tyr Ile Val
    50                  55                  60

Glu Thr Pro Ser Ser Asp Asn Gly Thr Cys Phe Pro Gly Asp Phe Ile
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Thr Ser Ser Trp Pro Asn His Asp Ser
            100                 105                 110

Asn Lys Gly Val Thr Ala Ala Cys Pro His Ala Gly Ala Lys Ser Phe
        115                 120                 125

Tyr Lys Asn Leu Ile Trp Leu Val Lys Lys Gly Asn Ser Tyr Pro Lys
    130                 135                 140

Leu Ser Lys Ser Tyr Ile Asn Asp Lys Gly Lys Glu Val Leu Val Leu
145                 150                 155                 160

Trp Gly Ile His His Pro Ser Thr Ser Ala Asp Gln Gln Ser Leu Tyr
                165                 170                 175

Gln Asn Ala Asp Thr Tyr Val Phe Val Gly Ser Ser Arg Tyr Ser Lys
            180                 185                 190

Lys Phe Lys Pro Glu Ile Ala Ile Arg Pro Lys Val Arg Asp Gln Glu
        195                 200                 205

Gly Arg Met Asn Tyr Tyr Trp Thr Leu Val Glu Pro Gly Asp Lys Ile
    210                 215                 220

Thr Phe Glu Ala Thr Gly Asn Leu Val Val Pro Arg Tyr Ala Phe Ala
225                 230                 235                 240

Met Glu Arg Asn Ala Ser Gly Glu Ser Gln Val Arg Gln Gln Phe Ser
                245                 250                 255

Lys Asp Ile Glu Lys Leu Leu Asn Glu Gln Val Asn Lys Glu Met Gln
            260                 265                 270

Ser Ser Asn Leu Tyr Met Ser Met Ser Ser Trp Cys Tyr Thr His Ser
        275                 280                 285

Leu Asp Gly Ala Gly Leu Phe Leu Phe Asp His Ala Ala Glu Glu Tyr
```

```
                290              295              300
Glu His Ala Lys Lys Leu Ile Ile Phe Leu Asn Glu Asn Asn Val Pro
305              310              315              320

Val Gln Leu Thr Ser Ile Ser Ala Pro Glu His Lys Phe Glu Gly Leu
            325              330              335

Thr Gln Ile Phe Gln Lys Ala Tyr Glu His Glu Gln His Ile Ser Glu
            340              345              350

Ser Ile Asn Asn Ile Val Asp His Ala Ile Lys Ser Lys Asp His Ala
            355              360              365

Thr Phe Asn Phe Leu Gln Trp Tyr Val Ala Glu Gln His Glu Glu Glu
            370              375              380

Val Leu Phe Lys Asp Ile Leu Asp Lys Ile Glu Leu Ile Gly Asn Glu
385              390              395              400

Asn His Gly Leu Tyr Leu Ala Asp Gln Tyr Val Lys Gly Ile Ala Lys
            405              410              415

Ser Arg Lys Ser Gly Ser
            420

<210> SEQ ID NO 107
<211> LENGTH: 1269
<212> TYPE: DNA
<213> ORGANISM: Artificial Sequence
<220> FEATURE:
<223> OTHER INFORMATION: Synthetic

<400> SEQUENCE: 107
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt     300 cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaggcgtt     540
ccgctccatg gcgaaggcgt accggggcac caccaggttg ccggtggcct cgaaggtgat     600
cttgtcgccg ggctccacca gggtccagta gtagttcatc cggccctcct ggtcccgcac     660
cttgggccgg atggcgatct cgggcttgaa cttcttgctg taccggctgc tgcccacgaa     720
cacgtaggtg tcggcgttct ggtacaggct ctgctggtcg cgctggtgc tggggtggtg     780 gatgcccac agcaccagca cctccttgcc cttgtcgttg atgtagctct tgctcagctt     840
ggggtagctg ttgcccttct tcaccagcca gatcaggttc ttgtagaagc tcttggcgcc     900
ggcgtggggg caggcggcgg tcacgccctt gttgctgtcg tggttgggcc agctgctggt     960
cttggggaag atctcgaacc gctcgaagct gctcacgctg ctcagctgct cccgcagctc    1020
ctcgtagtcg atgaagtcgc cggggaagca ggtgccgttg tcgctgctgg gggtctccac    1080
gatgtagctc cagctgctgg cggtgctcag gctctcgcac tcggggttgc ccagaatcca    1140
gccggcgatg ttgcacttgc ccaggtgcag gggggccacg gctagcacgc cctgaggcag    1200
cagcaggttg ctcaccacca gcagcagcag cagtctgctg cccttctggc tgctgccctt    1260
gctgtccat                                                            1269
```

<210> SEQ ID NO 108
<211> LENGTH: 1269
<212> TYPE: DNA
<213> ORGANISM: Artificial Sequence
<220> FEATURE:
<223> OTHER INFORMATION: Synthetic

<400> SEQUENCE: 108

| | |
|---|---|
| atggacagca agggcagcag ccagaagggc agcagactgc tgctgctgct ggtggtgagc | 60 |
| aacctgctgc tgcctcaggg cgtgctagcc atcgcccctc tgcagctggg caagtgtaat | 120 |
| atcgccggat ggctgctggg aaaccccgag tgtgattctc tgctgcctgc caagagctgg | 180 |
| agctacatcg tggagacccc caattctgag aatggcgcct gcttccctgg cgacttcatc | 240 |
| gattacgagg agctgaagga gcagctgagt tctgtctcta gcctggagag attcgagatc | 300 |
| ttccccaagg agagcagctg gcccaatcac aataccctga agggagtgac agccgcctgt | 360 |
| agccacagag gcaagagcag cttctaccgg aatctgctgt ggctgaccaa gaccggcgat | 420 |
| agctacccca agctgaacaa cagctacgtg aacaacaagg gcaaggaagt gctggtgctg | 480 |
| tggggagtgc accaccctag cagcagcaat gagcagcaga gcctgtacca caacgtgaac | 540 |
| gcctatgtga gcgtggtgtc cagcaactac aaccggagat tcacccctga atcgccgcc | 600 |
| agacccaaag tgagagacca gcccggcagg atgaattact actggaccct gctggagcct | 660 |
| ggcgatacca tcatctttga ggccaccggc aatctgattg ccccttggta cgcctttgcc | 720 |
| ctgagcagag gcgcctccgg agagagccag gtgaggcagc agttcagcaa ggacatcgag | 780 |
| aagctgctga cgagcaggt gaacaaggag atgcagagca gcaacctgta catgagcatg | 840 |
| agcagctggt gctacacccca cagcctggac ggcgccggcc tgttcctgtt cgaccacgcc | 900 |
| gccgaggagt acgagcacgc caagaagctg atcatcttcc tgaacgagaa caacgtgccc | 960 |
| gtgcagctga ccagcatcag cgcccccgag cacaagttcg agggcctgac ccagatcttc | 1020 |
| cagaaggcct acgagcacga gcagcacatc agcgagagca tcaacaacat cgtggaccac | 1080 |
| gccatcaaga gcaaggacca cgccaccttc aacttcctgc agtggtacgt ggccgagcag | 1140 |
| cacgaggagg aggtgctgtt caaggacatc ctggacaaga tcgagctgat cggcaacgag | 1200 |
| aaccacggcc tgtacctggc cgaccagtac gtgaagggca tcgccaagag caggaagagc | 1260 |
| ggatcctag | 1269 |

<210> SEQ ID NO 109
<211> LENGTH: 422
<212> TYPE: PRT
<213> ORGANISM: Artificial Sequence
<220> FEATURE:
<223> OTHER INFORMATION: Synthetic

<400> SEQUENCE: 109

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ile Ala
            20                  25                  30

Pro Leu Gln Leu Gly Lys Cys Asn Ile Ala Gly Trp Leu Leu Gly Asn
        35                  40                  45

Pro Glu Cys Asp Ser Leu Leu Pro Ala Lys Ser Trp Ser Tyr Ile Val
    50                  55                  60

Glu Thr Pro Asn Ser Glu Asn Gly Ala Cys Phe Pro Gly Asp Phe Ile
65                  70                  75                  80

Asp Tyr Glu Glu Leu Lys Glu Gln Leu Ser Ser Val Ser Ser Leu Glu
                 85                  90                  95

Arg Phe Glu Ile Phe Pro Lys Glu Ser Ser Trp Pro Asn His Asn Thr
            100                 105                 110

Leu Lys Gly Val Thr Ala Ala Cys Ser His Arg Gly Lys Ser Ser Phe
        115                 120                 125

Tyr Arg Asn Leu Leu Trp Leu Thr Lys Thr Gly Asp Ser Tyr Pro Lys
    130                 135                 140

Leu Asn Asn Ser Tyr Val Asn Lys Gly Lys Glu Val Leu Val Leu
145                 150                 155                 160

Trp Gly Val His His Pro Ser Ser Asn Glu Gln Gln Ser Leu Tyr
                165                 170                 175

His Asn Val Asn Ala Tyr Val Ser Val Val Ser Ser Asn Tyr Asn Arg
            180                 185                 190

Arg Phe Thr Pro Glu Ile Ala Ala Arg Pro Lys Val Arg Asp Gln Pro
        195                 200                 205

Gly Arg Met Asn Tyr Tyr Trp Thr Leu Leu Glu Pro Gly Asp Thr Ile
    210                 215                 220

Ile Phe Glu Ala Thr Gly Asn Leu Ile Ala Pro Trp Tyr Ala Phe Ala
225                 230                 235                 240

Leu Ser Arg Gly Ala Ser Gly Glu Ser Gln Val Arg Gln Gln Phe Ser
                245                 250                 255

Lys Asp Ile Glu Lys Leu Leu Asn Glu Gln Val Asn Lys Glu Met Gln
            260                 265                 270

Ser Ser Asn Leu Tyr Met Ser Met Ser Ser Trp Cys Tyr Thr His Ser
        275                 280                 285

Leu Asp Gly Ala Gly Leu Phe Leu Phe Asp His Ala Ala Glu Glu Tyr
    290                 295                 300

Glu His Ala Lys Lys Leu Ile Ile Phe Leu Asn Glu Asn Asn Val Pro
305                 310                 315                 320

Val Gln Leu Thr Ser Ile Ser Ala Pro Glu His Lys Phe Glu Gly Leu
                325                 330                 335

Thr Gln Ile Phe Gln Lys Ala Tyr Glu His Glu Gln His Ile Ser Glu
            340                 345                 350

Ser Ile Asn Asn Ile Val Asp His Ala Ile Lys Ser Lys Asp His Ala
        355                 360                 365

Thr Phe Asn Phe Leu Gln Trp Tyr Val Ala Glu Gln His Glu Glu Glu
    370                 375                 380

Val Leu Phe Lys Asp Ile Leu Asp Lys Ile Glu Leu Ile Gly Asn Glu
385                 390                 395                 400

Asn His Gly Leu Tyr Leu Ala Asp Gln Tyr Val Lys Gly Ile Ala Lys
                405                 410                 415

Ser Arg Lys Ser Gly Ser
            420

<210> SEQ ID NO 110
<211> LENGTH: 1269
<212> TYPE: DNA
<213> ORGANISM: Artificial Sequence
<220> FEATURE:
<223> OTHER INFORMATION: Synthetic

<400> SEQUENCE: 110
ctaggatccg ctcttcctgc tcttggcgat gcccttcacg tactggtcgg ccaggtacag    60

```
gccgtggttc tcgttgccga tcagctcgat cttgtccagg atgtccttga acagcacctc    120
ctcctcgtgc tgctcggcca cgtaccactg caggaagttg aaggtggcgt ggtccttgct    180
cttgatggcg tggtccacga tgttgttgat gctctcgctg atgtgctgct cgtgctcgta    240
ggccttctgg aagatctggg tcaggccctc gaacttgtgc tcgggggcgc tgatgctggt    300
cagctgcacg ggcacgttgt tctcgttcag gaagatgatc agcttcttgg cgtgctcgta    360
ctcctcggcg cgtggtcga acaggaacag gccggcgccg tccaggctgt gggtgtagca    420
ccagctgctc atgctcatgt acaggttgct gctctgcatc tccttgttca cctgctcgtt    480
cagcagcttc tcgatgtcct tgctgaactg ctgcctcacc tggctctctc cggaggcgcc    540
tctgctcagg gcaaaggcgt accaaggggc aatcagattg ccggtggcct caaagatgat    600
ggtatcgcca ggctccagca gggtccagta gtaattcatc ctgccgggct ggtctctcac    660
tttgggtctg gcggcgattt caggggtgaa tctccggttg tagttgctgg acaccacgct    720
cacataggcg ttcacgttgt ggtacaggct ctgctgctca ttgctgctgc tagggtggtg    780
cactccccac agcaccagca cttccttgcc cttgttgttc acgtagctgt tgttcagctt    840
ggggtagcta tcgccggtct tggtcagcca cagcagattc cggtagaagc tgctcttgcc    900
tctgtggcta caggcggctg tcactccctt cagggtattg tgattgggcc agctgctctc    960
cttggggaag atctcgaatc tctccaggct agagacagaa ctcagctgct ccttcagctc    1020
ctcgtaatcg atgaagtcgc cagggaagca ggcgccattc tcagaattgg gggtctccac    1080
gatgtagctc cagctcttgg caggcagcag agaatcacac tcggggtttc ccagcagcca    1140
tccggcgata ttacacttgc ccagctgcag aggggcgatg ctagcacgc ctgaggcag     1200 cagcaggttg ctcaccacca gcagcagcag cagtctgctg cccttctggc tgctgccctt    1260
gctgtccat                                                           1269
```

<210> SEQ ID NO 111  
<211> LENGTH: 1269  
<212> TYPE: DNA  
<213> ORGANISM: Artificial Sequence  
<220> FEATURE:  
<223> OTHER INFORMATION: Synthetic

<400> SEQUENCE: 111

```
atggacagca agggcagcag ccagaagggc agcagactgc tgctgctgct ggtggtgagc    60
aacctgctgc tgcctcaggg cgtgctagcc attgccccc tgcagctggg caagtgcagc    120
attgccggct ggattctggg caaccccgag tgcgagagcc tgttcagcaa gaagagctgg    180
tcctacattg ccgagacacc caacagcgag aacggcacct gtttccccgg ctacttcgcc    240
gactacgagg aactgcggga gcagctgagc agcgtgtcca gcttcgagcg gttcgagatc    300
ttccccaaag agcggagctg gcccaagcac aacgtgacca gaggcgtgac cgccagctgc    360
tctcacaagg gcaagagcag cttctaccgg aacctgctgt ggctgaccga agaacggc     420 agctacccca acctgagcaa gagctacgtg aacaacaaag agaaagaggt cctggtcctc    480
tggggcgtgc accaccctag caacatcgag gaccagaaaa ccatctaccg gaaagaaaac    540
gcctacgtgt ccgtggtgtc cagcaactac aaccggcggt tcaccccga gatcgccgag    600 aggcctaaag tgcggggcca ggccggcaga atcaactact actggaccct gctggaaccc    660
ggcgacacca tcatcttcga ggccaacggc aacctgatcg cccttggca cgcctttgcc    720 ctgagcagag cgcctccgg agagagccag gtgaggcagc agttcagcaa ggacatcgag    780
aagctgctga cgagcaggt gaacaaggag atgcagagca gcaacctgta catgagcatg    840
```

```
agcagctggt gctacaccca cagcctggac ggcgccggcc tgttcctgtt cgaccacgcc    900
gccgaggagt acgagcacgc caagaagctg atcatcttcc tgaacgagaa caacgtgccc    960
gtgcagctga ccagcatcag cgcccccgag cacaagttcg agggcctgac ccagatcttc   1020
cagaaggcct acgagcacga gcagcacatc agcgagagca tcaacaacat cgtggaccac   1080
gccatcaaga gcaaggacca cgccaccttc aacttcctgc agtggtacgt ggccgagcag   1140
cacgaggagg aggtgctgtt caaggacatc ctggacaaga tcgagctgat cggcaacgag   1200
aaccacggcc tgtacctggc cgaccagtac gtgaagggca tcgccaagag caggaagagc   1260
ggatcctag                                                           1269
```

<210> SEQ ID NO 112
<211> LENGTH: 422
<212> TYPE: PRT
<213> ORGANISM: Artificial Sequence
<220> FEATURE:
<223> OTHER INFORMATION: Synthetic

<400> SEQUENCE: 112

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ile Ala
            20                  25                  30

Pro Leu Gln Leu Gly Lys Cys Ser Ile Ala Gly Trp Ile Leu Gly Asn
        35                  40                  45

Pro Glu Cys Glu Ser Leu Phe Ser Lys Lys Ser Trp Ser Tyr Ile Ala
    50                  55                  60

Glu Thr Pro Asn Ser Glu Asn Gly Thr Cys Phe Pro Gly Tyr Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Arg Ser Trp Pro Lys His Asn Val
            100                 105                 110

Thr Arg Gly Val Thr Ala Ser Cys Ser His Lys Gly Lys Ser Ser Phe
        115                 120                 125

Tyr Arg Asn Leu Leu Trp Leu Thr Glu Lys Asn Gly Ser Tyr Pro Asn
    130                 135                 140

Leu Ser Lys Ser Tyr Val Asn Asn Lys Glu Lys Glu Val Leu Val Leu
145                 150                 155                 160

Trp Gly Val His His Pro Ser Asn Ile Glu Asp Gln Lys Thr Ile Tyr
                165                 170                 175

Arg Lys Glu Asn Ala Tyr Val Ser Val Val Ser Ser Asn Tyr Asn Arg
            180                 185                 190

Arg Phe Thr Pro Glu Ile Ala Glu Arg Pro Lys Val Arg Gly Gln Ala
        195                 200                 205

Gly Arg Ile Asn Tyr Tyr Trp Thr Leu Leu Glu Pro Gly Asp Thr Ile
    210                 215                 220

Ile Phe Glu Ala Asn Gly Asn Leu Ile Ala Pro Trp His Ala Phe Ala
225                 230                 235                 240

Leu Ser Arg Gly Ala Ser Gly Glu Ser Gln Val Arg Gln Gln Phe Ser
                245                 250                 255

Lys Asp Ile Glu Lys Leu Leu Asn Glu Gln Val Asn Lys Glu Met Gln
            260                 265                 270

Ser Ser Asn Leu Tyr Met Ser Met Ser Ser Trp Cys Tyr Thr His Ser
```

```
                275                 280                 285
Leu Asp Gly Ala Gly Leu Phe Leu Phe Asp His Ala Ala Glu Glu Tyr
        290                 295                 300
Glu His Ala Lys Lys Leu Ile Ile Phe Leu Asn Glu Asn Asn Val Pro
305                 310                 315                 320
Val Gln Leu Thr Ser Ile Ser Ala Pro Glu His Lys Phe Glu Gly Leu
                325                 330                 335
Thr Gln Ile Phe Gln Lys Ala Tyr Glu His Glu Gln His Ile Ser Glu
            340                 345                 350
Ser Ile Asn Asn Ile Val Asp His Ala Ile Lys Ser Lys Asp His Ala
                355                 360                 365
Thr Phe Asn Phe Leu Gln Trp Tyr Val Ala Glu Gln His Glu Glu Glu
        370                 375                 380
Val Leu Phe Lys Asp Ile Leu Asp Lys Ile Glu Leu Ile Gly Asn Glu
385                 390                 395                 400
Asn His Gly Leu Tyr Leu Ala Asp Gln Tyr Val Lys Gly Ile Ala Lys
                405                 410                 415
Ser Arg Lys Ser Gly Ser
            420
```

<210> SEQ ID NO 113
<211> LENGTH: 1269
<212> TYPE: DNA
<213> ORGANISM: Artificial Sequence
<220> FEATURE:
<223> OTHER INFORMATION: Synthetic

<400> SEQUENCE: 113

```
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcggggcgc tgatgctggt   300
cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggcgcc   540
tctgctcagg gcaaaggcgt gccaaggggc gatcaggttg ccgttggcct cgaagatgat   600
ggtgtcgccg ggttccagca gggtccagta gtagttgatt ctgccggcct ggccccgcac   660
tttaggcctc tcggcgatct cggggggtgaa ccgccggttg tagttgctgg acaccacgga   720
cacgtaggcg ttttctttcc ggtagatggt tttctggtcc tcgatgttgc tagggtggtg   780
cacgccccag aggaccagga cctctttctc tttgttgttc acgtagctct tgctcaggtt   840
ggggtagctg ccgttcttct cggtcagcca cagcaggttc cggtagaagc tgctcttgcc   900
cttgtgagag cagctggcgg tcacgcctct ggtcacgttg tgcttgggcc agctccgctc   960
tttgggaag atctcgaacc gctcgaagct ggacacgctg ctcagctgct cccgcagttc  1020
ctcgtagtcg gcgaagtagc cggggaaaca ggtgccgttc tcgctgttgg gtgtctcggc  1080
aatgtaggac cagctcttct tgctgaacag gctctcgcac tcggggttgc ccagaatcca  1140
gccggcaatg ctgcacttgc ccagctgcag gggggcaatg ctagcacgc cctgaggcag  1200
```

```
cagcaggttg ctcaccacca gcagcagcag cagtctgctg cccttctggc tgctgccctt    1260
gctgtccat                                                            1269
```

<210> SEQ ID NO 114
<211> LENGTH: 1269
<212> TYPE: DNA
<213> ORGANISM: Artificial Sequence
<220> FEATURE:
<223> OTHER INFORMATION: Synthetic

<400> SEQUENCE: 114

```
atggacagca agggcagcag ccagaagggc agcagactgc tgctgctgct ggtggtgagc     60
aacctgctgc tgcctcaggg cgtgctagcc atcgcccctc tgcagctggg caactgcagc    120
gtggctggct ggattctggg gaatccaaag tgtgagagtc tgttttcaaa agaatcttgg    180
agttacatcg cagagacccc caaccctgaa atggaacat gcttccctgg ctatttcgcc     240
gattatgagg aactgaggga gcagctgagc tccgtgtcta gtttcgagcg ctttgaaatt    300
ttcccaaagg aatcaagctg gcccaaccac accgtgacaa aggcgtcac cacatcatgt     360 agccataacg ggaagtcctc tttttaccgc aatctgctgt ggctgacaga aagaacggc     420 ctgtacccaa atctgtccaa gtcttacgtg aacaataagg agaaggaagt gctggtcctg    480
tggggcgtcc accatcccag caacatccga gaccagcggg caatctacca cacagagaat    540
gcctatgtga gcgtggtcag ttcacattac agccggcggt tcaccccga tcgccaag      600 agaccaaaag tgaggggcca ggaagggcga attaactact attggactct gctggagcca    660
ggagatacca tcattttcga agccaacggc aatctgatcg ctcccctggta tgcatttgcc    720 ctgtcccgcg gagcctccgg agagagccag gtgaggcagc agttcagcaa ggacatcgag    780
aagctgctga cgagcaggt gaacaaggag atgcagagca gcaacctgta catgagcatg    840
agcagctggt gctacacccca gcctggac ggcgccggcc tgttcctgtt cgaccacgcc    900
gccgaggagt acgagcacgc caagaagctg atcatcttcc tgaacgagaa caacgtgccc    960
gtgcagctga ccagcatcag cgcccccgag cacaagttcg agggcctgac ccagatcttc   1020
cagaaggcct acgagcacga gcagcacatc agcgagagca tcaacaacat cgtgaccac    1080 gccatcaaga gcaaggacca cgccaccttc aacttcctgc agtggtacgt ggccgagcag   1140
cacgaggagg aggtgctgtt caaggacatc ctggacaaga tcgagctgat cggcaacgag   1200
aaccacggcc tgtacctggc cgaccagtac gtgaagggca tcgccaagag caggaagagc   1260
ggatcctag                                                           1269
```

<210> SEQ ID NO 115
<211> LENGTH: 422
<212> TYPE: PRT
<213> ORGANISM: Artificial Sequence
<220> FEATURE:
<223> OTHER INFORMATION: Synthetic

<400> SEQUENCE: 115

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ile Ala
            20                  25                  30

Pro Leu Gln Leu Gly Asn Cys Ser Val Ala Gly Trp Ile Leu Gly Asn
        35                  40                  45

Pro Lys Cys Glu Ser Leu Phe Ser Lys Glu Ser Trp Ser Tyr Ile Ala
    50                  55                  60
```

```
Glu Thr Pro Asn Pro Glu Asn Gly Thr Cys Phe Pro Gly Tyr Phe Ala
 65                  70                  75                  80

Asp Tyr Glu Glu Leu Arg Glu Gln Leu Ser Ser Val Ser Ser Phe Glu
             85                  90                  95

Arg Phe Glu Ile Phe Pro Lys Glu Ser Ser Trp Pro Asn His Thr Val
            100                 105                 110

Thr Lys Gly Val Thr Thr Ser Cys Ser His Asn Gly Lys Ser Ser Phe
        115                 120                 125

Tyr Arg Asn Leu Leu Trp Leu Thr Glu Lys Asn Gly Leu Tyr Pro Asn
    130                 135                 140

Leu Ser Lys Ser Tyr Val Asn Asn Lys Glu Lys Glu Val Leu Val Leu
145                 150                 155                 160

Trp Gly Val His His Pro Ser Asn Ile Arg Asp Gln Arg Ala Ile Tyr
                165                 170                 175

His Thr Glu Asn Ala Tyr Val Ser Val Val Ser Ser His Tyr Ser Arg
            180                 185                 190

Arg Phe Thr Pro Glu Ile Ala Lys Arg Pro Lys Val Arg Gly Gln Glu
        195                 200                 205

Gly Arg Ile Asn Tyr Tyr Trp Thr Leu Leu Glu Pro Gly Asp Thr Ile
210                 215                 220

Ile Phe Glu Ala Asn Gly Asn Leu Ile Ala Pro Trp Tyr Ala Phe Ala
225                 230                 235                 240

Leu Ser Arg Gly Ala Ser Gly Glu Ser Gln Val Arg Gln Gln Phe Ser
                245                 250                 255

Lys Asp Ile Glu Lys Leu Leu Asn Glu Gln Val Asn Lys Glu Met Gln
            260                 265                 270

Ser Ser Asn Leu Tyr Met Ser Met Ser Ser Trp Cys Tyr Thr His Ser
        275                 280                 285

Leu Asp Gly Ala Gly Leu Phe Leu Phe Asp His Ala Ala Glu Glu Tyr
    290                 295                 300

Glu His Ala Lys Lys Leu Ile Ile Phe Leu Asn Glu Asn Asn Val Pro
305                 310                 315                 320

Val Gln Leu Thr Ser Ile Ser Ala Pro Glu His Lys Phe Glu Gly Leu
                325                 330                 335

Thr Gln Ile Phe Gln Lys Ala Tyr Glu His Glu Gln His Ile Ser Glu
            340                 345                 350

Ser Ile Asn Asn Ile Val Asp His Ala Ile Lys Ser Lys Asp His Ala
        355                 360                 365

Thr Phe Asn Phe Leu Gln Trp Tyr Val Ala Glu Gln His Glu Glu Glu
    370                 375                 380

Val Leu Phe Lys Asp Ile Leu Asp Lys Ile Glu Leu Ile Gly Asn Glu
385                 390                 395                 400

Asn His Gly Leu Tyr Leu Ala Asp Gln Tyr Val Lys Gly Ile Ala Lys
                405                 410                 415

Ser Arg Lys Ser Gly Ser
            420

<210> SEQ ID NO 116
<211> LENGTH: 1269
<212> TYPE: DNA
<213> ORGANISM: Artificial Sequence
<220> FEATURE:
<223> OTHER INFORMATION: Synthetic

<400> SEQUENCE: 116
```

```
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt      300 cagctgcacg gcacgttgt tctcgttcag gaagatgatc agcttcttgg cgtgctcgta      360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaggctcc     540
gcgggacagg gcaaatgcat accagggagc gatcagattg ccgttggctt cgaaaatgat     600
ggtatctcct ggctccagca gagtccaata gtagttaatt cgcccttcct ggcccctcac     660
ttttggtctc ttggcgatct cggggtgaa ccgccggctg taatgtgaac tgaccacgct      720
cacataggca ttctctgtgt ggtagattgc ccgctggtct cggatgttgc tgggatggtg     780
gacgccccac aggaccagca cttccttctc cttattgttc acgtaagact tggacagatt     840
tgggtacagg ccgttcttct ctgtcagcca cagcagattg cggtaaaaag aggacttccc     900
gttatggcta catgatgtgg tgacgccttt tgtcacggtg tggttgggcc agcttgattc     960
ctttgggaaa atttcaaagc gctcgaaact agacacggag ctcagctgct ccctcagttc    1020
ctcataatcg gcgaaatagc cagggaagca tgttccattt tcagggttgg gggtctctgc    1080
gatgtaactc caagattctt ttgaaaacag actctcacac tttggattcc ccagaatcca    1140
gccagccacg ctgcagttgc ccagctgcag agggcgatg gctagcacgc cctgaggcag    1200
cagcaggttg ctcaccacca gcagcagcag cagtctgctg cccttctggc tgctgcccttt   1260 gctgtccat                                                             1269
```

<210> SEQ ID NO 117
<211> LENGTH: 1269
<212> TYPE: DNA
<213> ORGANISM: Artificial Sequence
<220> FEATURE:
<223> OTHER INFORMATION: Synthetic

<400> SEQUENCE: 117

```
atggacagca agggcagcag ccagaagggc agcagactgc tgctgctgct ggtggtgagc      60
aacctgctgc tgcctcaggg cgtgctagcc attgccccctc tgcagctggg caattgttct    120
atcgccggct ggattctggg aaatcccgag tgcgagagcc tgttcagcaa gaagtcctgg    180
tcctatatcg ccgagacacc caacagcgag aatggcacct gttttccctgg ctacttcgcc    240 gattacgagg aactgagaga gcagctgtcc tctgtctcca gcttcgagcg gttcgagatc    300
ttccccaaag agtccagctg gcccaatcac acagtgacca agggcgtgac cgcctcttgt    360
agccacaagg gcagaagcag cttctaccgg aacctgctgt ggctgaccaa gaagaacggc    420
agctacccca atctgagcaa gagctacgtg aacaacaaag aaaagaggt gctggtcctc    480 tggggagtgc accaccctag caacatcgga gatcagcggg ccatctacca caccgagaac    540
gcctatgtgt ccgtggtgtc cagccactac aacagaagat tcaccccccga gatcgccaaa    600 agacccaaag tgcgggacca ggaaggcaga atcaactact actggaccct gctggaacct    660
ggcgacacca tcatcttcga ggccaacggc aatctgatcg ccccttggta tgcctttgcc    720
```

```
ctgagcagag gcgcctccgg agagagccag gtgaggcagc agttcagcaa ggacatcgag    780
aagctgctga acgagcaggt gaacaaggag atgcagagca gcaacctgta catgagcatg    840
agcagctggt gctacaccca cagcctggac ggcgccggcc tgttcctgtt cgaccacgcc    900
gccgaggagt acgagcacgc caagaagctg atcatcttcc tgaacgagaa caacgtgccc    960
gtgcagctga ccagcatcag cgcccccgag cacaagttcg agggcctgac ccagatcttc   1020
cagaaggcct acgagcacga gcagcacatc agcgagagca tcaacaacat cgtggaccac   1080
gccatcaaga gcaaggacca cgccaccttc aacttcctgc agtggtacgt ggccgagcag   1140
cacgaggagg aggtgctgtt caaggacatc ctggacaaga tcgagctgat cggcaacgag   1200
aaccacggcc tgtacctggc cgaccagtac gtgaagggca tcgccaagag caggaagagc   1260
ggatcctag                                                          1269
```

<210> SEQ ID NO 118
<211> LENGTH: 422
<212> TYPE: PRT
<213> ORGANISM: Artificial Sequence
<220> FEATURE:
<223> OTHER INFORMATION: Synthetic

<400> SEQUENCE: 118

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Ile Ala
            20                  25                  30

Pro Leu Gln Leu Gly Asn Cys Ser Ile Ala Gly Trp Ile Leu Gly Asn
        35                  40                  45

Pro Glu Cys Glu Ser Leu Phe Ser Lys Ser Trp Ser Tyr Ile Ala
    50                  55                  60

Glu Thr Pro Asn Ser Glu Asn Gly Thr Cys Phe Pro Gly Tyr Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Ser Ser Trp Pro Asn His Thr Val
            100                 105                 110

Thr Lys Gly Val Thr Ala Ser Cys Ser His Lys Gly Arg Ser Ser Phe
        115                 120                 125

Tyr Arg Asn Leu Leu Trp Leu Thr Lys Lys Asn Gly Ser Tyr Pro Asn
    130                 135                 140

Leu Ser Lys Ser Tyr Val Asn Asn Lys Glu Lys Glu Val Leu Val Leu
145                 150                 155                 160

Trp Gly Val His His Pro Ser Asn Ile Gly Asp Gln Arg Ala Ile Tyr
                165                 170                 175

His Thr Glu Asn Ala Tyr Val Ser Val Val Ser Ser His Tyr Asn Arg
            180                 185                 190

Arg Phe Thr Pro Glu Ile Ala Lys Arg Pro Lys Val Arg Asp Gln Glu
        195                 200                 205

Gly Arg Ile Asn Tyr Tyr Trp Thr Leu Leu Glu Pro Gly Asp Thr Ile
    210                 215                 220

Ile Phe Glu Ala Asn Gly Asn Leu Ile Ala Pro Trp Tyr Ala Phe Ala
225                 230                 235                 240

Leu Ser Arg Gly Ala Ser Gly Glu Ser Gln Val Arg Gln Phe Ser
                245                 250                 255

Lys Asp Ile Glu Lys Leu Leu Asn Glu Gln Val Asn Lys Glu Met Gln
```

|     |     |     |     | 260 |     |     |     |     | 265 |     |     |     |     | 270 |     |
| --- | --- | --- | --- | --- | --- | --- | --- | --- | --- | --- | --- | --- | --- | --- | --- |
| Ser | Ser | Asn | Leu | Tyr | Met | Ser | Met | Ser | Ser | Trp | Cys | Tyr | Thr | His | Ser |
|     |     | 275 |     |     |     |     | 280 |     |     |     |     | 285 |     |     |     |
| Leu | Asp | Gly | Ala | Gly | Leu | Phe | Leu | Phe | Asp | His | Ala | Ala | Glu | Glu | Tyr |
|     |     | 290 |     |     |     |     | 295 |     |     |     |     | 300 |     |     |     |
| Glu | His | Ala | Lys | Lys | Leu | Ile | Ile | Phe | Leu | Asn | Glu | Asn | Asn | Val | Pro |
| 305 |     |     |     |     | 310 |     |     |     |     | 315 |     |     |     |     | 320 |
| Val | Gln | Leu | Thr | Ser | Ile | Ser | Ala | Pro | Glu | His | Lys | Phe | Glu | Gly | Leu |
|     |     |     |     | 325 |     |     |     |     | 330 |     |     |     |     | 335 |     |
| Thr | Gln | Ile | Phe | Gln | Lys | Ala | Tyr | Glu | His | Glu | Gln | His | Ile | Ser | Glu |
|     |     |     | 340 |     |     |     |     | 345 |     |     |     |     | 350 |     |     |
| Ser | Ile | Asn | Asn | Ile | Val | Asp | His | Ala | Ile | Lys | Ser | Lys | Asp | His | Ala |
|     |     | 355 |     |     |     |     | 360 |     |     |     |     | 365 |     |     |     |
| Thr | Phe | Asn | Phe | Leu | Gln | Trp | Tyr | Val | Ala | Glu | Gln | His | Glu | Glu | Glu |
|     |     | 370 |     |     |     |     | 375 |     |     |     |     | 380 |     |     |     |
| Val | Leu | Phe | Lys | Asp | Ile | Leu | Asp | Lys | Ile | Glu | Leu | Ile | Gly | Asn | Glu |
| 385 |     |     |     |     | 390 |     |     |     |     | 395 |     |     |     |     | 400 |
| Asn | His | Gly | Leu | Tyr | Leu | Ala | Asp | Gln | Tyr | Val | Lys | Gly | Ile | Ala | Lys |
|     |     |     |     | 405 |     |     |     |     | 410 |     |     |     |     | 415 |     |
| Ser | Arg | Lys | Ser | Gly | Ser |     |     |     |     |     |     |     |     |     |     |
|     |     |     | 420 |     |     |     |     |     |     |     |     |     |     |     |     |

<210> SEQ ID NO 119
<211> LENGTH: 1269
<212> TYPE: DNA
<213> ORGANISM: Artificial Sequence
<220> FEATURE:
<223> OTHER INFORMATION: Synthetic

<400> SEQUENCE: 119

```
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt     300
cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaggcgcc     540
tctgctcagg gcaaaggcat accaggggc gatcagattg ccgttggcct cgaagatgat     600
ggtgtcgcca ggttccagca gggtccagta gtagttgatt ctgccttcct ggtcccgcac     660
tttgggtctt ttggcgatct cggggtgaa tcttctgttg tagtggctgg acaccacgga     720
cacataggcg ttctcggtgt ggtagatggc ccgctgatct ccgatgttgc tagggtggtg     780
cactccccag aggaccagca cctcttttc tttgttgttc acgtagctct tgctcagatt     840
ggggtagctg ccgttcttct tggtcagcca cagcaggttc cggtagaagc tgcttctgcc     900
cttgtggcta caagaggcgg tcacgccctt ggtcactgtg tgattgggcc agctggactc     960
tttggggaag atctcgaacc gctcgaagct ggagacagag acagctgct ctctcagttc    1020
ctcgtaatcg gcgaagtagc cagggaaaca ggtgccattc tcgctgttgg gtgtctcggc    1080
gatataggac caggacttct tgctgaacag gctctcgcac tcgggatttc ccagaatcca    1140
```

```
gccggcgata gaacaattgc ccagctgcag aggggcaatg ctagcacgc cctgaggcag    1200 cagcaggttg ctcaccacca gcagcagcag cagtctgctg cccttctggc tgctgccctt    1260
gctgtccat                                                             1269
```

<210> SEQ ID NO 120
<211> LENGTH: 1269
<212> TYPE: DNA
<213> ORGANISM: Artificial Sequence
<220> FEATURE:
<223> OTHER INFORMATION: Synthetic

<400> SEQUENCE: 120

```
atggacagca agggcagcag ccagaagggc agcagactgc tgctgctgct ggtggtgagc      60
aacctgctgc tgcctcaggg cgtgctagcc atcgctcctc tgcagctggg gaaatgcagc     120
atcgcagggt ggattctggg aaacccagag tgtgaaagtc tgttttcaaa gaaatcttgg     180
agttacattg ccgagacacc caacagcgaa aatggcactt gcttccctgg gtatttcgct     240
gattatgagg aactgcgcga gcagctgagc tccgtgtcta gtttcgagcg atttgaaatc     300
ttccccaagg aatcaagctg gcctaagcac aacgtgacca agggggtcac agcctcatgt     360
agccataagg gaaaatcctc tttttaccgc aatctgctgt ggctgacaga gaagaacggg     420
tcctacccaa atctgtccaa gtcttacgtg aacaataagg agaaggaagt gctggtcctg     480
tggggcgtcc accatccctc taacatcgag gaccagaaga ctatctacag gaaagaaaac     540
gcatatgtga gtgtggtcag ttcacactac aatcggcggt tcaccccgga gatcgccaag     600
aggcccaaag tgcgcaacca ggaaggccgc attaattact attggaccct gctggagcca     660
ggcgatacaa tcattttcga agccaacggg aatctgatcg ctcccctggt atgcatttgcc    720 ctgtcccgag gagcctccgg agagagccag gtgaggcagc agttcagcaa ggacatcgag     780
aagctgctga cgagcaggt gaacaaggag atgcagagca gcaacctgta catgagcatg     840
agcagctggt gctacacccca gcctggac ggcgccggcc tgttcctgtt cgaccacgcc     900
gccgaggagt acgagcacgc caagaagctg atcatcttcc tgaacgagaa caacgtgccc     960
gtgcagctga ccagcatcag cgcccccgag cacaagttcg agggcctgac ccagatcttc    1020
cagaaggcct acgagcacga gcagcacatc agcgagagca tcaacaacat cgtggaccac    1080
gccatcaaga gcaaggacca cgccaccttc aacttcctgc agtggtacgt ggccgagcag    1140
cacgaggagg aggtgctgtt caaggacatc ctggacaaga tcgagctgat cggcaacgag    1200
aaccacggcc tgtacctggc cgaccagtac gtgaagggca tcgccaagag caggaagagc    1260
ggatcctag                                                            1269
```

<210> SEQ ID NO 121
<211> LENGTH: 422
<212> TYPE: PRT
<213> ORGANISM: Artificial Sequence
<220> FEATURE:
<223> OTHER INFORMATION: Synthetic

<400> SEQUENCE: 121

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ile Ala
            20                  25                  30

Pro Leu Gln Leu Gly Lys Cys Ser Ile Ala Gly Trp Ile Leu Gly Asn
        35                  40                  45
```

Pro Glu Cys Glu Ser Leu Phe Ser Lys Lys Ser Trp Ser Tyr Ile Ala
50                  55                  60

Glu Thr Pro Asn Ser Glu Asn Gly Thr Cys Phe Pro Gly Tyr Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Ser Ser Trp Pro Lys His Asn Val
                100                 105                 110

Thr Lys Gly Val Thr Ala Ser Cys Ser His Lys Gly Lys Ser Ser Phe
                115                 120                 125

Tyr Arg Asn Leu Leu Trp Leu Thr Glu Lys Asn Gly Ser Tyr Pro Asn
130                 135                 140

Leu Ser Lys Ser Tyr Val Asn Asn Lys Glu Lys Glu Val Leu Val Leu
145                 150                 155                 160

Trp Gly Val His His Pro Ser Asn Ile Glu Asp Gln Lys Thr Ile Tyr
                165                 170                 175

Arg Lys Glu Asn Ala Tyr Val Ser Val Val Ser Ser His Tyr Asn Arg
                180                 185                 190

Arg Phe Thr Pro Glu Ile Ala Lys Arg Pro Lys Val Arg Asn Gln Glu
                195                 200                 205

Gly Arg Ile Asn Tyr Tyr Trp Thr Leu Leu Glu Pro Gly Asp Thr Ile
210                 215                 220

Ile Phe Glu Ala Asn Gly Asn Leu Ile Ala Pro Trp Tyr Ala Phe Ala
225                 230                 235                 240

Leu Ser Arg Gly Ala Ser Gly Glu Ser Gln Val Arg Gln Gln Phe Ser
                245                 250                 255

Lys Asp Ile Glu Lys Leu Leu Asn Glu Gln Val Asn Lys Glu Met Gln
                260                 265                 270

Ser Ser Asn Leu Tyr Met Ser Met Ser Ser Trp Cys Tyr Thr His Ser
                275                 280                 285

Leu Asp Gly Ala Gly Leu Phe Leu Phe Asp His Ala Ala Glu Glu Tyr
                290                 295                 300

Glu His Ala Lys Lys Leu Ile Ile Phe Leu Asn Glu Asn Asn Val Pro
305                 310                 315                 320

Val Gln Leu Thr Ser Ile Ser Ala Pro Glu His Lys Phe Glu Gly Leu
                325                 330                 335

Thr Gln Ile Phe Gln Lys Ala Tyr Glu His Glu Gln His Ile Ser Glu
                340                 345                 350

Ser Ile Asn Asn Ile Val Asp His Ala Ile Lys Ser Lys Asp His Ala
                355                 360                 365

Thr Phe Asn Phe Leu Gln Trp Tyr Val Ala Glu Gln His Glu Glu Glu
                370                 375                 380

Val Leu Phe Lys Asp Ile Leu Asp Lys Ile Glu Leu Ile Gly Asn Glu
385                 390                 395                 400

Asn His Gly Leu Tyr Leu Ala Asp Gln Tyr Val Lys Gly Ile Ala Lys
                405                 410                 415

Ser Arg Lys Ser Gly Ser
                420

<210> SEQ ID NO 122
<211> LENGTH: 1269
<212> TYPE: DNA
<213> ORGANISM: Artificial Sequence
<220> FEATURE:

<223> OTHER INFORMATION: Synthetic

<400> SEQUENCE: 122

```
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt      300
cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaggctcc     540
tcgggacagg gcaaatgcat accagggagc gatcagattc ccgttggctt cgaaaatgat     600
tgtatcgcct ggctccagca gggtccaata gtaattaatg cggccttcct ggttgcgcac     660
tttgggcctc ttggcgatct cggggtgaa ccgccgattg tagtgtgaac tgaccacact      720
cacatatgcg ttttctttcc tgtagatagt cttctggtcc tcgatgttag agggatggtg     780
gacgccccac aggaccagca cttccttctc cttattgttc acgtaagact tggacagatt     840
tgggtaggac ccgttcttct ctgtcagcca cagcagattg cggtaaaaag aggattttcc     900
cttatggcta catgaggctg tgaccccttt ggtcacgttg tgcttaggcc agcttgattc     960
cttggggaag atttcaaatc gctcgaaact agacacggag ctcagctgct cgcgcagttc    1020
ctcataatca gcgaaatacc cagggaagca agtgccattt cgctgttgg gtgtctcggc     1080
aatgtaactc caagatttct ttgaaaacag actttcacac tctgggtttc ccagaatcca    1140
ccctgcgatg ctgcatttcc ccagctgcag aggagcgatg ctagcacgc cctgaggcag     1200
cagcaggttg ctcaccacca gcagcagcag cagtctgctg cccttctggc tgctgcccctt   1260
gctgtccat                                                           1269
```

<210> SEQ ID NO 123
<211> LENGTH: 1269
<212> TYPE: DNA
<213> ORGANISM: Artificial Sequence
<220> FEATURE:
<223> OTHER INFORMATION: Synthetic

<400> SEQUENCE: 123

```
atggacagca agggcagcag ccagaagggc agcagactgc tgctgctgct ggtggtgagc      60
aacctgctgc tgcctcaggg cgtgctagcc atcgccccac tgcagctggg caagtgcaac     120
atcgctggct ggattctggg gaatcccgag tgtgaatcac tgctgagcaa ccgctcatgg     180
agctacatcg ctgagacccc taacagcgaa aatggaattt gcttcccagg cgactttgca     240
gattatgagg aactgcggga gcagctgagc tccgtgtcta gtttcgagag atttgaaatc     300
ttccccaaag aatcaagctg gcctaagcac aacattacca ggggcgtgac agtcgcctgt     360
agccatgcta agaaatcctc tttctacaag aacctgctgt ggctgacaga ggccaatggc     420
ctgtacccct ccctgtctaa aagttatgtg aatgaccgcg agaaggaagt gctggtcctg     480
tggggcgtcc accatcctag caacatcgag gatcagagga cactgtaccg caaggaaaat     540
gcctatgtga gcgtcgtcag ttcaaactac aatcggagat tactccaga gattgctgaa     600
cgaccaaaag tgcgaggaca gcctggacga atgaactact attggaccct gctggagcca     660
```

```
ggagataaga tcatttttga agcaaacggc aatctgatcg cccctggta tgcattcgcc      720 ctgtcaagag gaccttccgg agagagccag gtgaggcagc agttcagcaa ggacatcgag      780
aagctgctga cgagcaggt gaacaaggag atgcagagca gcaacctgta catgagcatg      840
agcagctggt gctacaccca cagcctggac ggcgccggcc tgttcctgtt cgaccacgcc      900
gccgaggagt acgagcacgc caagaagctg atcatcttcc tgaacgagaa caacgtgccc      960
gtgcagctga ccagcatcag cgcccccgag cacaagttcg agggcctgac ccagatcttc     1020
cagaaggcct acgagcacga gcagcacatc agcgagagca tcaacaacat cgtggaccac     1080
gccatcaaga gcaaggacca cgccaccttc aacttcctgc agtggtacgt ggccgagcag     1140
cacgaggagg aggtgctgtt caaggacatc ctggacaaga tcgagctgat cggcaacgag     1200
aaccacggcc tgtacctggc cgaccagtac gtgaagggca tcgccaagag caggaagagc     1260
ggatcctag                                                              1269
```

<210> SEQ ID NO 124
<211> LENGTH: 422
<212> TYPE: PRT
<213> ORGANISM: Artificial Sequence
<220> FEATURE:
<223> OTHER INFORMATION: Synthetic

<400> SEQUENCE: 124

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Ile Ala
            20                  25                  30

Pro Leu Gln Leu Gly Lys Cys Asn Ile Ala Gly Trp Ile Leu Gly Asn
        35                  40                  45

Pro Glu Cys Glu Ser Leu Leu Ser Asn Arg Ser Trp Ser Tyr Ile Ala
    50                  55                  60

Glu Thr Pro Asn Ser Glu Asn Gly Ile Cys Phe Pro Gly Asp Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Ser Ser Trp Pro Lys His Asn Ile
            100                 105                 110

Thr Arg Gly Val Thr Val Ala Cys Ser His Ala Lys Lys Ser Ser Phe
        115                 120                 125

Tyr Lys Asn Leu Leu Trp Leu Thr Glu Ala Asn Gly Leu Tyr Pro Ser
    130                 135                 140

Leu Ser Lys Ser Tyr Val Asn Asp Arg Glu Lys Glu Val Leu Val Leu
145                 150                 155                 160

Trp Gly Val His His Pro Ser Asn Ile Glu Asp Gln Arg Thr Leu Tyr
                165                 170                 175

Arg Lys Glu Asn Ala Tyr Val Ser Val Val Ser Ser Asn Tyr Asn Arg
            180                 185                 190

Arg Phe Thr Pro Glu Ile Ala Glu Arg Pro Lys Val Arg Gly Gln Pro
        195                 200                 205

Gly Arg Met Asn Tyr Tyr Trp Thr Leu Leu Glu Pro Gly Asp Lys Ile
    210                 215                 220

Ile Phe Glu Ala Asn Gly Asn Leu Ile Ala Pro Trp Tyr Ala Phe Ala
225                 230                 235                 240

Leu Ser Arg Gly Pro Ser Gly Glu Ser Gln Val Arg Gln Gln Phe Ser
```

```
                    245                 250                 255
Lys Asp Ile Glu Lys Leu Leu Asn Glu Gln Val Asn Lys Glu Met Gln
            260                 265                 270

Ser Ser Asn Leu Tyr Met Ser Met Ser Ser Trp Cys Tyr Thr His Ser
        275                 280                 285

Leu Asp Gly Ala Gly Leu Phe Leu Phe Asp His Ala Ala Glu Glu Tyr
    290                 295                 300

Glu His Ala Lys Lys Leu Ile Ile Phe Leu Asn Glu Asn Asn Val Pro
305                 310                 315                 320

Val Gln Leu Thr Ser Ile Ser Ala Pro Glu His Lys Phe Glu Gly Leu
                325                 330                 335

Thr Gln Ile Phe Gln Lys Ala Tyr Glu His Glu Gln His Ile Ser Glu
            340                 345                 350

Ser Ile Asn Asn Ile Val Asp His Ala Ile Lys Ser Lys Asp His Ala
        355                 360                 365

Thr Phe Asn Phe Leu Gln Trp Tyr Val Ala Glu Gln His Glu Glu Glu
    370                 375                 380

Val Leu Phe Lys Asp Ile Leu Asp Lys Ile Glu Leu Ile Gly Asn Glu
385                 390                 395                 400

Asn His Gly Leu Tyr Leu Ala Asp Gln Tyr Val Lys Gly Ile Ala Lys
                405                 410                 415

Ser Arg Lys Ser Gly Ser
            420

<210> SEQ ID NO 125
<211> LENGTH: 1269
<212> TYPE: DNA
<213> ORGANISM: Artificial Sequence
<220> FEATURE:
<223> OTHER INFORMATION: Synthetic

<400> SEQUENCE: 125
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aagtggcgt ggtccttgct     180 cttgatggcg tggtccacga tgttgttgat gctctcgctg atgtgctgct cgtgctcgta     240
ggccttctgg aagatctggg tcaggccctc gaacttgtgc tcggggcgc tgatgctggt     300 cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaaggtcc     540
tcttgacagg gcgaatgcat accagggggc gatcagattg ccgtttgctt caaaaatgat     600
cttatctcct ggctccagca gggtccaata gtagttcatt cgtccaggct gtcctcgcac     660
ttttggtcgt tcagcaatct ctggagtaaa tctccgattg tagtttgaac tgacgacgct     720
cacataggca ttttccttgc ggtacagtgt cctctgatcc tcgatgttgc taggatggtg     780
gacgccccac aggaccagca cttccttctc gcggtcattc acataacttt tagacaggga     840
ggggtacagg ccattggcct ctgtcagcca cagcaggttc ttgtagaaag aggatttctt     900
agcatggcta caggcgactg tcacgcccct ggtaatgttg tgcttaggcc agcttgattc     960
tttggggaag atttcaaatc tctcgaaact agacacggag ctcagctgct cccgcagttc    1020
```

```
ctcataatct gcaaagtcgc ctgggaagca aattccattt tcgctgttag gggtctcagc    1080
gatgtagctc catgagcggt tgctcagcag tgattcacac tcgggattcc ccagaatcca    1140
gccagcgatg ttgcacttgc ccagctgcag tggggcgatg gctagcacgc cctgaggcag    1200
cagcaggttg ctcaccacca gcagcagcag cagtctgctg cccttctggc tgctgccctt    1260
gctgtccat                                                            1269
```

<210> SEQ ID NO 126
<211> LENGTH: 1266
<212> TYPE: DNA
<213> ORGANISM: Artificial Sequence
<220> FEATURE:
<223> OTHER INFORMATION: Synthetic

<400> SEQUENCE: 126

```
atggacagca agggcagcag ccagaagggc agcagactgc tgctgctgct ggtggtgagc      60
aacctgctgc tgcctcaggg cgtgctagcc atcgccccac tgcagctggg aaaatgcaac    120
atcgctggat ggattctggg caatcccgag tgtgaatcac tgctgagcga gcgctcttgg    180
agttacatcg tggagacccc taacagcgaa aatgggacat gcttcccagg agactttatt    240
gattatgagg aactgcgcga gcagctgagc tccgtgtcta gtttcgagcg atttgaaatc    300
ttctctaagg aatcaagctg gccaaaacac accacaggcg gggtgactgc cgcttgtagt    360
catgccggca gtcctctctt ctaccggaac ctgctgtggc tgaccgagaa agacgggtcc    420
taccccaacc tgaacaactc ttacgtgaat aagaagggca aggaagtgct ggtcctgtgg    480
ggggtccacc atcctagcaa catcaaggat cagcagacac tgtaccagaa agagaatgcc    540
tatgtgtccg tggtcagttc aaactacaat cggcggttca cccccgagat cgctgaaagg    600
cctaaggtcc gcggacaggc aggccgaatt aactactatt ggactctgct gaaacccggg    660
gacaccatca tgttcgaggc aaacggaaat ctgattgccc cttggtatgc ttttgcactg    720
tctcgcgggg cctccggaga gagccaggtg aggcagcagt tcagcaagga catcgagaag    780
ctgctgaacg agcaggtgaa caaggagatg cagagcagca acctgtacat gagcatgagc    840
agctggtgct acacccacag cctggacggc gccggcctgt tcctgttcga ccacgccgcc    900
gaggagtacg agcacgccaa gaagctgatc atcttcctga cgagaacaa cgtgcccgtg    960 cagctgacca gcatcagcgc ccccgagcac aagttcgagg gcctgaccca gatcttccag   1020
aaggcctacg agcacgagca gcacatcagc gagagcatca caacatcgt ggaccacgcc    1080 atcaagagca aggaccacgc caccttcaac ttcctgcagt ggtacgtggc cgagcagcac   1140
gaggaggagg tgctgttcaa ggacatcctg gacaagatcg agctgatcgg caacgagaac   1200
cacggcctgt acctggccga ccagtacgtg aagggcatcg ccaagagcag gaagagcgga   1260
tcctag                                                             1266
```

<210> SEQ ID NO 127
<211> LENGTH: 421
<212> TYPE: PRT
<213> ORGANISM: Artificial Sequence
<220> FEATURE:
<223> OTHER INFORMATION: Synthetic

<400> SEQUENCE: 127

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ile Ala
            20                  25                  30
```

Pro Leu Gln Leu Gly Lys Cys Asn Ile Ala Gly Trp Ile Leu Gly Asn
    35                  40                  45

Pro Glu Cys Glu Ser Leu Leu Ser Glu Arg Ser Trp Ser Tyr Ile Val
 50                  55                  60

Glu Thr Pro Asn Ser Glu Asn Gly Thr Cys Phe Pro Gly Asp Phe Ile
 65                  70                  75                  80

Asp Tyr Glu Glu Leu Arg Glu Gln Leu Ser Ser Val Ser Ser Phe Glu
                85                  90                  95

Arg Phe Glu Ile Phe Ser Lys Glu Ser Ser Trp Pro Lys His Thr Thr
            100                 105                 110

Gly Gly Val Thr Ala Ala Cys Ser His Ala Gly Lys Ser Ser Phe Tyr
            115                 120                 125

Arg Asn Leu Leu Trp Leu Thr Glu Lys Asp Gly Ser Tyr Pro Asn Leu
        130                 135                 140

Asn Asn Ser Tyr Val Asn Lys Lys Gly Lys Glu Val Leu Val Leu Trp
145                 150                 155                 160

Gly Val His His Pro Ser Asn Ile Lys Asp Gln Gln Thr Leu Tyr Gln
                165                 170                 175

Lys Glu Asn Ala Tyr Val Ser Val Val Ser Ser Asn Tyr Asn Arg Arg
            180                 185                 190

Phe Thr Pro Glu Ile Ala Glu Arg Pro Lys Val Arg Gly Gln Ala Gly
        195                 200                 205

Arg Ile Asn Tyr Tyr Trp Thr Leu Leu Lys Pro Gly Asp Thr Ile Met
    210                 215                 220

Phe Glu Ala Asn Gly Asn Leu Ile Ala Pro Trp Tyr Ala Phe Ala Leu
225                 230                 235                 240

Ser Arg Gly Ala Ser Gly Glu Ser Gln Val Arg Gln Gln Phe Ser Lys
                245                 250                 255

Asp Ile Glu Lys Leu Leu Asn Glu Gln Val Asn Lys Glu Met Gln Ser
            260                 265                 270

Ser Asn Leu Tyr Met Ser Met Ser Ser Trp Cys Tyr Thr His Ser Leu
        275                 280                 285

Asp Gly Ala Gly Leu Phe Leu Phe Asp His Ala Ala Glu Glu Tyr Glu
    290                 295                 300

His Ala Lys Lys Leu Ile Ile Phe Leu Asn Glu Asn Asn Val Pro Val
305                 310                 315                 320

Gln Leu Thr Ser Ile Ser Ala Pro Glu His Lys Phe Glu Gly Leu Thr
                325                 330                 335

Gln Ile Phe Gln Lys Ala Tyr Glu His Glu Gln His Ile Ser Glu Ser
            340                 345                 350

Ile Asn Asn Ile Val Asp His Ala Ile Lys Ser Lys Asp His Ala Thr
        355                 360                 365

Phe Asn Phe Leu Gln Trp Tyr Val Ala Glu Gln His Glu Glu Glu Val
    370                 375                 380

Leu Phe Lys Asp Ile Leu Asp Lys Ile Glu Leu Ile Gly Asn Glu Asn
385                 390                 395                 400

His Gly Leu Tyr Leu Ala Asp Gln Tyr Val Lys Gly Ile Ala Lys Ser
                405                 410                 415

Arg Lys Ser Gly Ser
            420

<210> SEQ ID NO 128
<211> LENGTH: 1266

<212> TYPE: DNA
<213> ORGANISM: Artificial Sequence
<220> FEATURE:
<223> OTHER INFORMATION: Synthetic

<400> SEQUENCE: 128

```
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgcg tgatgctggt     300
cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaggcccc     540
gcgagacagt gcaaaagcat accaaggggc aatcagattt ccgtttgcct cgaacatgat     600
ggtgtccccg ggtttcagca gagtccaata gtagttaatt cggcctgcct gtccgcggac     660
cttaggcctt tcagcgatct cggggggtgaa ccgccgattg tagtttgaac tgaccacgga     720
cacataggca ttctctttct ggtacagtgt ctgctgatcc ttgatgttgc taggatggtg     780
gaccccccac aggaccagca cttccttgcc cttcttattc acgtaagagt tgttcaggtt     840
ggggtaggac ccgtctttct cggtcagcca cagcaggttc cggtagaaag aggacttgcc     900
ggcatgacta caagcggcag tcaccccgcc tgtggtgtgt tttggccagc ttgattcctt     960
agagaagatt tcaaatcgct cgaaactaga cacggagctc agctgctcgc gcagttcctc    1020
ataatcaata aagtctcctg ggaagcatgt cccattttcg ctgttagggg tctccacgat    1080
gtaactccaa gagcgctcgc tcagcagtga ttcacactcg ggattgccca gaatccatcc    1140
agcgatgttg cattttccca gctgcagtgg ggcgatggct agcacgccct gaggcagcag    1200
caggttgctc accaccagca gcagcagcag tctgctgccc ttctggctgc tgcccttgct    1260
gtccat                                                              1266
```

<210> SEQ ID NO 129
<211> LENGTH: 1269
<212> TYPE: DNA
<213> ORGANISM: Artificial Sequence
<220> FEATURE:
<223> OTHER INFORMATION: Synthetic

<400> SEQUENCE: 129

```
atggacagca agggcagcag ccagaagggc agcagactgc tgctgctgct ggtggtgagc      60
aacctgctgc tgcctcaggg cgtgctagcc atcgcccctc tgcagctggg caagtgctct     120
atcgctggct ggattctggg gaatccagag tgtgaaagtc tgttttcaaa gaaatcttgg     180
agttacattg ctgagacccc caacagcgaa atggaacat gcttccctgg ctatttcgca      240
gattatgagg aactgaggga gcagctgagc tccgtgtcta gtttcgagag atttgaaatc     300
ttccccaaag aaaggagctg gcctaagcac aacgtgaccc gggagtcac agcctcatgt      360
agccataagg gcaaatcaag cttttacaga aatctgctgt ggctgacaga gaaaaacggg     420
tcctacccaa atctgtccaa gtcttatgtg aacaataagg agaaagaagt gctggtcctg     480
tggggcgtcc accatcccag caacatcgag gaccagaaga ctatttaccg aaaagaaaat     540
```

```
gcctatgtgt ccgtggtctc ctctaactac aatcggagat ttaccccaga gatcgctgaa      600
aggccaaagg tgcgaggaca ggcaggacga attaactact attggactct gctggagcca      660
ggggatacca tcattttcga agccaacgga aatctgatcg ctccctggta tgcatttgcc      720
ctgagtcggg gagcctccgg agagagccag gtgaggcagc agttcagcaa ggacatcgag      780
aagctgctga acgagcaggt gaacaaggag atgcagagca gcaacctgta catgagcatg      840
agcagctggt gctacaccca agcctggacg gcgccggcc tgttcctgtt cgaccacgcc      900
gccgaggagt acgagcacgc caagaagctg atcatcttcc tgaacgagaa caacgtgccc      960
gtgcagctga ccagcatcag cgcccccgag cacaagttcg agggcctgac ccagatcttc     1020
cagaaggcct acgagcacga gcagcacatc agcgagagca tcaacaacat cgtggaccac     1080
gccatcaaga gcaaggacca cgccaccttc aacttcctgc agtggtacgt ggccgagcag     1140
cacgaggagg aggtgctgtt caaggacatc ctggacaaga tcgagctgat cggcaacgag     1200
aaccacggcc tgtacctggc cgaccagtac gtgaagggca tcgccaagag caggaagagc     1260
ggatcctag                                                              1269
```

<210> SEQ ID NO 130
<211> LENGTH: 422
<212> TYPE: PRT
<213> ORGANISM: Artificial Sequence
<220> FEATURE:
<223> OTHER INFORMATION: Synthetic

<400> SEQUENCE: 130

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ile Ala
            20                  25                  30

Pro Leu Gln Leu Gly Lys Cys Ser Ile Ala Gly Trp Ile Leu Gly Asn
        35                  40                  45

Pro Glu Cys Glu Ser Leu Phe Ser Lys Lys Ser Trp Ser Tyr Ile Ala
    50                  55                  60

Glu Thr Pro Asn Ser Glu Asn Gly Thr Cys Phe Pro Gly Tyr Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Arg Ser Trp Pro Lys His Asn Val
            100                 105                 110

Thr Arg Gly Val Thr Ala Ser Cys Ser His Lys Gly Lys Ser Ser Phe
        115                 120                 125

Tyr Arg Asn Leu Leu Trp Leu Thr Glu Lys Asn Gly Ser Tyr Pro Asn
    130                 135                 140

Leu Ser Lys Ser Tyr Val Asn Asn Lys Glu Lys Glu Val Leu Val Leu
145                 150                 155                 160

Trp Gly Val His His Pro Ser Asn Ile Glu Asp Gln Lys Thr Ile Tyr
                165                 170                 175

Arg Lys Glu Asn Ala Tyr Val Ser Val Val Ser Ser Asn Tyr Asn Arg
            180                 185                 190

Arg Phe Thr Pro Glu Ile Ala Glu Arg Pro Lys Val Arg Gly Gln Ala
        195                 200                 205

Gly Arg Ile Asn Tyr Tyr Trp Thr Leu Leu Glu Pro Gly Asp Thr Ile
    210                 215                 220

Ile Phe Glu Ala Asn Gly Asn Leu Ile Ala Pro Trp Tyr Ala Phe Ala
```

```
                225                 230                 235                 240
Leu Ser Arg Gly Ala Ser Gly Glu Ser Gln Val Arg Gln Gln Phe Ser
                    245                 250                 255

Lys Asp Ile Glu Lys Leu Leu Asn Glu Gln Val Asn Lys Glu Met Gln
                260                 265                 270

Ser Ser Asn Leu Tyr Met Ser Met Ser Ser Trp Cys Tyr Thr His Ser
                275                 280                 285

Leu Asp Gly Ala Gly Leu Phe Leu Phe Asp His Ala Ala Glu Glu Tyr
                290                 295                 300

Glu His Ala Lys Lys Leu Ile Ile Phe Leu Asn Glu Asn Asn Val Pro
305                 310                 315                 320

Val Gln Leu Thr Ser Ile Ser Ala Pro Glu His Lys Phe Glu Gly Leu
                325                 330                 335

Thr Gln Ile Phe Gln Lys Ala Tyr Glu His Glu Gln His Ile Ser Glu
                340                 345                 350

Ser Ile Asn Asn Ile Val Asp His Ala Ile Lys Ser Lys Asp His Ala
                355                 360                 365

Thr Phe Asn Phe Leu Gln Trp Tyr Val Ala Glu Gln His Glu Glu Glu
                370                 375                 380

Val Leu Phe Lys Asp Ile Leu Asp Lys Ile Glu Leu Ile Gly Asn Glu
385                 390                 395                 400

Asn His Gly Leu Tyr Leu Ala Asp Gln Tyr Val Lys Gly Ile Ala Lys
                405                 410                 415

Ser Arg Lys Ser Gly Ser
                420

<210> SEQ ID NO 131
<211> LENGTH: 1269
<212> TYPE: DNA
<213> ORGANISM: Artificial Sequence
<220> FEATURE:
<223> OTHER INFORMATION: Synthetic

<400> SEQUENCE: 131
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcgggggcgc tgatgctggt     300
cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaggctcc     540
ccgactcagg gcaaatgcat accagggagc gatcagattt ccgttggctt cgaaaatgat     600 ggtatccct ggctccagca gagtccaata gtagttaatt cgtcctgcct gtcctcgcac      660
ctttggcctt tcagcgatct ctggggtaaa tctccgattg tagttagagg agaccacgga     720
cacataggca ttttctttc ggtaaatagt cttctggtcc tcgatgttgc tgggatggtg      780
gacgccccac aggaccagca cttctttctc cttattgttc acataagact tggacagatt     840
tgggtaggac ccgttttct ctgtcagcca cagcagattt ctgtaaaagc ttgatttgcc      900
cttatggcta catgaggctg tgactccccg ggtcacgttg tgcttaggcc agctccttc      960
```

```
tttgggaag atttcaaatc tctcgaaact agacacggag ctcagctgct ccctcagttc   1020
ctcataatct gcgaaatagc cagggaagca tgttccattt tcgctgttgg gggtctcagc   1080
aatgtaactc caagatttct ttgaaaacag actttcacac tctggattcc ccagaatcca   1140
gccagcgata gagcacttgc ccagctgcag aggggcgatg gctagcacgc cctgaggcag   1200
cagcaggttg ctcaccacca gcagcagcag cagtctgctg cccttctggc tgctgccctt   1260
gctgtccat                                                            1269
```

<210> SEQ ID NO 132
<211> LENGTH: 1269
<212> TYPE: DNA
<213> ORGANISM: Artificial Sequence
<220> FEATURE:
<223> OTHER INFORMATION: Synthetic

<400> SEQUENCE: 132

```
atggacagca agggcagcag ccagaagggc agcagactgc tgctgctgct ggtggtgagc     60
aacctgctgc tgcctcaggg cgtgctagcc atcgctcctc tgcagctggg aaagtgcaac   120
atcgcaggat ggattctggg caatccagag tgtgaatccc tgctgtctaa acggtcttgg   180
agttacattg ccgagacacc caactctgaa atggggcct gcttccctgg agactttgct    240
gattatgagg aactgagaga gcagctgagc tccgtgtcta gtttcgagag atttgaaatc   300
ttccccaagg aaaggtcctg gcctaaacac aacattacta gggggggtgac cgccgcttgt   360 tctcatgccg gaaaatcaag cttctacaag aatctgctgt ggctgacaga gactgacggc   420
tcctacccaa agctgtcaaa agctatgtg aacaataagg agaaagaagt gctggtcctg    480
tggggcgtcc accatcccag taacatcgag gatcagaaaa ctctgtaccg caaggaaaat   540
gcttatgtga gcgtggtctc ctctaactac aatcggagat ttacccccaga gatcgcagaa   600 aggccaaagg tgcgaggaca ggcaggacga attaactact attggactct gctggagcca   660
ggcgacacca tcattttcga agcaaacggg aatctgatcg cccctggta tgcttttgca     720 ctgtcccgcg atgcctccgg agagagccag gtgaggcagc agttcagcaa ggacatcgag   780
aagctgctga cgagcaggt gaacaaggag atgcagagca gcaacctgta catgagcatg    840
agcagctggt gctacaccca gcctggac ggcgccggcc tgttcctgtt cgaccacgcc      900
gccgaggagt acgagcacgc caagaagctg atcatcttcc tgaacgagaa caacgtgccc   960
gtgcagctga ccagcatcag cgcccccgag cacaagttcg agggcctgac ccagatcttc   1020
cagaaggcct acgagcacga gcagcacatc agcgagagca tcaacaacat cgtggaccac   1080
gccatcaaga gcaaggacca cgccaccttc aacttcctgc agtggtacgt ggccgagcag   1140
cacgaggagg aggtgctgtt caaggacatc ctggacaaga tcgagctgat cggcaacgag   1200
aaccacggcc tgtacctggc cgaccagtac gtgaagggca tcgccaagag caggaagagc   1260
ggatcctag                                                            1269
```

<210> SEQ ID NO 133
<211> LENGTH: 422
<212> TYPE: PRT
<213> ORGANISM: Artificial Sequence
<220> FEATURE:
<223> OTHER INFORMATION: Synthetic

<400> SEQUENCE: 133

```
Met Asp Ser Lys Gly Ser Ser Gln Lys Gly Ser Arg Leu Leu Leu Leu
1               5                   10                  15
```

Leu Val Val Ser Asn Leu Leu Pro Gln Gly Val Leu Ala Ile Ala
            20              25              30

Pro Leu Gln Leu Gly Lys Cys Asn Ile Ala Gly Trp Ile Leu Gly Asn
        35              40              45

Pro Glu Cys Glu Ser Leu Leu Ser Lys Arg Ser Trp Ser Tyr Ile Ala
50              55              60

Glu Thr Pro Asn Ser Glu Asn Gly Ala Cys Phe Pro Gly Asp Phe Ala
65              70              75              80

Asp Tyr Glu Glu Leu Arg Glu Gln Leu Ser Ser Val Ser Ser Phe Glu
            85              90              95

Arg Phe Glu Ile Phe Pro Lys Glu Arg Ser Trp Pro Lys His Asn Ile
            100             105             110

Thr Arg Gly Val Thr Ala Ala Cys Ser His Ala Gly Lys Ser Ser Phe
        115             120             125

Tyr Lys Asn Leu Leu Trp Leu Thr Glu Thr Asp Gly Ser Tyr Pro Lys
130             135             140

Leu Ser Lys Ser Tyr Val Asn Asn Lys Glu Lys Glu Val Leu Val Leu
145             150             155             160

Trp Gly Val His His Pro Ser Asn Ile Glu Asp Gln Lys Thr Leu Tyr
            165             170             175

Arg Lys Glu Asn Ala Tyr Val Ser Val Ser Ser Asn Tyr Asn Arg
            180             185             190

Arg Phe Thr Pro Glu Ile Ala Glu Arg Pro Lys Val Arg Gly Gln Ala
        195             200             205

Gly Arg Ile Asn Tyr Tyr Trp Thr Leu Leu Glu Pro Gly Asp Thr Ile
        210             215             220

Ile Phe Glu Ala Asn Gly Asn Leu Ile Ala Pro Trp Tyr Ala Phe Ala
225             230             235             240

Leu Ser Arg Asp Ala Ser Gly Glu Ser Gln Val Arg Gln Gln Phe Ser
            245             250             255

Lys Asp Ile Glu Lys Leu Leu Asn Glu Gln Val Asn Lys Glu Met Gln
            260             265             270

Ser Ser Asn Leu Tyr Met Ser Met Ser Ser Trp Cys Tyr Thr His Ser
        275             280             285

Leu Asp Gly Ala Gly Leu Phe Leu Phe Asp His Ala Ala Glu Glu Tyr
290             295             300

Glu His Ala Lys Lys Leu Ile Ile Phe Leu Asn Glu Asn Asn Val Pro
305             310             315             320

Val Gln Leu Thr Ser Ile Ser Ala Pro Glu His Lys Phe Glu Gly Leu
            325             330             335

Thr Gln Ile Phe Gln Lys Ala Tyr Glu His Glu Gln His Ile Ser Glu
            340             345             350

Ser Ile Asn Asn Ile Val Asp His Ala Ile Lys Ser Lys Asp His Ala
        355             360             365

Thr Phe Asn Phe Leu Gln Trp Tyr Val Ala Glu Gln His Glu Glu Glu
        370             375             380

Val Leu Phe Lys Asp Ile Leu Asp Lys Ile Glu Leu Ile Gly Asn Glu
385             390             395             400

Asn His Gly Leu Tyr Leu Ala Asp Gln Tyr Val Lys Gly Ile Ala Lys
            405             410             415

Ser Arg Lys Ser Gly Ser
            420

<210> SEQ ID NO 134
<211> LENGTH: 1269
<212> TYPE: DNA
<213> ORGANISM: Artificial Sequence
<220> FEATURE:
<223> OTHER INFORMATION: Synthetic

<400> SEQUENCE: 134

| | | | | | |
|---|---|---|---|---|---|
| ctaggatccg | ctcttcctgc | tcttggcgat | gcccttcacg | tactggtcgg | ccaggtacag | 60 |
| gccgtggttc | tcgttgccga | tcagctcgat | cttgtccagg | atgtccttga | acagcacctc | 120 |
| ctcctcgtgc | tgctcggcca | cgtaccactg | caggaagttg | aaggtggcgt | ggtccttgct | 180 |
| cttgatggcg | tggtccacga | tgttgttgat | gctctcgctg | atgtgctgct | cgtgctcgta | 240 |
| ggccttctgg | aagatctggg | tcaggccctc | gaacttgtgc | tcgggggcgc | tgatgctggt | 300 |
| cagctgcacg | ggcacgttgt | tctcgttcag | gaagatgatc | agcttcttgg | cgtgctcgta | 360 |
| ctcctcggcg | gcgtggtcga | acaggaacag | gccggcgccg | tccaggctgt | gggtgtagca | 420 |
| ccagctgctc | atgctcatgt | acaggttgct | gctctgcatc | tccttgttca | cctgctcgtt | 480 |
| cagcagcttc | tcgatgtcct | tgctgaactg | ctgcctcacc | tggctctctc | cggaggcatc | 540 |
| gcgggacagt | gcaaaagcat | accagggggc | gatcagattc | ccgtttgctt | cgaaaatgat | 600 |
| ggtgtcgcct | ggctccagca | gagtccaata | gtagttaatt | cgtcctgcct | gtcctcgcac | 660 |
| cttggcctt | tctgcgatct | ctggggtaaa | tctccgattg | tagttagagg | agaccacgct | 720 |
| cacataagca | ttttccttgc | ggtacagagt | tttctgatcc | tcgatgttac | tgggatggtg | 780 |
| gacgccccac | aggaccagca | cttctttctc | cttattgttc | acatagcttt | ttgacagctt | 840 |
| tgggtaggag | ccgtcagtct | ctgtcagcca | cagcagattc | ttgtagaagc | ttgattttcc | 900 |
| ggcatgagaa | caagcggcgg | tcaccccct | agtaatgttg | tgtttaggcc | aggacctttc | 960 |
| cttggggaag | atttcaaatc | tctcgaaact | agacacggag | ctcagctgct | ctctcagttc | 1020 |
| ctcataatca | gcaaagtctc | cagggaagca | ggcccatttt | tcagagttgg | gtgtctcggc | 1080 |
| aatgtaactc | caagaccgtt | tagacagcag | ggattcacac | tctggattgc | ccagaatcca | 1140 |
| tcctgcgatg | ttgcactttc | ccagctgcag | aggagcgatg | gctagcacgc | cctgaggcag | 1200 |
| cagcaggttg | ctcaccacca | gcagcagcag | cagtctgctg | cccttctggc | tgctgccctt | 1260 |
| gctgtccat | | | | | | 1269 |

<210> SEQ ID NO 135
<211> LENGTH: 1266
<212> TYPE: DNA
<213> ORGANISM: Artificial Sequence
<220> FEATURE:
<223> OTHER INFORMATION: Synthetic

<400> SEQUENCE: 135

| | | | | | |
|---|---|---|---|---|---|
| atggacagca | agggcagcag | ccagaagggc | agcagactgc | tgctgctgct | ggtggtgagc | 60 |
| aacctgctgc | tgcctcaggg | cgtgctagcc | attgcccctc | tgcagctggg | aaattgtagc | 120 |
| gtggccggct | ggattctggg | caatcctgag | tgcgagctgc | tgatttccaa | agagtcctgg | 180 |
| tcctacatcg | tggagaagcc | caaccctgag | aatggcacct | gcttccctgg | ccacttcgcc | 240 |
| gattacgagg | aactgagaga | acagctgtcc | agcgtgtcca | gcttcgagag | attcgagatc | 300 |
| ttccccaaag | agagcagctg | gcccaatcat | acagtgaccg | gcgtgagcgc | ctcttgtagc | 360 |
| cacaatggcg | agagcagctt | ctacagaaac | ctgctgtggc | tgaccggcaa | gaacggcctg | 420 |
| taccccaacc | tgagcaagag | ctacgccaac | aacaaagaaa | agaagtgct | ggtcctctgg | 480 |

```
ggagtgcacc accctcctaa catcggcatc cagaaggccc tgtaccacac cgagaatgcc    540
tacgtgtccg tggtgtccag ccactacagc agaaagttca cccccgagat cgccaaaaga    600
cccaaagtgc gggaccagga aggcaggatc aactactact ggaccctgct ggaacctggc    660
gacaccatca tcttcgaggc caacggcaat ctgatcgccc tagatacgc ctttgccctg    720
agcagaggcg cctccggaga gagccaggtg aggcagcagt tcagcaagga catcgagaag    780
ctgctgaacg agcaggtgaa caaggagatg cagagcagca acctgtacat gagcatgagc    840
agctggtgct acacccacag cctggacggc gccggcctgt tcctgttcga ccacgccgcc    900
gaggagtacg agcacgccaa gaagctgatc atcttcctga cgagaacaa cgtgcccgtg    960
cagctgacca gcatcagcgc ccccgagcac aagttcgagg gcctgaccca gatcttccag   1020
aaggcctacg agcacgagca gcacatcagc gagagcatca acaacatcgt ggaccacgcc   1080
atcaagagca aggaccacgc caccttcaac ttcctgcagt ggtacgtggc cgagcagcac   1140
gaggaggagg tgctgttcaa ggacatcctg gacaagatcg agctgatcgg caacgagaac   1200
cacggcctgt acctggccga ccagtacgtg aagggcatcg ccaagagcag gaagagcgga   1260
tcctag                                                              1266

<210> SEQ ID NO 136
<211> LENGTH: 421
<212> TYPE: PRT
<213> ORGANISM: Artificial Sequence
<220> FEATURE:
<223> OTHER INFORMATION: Synthetic

<400> SEQUENCE: 136

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Ile Ala
            20                  25                  30

Pro Leu Gln Leu Gly Asn Cys Ser Val Ala Gly Trp Ile Leu Gly Asn
        35                  40                  45

Pro Glu Cys Glu Leu Leu Ile Ser Lys Glu Ser Trp Ser Tyr Ile Val
    50                  55                  60

Glu Lys Pro Asn Pro Glu Asn Gly Thr Cys Phe Pro Gly His Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Ser Ser Trp Pro Asn His Thr Val
            100                 105                 110

Thr Gly Val Ser Ala Ser Cys Ser His Asn Gly Glu Ser Ser Phe Tyr
        115                 120                 125

Arg Asn Leu Leu Trp Leu Thr Gly Lys Asn Gly Leu Tyr Pro Asn Leu
    130                 135                 140

Ser Lys Ser Tyr Ala Asn Asn Lys Glu Lys Glu Val Leu Val Leu Trp
145                 150                 155                 160

Gly Val His His Pro Pro Asn Ile Gly Ile Gln Lys Ala Leu Tyr His
                165                 170                 175

Thr Glu Asn Ala Tyr Val Ser Val Val Ser Ser His Tyr Ser Arg Lys
            180                 185                 190

Phe Thr Pro Glu Ile Ala Lys Arg Pro Lys Val Arg Asp Gln Glu Gly
        195                 200                 205

Arg Ile Asn Tyr Tyr Trp Thr Leu Leu Glu Pro Gly Asp Thr Ile Ile
```

```
              210                 215                 220
Phe Glu Ala Asn Gly Asn Leu Ile Ala Pro Arg Tyr Ala Phe Ala Leu
225                 230                 235                 240

Ser Arg Gly Ala Ser Gly Glu Ser Gln Val Arg Gln Gln Phe Ser Lys
                245                 250                 255

Asp Ile Glu Lys Leu Leu Asn Glu Gln Val Asn Lys Glu Met Gln Ser
                260                 265                 270

Ser Asn Leu Tyr Met Ser Met Ser Ser Trp Cys Tyr Thr His Ser Leu
            275                 280                 285

Asp Gly Ala Gly Leu Phe Leu Phe Asp His Ala Ala Glu Glu Tyr Glu
                290                 295                 300

His Ala Lys Lys Leu Ile Ile Phe Leu Asn Glu Asn Asn Val Pro Val
305                 310                 315                 320

Gln Leu Thr Ser Ile Ser Ala Pro Glu His Lys Phe Glu Gly Leu Thr
                325                 330                 335

Gln Ile Phe Gln Lys Ala Tyr Glu His Glu Gln His Ile Ser Glu Ser
                340                 345                 350

Ile Asn Asn Ile Val Asp His Ala Ile Lys Ser Lys Asp His Ala Thr
            355                 360                 365

Phe Asn Phe Leu Gln Trp Tyr Val Ala Glu Gln His Glu Glu Glu Val
        370                 375                 380

Leu Phe Lys Asp Ile Leu Asp Lys Ile Glu Leu Ile Gly Asn Glu Asn
385                 390                 395                 400

His Gly Leu Tyr Leu Ala Asp Gln Tyr Val Lys Gly Ile Ala Lys Ser
                405                 410                 415

Arg Lys Ser Gly Ser
            420

<210> SEQ ID NO 137
<211> LENGTH: 1266
<212> TYPE: DNA
<213> ORGANISM: Artificial Sequence
<220> FEATURE:
<223> OTHER INFORMATION: Synthetic

<400> SEQUENCE: 137
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt     300 cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaggcgcc     540
tctgctcagg gcaaaggcgt atctaggggc gatcagattg ccgttggcct cgaagatgat     600
ggtgtcgcca ggttccagca gggtccagta gtagttgatc ctgccttcct ggtcccgcac     660
tttgggtctt ttggcgatct cgggggtgaa ctttctgctg tagtggctgg acaccacgga     720
cacgtaggca ttctcggtgt ggtacagggc cttctggatg ccgatgttag gagggtggtg     780
cactccccag aggaccagca cttcttttc tttgttgttg gcgtagctct tgctcaggtt     840
```

| | | | | | |
|---|---|---|---|---|---|
| ggggtacagg | ccgttcttgc | cggtcagcca | cagcaggttt | ctgtagaagc | tgctctcgcc | 900 |
| attgtggcta | caagaggcgc | tcacgccggt | cactgtatga | ttgggccagc | tgctctcttt | 960 |
| ggggaagatc | tcgaatctct | cgaagctgga | cacgctggac | agctgttctc | tcagttcctc | 1020 |
| gtaatcggcg | aagtggccag | ggaagcaggt | gccattctca | gggttgggct | tctccacgat | 1080 |
| gtaggaccag | gactctttgg | aaatcagcag | ctcgcactca | ggattgccca | gaatccagcc | 1140 |
| ggccacgcta | caatttccca | gctgcagagg | ggcaatggct | agcacgccct | gaggcagcag | 1200 |
| caggttgctc | accaccagca | gcagcagcag | tctgctgccc | ttctggctgc | tgcccttgct | 1260 |
| gtccat | | | | | | 1266 |

<210> SEQ ID NO 138
<211> LENGTH: 1269
<212> TYPE: DNA
<213> ORGANISM: Artificial Sequence
<220> FEATURE:
<223> OTHER INFORMATION: Synthetic

<400> SEQUENCE: 138

| | | | | | |
|---|---|---|---|---|---|
| atggacagca | agggcagcag | ccagaagggc | agcagactgc | tgctgctgct | ggtggtgagc | 60 |
| aacctgctgc | tgcctcaggg | cgtgctagcc | atcgctcctc | tgcagctggg | gaagtgcagc | 120 |
| atcgcagggt | ggattctggg | aaatccagag | tgtgaatccc | tgttttctaa | gaaaagctgg | 180 |
| tcctacattg | ccgagacacc | caactccgaa | atggcactt | gtttccctgg | gtatttcgct | 240 |
| gattatgagg | aactgcgcga | gcagctgagc | tccgtgtcta | gtttcgagcg | atttgaaatc | 300 |
| ttccccaagg | aatcaagctg | gcctaaacac | aacgtgaccc | gggggtcac | agcctcttgc | 360 |
| agtcataagg | gaaaatgttc | tttctacaga | aatctgctgt | ggctgacaga | gaagaacggg | 420 |
| agttacccaa | atctgtcaaa | gagctacgtg | aacaataagg | agaaagaagt | gctggtcctg | 480 |
| tggggcgtcc | accatccctc | taacatcgag | gaccagaaga | ctatctaccg | aaaagaaaac | 540 |
| gcatatgtga | gcgtggtctc | ctctcactac | aatcggcgt | tcacccccga | gatcgccaag | 600 |
| aggcccaaag | tgcgcgacca | ggaaggccgc | attaactact | attggaccct | gctggagcca | 660 |
| ggcgatacaa | tcattttcga | agccaacggg | aatctgatcg | ctcccctggta | tgcatttgcc | 720 |
| ctgtcaagag | gagcctccgg | agagagccag | gtgaggcagc | agttcagcaa | ggacatcgag | 780 |
| aagctgctga | cgagcaggt | gaacaaggag | atgcagagca | gcaacctgta | catgagcatg | 840 |
| agcagctggt | gctacaccca | cagcctggac | ggcgcggcc | tgttcctgtt | cgaccacgcc | 900 |
| gccgaggagt | acgagcacgc | caagaagctg | atcatcttcc | tgaacgagaa | caacgtgccc | 960 |
| gtgcagctga | ccagcatcag | cgcccccgag | cacaagttcg | agggcctgac | ccagatcttc | 1020 |
| cagaaggcct | acgagcacga | gcagcacatc | agcgagagca | tcaacaacat | cgtggaccac | 1080 |
| gccatcaaga | gcaaggacca | cgccaccttc | aacttcctgc | agtggtacgt | ggccgagcag | 1140 |
| cacgaggagg | aggtgctgtt | caaggacatc | ctggacaaga | tcgagctgat | cggcaacgag | 1200 |
| aaccacggcc | tgtacctggc | cgaccagtac | gtgaagggca | tcgccaagag | caggaagagc | 1260 |
| ggatcctag | | | | | | 1269 |

<210> SEQ ID NO 139
<211> LENGTH: 422
<212> TYPE: PRT
<213> ORGANISM: Artificial Sequence
<220> FEATURE:
<223> OTHER INFORMATION: Synthetic

<400> SEQUENCE: 139

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Ile Ala
            20                  25                  30

Pro Leu Gln Leu Gly Lys Cys Ser Ile Ala Gly Trp Ile Leu Gly Asn
                35                  40                  45

Pro Glu Cys Glu Ser Leu Phe Ser Lys Ser Trp Ser Tyr Ile Ala
    50                  55                  60

Glu Thr Pro Asn Ser Glu Asn Gly Thr Cys Phe Pro Gly Tyr Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Ser Ser Trp Pro Lys His Asn Val
                100                 105                 110

Thr Arg Gly Val Thr Ala Ser Cys Ser His Lys Gly Lys Cys Ser Phe
            115                 120                 125

Tyr Arg Asn Leu Leu Trp Leu Thr Glu Lys Asn Gly Ser Tyr Pro Asn
    130                 135                 140

Leu Ser Lys Ser Tyr Val Asn Asn Lys Glu Lys Glu Val Leu Val Leu
145                 150                 155                 160

Trp Gly Val His His Pro Ser Asn Ile Glu Asp Gln Lys Thr Ile Tyr
                165                 170                 175

Arg Lys Glu Asn Ala Tyr Val Ser Val Val Ser Ser His Tyr Asn Arg
                180                 185                 190

Arg Phe Thr Pro Glu Ile Ala Lys Arg Pro Lys Val Arg Asp Gln Glu
            195                 200                 205

Gly Arg Ile Asn Tyr Tyr Trp Thr Leu Leu Glu Pro Gly Asp Thr Ile
    210                 215                 220

Ile Phe Glu Ala Asn Gly Asn Leu Ile Ala Pro Trp Tyr Ala Phe Ala
225                 230                 235                 240

Leu Ser Arg Gly Ala Ser Gly Glu Ser Gln Val Arg Gln Gln Phe Ser
                245                 250                 255

Lys Asp Ile Glu Lys Leu Leu Asn Glu Gln Val Asn Lys Glu Met Gln
                260                 265                 270

Ser Ser Asn Leu Tyr Met Ser Met Ser Ser Trp Cys Tyr Thr His Ser
            275                 280                 285

Leu Asp Gly Ala Gly Leu Phe Leu Phe Asp His Ala Ala Glu Glu Tyr
    290                 295                 300

Glu His Ala Lys Lys Leu Ile Ile Phe Leu Asn Glu Asn Asn Val Pro
305                 310                 315                 320

Val Gln Leu Thr Ser Ile Ser Ala Pro Glu His Lys Phe Glu Gly Leu
                325                 330                 335

Thr Gln Ile Phe Gln Lys Ala Tyr Glu His Glu Gln His Ile Ser Glu
            340                 345                 350

Ser Ile Asn Asn Ile Val Asp His Ala Ile Lys Ser Lys Asp His Ala
    355                 360                 365

Thr Phe Asn Phe Leu Gln Trp Tyr Val Ala Glu Gln His Glu Glu Glu
    370                 375                 380

Val Leu Phe Lys Asp Ile Leu Asp Lys Ile Glu Leu Ile Gly Asn Glu
385                 390                 395                 400

Asn His Gly Leu Tyr Leu Ala Asp Gln Tyr Val Lys Gly Ile Ala Lys
                405                 410                 415
```

Ser Arg Lys Ser Gly Ser
         420

<210> SEQ ID NO 140
<211> LENGTH: 1269
<212> TYPE: DNA
<213> ORGANISM: Artificial Sequence
<220> FEATURE:
<223> OTHER INFORMATION: Synthetic

<400> SEQUENCE: 140

```
ctaggatccg ctcttcctgc tcttggcgat gcccttcacg tactggtcgg ccaggtacag     60
gccgtggttc tcgttgccga tcagctcgat cttgtccagg atgtccttga acagcacctc    120
ctcctcgtgc tgctcggcca cgtaccactg caggaagttg aaggtggcgt ggtccttgct    180
cttgatggcg tggtccacga tgttgttgat gctctcgctg atgtgctgct cgtgctcgta    240
ggccttctgg aagatctggg tcaggccctc gaacttgtgc tcggggcgc tgatgctggt    300
cagctgcacg ggcacgttgt tctcgttcag gaagatgatc agcttcttgg cgtgctcgta    360
ctcctcggcg cgtggtcga acaggaacag gccggcgccg tccaggctgt gggtgtagca    420
ccagctgctc atgctcatgt acaggttgct gctctgcatc tccttgttca cctgctcgtt    480
cagcagcttc tcgatgtcct tgctgaactg ctgcctcacc tggctctctc cggaggctcc    540
tcttgacagg gcaaatgcat accagggagc gatcagattc cgttggcttt cgaaaatgat    600
tgtatcgcct ggctccagca gggtccaata gtagttaatg cggccttcct ggtcgcgcac    660
tttgggcctc ttggcgatct cggggggtgaa ccgccgattg tagtgagagg agaccacgct    720
cacatatgcg ttttctttc ggtagatagt cttctggtcc tcgatgttag agggatggtg    780
gacgccccac aggaccagca cttctttctc cttattgttc acgtagctct ttgacagatt    840
tgggtaactc ccgttcttct ctgtcagcca cagcagattt ctgtagaaag aacattttcc    900
cttatgactg caagaggctg tgaccccccg ggtcacgttg tgtttaggcc agcttgattc    960
cttggggaag atttcaaatc gctcgaaact agacacggag ctcagctgct cgcgcagttc   1020
ctcataatca gcgaaatacc cagggaaaca agtgccattt cggagttgg gtgtctcggc   1080
aatgtaggac cagcttttct tagaaaacag ggattcacac tctggatttc ccagaatcca   1140
ccctgcgatg ctgcacttcc ccagctgcag aggagcgatg ctagcacgc cctgaggcag   1200
cagcaggttg ctcaccacca gcagcagcag cagtctgctg cccttctggc tgctgccctt   1260
gctgtccat                                                          1269
```

<210> SEQ ID NO 141
<211> LENGTH: 1269
<212> TYPE: DNA
<213> ORGANISM: Artificial Sequence
<220> FEATURE:
<223> OTHER INFORMATION: Synthetic

<400> SEQUENCE: 141

```
atggacagca agggcagcag ccagaagggc agcagactgc tgctgctgct ggtggtgagc     60
aacctgctgc tgcctcaggg cgtgctagcc atcgccctc tgcagctggg caagtgcaac    120
atcgctggct ggattctggg gaatccagag tgtgaatctc tgtttagtaa gaaaagctgg    180
tcctacattg ctgagacccc caacagcgaa atggaacat gcttccctgg ctatttcgca    240
gattatgagg aactgaggga gcagctgagc tccgtgtcta gtttcgagag atttgaaatc    300
ttccccaagg aaaggtcttg gcctaaacac aacattaccc ggggcgtgac agccgcttgt    360
```

```
agtcataagg ggaaatcaag cttttacaga aacctgctgt ggctgacaga gaagaatggc    420
tcatacccaa acctgaacaa gagctatgtg aacaataagg agaaagaagt gctggtcctg    480
tggggcgtcc accatccctc taacatcgag gaccagaaga ctctgtaccg aaaagaaaat    540
gcctatgtgt ccgtggtctc ctctaactac aatcggcggt tcacccccga gatcgctgaa    600
aggccaaagg tgcgcggaca ggcaggacgc attaactact attggactct gctggagcca    660
ggagatacca tcattttcga agcaaacggc aatctgatcg cccctggca cgcttttgca    720 ctgagccggg gagcctccgg agagagccag gtgaggcagc agttcagcaa ggacatcgag    780
aagctgctga cgagcaggt gaacaaggag atgcagagca gcaacctgta catgagcatg    840
agcagctggt gctacaccca cagcctggac ggcgccggcc tgttcctgtt cgaccacgcc    900
gccgaggagt acgagcacgc caagaagctg atcatcttcc tgaacgagaa caacgtgccc    960
gtgcagctga ccagcatcag cgcccccgag cacaagttcg agggcctgac ccagatcttc   1020
cagaaggcct acgagcacga gcagcacatc agcgagagca tcaacaacat cgtggaccac   1080
gccatcaaga gcaaggacca cgccaccttc aacttcctgc agtggtacgt ggccgagcag   1140
cacgaggagg aggtgctgtt caaggacatc ctggacaaga tcgagctgat cggcaacgag   1200
aaccacggcc tgtacctggc cgaccagtac gtgaagggca tcgccaagag caggaagagc   1260
ggatcctag                                                            1269
```

<210> SEQ ID NO 142
<211> LENGTH: 422
<212> TYPE: PRT
<213> ORGANISM: Artificial Sequence
<220> FEATURE:
<223> OTHER INFORMATION: Synthetic

<400> SEQUENCE: 142

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Ile Ala
            20                  25                  30

Pro Leu Gln Leu Gly Lys Cys Asn Ile Ala Gly Trp Ile Leu Gly Asn
        35                  40                  45

Pro Glu Cys Glu Ser Leu Phe Ser Lys Lys Ser Trp Ser Tyr Ile Ala
    50                  55                  60

Glu Thr Pro Asn Ser Glu Asn Gly Thr Cys Phe Pro Gly Tyr Phe Ala
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Glu Arg Ser Trp Pro Lys His Asn Ile
            100                 105                 110

Thr Arg Gly Val Thr Ala Ala Cys Ser His Lys Gly Lys Ser Ser Phe
        115                 120                 125

Tyr Arg Asn Leu Leu Trp Leu Thr Glu Lys Asn Gly Ser Tyr Pro Asn
    130                 135                 140

Leu Asn Lys Ser Tyr Val Asn Lys Glu Lys Glu Val Leu Val Leu
145                 150                 155                 160

Trp Gly Val His His Pro Ser Asn Ile Glu Asp Gln Lys Thr Leu Tyr
                165                 170                 175

Arg Lys Glu Asn Ala Tyr Val Ser Val Val Ser Ser Asn Tyr Asn Arg
            180                 185                 190

Arg Phe Thr Pro Glu Ile Ala Glu Arg Pro Lys Val Arg Gly Gln Ala

```
                195                 200                 205
Gly Arg Ile Asn Tyr Tyr Trp Thr Leu Leu Glu Pro Gly Asp Thr Ile
    210                 215                 220

Ile Phe Glu Ala Asn Gly Asn Leu Ile Ala Pro Trp His Ala Phe Ala
225                 230                 235                 240

Leu Ser Arg Gly Ala Ser Gly Glu Ser Gln Val Arg Gln Gln Phe Ser
                245                 250                 255

Lys Asp Ile Glu Lys Leu Leu Asn Glu Gln Val Asn Lys Glu Met Gln
            260                 265                 270

Ser Ser Asn Leu Tyr Met Ser Met Ser Ser Trp Cys Tyr Thr His Ser
        275                 280                 285

Leu Asp Gly Ala Gly Leu Phe Leu Phe Asp His Ala Ala Glu Glu Tyr
    290                 295                 300

Glu His Ala Lys Lys Leu Ile Ile Phe Leu Asn Glu Asn Asn Val Pro
305                 310                 315                 320

Val Gln Leu Thr Ser Ile Ser Ala Pro Glu His Lys Phe Glu Gly Leu
                325                 330                 335

Thr Gln Ile Phe Gln Lys Ala Tyr Glu His Glu Gln His Ile Ser Glu
            340                 345                 350

Ser Ile Asn Asn Ile Val Asp His Ala Ile Lys Ser Lys Asp His Ala
        355                 360                 365

Thr Phe Asn Phe Leu Gln Trp Tyr Val Ala Glu Gln His Glu Glu Glu
    370                 375                 380

Val Leu Phe Lys Asp Ile Leu Asp Lys Ile Glu Leu Ile Gly Asn Glu
385                 390                 395                 400

Asn His Gly Leu Tyr Leu Ala Asp Gln Tyr Val Lys Gly Ile Ala Lys
                405                 410                 415

Ser Arg Lys Ser Gly Ser
            420

<210> SEQ ID NO 143
<211> LENGTH: 1269
<212> TYPE: DNA
<213> ORGANISM: Artificial Sequence
<220> FEATURE:
<223> OTHER INFORMATION: Synthetic

<400> SEQUENCE: 143
ctaggatccg ctcttcctgc tcttggcgat gcccttcacg tactggtcgg ccaggtacag     60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcggggcgc tgatgctggt   300 cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggctcc   540
ccggctcagt gcaaaagcgt gccagggggc gatcagattg ccgtttgctt cgaaaatgat   600
ggtatctcct ggctccagca gagtccaata gtagttaatg cgtcctgcct gtccgcgcac   660
ctttggcctt tcagcgatct cggggggtgaa ccgccgattg tagttagagg agaccacgga   720
cacataggca ttttcttttc ggtacagagt cttctggtcc tcgatgttag agggatggtg   780
```

```
gacgccccac aggaccagca cttctttctc cttattgttc acatagctct tgttcaggtt      840
tgggtatgag ccattcttct ctgtcagcca cagcaggttc ctgtaaaagc ttgatttccc      900
cttatgacta caagcggctg tcacgccccg ggtaatgttg tgtttaggcc aagacctttc      960
cttggggaag atttcaaatc tctcgaaact agacacggag ctcagctgct ccctcagttc     1020
ctcataatct gcgaaatagc cagggaagca tgttccattt tcgctgttgg gggtctcagc     1080
aatgtaggac cagcttttct tactaaacag agattcacac tctggattcc ccagaatcca     1140
gccagcgatg ttgcacttgc ccagctgcag aggggcgatg ctagcacgc cctgaggcag      1200 cagcaggttg ctcaccacca gcagcagcag cagtctgctg cccttctggc tgctgccctt     1260
gctgtccat                                                             1269
```

<210> SEQ ID NO 144
<211> LENGTH: 1266
<212> TYPE: DNA
<213> ORGANISM: Artificial Sequence
<220> FEATURE:
<223> OTHER INFORMATION: Synthetic

<400> SEQUENCE: 144

```
atggacagca agggcagcag ccagaagggc agcagactgc tgctgctgct ggtggtgagc        60
aacctgctgc tgcctcaggg cgtgctagcc gtgaagcctc tgatcctgag agattgtagc       120
gtggctggat ggctgctggg caaccctatg tgcgacgagt tcatcaacgt gcccgagtgg       180
agctatatcg tggagaaggc caaccccacc aacgatctgt gtttccccgg cagcttcaac       240
gattacgagg aactgaagca cctgctgtcc cggatcaacc acttcgagaa gatccagatc       300
atccccaagt cctcttggag cgatcacgaa gcctctagcg gagtgtctag cgcctgtcct       360
tacctgggca gccccagctt cttcagaaac gtggtgtggc tgatcaagaa gaacagcacc       420
taccccacca tcaagaagag ctacaacaac accaaccagg aagatctgct ggtcctgtgg       480
ggaatccacc accctaatga tgccgccgag cagaccagac tgtaccagaa ccccaccacc       540
tatatcagca tcggcaccag caccctgaat cagagactgg tgcccaagat cgccaccaga       600
tccaaggtga acgccagag cggcaggatg gaattcttct ggaccatcct gaagcccaac       660
gacgccatca acttcgagag caacggcaac tttatcgccc tgagtacgc ctacaagatc       720 gtgaagaagg gctccggaga gagccaggtg aggcagcagt tcagcaagga catcgagaag       780
ctgctgaacg agcaggtgaa caaggagatg cagagcagca acctgtacat gagcatgagc       840
agctggtgct acacccacag cctggacggc gccggcctgt tcctgttcga ccacgccgcc       900
gaggagtacg agcacgccaa gaagctgatc atcttcctga cgagaacaa cgtgcccgtg       960 cagctgacca gcatcagcgc ccccgagcac aagttcgagg cctgaccca gatcttccag      1020 aaggcctacg agcacgagca gcacatcagc gagagcatca acaacatcgt ggaccacgcc      1080
atcaagagca aggaccacgc cacccttcaac ttcctgcagt ggtacgtggc cgagcagcac      1140
gaggaggagg tgctgttcaa ggacatcctg gacaagatcg agctgatcgg caacgagaac      1200
cacggcctgt acctggccga ccagtacgtg aagggcatcg ccaagagcag gaagagcgga      1260
tcctag                                                                1266
```

<210> SEQ ID NO 145
<211> LENGTH: 421
<212> TYPE: PRT
<213> ORGANISM: Artificial Sequence
<220> FEATURE:

<223> OTHER INFORMATION: Synthetic

<400> SEQUENCE: 145

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Val Lys
            20                  25                  30

Pro Leu Ile Leu Arg Asp Cys Ser Val Ala Gly Trp Leu Leu Gly Asn
        35                  40                  45

Pro Met Cys Asp Glu Phe Ile Asn Val Pro Glu Trp Ser Tyr Ile Val
    50                  55                  60

Glu Lys Ala Asn Pro Thr Asn Asp Leu Cys Phe Pro Gly Ser Phe Asn
65                  70                  75                  80

Asp Tyr Glu Glu Leu Lys His Leu Leu Ser Arg Ile Asn His Phe Glu
                85                  90                  95

Lys Ile Gln Ile Ile Pro Lys Ser Ser Trp Ser Asp His Glu Ala Ser
            100                 105                 110

Ser Gly Val Ser Ser Ala Cys Pro Tyr Leu Gly Ser Pro Ser Phe Phe
        115                 120                 125

Arg Asn Val Val Trp Leu Ile Lys Lys Asn Ser Thr Tyr Pro Thr Ile
    130                 135                 140

Lys Lys Ser Tyr Asn Asn Thr Asn Gln Glu Asp Leu Leu Val Leu Trp
145                 150                 155                 160

Gly Ile His His Pro Asn Asp Ala Ala Glu Gln Thr Arg Leu Tyr Gln
                165                 170                 175

Asn Pro Thr Thr Tyr Ile Ser Ile Gly Thr Ser Thr Leu Asn Gln Arg
            180                 185                 190

Leu Val Pro Lys Ile Ala Thr Arg Ser Lys Val Asn Gly Gln Ser Gly
        195                 200                 205

Arg Met Glu Phe Phe Trp Thr Ile Leu Lys Pro Asn Asp Ala Ile Asn
    210                 215                 220

Phe Glu Ser Asn Gly Asn Phe Ile Ala Pro Glu Tyr Ala Tyr Lys Ile
225                 230                 235                 240

Val Lys Lys Gly Ser Gly Glu Ser Gln Val Arg Gln Gln Phe Ser Lys
                245                 250                 255

Asp Ile Glu Lys Leu Leu Asn Glu Gln Val Asn Lys Glu Met Gln Ser
            260                 265                 270

Ser Asn Leu Tyr Met Ser Met Ser Ser Trp Cys Tyr Thr His Ser Leu
        275                 280                 285

Asp Gly Ala Gly Leu Phe Leu Phe Asp His Ala Ala Glu Glu Tyr Glu
    290                 295                 300

His Ala Lys Lys Leu Ile Ile Phe Leu Asn Glu Asn Val Pro Val
305                 310                 315                 320

Gln Leu Thr Ser Ile Ser Ala Pro Glu His Lys Phe Glu Gly Leu Thr
                325                 330                 335

Gln Ile Phe Gln Lys Ala Tyr Glu His Gln His Ile Ser Glu Ser
            340                 345                 350

Ile Asn Asn Ile Val Asp His Ala Ile Lys Ser Lys Asp His Ala Thr
        355                 360                 365

Phe Asn Phe Leu Gln Trp Tyr Val Ala Glu Gln His Glu Glu Val
    370                 375                 380

Leu Phe Lys Asp Ile Leu Asp Lys Ile Glu Leu Ile Gly Asn Glu Asn
385                 390                 395                 400
```

His Gly Leu Tyr Leu Ala Asp Gln Tyr Val Lys Gly Ile Ala Lys Ser
            405                 410                 415

Arg Lys Ser Gly Ser
        420

<210> SEQ ID NO 146
<211> LENGTH: 1266
<212> TYPE: DNA
<213> ORGANISM: Artificial Sequence
<220> FEATURE:
<223> OTHER INFORMATION: Synthetic

<400> SEQUENCE: 146
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcggggcgc tgatgctggt   300 cagctgcacg ggcacgttgt tctcgttcag gaagatgatc agcttcttgg cgtgctcgta   360
ctcctcggcg cgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggagccctt   540
cttcacgatc ttgtaggcgt actcaggggc gataaagttg ccgttgctct cgaagttgat   600
ggcgtcgttg gcttcagga tggtccagaa gaattccatc ctgccgctct ggccgttcac   660
cttggatctg gtggcgatct tgggcaccag tctctgattc agggtgctgg tgccgatgct   720
gatataggtg gtggggttct ggtacagtct ggtctgctcg gcggcatcat tagggtggtg   780
gattccccac aggaccagca gatcttcctg gttggtgttg ttgtagctct tcttgatggt   840
ggggtaggtg ctgttcttct tgatcagcca ccacgtttt ctgaagaagc tggggctgcc   900
caggtaagga caggcgctag acactccgct agaggcttcg tgatcgctcc aagaggactt   960
ggggatgatc tggatcttct cgaagtggtt gatccgggac agcaggtgct tcagttcctc  1020
gtaatcgttg aagctgccgg ggaaacacag atcgttggtg gggttggcct tctccacgat  1080
atagctccac tcgggcacgt tgatgaactc gtcgcacata gggttgccca gcagccatcc  1140
agccacgcta caatctctca ggatcagagg cttcacggct agcacgccct gaggcagcag  1200
caggttgctc accaccagca gcagcagcag tctgctgccc ttctggctgc tgcccttgct  1260
gtccat                                                            1266

<210> SEQ ID NO 147
<211> LENGTH: 1263
<212> TYPE: DNA
<213> ORGANISM: Artificial Sequence
<220> FEATURE:
<223> OTHER INFORMATION: Synthetic

<400> SEQUENCE: 147
atggacagta aggggtcttc acagaaaggg tcacggctgc tgctgctgct ggtcgtcagt    60
aacctgctgc tgcctcaggg agtgctagcc gtgaaacccc tgattctgcg cgactgtagc   120
gtggccggat ggctgctggg caaccctatg tgcgatgagt ttattaacgt ccctgagtgg   180
agctacatcg tggagaaggc atccccagcc aacgacctgt gcttccccgg caacttcaat   240
gattatgagg aactgaaaca cctgctgtct cgaatcaacc atttcgaaaa gatccagatc   300

```
atcccaaaga gctcctggag caatcacgac gcctctagtg gagtctcaag cgcttgtccc    360
tatctgggcc ggtcctcttt ctttagaaac gtggtctggc tgatcaagaa aaattctgcc    420
taccctacaa ttaagagaag ttacaacaac actaatcagg aggacctgct ggtgctgtgg    480
ggcgtccacc atcctaacga tgccgctgaa cagaccaaac tgtaccagaa tccaaccaca    540
tatatcagtg tggggacttc aaccctgaac cagaggctgg tgcccgagat tgcaacccgc    600
cctaaggtca atggccagtc cgggcggatg gaattctttt ggacaatcct gaaacccaac    660
gatgctatta atttcgagag caacgggaat tttatcgctc ctgaatacgc atataagatt    720
gtgaagaaag gctccggaga aagtcaggtg aggcagcagt tcagtaagga tatcgagaaa    780
ctgctgaacg aacaggtgaa caaggagatg cagtctagta acctgtacat gagtatgtca    840
agctggtgtt atacccactc actggacgga gccggcctgt tcctgtttga tcacgcagcc    900
gaggaatacg aacatgctaa gaaactgatc atttttctga cgagaacaa cgtcccagtg    960 cagctgacaa gtatctcagc ccccgagcat aagttcgaag gcctgactca gatctttcag    1020
aaagcctacg aacacgagca gcatattagc gagtccatca caatattgt ggaccacgca    1080 attaagagca agatcatgc caccttcaat tttctgcagt ggtacgtggc cgagcagcac    1140
gaggaagagg tgctgttcaa ggacatcctg gataaaatcg aactgattgg caacgagaat    1200
catgggctgt acctggcaga ccagtatgtg aagggcattg ctaagtcaag aaaaagctga    1260
tga                                                                  1263
```

<210> SEQ ID NO 148
<211> LENGTH: 419
<212> TYPE: PRT
<213> ORGANISM: Artificial Sequence
<220> FEATURE:
<223> OTHER INFORMATION: Synthetic

<400> SEQUENCE: 148

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Val Lys
            20                  25                  30

Pro Leu Ile Leu Arg Asp Cys Ser Val Ala Gly Trp Leu Leu Gly Asn
        35                  40                  45

Pro Met Cys Asp Glu Phe Ile Asn Val Pro Glu Trp Ser Tyr Ile Val
    50                  55                  60

Glu Lys Ala Ser Pro Ala Asn Asp Leu Cys Phe Pro Gly Asn Phe Asn
65                  70                  75                  80

Asp Tyr Glu Glu Leu Lys His Leu Leu Ser Arg Ile Asn His Phe Glu
                85                  90                  95

Lys Ile Gln Ile Ile Pro Lys Ser Ser Trp Ser Asn His Asp Ala Ser
            100                 105                 110

Ser Gly Val Ser Ser Ala Cys Pro Tyr Leu Gly Arg Ser Ser Phe Phe
        115                 120                 125

Arg Asn Val Val Trp Leu Ile Lys Lys Asn Ser Ala Tyr Pro Thr Ile
    130                 135                 140

Lys Arg Ser Tyr Asn Asn Thr Asn Gln Glu Asp Leu Leu Val Leu Trp
145                 150                 155                 160

Gly Val His His Pro Asn Asp Ala Ala Glu Gln Thr Lys Leu Tyr Gln
                165                 170                 175

Asn Pro Thr Thr Tyr Ile Ser Val Gly Thr Ser Thr Leu Asn Gln Arg

|  | 180 |  |  |  | 185 |  |  |  | 190 |  |  |
|---|---|---|---|---|---|---|---|---|---|---|---|
| Leu | Val | Pro | Glu | Ile | Ala | Thr | Arg | Pro | Lys | Val | Asn | Gly | Gln | Ser | Gly |
|  |  | 195 |  |  |  |  | 200 |  |  |  |  | 205 |  |  |  |
| Arg | Met | Glu | Phe | Phe | Trp | Thr | Ile | Leu | Lys | Pro | Asn | Asp | Ala | Ile | Asn |
|  | 210 |  |  |  |  | 215 |  |  |  |  | 220 |  |  |  |  |
| Phe | Glu | Ser | Asn | Gly | Asn | Phe | Ile | Ala | Pro | Glu | Tyr | Ala | Tyr | Lys | Ile |
| 225 |  |  |  |  | 230 |  |  |  |  | 235 |  |  |  |  | 240 |
| Val | Lys | Lys | Gly | Ser | Gly | Glu | Ser | Gln | Val | Arg | Gln | Gln | Phe | Ser | Lys |
|  |  |  |  | 245 |  |  |  |  | 250 |  |  |  |  | 255 |  |
| Asp | Ile | Glu | Lys | Leu | Leu | Asn | Glu | Gln | Val | Asn | Lys | Glu | Met | Gln | Ser |
|  |  |  | 260 |  |  |  |  | 265 |  |  |  |  | 270 |  |  |
| Ser | Asn | Leu | Tyr | Met | Ser | Met | Ser | Ser | Trp | Cys | Tyr | Thr | His | Ser | Leu |
|  | 275 |  |  |  |  | 280 |  |  |  |  | 285 |  |  |  |  |
| Asp | Gly | Ala | Gly | Leu | Phe | Leu | Phe | Asp | His | Ala | Ala | Glu | Glu | Tyr | Glu |
|  | 290 |  |  |  |  | 295 |  |  |  |  | 300 |  |  |  |  |
| His | Ala | Lys | Lys | Leu | Ile | Ile | Phe | Leu | Asn | Glu | Asn | Asn | Val | Pro | Val |
| 305 |  |  |  |  | 310 |  |  |  |  | 315 |  |  |  |  | 320 |
| Gln | Leu | Thr | Ser | Ile | Ser | Ala | Pro | Glu | His | Lys | Phe | Glu | Gly | Leu | Thr |
|  |  |  | 325 |  |  |  |  | 330 |  |  |  |  | 335 |  |  |
| Gln | Ile | Phe | Gln | Lys | Ala | Tyr | Glu | His | Glu | Gln | His | Ile | Ser | Glu | Ser |
|  |  | 340 |  |  |  |  | 345 |  |  |  |  | 350 |  |  |  |
| Ile | Asn | Asn | Ile | Val | Asp | His | Ala | Ile | Lys | Ser | Lys | Asp | His | Ala | Thr |
|  | 355 |  |  |  |  | 360 |  |  |  |  | 365 |  |  |  |  |
| Phe | Asn | Phe | Leu | Gln | Trp | Tyr | Val | Ala | Glu | Gln | His | Glu | Glu | Glu | Val |
|  | 370 |  |  |  |  | 375 |  |  |  |  | 380 |  |  |  |  |
| Leu | Phe | Lys | Asp | Ile | Leu | Asp | Lys | Ile | Glu | Leu | Ile | Gly | Asn | Glu | Asn |
| 385 |  |  |  |  | 390 |  |  |  |  | 395 |  |  |  |  | 400 |
| His | Gly | Leu | Tyr | Leu | Ala | Asp | Gln | Tyr | Val | Lys | Gly | Ile | Ala | Lys | Ser |
|  |  |  |  | 405 |  |  |  |  | 410 |  |  |  |  | 415 |  |
| Arg | Lys | Ser |  |  |  |  |  |  |  |  |  |  |  |  |  |

<210> SEQ ID NO 149
<211> LENGTH: 1263
<212> TYPE: DNA
<213> ORGANISM: Artificial Sequence
<220> FEATURE:
<223> OTHER INFORMATION: Synthetic

<400> SEQUENCE: 149

| tcatcagctt | tttcttgact | tagcaatgcc | cttcacatac | tggtctgcca | ggtacagccc | 60 |
| atgattctcg | ttgccaatca | gttcgatttt | atccaggatg | tccttgaaca | gcacctcttc | 120 |
| ctcgtgctgc | tcggccacgt | accactgcag | aaaattgaag | gtggcatgat | ctttgctctt | 180 |
| aattgcgtgg | tccacaatat | tgttgatgga | ctcgctaata | tgctgctcgt | gttcgtaggc | 240 |
| tttctgaaag | atctgagtca | ggccttcgaa | cttatgctcg | ggggctgaga | tacttgtcag | 300 |
| ctgcactggg | acgttgttct | cgttcagaaa | aatgatcagt | tcttagcat | gttcgtattc | 360 |
| ctcggctgcg | tgatcaaaca | ggaacaggcc | ggctccgtcc | agtgagtggg | tataacacca | 420 |
| gcttgacata | tcatgtaca | ggttactaga | ctgcatctcc | ttgttcacct | gttcgttcag | 480 |
| cagtttctcg | atatccttac | tgaactgctg | cctcacctga | ctttctccgg | agcctttctt | 540 |
| cacaatctta | tatgcgtatt | caggagcgat | aaaattcccg | ttgctctcga | aattaatagc | 600 |
| atcgttgggt | ttcaggattg | tccaaaagaa | ttccatccgc | ccggactggc | cattgacctt | 660 |
| agggcgggtt | gcaatctcgg | gcaccagcct | ctggttcagg | gttgaagtcc | ccacactgat | 720 |

atatgtggtt ggattctggt acagtttggt ctgttcagcg gcatcgttag gatggtggac 780
gccccacagc accagcaggt cctcctgatt agtgttgttg taacttctct taattgtagg 840
gtaggcagaa tttttcttga tcagccagac cacgtttcta aagaaagagg accggcccag 900
atagggacaa gcgcttgaga ctccactaga ggcgtcgtga ttgctccagg agctctttgg 960
gatgatctgg atcttttcga aatggttgat tcgagacagc aggtgtttca gttcctcata 1020
atcattgaag ttgccgggga agcacaggtc gttggctggg gatgccttct ccacgatgta 1080
gctccactca gggacgttaa taaactcatc gcacataggg ttgcccagca gccatccggc 1140
cacgctacag tcgcgcagaa tcaggggttt cacggctagc actccctgag gcagcagcag 1200
gttactgacg accagcagca gcagcagccg tgaccctttc tgtgaagacc ccttactgtc 1260
cat 1263

<210> SEQ ID NO 150
<211> LENGTH: 1263
<212> TYPE: DNA
<213> ORGANISM: Artificial Sequence
<220> FEATURE:
<223> OTHER INFORMATION: Synthetic
<400> SEQUENCE: 150
atggacagta aggggtcttc acagaaaggg tcacggctgc tgctgctgct ggtcgtcagt 60
aacctgctgc tgcctcaggg agtgctagcc gtgaagcctc tgattctgaa agactgctcc 120
gtcgctggat ggctgctggg gaaccctatg tgtgatgagt ttattaacgt gcctgagtgg 180
agctacatcg tggagaaggc caaccccgct aatgacctgt gcttccctgg caacttcaat 240
gattatgagg aactgaaaca cctgctgagc cgaatcaacc attttgagaa gattcagatc 300
attcccaaag actcatggag cgatcacgaa gcttccctgg gagtgagctc cgcatgtcct 360
tatcagggca actctagttt ctttagaaat gtggtctggc tgatcaagaa aggcaacgcc 420
tacccaacaa ttaagaaatc ttacaacaac actaatcagg aagacctgct ggtcctgtgg 480
ggcatccacc atccaaacga tgaggccgaa cagaccaggc tgtaccagaa tcccaccaca 540
tatatctcca ttggcacttc taccctgaac cagcggctgg tgcccaagat cgccaccaga 600
agtaaagtca atggccagtc agggcgcatc gacttctttt ggacaattct gaagcctaac 660
gatgctatta atttcgagtc caacgggaat tttatcgcac cagaatacgc ctataagatt 720
gtgaagaaag gctccggaga aagtcaggtg aggcagcagt tcagtaagga tatcgagaaa 780
ctgctgaacg aacaggtgaa caaggagatg cagtctagta acctgtacat gagtatgtca 840
agctggtgtt atacccactc actggacgga gccggcctgt tcctgtttga tcacgcagcc 900
gaggaatacg aacatgctaa gaaactgatc atttttctga acgagaacaa cgtcccagtg 960
cagctgacaa gtatctcagc cccgagcat aagttcgaag gcctgactca gatctttcag 1020
aaagcctacg aacacgagca gcatattagc gagtccatca acaatattgt ggaccacgca 1080
attaagagca aagatcatgc caccttcaat tttctgcagt ggtacgtggc cgagcagcac 1140
gaggaagagg tgctgttcaa ggacatcctg gataaaatcg aactgattgg caacgagaat 1200
catgggctgt acctggcaga ccagtatgtg aagggcattg ctaagtcaag aaaaagctga 1260
tga 1263

<210> SEQ ID NO 151
<211> LENGTH: 419
<212> TYPE: PRT

<213> ORGANISM: Artificial Sequence
<220> FEATURE:
<223> OTHER INFORMATION: Synthetic

<400> SEQUENCE: 151

```
Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Val Lys
                20                  25                  30

Pro Leu Ile Leu Lys Asp Cys Ser Val Ala Gly Trp Leu Leu Gly Asn
            35                  40                  45

Pro Met Cys Asp Glu Phe Ile Asn Val Pro Glu Trp Ser Tyr Ile Val
        50                  55                  60

Glu Lys Ala Asn Pro Ala Asn Asp Leu Cys Phe Pro Gly Asn Phe Asn
65                  70                  75                  80

Asp Tyr Glu Glu Leu Lys His Leu Leu Ser Arg Ile Asn His Phe Glu
                85                  90                  95

Lys Ile Gln Ile Ile Pro Lys Asp Ser Trp Ser Asp His Glu Ala Ser
            100                 105                 110

Leu Gly Val Ser Ser Ala Cys Pro Tyr Gln Gly Asn Ser Ser Phe Phe
        115                 120                 125

Arg Asn Val Val Trp Leu Ile Lys Lys Gly Asn Ala Tyr Pro Thr Ile
130                 135                 140

Lys Lys Ser Tyr Asn Asn Thr Asn Gln Glu Asp Leu Leu Val Leu Trp
                150                 155                 160
145

Gly Ile His His Pro Asn Asp Glu Ala Glu Gln Thr Arg Leu Tyr Gln
            165                 170                 175

Asn Pro Thr Thr Tyr Ile Ser Ile Gly Thr Ser Thr Leu Asn Gln Arg
        180                 185                 190

Leu Val Pro Lys Ile Ala Thr Arg Ser Lys Val Asn Gly Gln Ser Gly
    195                 200                 205

Arg Ile Asp Phe Phe Trp Thr Ile Leu Lys Pro Asn Asp Ala Ile Asn
210                 215                 220

Phe Glu Ser Asn Gly Asn Phe Ile Ala Pro Glu Tyr Ala Tyr Lys Ile
225                 230                 235                 240

Val Lys Lys Gly Ser Gly Glu Ser Gln Val Arg Gln Gln Phe Ser Lys
                245                 250                 255

Asp Ile Glu Lys Leu Leu Asn Glu Gln Val Asn Lys Glu Met Gln Ser
            260                 265                 270

Ser Asn Leu Tyr Met Ser Met Ser Ser Trp Cys Tyr Thr His Ser Leu
        275                 280                 285

Asp Gly Ala Gly Leu Phe Leu Phe Asp His Ala Ala Glu Glu Tyr Glu
    290                 295                 300

His Ala Lys Lys Leu Ile Ile Phe Leu Asn Glu Asn Val Pro Val
305                 310                 315                 320

Gln Leu Thr Ser Ile Ser Ala Pro Glu His Lys Phe Glu Gly Leu Thr
                325                 330                 335

Gln Ile Phe Gln Lys Ala Tyr Glu His Glu Gln His Ile Ser Glu Ser
            340                 345                 350

Ile Asn Asn Ile Val Asp His Ala Ile Lys Ser Lys Asp His Ala Thr
        355                 360                 365

Phe Asn Phe Leu Gln Trp Tyr Val Ala Glu Gln His Glu Glu Glu Val
    370                 375                 380

Leu Phe Lys Asp Ile Leu Asp Lys Ile Glu Leu Ile Gly Asn Glu Asn
```

| | | | |
|---|---|---|---|
| 385 | 390 | 395 | 400 |

His Gly Leu Tyr Leu Ala Asp Gln Tyr Val Lys Gly Ile Ala Lys Ser
                405                      410                      415

Arg Lys Ser

<210> SEQ ID NO 152
<211> LENGTH: 1263
<212> TYPE: DNA
<213> ORGANISM: Artificial Sequence
<220> FEATURE:
<223> OTHER INFORMATION: Synthetic

<400> SEQUENCE: 152

```
tcatcagctt tttcttgact tagcaatgcc cttcacatac tggtctgcca ggtacagccc     60
atgattctcg ttgccaatca gttcgatttt atccaggatg tccttgaaca gcacctcttc    120
ctcgtgctgc tcggccacgt accactgcag aaaattgaag gtggcatgat ctttgctctt    180
aattgcgtgg tccacaatat tgttgatgga ctcgctaata tgctgctcgt gttcgtaggc    240
tttctgaaag atctgagtca ggccttcgaa cttatgctcg ggggctgaga tacttgtcag    300
ctgcactggg acgttgttct cgttcagaaa aatgatcagt ttcttagcat gttcgtattc    360
ctcggctgcg tgatcaaaca ggaacaggcc ggctccgtcc agtgagtggg tataacacca    420
gcttgacata tcatgtaca ggttactaga ctgcatctcc ttgttcacct gttcgttcag    480
cagtttctcg atatccttac tgaactgctg cctcacctga ctttctccgg agcctttctt    540
cacaatctta taggcgtatt ctggtgcgat aaaattcccg ttggactcga attaatagc     600
atcgttaggc ttcagaattg tccaaaagaa gtcgatgcgc cctgactggc cattgacttt    660
acttctggtg gcgatcttgg gcaccagccg ctggttcagg gtagaagtgc caatggagat    720
atatgtggtg ggattctggt acagcctggt ctgttcggcc tcatcgtttg gatggtggat    780
gccccacagg accagcaggt cttcctgatt agtgttgttg taagatttct taattgttgg    840
gtaggcgttg cctttcttga tcagccagac cacatttcta agaaactag agttgccctg     900
ataaggacat gcggagctca ctcccaggga agcttcgtga tcgctccatg agtctttggg    960
aatgatctga atcttctcaa aatggttgat tcggctcagc aggtgtttca gttcctcata   1020
atcattgaag ttgccaggga agcacaggtc attagcgggg ttggccttct ccacgatgta   1080
gctccactca ggcacgttaa taaactcatc acacataggg ttccccagca gccatccagc   1140
gacggagcag tctttcagaa tcagaggctt cacggctagc actccctgag gcagcagcag   1200
gttactgacg accagcagca gcagcagccg tgacccttc tgtgaagacc ccttactgtc    1260
cat                                                                 1263
```

<210> SEQ ID NO 153
<211> LENGTH: 1260
<212> TYPE: DNA
<213> ORGANISM: Artificial Sequence
<220> FEATURE:
<223> OTHER INFORMATION: Synthetic

<400> SEQUENCE: 153

```
atggacagta agggtcttc acagaaaggg tcacggctgc tgctgctgct ggtcgtcagt     60
aacctgctgc tgcctcaggg agtgctagcc gtgaaacccc tgattctgaa agactgctct    120
gtggctggat ggctgctggg caaccctatg tgcgatgagt tcctgaatgt gtccgaatgg    180
tcttacatcg tggagaaggc cagtccagct aacggactgt gcttccccgg cgacttcaat    240
```

```
gattatgagg aactgaagca cctgctgtct aggatcaacc atttcgagaa gatcaagatc    300
atcccaaaga gctcctggtc caatcacgaa gcttctgggg tgtctagtgc atgtagttat    360
ctgggaaagc cctcattctt tcgcaacctg gtctggctga tcaagaaaaa caatacttac    420
ccccccatca aggtcaatta tactaacacc aatcaggaag acctgctggt cctgtggggc    480
atccaccatc ctaacgatga gacagaacag gtgaagatct accagaatcc aaccacatat    540
atttcagtcg gcacaagcac tctgaaccag cggctggtgc ctaagattgc caccagaagc    600
aaagtcaatg gccagtccgg gcgaatggag ttctttttgga caatcctgaa gcccaacgac    660
gctattaatt tcgatagcaa cggcaacttc atcgcacctg aatacgccta taaaattgtg    720
aagaaagggt ccggagaaag tcaggtgagg cagcagttca gtaaggatat cgagaaactg    780
ctgaacgaac aggtgaacaa ggagatgcag tctagtaacc tgtacatgag tatgtcaagc    840
tggtgttata cccactcact ggacggagcc ggcctgttcc tgtttgatca cgcagccgag    900
gaatacgaac atgctaagaa actgatcatt tttctgaacg agaacaacgt cccagtgcag    960
ctgacaagta tctcagcccc cgagcataag ttcgaaggcc tgactcagat ctttcagaaa   1020
gcctacgaac acgagcagca tattagcgag tccatcaaca atattgtgga ccacgcaatt   1080
aagagcaaag atcatgccac cttcaatttt ctgcagtggt acgtggccga gcagcacgag   1140
gaagaggtgc tgttcaagga catcctggat aaaatcgaac tgattggcaa cgagaatcat   1200
gggctgtacc tggcagacca gtatgtgaag ggcattgcta agtcaagaaa aagctgatga   1260
```

<210> SEQ ID NO 154  
<211> LENGTH: 418  
<212> TYPE: PRT  
<213> ORGANISM: Artificial Sequence  
<220> FEATURE:  
<223> OTHER INFORMATION: Synthetic

<400> SEQUENCE: 154

```
Met Asp Ser Lys Gly Ser Gln Lys Gly Ser Arg Leu Leu Leu
1               5                   10                  15

Leu Val Val Ser Asn Leu Leu Pro Gln Gly Val Leu Ala Val Lys
                20                  25                  30

Pro Leu Ile Leu Lys Asp Cys Ser Val Ala Gly Trp Leu Leu Gly Asn
            35                  40                  45

Pro Met Cys Asp Glu Phe Leu Asn Val Ser Glu Trp Ser Tyr Ile Val
        50                  55                  60

Glu Lys Ala Ser Pro Ala Asn Gly Leu Cys Phe Pro Gly Asp Phe Asn
65                  70                  75                  80

Asp Tyr Glu Glu Leu Lys His Leu Leu Ser Arg Ile Asn His Phe Glu
                85                  90                  95

Lys Ile Lys Ile Ile Pro Lys Ser Ser Trp Ser Asn His Glu Ala Ser
            100                 105                 110

Gly Val Ser Ser Ala Cys Ser Tyr Leu Gly Lys Pro Ser Phe Phe Arg
        115                 120                 125

Asn Leu Val Trp Leu Ile Lys Lys Asn Asn Thr Tyr Pro Pro Ile Lys
    130                 135                 140

Val Asn Tyr Thr Asn Thr Asn Gln Glu Asp Leu Leu Val Leu Trp Gly
145                 150                 155                 160

Ile His His Pro Asn Asp Glu Thr Glu Gln Val Lys Ile Tyr Gln Asn
                165                 170                 175

Pro Thr Thr Tyr Ile Ser Val Gly Thr Ser Thr Leu Asn Gln Arg Leu
            180                 185                 190
```

Val Pro Lys Ile Ala Thr Arg Ser Lys Val Asn Gly Gln Ser Gly Arg
            195                 200                 205

Met Glu Phe Phe Trp Thr Ile Leu Lys Pro Asn Asp Ala Ile Asn Phe
    210                 215                 220

Asp Ser Asn Gly Asn Phe Ile Ala Pro Glu Tyr Ala Tyr Lys Ile Val
225                 230                 235                 240

Lys Lys Gly Ser Gly Glu Ser Gln Val Arg Gln Gln Phe Ser Lys Asp
                245                 250                 255

Ile Glu Lys Leu Leu Asn Glu Gln Val Asn Lys Glu Met Gln Ser Ser
            260                 265                 270

Asn Leu Tyr Met Ser Met Ser Ser Trp Cys Tyr Thr His Ser Leu Asp
            275                 280                 285

Gly Ala Gly Leu Phe Leu Phe Asp His Ala Ala Glu Glu Tyr Glu His
        290                 295                 300

Ala Lys Lys Leu Ile Ile Phe Leu Asn Glu Asn Asn Val Pro Val Gln
305                 310                 315                 320

Leu Thr Ser Ile Ser Ala Pro Glu His Lys Phe Glu Gly Leu Thr Gln
                325                 330                 335

Ile Phe Gln Lys Ala Tyr Glu His Glu Gln His Ile Ser Glu Ser Ile
            340                 345                 350

Asn Asn Ile Val Asp His Ala Ile Lys Ser Lys Asp His Ala Thr Phe
        355                 360                 365

Asn Phe Leu Gln Trp Tyr Val Ala Glu Gln His Glu Glu Val Leu
    370                 375                 380

Phe Lys Asp Ile Leu Asp Lys Ile Glu Leu Ile Gly Asn Glu Asn His
385                 390                 395                 400

Gly Leu Tyr Leu Ala Asp Gln Tyr Val Lys Gly Ile Ala Lys Ser Arg
                405                 410                 415

Lys Ser

<210> SEQ ID NO 155
<211> LENGTH: 1260
<212> TYPE: DNA
<213> ORGANISM: Artificial Sequence
<220> FEATURE:
<223> OTHER INFORMATION: Synthetic

<400> SEQUENCE: 155
tcatcagctt tttcttgact tagcaatgcc cttcacatac tggtctgcca ggtacagccc      60
atgattctcg ttgccaatca gttcgatttt atccaggatg tccttgaaca gcacctcttc     120
ctcgtgctgc tcggccacgt accactgcag aaaattgaag gtggcatgat ctttgctctt     180
aattgcgtgg tccacaatat tgttgatgga ctcgctaata tgctgctcgt gttcgtaggc     240
tttctgaaag atctgagtca ggccttcgaa cttatgctcg ggggctgaga tacttgtcag     300
ctgcactggg acgttgttct cgttcagaaa aatgatcagt ttcttagcat gttcgtattc     360
ctcggctgcg tgatcaaaca ggaacaggcc ggctccgtcc agtgagtggg tataacacca     420
gcttgacata tcatgtaca ggttactaga ctgcatctcc ttgttcacct gttcgttcag     480
cagtttctcg atatccttac tgaactgctg cctcacctga ctttctccgg acctttctt     540
cacaatttta taggcgtatt caggtgcgat gaagttgccg ttgctatcga aattaatagc     600
gtcgttgggc ttcaggattg tccaaaagaa ctccattcgc ccggactggc cattgacttt     660
gcttctggtg gcaatcttag gcaccagccg ctggttcaga gtgcttgtgc cgactgaaat     720

| | |
|---|---|
| atatgtggtt ggattctggt agatcttcac ctgttctgtc tcatcgttag gatggtggat | 780 |
| gccccacagg accagcaggt cttcctgatt ggtgttagta taattgacct tgatgggggg | 840 |
| gtaagtattg ttttttcttga tcagccagac caggttgcga agaatgagg ctttcccag | 900 |
| ataactacat gcactagaca ccccagaagc ttcgtgattg gaccaggagc tctttgggat | 960 |
| gatcttgatc ttctcgaaat ggttgatcct agacagcagg tgcttcagtt cctcataatc | 1020 |
| attgaagtcg ccggggaagc acagtccgtt agctggactg gccttctcca cgatgtaaga | 1080 |
| ccattcggac acattcagga actcatcgca catagggttg cccagcagcc atccagccac | 1140 |
| agagcagtct ttcagaatca ggggtttcac ggctagcact ccctgaggca gcagcaggtt | 1200 |
| actgacgacc agcagcagca gcagccgtga ccctttctgt gaagacccct tactgtccat | 1260 |

<210> SEQ ID NO 156
<211> LENGTH: 1263
<212> TYPE: DNA
<213> ORGANISM: Artificial Sequence
<220> FEATURE:
<223> OTHER INFORMATION: Synthetic

<400> SEQUENCE: 156

| | |
|---|---|
| atggacagta aggggtcttc acagaaaggg tcacggctgc tgctgctgct ggtcgtcagt | 60 |
| aacctgctgc tgcctcaggg agtgctagcc gtcaaacccc tgattctgag agattgtagt | 120 |
| gtcgctggct ggctgctggg caaccctatg tgtgatgagt ttattaacgt ccctgaatgg | 180 |
| tcttacatcg tggagaaagc aagtcccgcc aacgacctgt gcttccctgg cgacttcaat | 240 |
| gattatgagg aactgaaaca cctgctgtcc cgaatcaacc attttgagaa gattcagatc | 300 |
| attcccaaaa gctcctggtc taatcacgaa gcctctagtg gagtctcaag cgcttgtcct | 360 |
| tatctgggca gtcctctttt ctttaggaac gtggtctggc tgatcaagaa aaattcaaca | 420 |
| tacccaacca tcaagcgcag ttataacaat actaaccagg aggacctgct ggtgctgtgg | 480 |
| ggcatccacc atccaaacga tgccgctgaa cagacaaagc tgtaccagaa tcccaccaca | 540 |
| tatatcagtg tcgggacttc aaccctgaac cagcggctgg tgcccaagat tgccaccaga | 600 |
| agcaaagtca atgccagtc cgggagaatg gaattctttt ggacaatcct gaagcctaac | 660 |
| gatgccatta atttcgagag caacgggaat tttatcgctc cagaatacgc atataaaatt | 720 |
| gtgaagaaag ctccggaga agtcaggtg aggcagcagt tcagtaagga tatcgagaaa | 780 |
| ctgctgaacg aacaggtgaa caaggagatg cagtctagta acctgtacat gagtatgtca | 840 |
| agctggtgtt atacccactc actggacgga gccggcctgt tcctgtttga tcacgcagcc | 900 |
| gaggaatacg aacatgctaa gaaactgatc attttttctga acgagaacaa cgtcccagtg | 960 |
| cagctgacaa gtatctcagc ccccgagcat aagttcgaag gcctgactca gatctttcag | 1020 |
| aaagcctacg aacacgagca gcatattagc gagtccatca caatattgt ggaccacgca | 1080 |
| attaagagca agatcatgc caccttcaat tttctgcagt ggtacgtggc cgagcagcac | 1140 |
| gaggaagagg tgctgttcaa ggacatcctg gataaaatcg aactgattgg caacgagaat | 1200 |
| catgggctgt acctggcaga ccagtatgtg aagggcattg ctaagtcaag aaaaagctga | 1260 |
| tga | 1263 |

<210> SEQ ID NO 157
<211> LENGTH: 419
<212> TYPE: PRT
<213> ORGANISM: Artificial Sequence
<220> FEATURE:
<223> OTHER INFORMATION: Synthetic

<400> SEQUENCE: 157

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Val Lys
            20                  25                  30

Pro Leu Ile Leu Arg Asp Cys Ser Val Ala Gly Trp Leu Leu Gly Asn
        35                  40                  45

Pro Met Cys Asp Glu Phe Ile Asn Val Pro Glu Trp Ser Tyr Ile Val
    50                  55                  60

Glu Lys Ala Ser Pro Ala Asn Asp Leu Cys Phe Pro Gly Asp Phe Asn
65                  70                  75                  80

Asp Tyr Glu Glu Leu Lys His Leu Leu Ser Arg Ile Asn His Phe Glu
                85                  90                  95

Lys Ile Gln Ile Ile Pro Lys Ser Ser Trp Ser Asn His Glu Ala Ser
            100                 105                 110

Ser Gly Val Ser Ser Ala Cys Pro Tyr Leu Gly Lys Ser Ser Phe Phe
        115                 120                 125

Arg Asn Val Val Trp Leu Ile Lys Lys Asn Ser Thr Tyr Pro Thr Ile
130                 135                 140

Lys Arg Ser Tyr Asn Asn Thr Asn Gln Glu Asp Leu Leu Val Leu Trp
145                 150                 155                 160

Gly Ile His His Pro Asn Asp Ala Ala Glu Gln Thr Lys Leu Tyr Gln
                165                 170                 175

Asn Pro Thr Thr Tyr Ile Ser Val Gly Thr Ser Thr Leu Asn Gln Arg
            180                 185                 190

Leu Val Pro Lys Ile Ala Thr Arg Ser Lys Val Asn Gly Gln Ser Gly
        195                 200                 205

Arg Met Glu Phe Phe Trp Thr Ile Leu Lys Pro Asn Asp Ala Ile Asn
210                 215                 220

Phe Glu Ser Asn Gly Asn Phe Ile Ala Pro Glu Tyr Ala Tyr Lys Ile
225                 230                 235                 240

Val Lys Lys Gly Ser Gly Glu Ser Gln Val Arg Gln Gln Phe Ser Lys
                245                 250                 255

Asp Ile Glu Lys Leu Leu Asn Glu Gln Val Asn Lys Glu Met Gln Ser
            260                 265                 270

Ser Asn Leu Tyr Met Ser Met Ser Ser Trp Cys Tyr Thr His Ser Leu
        275                 280                 285

Asp Gly Ala Gly Leu Phe Leu Phe Asp His Ala Ala Glu Glu Tyr Glu
290                 295                 300

His Ala Lys Lys Leu Ile Ile Phe Leu Asn Glu Asn Asn Val Pro Val
305                 310                 315                 320

Gln Leu Thr Ser Ile Ser Ala Pro Glu His Lys Phe Glu Gly Leu Thr
                325                 330                 335

Gln Ile Phe Gln Lys Ala Tyr Glu His Glu Gln His Ile Ser Glu Ser
            340                 345                 350

Ile Asn Asn Ile Val Asp His Ala Ile Lys Ser Lys Asp His Ala Thr
        355                 360                 365

Phe Asn Phe Leu Gln Trp Tyr Val Ala Glu Gln Glu His Glu Glu Val
370                 375                 380

Leu Phe Lys Asp Ile Leu Asp Lys Ile Glu Leu Ile Gly Asn Glu Asn
385                 390                 395                 400

His Gly Leu Tyr Leu Ala Asp Gln Tyr Val Lys Gly Ile Ala Lys Ser

Arg Lys Ser

<210> SEQ ID NO 158
<211> LENGTH: 1263
<212> TYPE: DNA
<213> ORGANISM: Artificial Sequence
<220> FEATURE:
<223> OTHER INFORMATION: Synthetic

<400> SEQUENCE: 158

```
tcatcagctt tttcttgact tagcaatgcc cttcacatac tggtctgcca ggtacagccc      60
atgattctcg ttgccaatca gttcgatttt atccaggatg tccttgaaca gcacctcttc    120
ctcgtgctgc tcggccacgt accactgcag aaaattgaag gtggcatgat ctttgctctt    180
aattgcgtgg tccacaatat tgttgatgga ctcgctaata tgctgctcgt gttcgtaggc    240
tttctgaaag atctgagtca ggccttcgaa cttatgctcg ggggctgaga tacttgtcag    300
ctgcactggg acgttgttct cgttcagaaa atgatcagt ttcttagcat gttcgtattc    360
ctcggctgcg tgatcaaaca ggaacaggcc ggctccgtcc agtgagtggg tataacacca    420
gcttgacata ctcatgtaca ggttactaga ctgcatctcc ttgttcacct gttcgttcag    480
cagtttctcg atatccttac tgaactgctg cctcacctga ctttctccgg agcctttctt    540
cacaattta tatgcgtatt ctggagcgat aaaattcccg ttgctctcga attaatggc      600
atcgttaggc ttcaggattg tccaaaagaa ttccattctc ccggactggc cattgacttt    660
gcttctggtg gcaatcttgg gcaccagccg ctggttcagg gttgaagtcc cgacactgat    720
atatgtggtg ggattctggt acagctttgt ctgttcagcg gcatcgtttg gatggtggat    780
gccccacagc accagcaggt cctcctggtt agtattgtta taactgcgct tgatggttgg    840
gtatgttgaa ttttcttga tcagccagac cacgttccta agaaagagg acttgcccag      900
ataaggacaa gcgcttgaga ctccactaga ggcttcgtga ttagaccagg agcttttggg    960
aatgatctga atcttctcaa atggttgat tcgggacagc aggtgtttca gttcctcata    1020
atcattgaag tcgccaggga agcacaggtc gttggcggga cttgctttct ccacgatgta    1080
agaccattca gggacgttaa taaactcatc acacataggg ttgcccagca gccagccagc    1140
gacactacaa tctctcagaa tcaggggttt gacggctagc actccctgag gcagcagcag    1200
gttactgacg accagcagca gcagcagccg tgacccttc tgtgaagacc ccttactgtc    1260
cat                                                                  1263
```

<210> SEQ ID NO 159
<211> LENGTH: 1263
<212> TYPE: DNA
<213> ORGANISM: Artificial Sequence
<220> FEATURE:
<223> OTHER INFORMATION: Synthetic

<400> SEQUENCE: 159

```
atggacagta aggggtcttc acagaaaggg tcacggctgc tgctgctgct ggtcgtcagt      60
aacctgctgc tgcctcaggg agtgctagcc gtcaaacctc tgattctgag agactgttcc    120
gtggctggat ggctgctggg caaccctatg tgcgatgagt ttatcaatgt ccccgagtgg    180
tcttacatcg tggagaaagc aagtcccgcc aacggactgt gcttccctgg cgacttcaat    240
gattatgagg aactgaaaca cctgctgtcc cggatcaacc atttgagaa gattcagatc    300
attcccaaaa gctcctggtc taatcacgaa gcctctagtg gggtctcaag cgcttgtcct    360
```

```
tatcaggaa   agtcctcttt   ctttaggaac   gtggtctggc   tgatcaagaa   aaattcaaca      420
tacccaacca  tcaagcgcag   ttataacaat   actaaccagg   aggacctgct   ggtgctgtgg      480
ggcatccacc  atccaaacga   tgccgctgaa   cagacacgac   tgtaccagaa   tcccaccaca      540
tatatcagtg  tcggcacttc   aaccctgaac   agcggctgg    tgcccaagat   tgccaccaga      600
agcaaagtca  atggccagtc   cgggagaatg   gaattctttt   ggacaatcct   gaagcctaac      660
gacgccatta  atttcgagag   caacggcaat   tttatcgctc   cagaatacgc   atataagatt      720
gtgaagaaag  ggtccggaga   aagtcaggtg   aggcagcagt   tcagtaagga   tatcgagaaa      780
ctgctgaacg  aacaggtgaa   caaggagatg   cagtctagta   acctgtacat   gagtatgtca      840
agctggtgtt  atacccactc   actggacgga   gccggcctgt   tcctgtttga   tcacgcagcc      900
gaggaatacg  aacatgctaa   gaaactgatc   attttctga    cgagaacaa    cgtcccagtg      960 cagctgacaa  gtatctcagc   ccccgagcat   aagttcgaag   gcctgactca   gatctttcag     1020
aaagcctacg  aacacgagca   gcatattagc   gagtccatca   acaatattgt   ggaccacgca     1080
attaagagca  aagatcatgc   caccttcaat   tttctgcagt   ggtacgtggc   cgagcagcac     1140
gaggaagagg  tgctgttcaa   ggacatcctg   gataaaatcg   aactgattgg   caacgagaat     1200
catgggctgt  acctggcaga   ccagtatgtg   aagggcattg   ctaagtcaag   aaaaagctga    1260
tga                                                                            1263
```

<210> SEQ ID NO 160
<211> LENGTH: 419
<212> TYPE: PRT
<213> ORGANISM: Artificial Sequence
<220> FEATURE:
<223> OTHER INFORMATION: Synthetic

<400> SEQUENCE: 160

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Val Lys
            20                  25                  30

Pro Leu Ile Leu Arg Asp Cys Ser Val Ala Gly Trp Leu Leu Gly Asn
        35                  40                  45

Pro Met Cys Asp Glu Phe Ile Asn Val Pro Glu Trp Ser Tyr Ile Val
    50                  55                  60

Glu Lys Ala Ser Pro Ala Asn Gly Leu Cys Phe Pro Gly Asp Phe Asn
65                  70                  75                  80

Asp Tyr Glu Glu Leu Lys His Leu Leu Ser Arg Ile Asn His Phe Glu
                85                  90                  95

Lys Ile Gln Ile Ile Pro Lys Ser Ser Trp Ser Asn His Glu Ala Ser
            100                 105                 110

Ser Gly Val Ser Ser Ala Cys Pro Tyr Gln Gly Lys Ser Ser Phe Phe
        115                 120                 125

Arg Asn Val Val Trp Leu Ile Lys Lys Asn Ser Thr Tyr Pro Thr Ile
    130                 135                 140

Lys Arg Ser Tyr Asn Asn Thr Asn Gln Glu Asp Leu Leu Val Leu Trp
145                 150                 155                 160

Gly Ile His His Pro Asn Asp Ala Ala Glu Gln Thr Arg Leu Tyr Gln
                165                 170                 175

Asn Pro Thr Thr Tyr Ile Ser Val Gly Thr Ser Thr Leu Asn Gln Arg
            180                 185                 190
```

```
Leu Val Pro Lys Ile Ala Thr Arg Ser Lys Val Asn Gly Gln Ser Gly
            195                 200                 205

Arg Met Glu Phe Phe Trp Thr Ile Leu Lys Pro Asn Asp Ala Ile Asn
    210                 215                 220

Phe Glu Ser Asn Gly Asn Phe Ile Ala Pro Glu Tyr Ala Tyr Lys Ile
225                 230                 235                 240

Val Lys Lys Gly Ser Gly Ser Gln Val Arg Gln Phe Ser Lys
                245                 250                 255

Asp Ile Glu Lys Leu Leu Asn Glu Gln Val Asn Lys Glu Met Gln Ser
            260                 265                 270

Ser Asn Leu Tyr Met Ser Met Ser Ser Trp Cys Tyr Thr His Ser Leu
        275                 280                 285

Asp Gly Ala Gly Leu Phe Leu Phe Asp His Ala Ala Glu Glu Tyr Glu
        290                 295                 300

His Ala Lys Lys Leu Ile Ile Phe Leu Asn Glu Asn Asn Val Pro Val
305                 310                 315                 320

Gln Leu Thr Ser Ile Ser Ala Pro Glu His Lys Phe Glu Gly Leu Thr
                325                 330                 335

Gln Ile Phe Gln Lys Ala Tyr Glu His Glu Gln His Ile Ser Glu Ser
            340                 345                 350

Ile Asn Asn Ile Val Asp His Ala Ile Lys Ser Lys Asp His Ala Thr
        355                 360                 365

Phe Asn Phe Leu Gln Trp Tyr Val Ala Glu Gln His Glu Glu Glu Val
        370                 375                 380

Leu Phe Lys Asp Ile Leu Asp Lys Ile Glu Leu Ile Gly Asn Glu Asn
385                 390                 395                 400

His Gly Leu Tyr Leu Ala Asp Gln Tyr Val Lys Gly Ile Ala Lys Ser
                405                 410                 415

Arg Lys Ser

<210> SEQ ID NO 161
<211> LENGTH: 1263
<212> TYPE: DNA
<213> ORGANISM: Artificial Sequence
<220> FEATURE:
<223> OTHER INFORMATION: Synthetic

<400> SEQUENCE: 161
tcatcagctt tttcttgact tagcaatgcc cttcacatac tggtctgcca ggtacagccc      60
atgattctcg ttgccaatca gttcgatttt atccaggatg tccttgaaca gcacctcttc     120
ctcgtgctgc tcggccacgt accactgcag aaaattgaag gtggcatgat ctttgctctt     180
aattgcgtgg tccacaatat tgttgatgga ctcgctaata tgctgctcgt gttcgtaggc     240
tttctgaaag atctgagtca ggccttcgaa cttatgctcg ggggctgaga tacttgtcag     300
ctgcactggg acgttgttct cgttcagaaa atgatcagt ttcttagcat gttcgtattc     360
ctcggctgcg tgatcaaaca ggaacaggcc ggctccgtcc agtgagtggg tataacacca     420
gcttgacata tcatgtaca ggttactaga ctgcatctcc ttgttcacct gttcgttcag     480
cagtttctcg atatccttac tgaactgctg cctcacctga cttctccgg accctttctt      540 cacaatctta tatgcgtatt ctggagcgat aaaattgccg ttgctctcga aattaatggc     600
gtcgttaggc ttcaggattg tccaaaagaa ttccattctc ccggactggc cattgacttt     660
gcttctggtg gcaatcttgg gcaccagccg ctggttcagg gttgaagtgc cgacactgat     720
atatgtggtg ggattctggt acagtcgtgt ctgttcagcg gcatcgtttg gatggtggat     780
```

```
gccccacagc accagcaggt cctcctggtt agtattgtta taactgcgct tgatggttgg      840
gtatgttgaa tttttcttga tcagccagac cacgttccta agaaagagg actttccctg       900 ataaggacaa gcgcttgaga ccccactaga ggcttcgtga ttagaccagg agcttttggg      960
aatgatctga atcttctcaa aatggttgat ccgggacagc aggtgtttca gttcctcata     1020
atcattgaag tcgccaggga agcacagtcc gttggcggga cttgctttct ccacgatgta     1080
agaccactcg gggacattga taaactcatc gcacataggg ttgcccagca gccatccagc     1140
cacggaacag tctctcagaa tcagaggttt gacggctagc actccctgag gcagcagcag     1200
gttactgacg accagcagca gcagcagccg tgaccctttc tgtgaagacc ccttactgtc     1260
cat                                                                   1263
```

<210> SEQ ID NO 162
<211> LENGTH: 1251
<212> TYPE: DNA
<213> ORGANISM: Artificial Sequence
<220> FEATURE:
<223> OTHER INFORMATION: Synthetic

<400> SEQUENCE: 162

```
atggacagca agggcagcag ccagaagggc agcagactgc tgctgctgct ggtggtgagc       60
aacctgctgc tgcctcaggg cgtgctagcc accagatcc tggatggcga aaactgtaca      120
ctgattgacg ctctgctggg agaccctcag tgcgatggct tccagaataa gaaatgggat      180
ctgtttgtgg agaggtctaa ggcatacagt aactgtttcc cctatgacgt gcctgattat     240
gcaagcctgc gctccctggt cgcctctagt ggcacactgg agttcaacaa tgaaagcttt     300
aattggacag gggtgactca gaacggaact tcaagcgcct gcatccggag atctaacaac     360
agtttctttt caagactgaa ctggctgacc cagctgaatt tcaagtaccc tgctctgaac     420
gtgacaatgc caaacaatga gcagtttgac aagctgtata tctggggcgt gcaccatccc     480
gtcaccgaca aagatcagat cttcctgtac gcacagtcct ctggcaggat taccgtgtca     540
acaaagcgca gccagcaggc cgtcatccct aatattgggt acaggccacg catccgaaac     600
attcccagcc gcatctccat ctactggact atcgtgaaac caggcgatat cctgctgatt     660
aactccaccg gaaatctgat tgcccccggg ggctatttca agattagaag tggggcctcc     720
ggagagagcc aggtgaggca gcagttcagc aaggacatcg agaagctgct gaacgagcag     780
gtgaacaagg agatgcagag cagcaacctg tacatgagca tgagcagctg gtgctacacc     840
cacagcctgg acgcgccgg cctgttcctg ttcgaccacg ccgccgagga gtacgagcac     900
gccaagaagc tgatcatctt cctgaacgag aacaacgtgc ccgtgcagct gaccagcatc     960
agcgcccccg agcacaagtt cgagggcctg acccagatct tccagaaggc ctacgagcac    1020
gagcagcaca tcagcgagag catcaacaac atcgtggacc acgccatcaa gagcaaggac    1080
cacgccacct tcaacttcct gcagtggtac gtggccgagc agcacgagga ggaggtgctg    1140
ttcaaggaca tcctggacaa gatcgagctg atcggcaacg agaaccacgg cctgtacctg    1200
gccgaccagt acgtgaaggg catcgccaag agcaggaaga gcggatccta g             1251
```

<210> SEQ ID NO 163
<211> LENGTH: 416
<212> TYPE: PRT
<213> ORGANISM: Artificial Sequence
<220> FEATURE:
<223> OTHER INFORMATION: Synthetic

<400> SEQUENCE: 163

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala His Gln
            20                  25                  30

Ile Leu Asp Gly Glu Asn Cys Thr Leu Ile Asp Ala Leu Leu Gly Asp
            35                  40                  45

Pro Gln Cys Asp Gly Phe Gln Asn Lys Lys Trp Asp Leu Phe Val Glu
        50                  55                  60

Arg Ser Lys Ala Tyr Ser Asn Cys Phe Pro Tyr Asp Val Pro Asp Tyr
65                  70                  75                  80

Ala Ser Leu Arg Ser Leu Val Ala Ser Ser Gly Thr Leu Glu Phe Asn
                85                  90                  95

Asn Glu Ser Phe Asn Trp Thr Gly Val Thr Gln Asn Gly Thr Ser Ser
            100                 105                 110

Ala Cys Ile Arg Arg Ser Asn Asn Ser Phe Phe Ser Arg Leu Asn Trp
        115                 120                 125

Leu Thr Gln Leu Asn Phe Lys Tyr Pro Ala Leu Asn Val Thr Met Pro
130                 135                 140

Asn Asn Glu Gln Phe Asp Lys Leu Tyr Ile Trp Gly Val His His Pro
145                 150                 155                 160

Val Thr Asp Lys Asp Gln Ile Phe Leu Tyr Ala Gln Ser Ser Gly Arg
                165                 170                 175

Ile Thr Val Ser Thr Lys Arg Ser Gln Gln Ala Val Ile Pro Asn Ile
            180                 185                 190

Gly Tyr Arg Pro Arg Ile Arg Asn Ile Pro Ser Arg Ile Ser Ile Tyr
        195                 200                 205

Trp Thr Ile Val Lys Pro Gly Asp Ile Leu Leu Ile Asn Ser Thr Gly
210                 215                 220

Asn Leu Ile Ala Pro Arg Gly Tyr Phe Lys Ile Arg Ser Gly Ala Ser
225                 230                 235                 240

Gly Glu Ser Gln Val Arg Gln Gln Phe Ser Lys Asp Ile Glu Lys Leu
                245                 250                 255

Leu Asn Glu Gln Val Asn Lys Glu Met Gln Ser Ser Asn Leu Tyr Met
            260                 265                 270

Ser Met Ser Ser Trp Cys Tyr Thr His Ser Leu Asp Gly Ala Gly Leu
        275                 280                 285

Phe Leu Phe Asp His Ala Ala Glu Glu Tyr Glu His Ala Lys Lys Leu
290                 295                 300

Ile Ile Phe Leu Asn Glu Asn Asn Val Pro Val Gln Leu Thr Ser Ile
305                 310                 315                 320

Ser Ala Pro Glu His Lys Phe Glu Gly Leu Thr Gln Ile Phe Gln Lys
                325                 330                 335

Ala Tyr Glu His Glu Gln His Ile Ser Glu Ser Ile Asn Asn Ile Val
            340                 345                 350

Asp His Ala Ile Lys Ser Lys Asp His Ala Thr Phe Asn Phe Leu Gln
        355                 360                 365

Trp Tyr Val Ala Glu Gln His Glu Glu Val Leu Phe Lys Asp Ile
370                 375                 380

Leu Asp Lys Ile Glu Leu Ile Gly Asn Glu Asn His Gly Leu Tyr Leu
385                 390                 395                 400

Ala Asp Gln Tyr Val Lys Gly Ile Ala Lys Ser Arg Lys Ser Gly Ser
                405                 410                 415
```

<210> SEQ ID NO 164
<211> LENGTH: 1251
<212> TYPE: DNA
<213> ORGANISM: Artificial Sequence
<220> FEATURE:
<223> OTHER INFORMATION: Synthetic

<400> SEQUENCE: 164

```
ctaggatccg ctcttcctgc tcttggcgat gcccttcacg tactggtcgg ccaggtacag     60
gccgtggttc tcgttgccga tcagctcgat cttgtccagg atgtccttga acagcacctc    120
ctcctcgtgc tgctcggcca cgtaccactg caggaagttg aaggtggcgt ggtccttgct    180
cttgatggcg tggtccacga tgttgttgat gctctcgctg atgtgctgct cgtgctcgta    240
ggccttctgg aagatctggg tcaggccctc gaacttgtgc tcggggggcgc tgatgctggt    300
cagctgcacg ggcacgttgt tctcgttcag gaagatgatc agcttcttgg cgtgctcgta    360
ctcctcggcg cgtggtcga acaggaacag gccggcgccg tccaggctgt gggtgtagca    420
ccagctgctc atgctcatgt acaggttgct gctctgcatc tccttgttca cctgctcgtt    480
cagcagcttc tcgatgtcct tgctgaactg ctgcctcacc tggctctctc cggaggcccc    540
acttctaatc ttgaaatagc cccgggggc aatcagattt ccggtggagt taatcagcag    600
gatatcgcct ggtttcacga tagtccagta tgatggagatg cggctgggaa tgtttcggat    660
gcgtggcctg tacccaatat tagggatgac ggcctgctgg ctgcgctttg ttgacacggt    720
aatcctgcca gaggactgtg cgtacaggaa gatctgatct tgtcggtga cgggatggtg    780
cacgccccag atatacagct tgtcaaactg ctcattgttt ggcattgtca cgttcagagc    840
agggtacttg aaattcagct gggtcagcca gttcagtctt gaaagaaac tgttgttaga    900
tctccggatg caggcgcttg aagttccgtt ctgagtcacc cctgtccaat taaagctttc    960
attgttgaac tccagtgtgc cactagaggc gaccagggag cgcaggcttg cataatcagg   1020
cacgtcatag gggaaacagt tactgtatgc cttagacctc tccacaaaca gatcccattt   1080
cttattctgg aagccatcgc actgagggtc tcccagcaga gcgtcaatca gtgtacagtt   1140
ttcgccatcc aggatctggt gggctagcac gccctgaggc agcagcaggt tgctcaccac   1200
cagcagcagc agcagtctgc tgcccttctg gctgctgccc ttgctgtcca t            1251
```

<210> SEQ ID NO 165
<211> LENGTH: 1320
<212> TYPE: DNA
<213> ORGANISM: Artificial Sequence
<220> FEATURE:
<223> OTHER INFORMATION: Synthetic

<400> SEQUENCE: 165

```
atggacagca agggcagcag ccagaagggc agcagactgc tgctgctgct ggtggtgagc     60
aacctgctgc tgcctcaggg cgtgctagcc aaaacacgcg aaaactgtg ccccgactgt    120
ctgaactgca ccgacctgga tgtggcactg gacgaccta tgtgtgtcgg aaccacacca    180
tccgcaaaag cctctattct gcacgaggtg cggcccgtca cttctggctg cttccctatc    240
atgcatgacc ggaccaagat tagacagctg gccaacctgc tgagggggta cgaaaatatc    300
cgcctgtcca cacagaacgt gattgatgct gagaaggcac caggaggacc atatcgcctg    360
ggaacctccg ggtcttgtcc caatgctaca agtaaatcag gcttctttgc aactatggct    420
tgggcagtgc ctaaggacaa caacaagaac gctacaaatc ccctgactgt ggaagtccct    480
```

```
tacatctgcg cagaggggga agaccagatt accgtgtggg gatttcactc tgacgataag    540
acacagatga aaaacctgta cggggatagt aatcctcaga agttcaccag ctccgccaac    600
ggagtgacta cccattatgt cagtcagatc ggaggcttcc cagaccagac tgaggatggg    660
ggactgcccc agtcaggcag aatcgtggtc gactacatga tgcagaagcc tggaaaaact    720
ggcaccattg tgtatcagag aggagtcctg ctgccacaga aagtgtggtg tgcatcaggc    780
aggagctccg gagagagcca ggtgaggcag cagttcagca aggacatcga gaagctgctg    840
aacgagcagg tgaacaagga gatgcagagc agcaacctgt acatgagcat gagcagctgg    900
tgctacaccc acagcctgga cggcgccggc ctgttcctgt cgaccacgc cgccgaggag    960 tacgagcacg ccaagaagct gatcatcttc ctgaacgaga acaacgtgcc cgtgcagctg   1020
accagcatca gcgcccccga gcacaagttc gagggcctga cccagatctt ccagaaggcc   1080
tacgagcacg agcagcacat cagcgagagc atcaacaaca tcgtggacca cgccatcaag   1140
agcaaggacc acgccacctt caacttcctg cagtggtacg tggccgagca gcacgaggag   1200
gaggtgctgt tcaaggacat cctggacaag atcgagctga tcgcaacga gaaccacggc   1260 ctgtacctgg ccgaccagta cgtgaagggc atcgccaaga gcaggaagag cggatcctag   1320
```

<210> SEQ ID NO 166
<211> LENGTH: 439
<212> TYPE: PRT
<213> ORGANISM: Artificial Sequence
<220> FEATURE:
<223> OTHER INFORMATION: Synthetic

<400> SEQUENCE: 166

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Lys Thr
                20                  25                  30

Arg Gly Lys Leu Cys Pro Asp Cys Leu Asn Cys Thr Asp Leu Asp Val
            35                  40                  45

Ala Leu Gly Arg Pro Met Cys Val Gly Thr Thr Pro Ser Ala Lys Ala
        50                  55                  60

Ser Ile Leu His Glu Val Arg Pro Val Thr Ser Gly Cys Phe Pro Ile
65                  70                  75                  80

Met His Asp Arg Thr Lys Ile Arg Gln Leu Ala Asn Leu Leu Arg Gly
                85                  90                  95

Tyr Glu Asn Ile Arg Leu Ser Thr Gln Asn Val Ile Asp Ala Glu Lys
            100                 105                 110

Ala Pro Gly Gly Pro Tyr Arg Leu Gly Thr Ser Gly Ser Cys Pro Asn
        115                 120                 125

Ala Thr Ser Lys Ser Gly Phe Phe Ala Thr Met Ala Trp Ala Val Pro
    130                 135                 140

Lys Asp Asn Asn Lys Asn Ala Thr Asn Pro Leu Thr Val Glu Val Pro
145                 150                 155                 160

Tyr Ile Cys Ala Glu Gly Glu Asp Gln Ile Thr Val Trp Gly Phe His
                165                 170                 175

Ser Asp Asp Lys Thr Gln Met Lys Asn Leu Tyr Gly Asp Ser Asn Pro
            180                 185                 190

Gln Lys Phe Thr Ser Ser Ala Asn Gly Val Thr Thr His Tyr Val Ser
        195                 200                 205

Gln Ile Gly Gly Phe Pro Asp Gln Thr Glu Asp Gly Gly Leu Pro Gln
    210                 215                 220
```

```
Ser Gly Arg Ile Val Val Asp Tyr Met Met Gln Lys Pro Gly Lys Thr
225                 230                 235                 240

Gly Thr Ile Val Tyr Gln Arg Gly Val Leu Leu Pro Gln Lys Val Trp
            245                 250                 255

Cys Ala Ser Gly Arg Ser Ser Gly Glu Ser Gln Val Arg Gln Gln Phe
        260                 265                 270

Ser Lys Asp Ile Glu Lys Leu Leu Asn Glu Gln Val Asn Lys Glu Met
    275                 280                 285

Gln Ser Ser Asn Leu Tyr Met Ser Met Ser Ser Trp Cys Tyr Thr His
290                 295                 300

Ser Leu Asp Gly Ala Gly Leu Phe Leu Phe Asp His Ala Ala Glu Glu
305                 310                 315                 320

Tyr Glu His Ala Lys Lys Leu Ile Ile Phe Leu Asn Glu Asn Asn Val
            325                 330                 335

Pro Val Gln Leu Thr Ser Ile Ser Ala Pro Glu His Lys Phe Glu Gly
        340                 345                 350

Leu Thr Gln Ile Phe Gln Lys Ala Tyr Glu His Glu Gln His Ile Ser
    355                 360                 365

Glu Ser Ile Asn Asn Ile Val Asp His Ala Ile Lys Ser Lys Asp His
370                 375                 380

Ala Thr Phe Asn Phe Leu Gln Trp Tyr Val Ala Glu Gln His Glu Glu
385                 390                 395                 400

Glu Val Leu Phe Lys Asp Ile Leu Asp Lys Ile Glu Leu Ile Gly Asn
            405                 410                 415

Glu Asn His Gly Leu Tyr Leu Ala Asp Gln Tyr Val Lys Gly Ile Ala
        420                 425                 430

Lys Ser Arg Lys Ser Gly Ser
    435
```

<210> SEQ ID NO 167
<211> LENGTH: 1320
<212> TYPE: DNA
<213> ORGANISM: Artificial Sequence
<220> FEATURE:
<223> OTHER INFORMATION: Synthetic

<400> SEQUENCE: 167

```
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgctg atgtgctgct cgtgctcgta     240
ggccttctgg aagatctggg tcaggccctc gaacttgtgc tcggggcgc tgatgctggt     300
cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggagctcct     540
gcctgatgca caccacactt tctgtggcag caggactcct ctctgataca caatggtgcc     600
agttttttcca ggcttctgca tcatgtagtc gaccacgatt ctgcctgact ggggcagtcc     660
cccatcctca gtctggtctg ggaagcctcc gatctgactg acataatggg tagtcactcc     720
gttggcggag ctggtgaact tctgaggatt actatcccg tacaggtttt tcatctgtgt     780
```

| cttatcgtca gagtgaaatc cccacacggt aatctggtct tccccctctg cgcagatgta | 840 |
| agggacttcc acagtcaggg gatttgtagc gttcttgttg ttgtccttag gcactgccca | 900 |
| agccatagtt gcaaagaagc ctgatttact tgtagcattg ggacaagacc cggaggttcc | 960 |
| caggcgatat ggtcctcctg gtgccttctc agcatcaatc acgttctgtg tggacaggcg | 1020 |
| gatattttcg taccccctca gcaggttggc cagctgtcta atcttggtcc ggtcatgcat | 1080 |
| gatagggaag cagccagaag tgacgggccg cacctcgtgc agaatagagg cttttgcgga | 1140 |
| tggtgtggtt ccgacacaca taggtcgtcc cagtgccaca tccaggtcgg tgcagttcag | 1200 |
| acagtcgggg cacagttttc cgcgtgtttt ggctagcacg ccctgaggca gcagcaggtt | 1260 |
| gctcaccacc agcagcagca gcagtctgct gcccttctgg ctgctgccct tgctgtccat | 1320 |

<210> SEQ ID NO 168
<211> LENGTH: 1323
<212> TYPE: DNA
<213> ORGANISM: Artificial Sequence
<220> FEATURE:
<223> OTHER INFORMATION: Synthetic

<400> SEQUENCE: 168

| atggacagca agggcagcag ccagaagggc agcagactgc tgctgctgct ggtggtgagc | 60 |
| aacctgctgc tgcctcaggg cgtgctagcc gagacaagag gcaagctgtg ccccaagtgc | 120 |
| ctgaactgta ccgatctgga tgtggccctg ggcagaccta gtgtaccgg caagatccct | 180 |
| agcgccagag tgtctatcct gcacgaagtg cggcctgtga ccagcggctg cttccccatc | 240 |
| atgcacgacc ggaccaagat cagacagctg cccaatctgc tgagaggcta cgagcacatc | 300 |
| agactgagca cccacaacgt gatcaatgcc gagaatgccc ctgcggcccc ttacaagatc | 360 |
| ggcacctccg gcagctgtcc caacatcacc aacggcaacg gctttttgc cacaatggcc | 420 |
| tgggccgtgc ctaagaacga caagaacaag accgccacca ccctctgac aatcgaggtg | 480 |
| ccctacatct gtaccgaggg cgaggatcag atcacagtgt ggggcttcca cagcgacaac | 540 |
| gagactcaga tggccaagct gtacggcgac agcaagcccc agaagtttac cagcagcgcc | 600 |
| aatggcgtga ccacccacta cgtgtctcag atcggcggct ccctaatca gacagaggat | 660 |
| ggcggcctgc ctcagagcgg cagaatcgtg gtggactaca tggtgcagaa gtccggcaag | 720 |
| accggcacca tcacctacca gagaggcatc ctgctgcctc agaaagtgtg gtgtgccagc | 780 |
| ggcagatcct ccggagagag ccaggtgagg cagcagttca gcaaggacat cgagaagctg | 840 |
| ctgaacgagc aggtgaacaa ggagatgcag agcagcaacc tgtacatgag catgagcagc | 900 |
| tggtgctaca cccacagcct ggacggcgcc ggcctgttcc tgttcgacca cgccgccgag | 960 |
| gagtacgagc acgccaagaa gctgatcatc ttcctgaacg agaacaacgt gcccgtgcag | 1020 |
| ctgaccagca tcagcgcccc cgagcacaag ttcgagggcc tgacccagat cttccagaag | 1080 |
| gcctacgagc acgagcagca catcagcgag agcatcaaca catcgtgga ccacgccatc | 1140 |
| aagagcaagg accacgccac cttcaacttc ctgcagtggt acgtggccga gcagcacgag | 1200 |
| gaggaggtgc tgttcaagga catcctggac aagatcgagc tgatcggcaa cgagaaccac | 1260 |
| ggcctgtacc tggccgacca gtacgtgaag ggcatcgcca agagcaggaa gagcggatcc | 1320 |
| tag | 1323 |

<210> SEQ ID NO 169
<211> LENGTH: 440
<212> TYPE: PRT
<213> ORGANISM: Artificial Sequence
<220> FEATURE:
<223> OTHER INFORMATION: Synthetic

<400> SEQUENCE: 169

Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Glu Thr
            20                  25                  30

Arg Gly Lys Leu Cys Pro Lys Cys Leu Asn Cys Thr Asp Leu Asp Val
            35                  40                  45

Ala Leu Gly Arg Pro Lys Cys Thr Gly Lys Ile Pro Ser Ala Arg Val
50                  55                  60

Ser Ile Leu His Glu Val Arg Pro Val Thr Ser Gly Cys Phe Pro Ile
65                  70                  75                  80

Met His Asp Arg Thr Lys Ile Arg Gln Leu Pro Asn Leu Leu Arg Gly
                85                  90                  95

Tyr Glu His Ile Arg Leu Ser Thr His Asn Val Ile Asn Ala Glu Asn
            100                 105                 110

Ala Pro Gly Gly Pro Tyr Lys Ile Gly Thr Ser Gly Ser Cys Pro Asn
        115                 120                 125

Ile Thr Asn Gly Asn Gly Phe Phe Ala Thr Met Ala Trp Ala Val Pro
130                 135                 140

Lys Asn Asp Lys Asn Lys Thr Ala Thr Asn Pro Leu Thr Ile Glu Val
145                 150                 155                 160

Pro Tyr Ile Cys Thr Glu Gly Glu Asp Gln Ile Thr Val Trp Gly Phe
                165                 170                 175

His Ser Asp Asn Glu Thr Gln Met Ala Lys Leu Tyr Gly Asp Ser Lys
            180                 185                 190

Pro Gln Lys Phe Thr Ser Ser Ala Asn Gly Val Thr Thr His Tyr Val
        195                 200                 205

Ser Gln Ile Gly Gly Phe Pro Asn Gln Thr Glu Asp Gly Gly Leu Pro
210                 215                 220

Gln Ser Gly Arg Ile Val Val Asp Tyr Met Val Gln Lys Ser Gly Lys
225                 230                 235                 240

Thr Gly Thr Ile Thr Tyr Gln Arg Gly Ile Leu Leu Pro Gln Lys Val
                245                 250                 255

Trp Cys Ala Ser Gly Arg Ser Ser Gly Glu Ser Gln Val Arg Gln Gln
            260                 265                 270

Phe Ser Lys Asp Ile Glu Lys Leu Leu Asn Glu Gln Val Asn Lys Glu
        275                 280                 285

Met Gln Ser Ser Asn Leu Tyr Met Ser Met Ser Ser Trp Cys Tyr Thr
290                 295                 300

His Ser Leu Asp Gly Ala Gly Leu Phe Leu Asp His Ala Ala Glu
305                 310                 315                 320

Glu Tyr Glu His Ala Lys Lys Leu Ile Ile Phe Leu Asn Glu Asn Asn
                325                 330                 335

Val Pro Val Gln Leu Thr Ser Ile Ser Ala Pro Glu His Lys Phe Glu
            340                 345                 350

Gly Leu Thr Gln Ile Phe Gln Lys Ala Tyr Glu His Glu Gln His Ile
        355                 360                 365

Ser Glu Ser Ile Asn Asn Ile Val Asp His Ala Ile Lys Ser Lys Asp
370                 375                 380

His Ala Thr Phe Asn Phe Leu Gln Trp Tyr Val Ala Glu Gln His Glu
385                 390                 395                 400

Glu Glu Val Leu Phe Lys Asp Ile Leu Asp Lys Ile Glu Leu Ile Gly
            405                 410                 415

Asn Glu Asn His Gly Leu Tyr Leu Ala Asp Gln Tyr Val Lys Gly Ile
        420                 425                 430

Ala Lys Ser Arg Lys Ser Gly Ser
        435                 440

<210> SEQ ID NO 170
<211> LENGTH: 1323
<212> TYPE: DNA
<213> ORGANISM: Artificial Sequence
<220> FEATURE:
<223> OTHER INFORMATION: Synthetic

<400> SEQUENCE: 170

```
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggcctc gaacttgtgc tcggggcgc tgatgctggt    300 cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggatct   540
gccgctggca caccacactt tctgaggcag caggatgcct ctctggtagg tgatggtgcc   600
ggtcttgccg gacttctgca ccatgtagtc caccacgatt ctgccgctct gaggcaggcc   660
gccatcctct gtctgattag ggaagccgcc gatctgagac acgtagtggg tggtcacgcc   720 attgcgctg ctggtaaact tctggggctt gctgtcgccg tacagcttgg ccatctgagt   780
ctcgttgtcg ctgtggaagc cccacactgt gatctgatcc tcgccctcgg tacagatgta   840
gggcacctcg attgtcagag ggttggtggc ggtcttgttc ttgtcgttct taggcacggc   900
ccaggccatt gtggcaaaaa agccgttgcc gttggtgatg ttgggacagc tgccggaggt   960
gccgatcttg taagggccgc caggggcatt ctcggcattg atcacgttgt gggtgctcag  1020
tctgatgtgc tcgtagcctc tcagcagatt gggcagctgt ctgatcttgg tccggtcgtg  1080
catgatgggg aagcagccgc tggtcacagg ccgcacttcg tgcaggatag acactctggc  1140
gctagggatc ttgccggtac acttaggtct gcccagggcc acatccagat cggtacagtt  1200
caggcacttg ggcacagct tgcctcttgt ctcggctagc acgccctgag cagcagcag  1260 gttgctcacc accagcagca gcagcagtct gctgcccttc tggctgctgc ccttgctgtc  1320
cat                                                               1323
```

<210> SEQ ID NO 171
<211> LENGTH: 2604
<212> TYPE: DNA
<213> ORGANISM: Artificial Sequence
<220> FEATURE:
<223> OTHER INFORMATION: Synthetic

<400> SEQUENCE: 171

```
atggacagca agggcagcag ccagaagggc tccagactgc tgctgctcct ggtggtgtcc    60
aacctcctgc tgcctcaggg cgtgctagcc gtggctcctc tgcacctggg caagtgcaat   120
```

-continued

```
atcgccggct ggattctggg caaccccgag tgcgagagcc tgagcacagc cagcagctgg    180
tcctacatcg tggaaacccc tagcagcgac aacggcacct gtttccccgg cgacttcatc    240
gactacgagg aactgcgcga gcagctgagc agcgtgtcca gcttcgagag attcgagatc    300
ttccccaaga cctccagctg gcccaaccac gacagcaaca aaggcgtgac cgccgcctgt    360
cctcacgctg gcgccaagag cttctacaag aacctgatct ggctggtcaa gaagggcaac    420 agctaccccca agctgagcaa gagctacatc aacgacaagg gcaaagaggt gctggtcctc    480
tggggcatcc accaccctag cacaagcgcc gaccagcaga gcctgtacca aacgccgac     540 gcctacgtgt tcgtgggcag ctcccggtac agcaagaagt tcaagcccga gatcgccatc    600
cggcccaaag tgcgggacca ggaaggccgg atgaactact actggaccct ggtggaaccc    660
ggcgacaaga tcaccttcga ggccaccggc aatctggtgg tgcccagata cgccttcgcc    720
atggaaagaa cgccagcgg cgagagccaa gtccgacagc agttcagcaa ggacatcgag     780
aagctgctga cgagcaggt caacaaagag atgcagagca gcaacctgta catgagcatg    840
tccagctggt gttacaccca cagcctggac ggcgctggcc tgttcctgtt tgatcacgcc    900
gccgaggaat acgagcacgc caagaagctg atcatcttcc tgaacgagaa caacgtgccc    960
gtgcagctga ccagcatcag cgccccagag cacaagttcg agggcctgac ccagatcttc   1020
cagaaggcct acgaacacga gcagcacatc agcgagagca tcaacaatat cgtggaccac   1080
gccatcaaga gcaaggatca cgccaccttc aactttctgc aatggtacgt ggccgaacag   1140
cacgaggaag aagtgctgtt taaggacatc ctggacaaga tcgagctgat cggcaacgag   1200
aaccacggcc tgtacctggc cgaccagtac gtgaagggca ttgccaagag cagaaagagc   1260
cggaagcgga gatctggcag cggcgctcct gtgaagcaga ccctgaactt cgacctgctg   1320
aagctggccg gcgacgtgga aagcaacccct gggcccatgg actccaaggg ctcctcccag   1380
aaaggatctc ggctgctcct cctgctcgtg gtgtctaatc tgctgctgcc acagggtgtc   1440
ctggcccacc agatcctgga tggcgagaac tgcacctga tcgacgccct gctgggcgac    1500
cctcagtgcg acggcttcca gaacaagaag tgggacctgt cgtcgagcg gagcaaggcc    1560 tacagcaact gcttcccta cgacgtgccc gactacgcca gcctgagaag cctggtggcc    1620
agcagcggca ccctggaatt caacaacgag agcttcaact ggaacggcgt gacccagaac   1680
ggcaccagct ccgcctgcat cagaagaagc aacaacagct tcttctcccg gctgaactgg   1740
ctgacccacc tgaatttcaa gtaccccgcc ctgaacgtga ccatgcccaa caatgagcag   1800
ttcgacaagc tgtacatctg gggagtgcac caccccgtga ccgacaagga ccagatcttt   1860
ctgtacgccc agcccagcgg ccggatcacc gtgtctacca agagaagcca gcaggccgtg   1920
atccccaaca tcggcttccg gcccaggatc agaaacatcc ccagccggat cagcatctac   1980
tggacaatcg tgaagcctgg cgacatcctg ctgatcaaca gcaccggcaa cctgatcgcc   2040
cctcggggct acttcaagat cagaagcggc aagctccgga gaatctcaagt ccgccagcag  2100 ttttctaagg acatcgaaaa gctgctcaat gaacaggtca caaagagat gcagtcctct   2160 aacctgtata tgagtatgag ttcctggtgc tatacccact ctctcgacgg tgcagggctg    2220
ttcctcttcg accacgctgc agaggaatat gaacatgcta agaaactgat tatctttctc   2280
aacgaaaaca acgtgccagt ccagctcacc agtatctctg cccctgaaca taagtttgag   2340
gggctcactc agatctttca gaaagcttac gagcacgagc agcatatctc tgagtctatt   2400
aacaacatcg tcgaccatgc tatcaaatct aaagaccacg ctactttaa ctttctccaa    2460
```

-continued

```
tggtacgtcg cagagcagca tgaggaagag gtcctcttca aggacattct cgacaaaatt    2520
gaactcatcg aaacgaaaa ccatgggctc tacctggctg atcagtacgt caagggaatc    2580
gcaaaaagcc ggaagtcttg atga                                          2604
```

<210> SEQ ID NO 172
<211> LENGTH: 865
<212> TYPE: PRT
<213> ORGANISM: Artificial Sequence
<220> FEATURE:
<223> OTHER INFORMATION: Synthetic

<400> SEQUENCE: 172

```
Asp Ser Lys Gly Ser Ser Gln Lys Gly Ser Arg Leu Leu Leu Leu Leu
1               5                   10                  15

Val Val Ser Asn Leu Leu Pro Gln Gly Val Leu Ala Val Ala Pro
            20                  25                  30

Leu His Leu Gly Lys Cys Asn Ile Ala Gly Trp Ile Leu Gly Asn Pro
        35                  40                  45

Glu Cys Glu Ser Leu Ser Thr Ala Ser Ser Trp Ser Tyr Ile Val Glu
    50                  55                  60

Thr Pro Ser Ser Asp Asn Gly Thr Cys Phe Pro Gly Asp Phe Ile Asp
65                  70                  75                  80

Tyr Glu Glu Leu Arg Glu Gln Leu Ser Ser Val Ser Ser Phe Glu Arg
                85                  90                  95

Phe Glu Ile Phe Pro Lys Thr Ser Ser Trp Pro Asn His Asp Ser Asn
            100                 105                 110

Lys Gly Val Thr Ala Ala Cys Pro His Ala Gly Ala Lys Ser Phe Tyr
        115                 120                 125

Lys Asn Leu Ile Trp Leu Val Lys Lys Gly Asn Ser Tyr Pro Lys Leu
    130                 135                 140

Ser Lys Ser Tyr Ile Asn Asp Lys Gly Lys Glu Val Leu Val Leu Trp
145                 150                 155                 160

Gly Ile His His Pro Ser Thr Ser Ala Asp Gln Gln Ser Leu Tyr Gln
                165                 170                 175

Asn Ala Asp Ala Tyr Val Phe Val Gly Ser Ser Arg Tyr Ser Lys Lys
            180                 185                 190

Phe Lys Pro Glu Ile Ala Ile Arg Pro Lys Val Arg Asp Gln Glu Gly
        195                 200                 205

Arg Met Asn Tyr Tyr Trp Thr Leu Val Glu Pro Gly Asp Lys Ile Thr
    210                 215                 220

Phe Glu Ala Thr Gly Asn Leu Val Val Pro Arg Tyr Ala Phe Ala Met
225                 230                 235                 240

Glu Arg Asn Ala Ser Gly Glu Ser Gln Val Arg Gln Gln Phe Ser Lys
                245                 250                 255

Asp Ile Glu Lys Leu Leu Asn Glu Gln Val Asn Lys Glu Met Gln Ser
            260                 265                 270

Ser Asn Leu Tyr Met Ser Met Ser Ser Trp Cys Tyr Thr His Ser Leu
        275                 280                 285

Asp Gly Ala Gly Leu Phe Leu Phe Asp His Ala Ala Glu Glu Tyr Glu
    290                 295                 300

His Ala Lys Lys Leu Ile Ile Phe Leu Asn Glu Asn Asn Val Pro Val
305                 310                 315                 320

Gln Leu Thr Ser Ile Ser Ala Pro Glu His Lys Phe Glu Gly Leu Thr
                325                 330                 335
```

-continued

```
Gln Ile Phe Gln Lys Ala Tyr Glu His Glu Gln His Ile Ser Glu Ser
            340                 345                 350
Ile Asn Asn Ile Val Asp His Ala Ile Lys Ser Lys Asp His Ala Thr
            355                 360                 365
Phe Asn Phe Leu Gln Trp Tyr Val Ala Glu Gln His Glu Glu Glu Val
        370                 375                 380
Leu Phe Lys Asp Ile Leu Asp Lys Ile Glu Leu Ile Gly Asn Glu Asn
385                 390                 395                 400
His Gly Leu Tyr Leu Ala Asp Gln Tyr Val Lys Gly Ile Ala Lys Ser
                405                 410                 415
Arg Lys Ser Arg Lys Arg Ser Gly Ser Gly Ala Pro Val Lys Gln
            420                 425                 430
Thr Leu Asn Phe Asp Leu Leu Lys Leu Ala Gly Asp Val Glu Ser Asn
            435                 440                 445
Pro Gly Pro Met Asp Ser Lys Gly Ser Ser Gln Lys Gly Ser Arg Leu
        450                 455                 460
Leu Leu Leu Leu Val Val Ser Asn Leu Leu Pro Gln Gly Val Leu
465                 470                 475                 480
Ala His Gln Ile Leu Asp Gly Glu Asn Cys Thr Leu Ile Asp Ala Leu
                485                 490                 495
Leu Gly Asp Pro Gln Cys Asp Gly Phe Gln Asn Lys Lys Trp Asp Leu
            500                 505                 510
Phe Val Glu Arg Ser Lys Ala Tyr Ser Asn Cys Phe Pro Tyr Asp Val
        515                 520                 525
Pro Asp Tyr Ala Ser Leu Arg Ser Leu Val Ala Ser Ser Gly Thr Leu
530                 535                 540
Glu Phe Asn Asn Glu Ser Phe Asn Trp Asn Gly Val Thr Gln Asn Gly
545                 550                 555                 560
Thr Ser Ser Ala Cys Ile Arg Arg Ser Asn Asn Ser Phe Phe Ser Arg
                565                 570                 575
Leu Asn Trp Leu Thr His Leu Asn Phe Lys Tyr Pro Ala Leu Asn Val
            580                 585                 590
Thr Met Pro Asn Asn Glu Gln Phe Asp Lys Leu Tyr Ile Trp Gly Val
        595                 600                 605
His His Pro Val Thr Asp Lys Asp Gln Ile Phe Leu Tyr Ala Gln Pro
610                 615                 620
Ser Gly Arg Ile Thr Val Ser Thr Lys Arg Ser Gln Gln Ala Val Ile
625                 630                 635                 640
Pro Asn Ile Gly Phe Arg Pro Arg Ile Arg Asn Ile Pro Ser Arg Ile
                645                 650                 655
Ser Ile Tyr Trp Thr Ile Val Lys Pro Gly Asp Ile Leu Leu Ile Asn
            660                 665                 670
Ser Thr Gly Asn Leu Ile Ala Pro Arg Gly Tyr Phe Lys Ile Arg Ser
        675                 680                 685
Gly Ala Ser Gly Glu Ser Gln Val Arg Gln Phe Ser Lys Asp Ile
690                 695                 700
Glu Lys Leu Leu Asn Glu Gln Val Asn Lys Glu Met Gln Ser Ser Asn
705                 710                 715                 720
Leu Tyr Met Ser Met Ser Ser Trp Cys Tyr Thr His Ser Leu Asp Gly
                725                 730                 735
Ala Gly Leu Phe Leu Phe Asp His Ala Ala Glu Glu Tyr Glu His Ala
            740                 745                 750
Lys Lys Leu Ile Ile Phe Leu Asn Glu Asn Asn Val Pro Val Gln Leu
```

```
              755                 760                 765
Thr Ser Ile Ser Ala Pro Glu His Lys Phe Glu Gly Leu Thr Gln Ile
    770                 775                 780

Phe Gln Lys Ala Tyr Glu His Glu Gln His Ile Ser Glu Ser Ile Asn
785                 790                 795                 800

Asn Ile Val Asp His Ala Ile Lys Ser Lys Asp His Ala Thr Phe Asn
                805                 810                 815

Phe Leu Gln Trp Tyr Val Ala Glu Gln His Glu Glu Val Leu Phe
            820                 825                 830

Lys Asp Ile Leu Asp Lys Ile Glu Leu Ile Gly Asn Glu Asn His Gly
        835                 840                 845

Leu Tyr Leu Ala Asp Gln Tyr Val Lys Gly Ile Ala Lys Ser Arg Lys
    850                 855                 860

Ser
865

<210> SEQ ID NO 173
<211> LENGTH: 2604
<212> TYPE: DNA
<213> ORGANISM: Artificial Sequence
<220> FEATURE:
<223> OTHER INFORMATION: Synthetic

<400> SEQUENCE: 173
tcatcaagac ttccggcttt tgcgattcc cttgacgtac tgatcagcca ggtagagccc      60
atggttttcg tttccgatga gttcaatttt gtcgagaatg tccttgaaga ggacctcttc     120
ctcatgctgc tctgcgacgt accattggag aaagttaaaa gtagcgtggt ctttagattt     180
gatagcatgg tcgacgatgt tgttaataga ctcagagata tgctgctcgt gctcgtaagc     240
tttctgaaag atctgagtga gccccctcaaa cttatgttca ggggcagaga tactggtgag     300
ctggactggc acgttgtttt cgttgagaaa gataatcagt ttcttagcat gttcatattc     360
ctctgcagcg tggtcgaaga ggaacagccc tgcaccgtcg agagagtggg tatagcacca     420
ggaactcata tcatataca ggttagagga ctgcatctct tgttgacct gttcattgag      480 cagcttttcg atgtccttag aaaactgctg gcggacttga gattctccgg aggcgccgct     540
tctgatcttg aagtagcccc gaggggcgat caggttgccg gtgctgttga tcagcaggat     600
gtcgccaggc ttcacgattg tccagtagat gctgatccgg ctggggatgt ttctgatcct     660
gggccggaag ccgatgttgg ggatcacggc ctgctggctt ctcttggtag acacggtgat     720
ccggccgctg ggctgggcgt acagaaagat ctggtccttg tcggtcacgg ggtggtgcac     780
tccccagatg tacagcttgt cgaactgctc attgttgggc atggtcacgt tcagggcggg     840
gtacttgaaa ttcaggtggg tcagccagtt cagccgggag aagaagctgt tgttgcttct     900
tctgatgcag gcggagctgg tgccgttctg gtcacgccg ttccagttga agctctcgtt      960
gttgaattcc agggtgccgc tgctggccac caggcttctc aggctggcgt agtcgggcac    1020
gtcgtagggg aagcagttgc tgtaggcctt gctccgctcg acgaacaggt cccacttctt    1080
gttctggaag ccgtcgcact gagggtcgcc cagcagggcg tcgatcaggg tgcagttctc    1140
gccatccagg atctggtggg ccaggacacc ctgtggcagc agcagattag acaccacgag    1200
caggaggagc agccgagatc ctttctggga ggagcccttg gagtccatgg gcccagggtt    1260
gctttccacg tcgccggcca gcttcagcag gtcgaagttc agggtctgct tcacaggagc    1320
gccgctgcca gatctccgct tccggctctt tctgctcttg gcaatgccct tcacgtactg    1380
```

| | |
|---|---|
| gtcggccagg tacaggccgt ggttctcgtt gccgatcagc tcgatcttgt ccaggatgtc | 1440 |
| cttaaacagc acttcttcct cgtgctgttc ggccacgtac cattgcagaa agttgaaggt | 1500 |
| ggcgtgatcc ttgctcttga tggcgtggtc cacgatattg ttgatgctct cgctgatgtg | 1560 |
| ctgctcgtgt tcgtaggcct tctggaagat ctgggtcagg ccctcgaact tgtgctctgg | 1620 |
| ggcgctgatg ctggtcagct gcacgggcac gttgttctcg ttcaggaaga tgatcagctt | 1680 |
| cttggcgtgc tcgtattcct cggcggcgtg atcaaacagg aacaggccag cgccgtccag | 1740 |
| gctgtgggtg taacaccagc tggacatgct catgtacagg ttgctgctct gcatctcttt | 1800 |
| gttgacctgc tcgttcagca gcttctcgat gtccttgctg aactgctgtc ggacttggct | 1860 |
| ctcgccgctg gcgtttcttt ccatggcgaa ggcgtatctg ggcaccacca gattgccggt | 1920 |
| ggcctcgaag gtgatcttgt cgccgggttc caccagggtc cagtagtagt tcatccggcc | 1980 |
| ttcctggtcc cgcactttgg gccggatggc gatctcgggc ttgaacttct tgctgtaccg | 2040 |
| ggagctgccc acgaacacgt aggcgtcggc gttctggtac aggctctgct ggtcggcgct | 2100 |
| tgtgctaggg tggtggatgc cccagaggac cagcacctct ttgcccttgt cgttgatgta | 2160 |
| gctcttgctc agcttggggt agctgttgcc cttcttgacc agccagatca ggttcttgta | 2220 |
| gaagctcttg gcgccagcgt gaggacaggc ggcggtcacg cctttgttgc tgtcgtggtt | 2280 |
| gggccagctg gaggtcttgg ggaagatctc gaatctctcg aagctggaca cgctgctcag | 2340 |
| ctgctcgcgc agttcctcgt agtcgatgaa gtcgccgggg aaacaggtgc cgttgtcgct | 2400 |
| gctaggggtt ccacgatgt aggaccagct gctggctgtg ctcaggctct cgcactcggg | 2460 |
| gttgcccaga atccagccgg cgatattgca cttgcccagg tgcagaggag ccacggctag | 2520 |
| cacgccctga ggcagcagga ggttggacac caccaggagc agcagcagtc tggagccctt | 2580 |
| ctggctgctg cccttgctgt ccat | 2604 |

<210> SEQ ID NO 174
<211> LENGTH: 2727
<212> TYPE: DNA
<213> ORGANISM: Artificial Sequence
<220> FEATURE:
<223> OTHER INFORMATION: Synthetic

<400> SEQUENCE: 174

| | |
|---|---|
| atggacagca agggcagcag ccagaagggc tccagactgc tgctgctcct ggtggtgtcc | 60 |
| aacctcctgc tgcctcaggg cgtgctagcc gagacaagag gcaagctgtg ccccaagtgc | 120 |
| ctgaactgca ccgacctgga tgtggccctg gcagaccta agtgcaccgg caagatcccc | 180 |
| agcgccagag tgtccatcct gcacgaagtg cggcctgtga ccagcggctg cttccccatc | 240 |
| atgcacgacc ggaccaagat cagacagctg cccaacctgc tgcggggcta cgagcacatc | 300 |
| agactgagca cccacaacgt gatcaacgcc gagaatgccc tggcggccc ttacaagatc | 360 |
| ggcaccagcg gaagctgccc caacatcacc aacggcaacg cttttttcgc caccatggcc | 420 |
| tgggccgtgc caagaacga caagaacaag accgccacca ccctctgac catcgaggtg | 480 |
| ccctacatct gcaccgaggg cgaggaccag atcaccgtgt ggggcttcca cagcgacgac | 540 |
| gagactcaga tggccaagct gtacggcgac agcaagcccc agaagttcac cagcagcgcc | 600 |
| aacggcgtga ccacccacta tgtgtcccag atcggcggct ccctaaccca gacagaggat | 660 |
| ggcggcctgc cccagagcgg cagaatcgtg tggactaca tggtgcagaa gtccggcaag | 720 |
| accggcacaa tcacctacca gagaggcatc ctgctgcctc agaaagtgtg gtgcgccagc | 780 |
| ggcagatcta gcggcgaatc tcaagtccga cagcagttca gcaaggacat cgagaagctg | 840 |

```
ctgaacgagc aggtcaacaa agagatgcag agcagcaacc tgtacatgag catgagcagc    900
tggtgctaca cccacagcct ggacggcgct ggcctgttcc tgtttgatca cgccgccgag    960
gaatacgagc acgccaagaa gctgatcatc ttcctgaacg agaacaacgt gcccgtgcag   1020
ctgaccagca tcagcgcccc tgagcacaag ttcgagggcc tgacccagat cttccagaag   1080
gcctacgaac acgagcagca catctccgag agcatcaaca acatcgtgga ccacgccatc   1140
aagagcaagg atcacgccac cttcaacttt ctgcagtggt acgtggccga acagcacgag   1200
gaagaggtgc tgtttaagga catcctggac aagatcgagc tgatcggcaa cgagaaccac   1260
ggcctgtacc tggccgacca gtacgtgaag ggaatcgcca agagcagaaa gagccggaag   1320
cggagatctg gcagcggcgc tcctgtgaag cagaccctga acttcgacct gctgaagctg   1380
gccggcgacg tggaatctaa tcctgggccc atggatagca aaggctctag ccagaaaggc   1440
agccgactcc tgctcctgct ggtcgtcagt aacctgctgc tgccccaggg cgtcctcgcc   1500
aagacaagag gcaagctgtg ccccgactgc ctgaattgca ccgacctgga tgtggccctg   1560
ggcagaccta tgtgcgtggg cacaacacct agcgccaagg ccagcatcct gcacgaagtg   1620
cggcctgtga ccagcggctg cttccctatc atgcacgacc ggaccaagat caggcagctg   1680
gccaatctgc tgagaggcta cgagaacatc cggctgagca cccagaatgt gatcgatgcc   1740
gagaaggccc ctggcggccc ttacagactg gcacaagcg gcagctgtcc caacgccacc   1800
agcaagagcg cttttttcgc cacaatggcc tgggccgtgc caaggacaa caacaagaat   1860 gccaccaacc ctctgaccgt ggaagtgccc tacatctgcg ccgagggcga ggatcagatc   1920
acagtgtggg gcttccacag cgacgacaag acccagatga agaacctgta cggcgacagc   1980
aatcccagag agttcacctc cagcgccaat ggcgtgacca cccactacgt gtcccagatc   2040
ggcggcttcc ccgatcagac agaggatggc ggactgcccc agtccggcag aatcgtggtg   2100
gactacatga tgcagaagcc cggcaagacc ggcaccatcg tgtaccagag aggcgtgctg   2160
ctccctcaga aagtgtggtg cgcctctggc agaagctccg gagaatctca gtccgccag   2220 cagtttttcta aggacatcga aaagctgctc aatgaacagg tcaacaaaga gatgcagtcc   2280
tctaacctgt atatgagtat gagttcctgg tgctataccc actctctcga cggtgcaggg   2340
ctgttcctct tcgaccacgc tgcagaggaa tatgaacatg ctaagaaact gattatcttt   2400
ctcaacgaaa caacgtgcc agtccagctc accagtatct ctgcccctga acataagttt   2460 gagggggctca ctcagatctt tcagaaagct tacgagcacg agcagcatat ctctgagtct   2520
attaacaaca tcgtcgacca tgctatcaaa tctaaagacc acgctacttt taactttctc   2580
caatggtacg tcgcagagca gcatgaggaa gaggtcctct tcaaggacat tctcgacaaa   2640
attgaactca tcggaaacga aaaccatggg ctctacctgg ctgatcagta cgtcaaggga   2700
atcgcaaaaa gccggaagtc ttgatga                                         2727
```

<210> SEQ ID NO 175
<211> LENGTH: 907
<212> TYPE: PRT
<213> ORGANISM: Artificial Sequence
<220> FEATURE:
<223> OTHER INFORMATION: Synthetic

<400> SEQUENCE: 175

Met Asp Ser Lys Gly Ser Ser Gln Lys Gly Ser Arg Leu Leu Leu Leu
1               5                   10                  15

Leu Val Val Ser Asn Leu Leu Leu Pro Gln Gly Val Leu Ala Glu Thr

```
            20                  25                  30
Arg Gly Lys Leu Cys Pro Lys Cys Leu Asn Cys Thr Asp Leu Asp Val
        35                  40                  45
Ala Leu Gly Arg Pro Lys Cys Thr Gly Lys Ile Pro Ser Ala Arg Val
        50                  55                  60
Ser Ile Leu His Glu Val Arg Pro Val Thr Ser Gly Cys Phe Pro Ile
65                  70                  75                  80
Met His Asp Arg Thr Lys Ile Arg Gln Leu Pro Asn Leu Leu Arg Gly
                85                  90                  95
Tyr Glu His Ile Arg Leu Ser Thr His Asn Val Ile Asn Ala Glu Asn
                100                 105                 110
Ala Pro Gly Gly Pro Tyr Lys Ile Gly Thr Ser Gly Ser Cys Pro Asn
            115                 120                 125
Ile Thr Asn Gly Asn Gly Phe Phe Ala Thr Met Ala Trp Ala Val Pro
        130                 135                 140
Lys Asn Asp Lys Asn Lys Thr Ala Thr Asn Pro Leu Thr Ile Glu Val
145                 150                 155                 160
Pro Tyr Ile Cys Thr Glu Gly Glu Asp Gln Ile Thr Val Trp Gly Phe
                165                 170                 175
His Ser Asp Asp Glu Thr Gln Met Ala Lys Leu Tyr Gly Asp Ser Lys
                180                 185                 190
Pro Gln Lys Phe Thr Ser Ser Ala Asn Gly Val Thr Thr His Tyr Val
            195                 200                 205
Ser Gln Ile Gly Gly Phe Pro Asn Gln Thr Glu Asp Gly Gly Leu Pro
        210                 215                 220
Gln Ser Gly Arg Ile Val Val Asp Tyr Met Val Gln Lys Ser Gly Lys
225                 230                 235                 240
Thr Gly Thr Ile Thr Tyr Gln Arg Gly Ile Leu Leu Pro Gln Lys Val
                245                 250                 255
Trp Cys Ala Ser Gly Arg Ser Ser Gly Glu Ser Gln Val Arg Gln Gln
                260                 265                 270
Phe Ser Lys Asp Ile Glu Lys Leu Leu Asn Glu Gln Val Asn Lys Glu
            275                 280                 285
Met Gln Ser Ser Asn Leu Tyr Met Ser Met Ser Ser Trp Cys Tyr Thr
        290                 295                 300
His Ser Leu Asp Gly Ala Gly Leu Phe Leu Phe Asp His Ala Ala Glu
305                 310                 315                 320
Glu Tyr Glu His Ala Lys Lys Leu Ile Ile Phe Leu Asn Glu Asn Asn
                325                 330                 335
Val Pro Val Gln Leu Thr Ser Ile Ser Ala Pro Glu His Lys Phe Glu
            340                 345                 350
Gly Leu Thr Gln Ile Phe Gln Lys Ala Tyr Glu His Glu Gln His Ile
        355                 360                 365
Ser Glu Ser Ile Asn Asn Ile Val Asp His Ala Ile Lys Ser Lys Asp
        370                 375                 380
His Ala Thr Phe Asn Phe Leu Gln Trp Tyr Val Ala Glu Gln His Glu
385                 390                 395                 400
Glu Glu Val Leu Phe Lys Asp Ile Leu Asp Lys Ile Glu Leu Ile Gly
                405                 410                 415
Asn Glu Asn His Gly Leu Tyr Leu Ala Asp Gln Tyr Val Lys Gly Ile
                420                 425                 430
Ala Lys Ser Arg Lys Ser Arg Lys Arg Ser Gly Ser Gly Ala Pro
            435                 440                 445
```

-continued

```
Val Lys Gln Thr Leu Asn Phe Asp Leu Leu Lys Leu Ala Gly Asp Val
    450                 455                 460
Glu Ser Asn Pro Gly Pro Met Asp Ser Lys Gly Ser Gln Lys Gly
465                 470                 475                 480
Ser Arg Leu Leu Leu Leu Val Val Ser Asn Leu Leu Leu Pro Gln
                    485                 490                 495
Gly Val Leu Ala Lys Thr Arg Gly Lys Leu Cys Pro Asp Cys Leu Asn
                500                 505                 510
Cys Thr Asp Leu Asp Val Ala Leu Gly Arg Pro Met Cys Val Gly Thr
        515                 520                 525
Thr Pro Ser Ala Lys Ala Ser Ile Leu His Glu Val Arg Pro Val Thr
    530                 535                 540
Ser Gly Cys Phe Pro Ile Met His Asp Arg Thr Lys Ile Arg Gln Leu
545                 550                 555                 560
Ala Asn Leu Leu Arg Gly Tyr Glu Asn Ile Arg Leu Ser Thr Gln Asn
                    565                 570                 575
Val Ile Asp Ala Glu Lys Ala Pro Gly Gly Pro Tyr Arg Leu Gly Thr
                580                 585                 590
Ser Gly Ser Cys Pro Asn Ala Thr Ser Lys Ser Gly Phe Phe Ala Thr
        595                 600                 605
Met Ala Trp Ala Val Pro Lys Asp Asn Asn Lys Asn Ala Thr Asn Pro
    610                 615                 620
Leu Thr Val Glu Val Pro Tyr Ile Cys Ala Glu Gly Glu Asp Gln Ile
625                 630                 635                 640
Thr Val Trp Gly Phe His Ser Asp Asp Lys Thr Gln Met Lys Asn Leu
                    645                 650                 655
Tyr Gly Asp Ser Asn Pro Gln Lys Phe Thr Ser Ser Ala Asn Gly Val
                660                 665                 670
Thr Thr His Tyr Val Ser Gln Ile Gly Gly Phe Pro Asp Gln Thr Glu
        675                 680                 685
Asp Gly Gly Leu Pro Gln Ser Gly Arg Ile Val Val Asp Tyr Met Met
    690                 695                 700
Gln Lys Pro Gly Lys Thr Gly Thr Ile Val Tyr Gln Arg Gly Val Leu
705                 710                 715                 720
Leu Pro Gln Lys Val Trp Cys Ala Ser Gly Arg Ser Ser Gly Glu Ser
                    725                 730                 735
Gln Val Arg Gln Gln Phe Ser Lys Asp Ile Glu Lys Leu Leu Asn Glu
                740                 745                 750
Gln Val Asn Lys Glu Met Gln Ser Ser Asn Leu Tyr Met Ser Met Ser
        755                 760                 765
Ser Trp Cys Tyr Thr His Ser Leu Asp Gly Ala Gly Leu Phe Leu Phe
    770                 775                 780
Asp His Ala Ala Glu Glu Tyr Glu His Ala Lys Lys Leu Ile Ile Phe
785                 790                 795                 800
Leu Asn Glu Asn Asn Val Pro Val Gln Leu Thr Ser Ile Ser Ala Pro
                    805                 810                 815
Glu His Lys Phe Glu Gly Leu Thr Gln Ile Phe Gln Lys Ala Tyr Glu
                820                 825                 830
His Glu Gln His Ile Ser Glu Ser Ile Asn Asn Ile Val Asp His Ala
        835                 840                 845
Ile Lys Ser Lys Asp His Ala Thr Phe Asn Phe Leu Gln Trp Tyr Val
    850                 855                 860
```

Ala Glu Gln His Glu Glu Val Leu Phe Lys Asp Ile Leu Asp Lys
865                 870                 875                 880

Ile Glu Leu Ile Gly Asn Glu Asn His Gly Leu Tyr Leu Ala Asp Gln
            885                 890                 895

Tyr Val Lys Gly Ile Ala Lys Ser Arg Lys Ser
            900                 905

<210> SEQ ID NO 176
<211> LENGTH: 2727
<212> TYPE: DNA
<213> ORGANISM: Artificial Sequence
<220> FEATURE:
<223> OTHER INFORMATION: Synthetic

<400> SEQUENCE: 176

| | | | | | |
|---|---|---|---|---|---|
| tcatcaagac | ttccggcttt | tgcgattcc | cttgacgtac | tgatcagcca | ggtagagccc | 60 |
| atggttttcg | tttccgatga | gttcaatttt | gtcgagaatg | tccttgaaga | ggacctcttc | 120 |
| ctcatgctgc | tctgcgacgt | accattggag | aaagttaaaa | gtagcgtggt | ctttagattt | 180 |
| gatagcatgg | tcgacgatgt | tgttaataga | ctcagagata | tgctgctcgt | gctcgtaagc | 240 |
| tttctgaaag | atctgagtga | gcccctcaaa | cttatgttca | ggggcagaga | tactggtgag | 300 |
| ctggactggc | acgttgtttt | cgttgagaaa | gataatcagt | ttcttagcat | gttcatattc | 360 |
| ctctgcagcg | tggtcgaaga | ggaacagccc | tgcaccgtcg | agagagtggg | tatagcacca | 420 |
| ggaactcata | ctcatataca | ggttagagga | ctgcatctct | tgttgaccct | gttcattgag | 480 |
| cagcttttcg | atgtccttag | aaaactgctg | gcggacttga | gattctccgg | agcttctgcc | 540 |
| agaggcgcac | cacactttct | gagggagcag | cacgcctctc | tggtacacga | tggtgccggt | 600 |
| cttgccgggc | ttctgcatca | tgtagtccac | cacgattctg | ccggactggg | gcagtccgcc | 660 |
| atcctctgtc | tgatcgggga | agccgccgat | ctgggacacg | tagtgggtgg | tcacgccatt | 720 |
| ggcgctggag | gtgaacttct | ggggattgct | gtcgccgtac | aggttcttca | tctgggtctt | 780 |
| gtcgtcgctg | tggaagcccc | acactgtgat | ctgatcctcg | ccctcggcgc | agatgtaggg | 840 |
| cacttccacg | gtcagagggt | tggtggcatt | cttgttgttg | tccttgggca | cggcccaggc | 900 |
| cattgtggcg | aaaaagccgc | tcttgctggt | ggcgttggga | cagctgccgc | ttgtgcccag | 960 |
| tctgtaaggg | ccgccagggg | ccttctcggc | atcgatcaca | ttctgggtgc | tcagccggat | 1020 |
| gttctcgtag | cctctcagca | gattggccag | ctgcctgatc | ttggtccggt | cgtgcatgat | 1080 |
| agggaagcag | ccgctggtca | caggccgcac | ttcgtgcagg | atgctggcct | ggcgctagg | 1140 |
| tgttgtgccc | acgcacatag | gtctgcccag | ggccacatcc | aggtcggtgc | aattcaggca | 1200 |
| gtcgggggcac | agcttgcctc | ttgtcttggc | gaggacgccc | tggggcagca | gcaggttact | 1260 |
| gacgaccagc | aggagcagga | gtcggctgcc | tttctggcta | gagcctttgc | tatccatggg | 1320 |
| cccaggatta | gattccacgt | cgccggccag | cttcagcagg | tcgaagttca | gggtctgctt | 1380 |
| cacaggagcg | ccgctgccag | atctccgctt | ccggctcttt | ctgctcttgg | cgattccctt | 1440 |
| cacgtactgg | tcggccaggt | acaggccgtg | gttctcgttg | ccgatcagct | cgatcttgtc | 1500 |
| caggatgtcc | ttaaacagca | cctcttcctc | gtgctgttcg | gccacgtacc | actgcagaaa | 1560 |
| gttgaaggtg | gcgtgatcct | tgctcttgat | ggcgtggtcc | acgatgttgt | tgatgctctc | 1620 |
| ggagatgtgc | tgctcgtgtt | cgtaggcctt | ctggaagatc | tgggtcaggc | cctcgaactt | 1680 |
| gtgctcaggg | gcgctgatgc | tggtcagctg | cacgggcacg | ttgttctcgt | tcaggaagat | 1740 |
| gatcagcttc | ttggcgtgct | cgtattcctc | ggcggcgtga | tcaaacagga | acaggccagc | 1800 |

| | |
|---|---:|
| gccgtccagg ctgtgggtgt agcaccagct gctcatgctc atgtacaggt tgctgctctg | 1860 |
| catctctttg ttgacctgct cgttcagcag cttctcgatg tccttgctga actgctgtcg | 1920 |
| gacttgagat tcgccgctag atctgccgct ggcgcaccac actttctgag gcagcaggat | 1980 |
| gcctctctgg taggtgattg tgccggtctt gccggacttc tgcaccatgt agtccaccac | 2040 |
| gattctgccg ctctggggca ggccgccatc tctgtctgg ttagggaagc cgccgatctg | 2100 |
| ggacacatag tgggtggtca cgccgttggc gctgctggtg aacttctggg gcttgctgtc | 2160 |
| gccgtacagc ttggccatct gagtctcgtc gtcgctgtgg aagccccaca cggtgatctg | 2220 |
| gtcctcgccc tcggtgcaga tgtagggcac ctcgatggtc agagggttgg tggcggtctt | 2280 |
| gttcttgtcg ttcttgggca cggcccaggc catggtggcg aaaaagccgt tgccgttggt | 2340 |
| gatgttgggg cagcttccgc tggtgccgat cttgtaaggg ccgccagggg cattctcggc | 2400 |
| gttgatcacg ttgtgggtgc tcagtctgat gtgctcgtag ccccgcagca ggttgggcag | 2460 |
| ctgtctgatc ttggtccggt cgtgcatgat ggggaagcag ccgctggtca caggccgcac | 2520 |
| ttcgtgcagg atggacactc tggcgctggg gatcttgccg gtgcacttag gtctgcccag | 2580 |
| ggccacatcc aggtcggtgc agttcaggca cttggggcac agcttgcctc ttgtctcggc | 2640 |
| tagcacgccc tgaggcagca ggaggttgga caccaccagg agcagcagca gtctggagcc | 2700 |
| cttctggctg ctgcccttgc tgtccat | 2727 |

<210> SEQ ID NO 177
<211> LENGTH: 4011
<212> TYPE: DNA
<213> ORGANISM: Artificial Sequence
<220> FEATURE:
<223> OTHER INFORMATION: Synthetic

<400> SEQUENCE: 177

| | |
|---|---:|
| atggacagca agggcagcag ccagaagggc tccagactgc tgctgctcct ggtggtgtcc | 60 |
| aacctcctgc tgcctcaggg cgtgctagcc gtggctcctc tgcacctggg caagtgcaat | 120 |
| atcgccggct ggattctggg caaccccgag tgcgagagcc tgagcacagc cagcagctgg | 180 |
| tcctacatcg tggaaacccc tagcagcgac aacggcacct gtttccccgg cgacttcatc | 240 |
| gactacgagg aactgcgcga gcagctgagc agcgtgtcca gcttcgagag attcgagatc | 300 |
| ttccccaaga cctccagctg gcccaaccac gacagcaaca aaggcgtgac cgccgcctgt | 360 |
| cctcacgctg gcgccaagag cttctacaag aacctgatct ggctggtcaa gaagggcaac | 420 |
| agctacccca gctgagcaa gagctacatc aacgacaagg caaagaggt gctggtcctc | 480 |
| tggggcatcc accaccctag cacaagcgcc gaccagcaga gcctgtacca gaacgccgac | 540 |
| gcctacgtgt tcgtgggcag ctcccggtac agcaagaagt tcaagcccga gatcgccatc | 600 |
| cggcccaaag tgcgggacca ggaaggccgg atgaactact actggaccct ggtggaaccc | 660 |
| ggcgacaaga tcaccttcga ggccaccggc aatctggtgg tgcccagata cgccttcgcc | 720 |
| atggaaagaa acgccagcgg cgagagccaa gtccgacagc agttcagcaa ggacatcgag | 780 |
| aagctgctga cgagcaggt caacaaagag atgcagagca gcaacctgta catgagcatg | 840 |
| tccagctggt gttacaccca cagcctggac ggcgctggcc tgttcctgtt tgatcacgcc | 900 |
| gccgaggaat acgagcacgc caagaagctg atcatcttcc tgaacgagaa caacgtgccc | 960 |
| gtgcagctga ccagcatcag cgccccagag cacaagttcg agggcctgac ccagatcttc | 1020 |
| cagaaggcct acgaacacga gcagcacatc agcgagagca tcaacaatat cgtggaccac | 1080 |
| gccatcaaga gcaaggatca cgccaccttc aactttctgc aatggtacgt ggccgaacag | 1140 |

```
cacgaggaag aagtgctgtt taaggacatc ctggacaaga tcgagctgat cggcaacgag   1200
aaccacggcc tgtacctggc cgaccagtac gtgaagggca ttgccaagag cagaaagagc   1260
cggaagcgga gatctggcag cggcgctcct gtgaagcaga ccctgaactt cgacctgctg   1320
aagctggccg cgacgtggaa aagcaaccct gggcccatgg actccaaggg ctcctcccag   1380
aaaggatctc ggctgctcct cctgctcgtg gtgtctaatc tgctgctgcc acagggtgtc   1440
ctggcccacc agatcctgga tggcgagaac tgcaccctga tcgacgccct gctgggcgac   1500
cctcagtgcg acggcttcca gaacaagaag tgggacctgt tcgtcgagcg gagcaaggcc   1560
tacagcaact gcttccccta cgacgtgccc gactacgcca gcctgagaag cctggtggcc   1620
agcagcggca ccctggaatt caacaacgag agcttcaact ggaacggcgt gacccagaac   1680
ggcaccagct ccgcctgcat cagaagaagc aacaacagct tcttctcccg gctgaactgg   1740
ctgacccacc tgaatttcaa gtaccccgcc ctgaacgtga ccatgcccaa caatgagcag   1800
ttcgacaagc tgtacatctg gggagtgcac acccccgtga ccgacaagga ccagatcttt   1860
ctgtacgccc agcccagcgg ccggatcacc gtgtctacca agagaagcca gcaggccgtg   1920
atccccaaca tcggcttccg gcccaggatc agaaacatcc ccagccggat cagcatctac   1980
tggacaatcg tgaagcctgg cgacatcctg ctgatcaaca gcaccggcaa cctgatcgcc   2040
cctcggggct acttcaagat cagaagcggc gcctccggag agtcccaagt gcgccagcag   2100
ttttccaagg atattgagaa actcctcaat gaacaggtca caaggaaat gcagtcctcc   2160 aacctctaca tgtctatgtc ctcttggtgc tacacacact ccctggatgg ggccggactg   2220
tttctgttcg accatgccgc tgaagagtat gaacacgcca aaaaactcat cattttctc   2280 aatgagaaca atgtccctgt ccagctcacc tccatctccg ctcccgagca caaatttgaa   2340
ggactcacac agatttttca gaaagcctat gagcatgaac agcacatttc cgagtccatc   2400
aacaacattg tcgatcatgc cattaagtcc aaggaccatg ctacattcaa tttcctccaa   2460
tggtatgtcg ctgagcagca tgaagaggaa gtcctgttca agatatcct cgataagatc   2520 gaactcattg ggaatgagaa tcacgggctc tatctcgccg atcagtatgt gaaagggatc   2580
gctaagtccc ggaagtccag aaagcggaga agcggctctg gcgccccagt caaacagaca   2640
ctgaattttg atctgctcaa gctcgctggg gacgtcgagt ccaatccagg gcccatggat   2700
agcaaaggct ctagccagaa aggcagccga ctcctgctcc tgctggtcgt cagtaacctg   2760
ctgctgcccc agggcgtcct cgccaagaca agaggcaagc tgtgccccga ctgcctgaat   2820
tgcaccgacc tggatgtggc cctgggcaga cctatgtgcg tgggcacaac acctagcgcc   2880
aaggccagca tcctgcacga agtgcggcct gtgaccagcg gctgcttccc tatcatgcac   2940
gaccggacca agatcaggca gctggccaat ctgctgagag ctacgagaa catccggctg   3000 agcacccaga atgtgatcga tgccgagaag gcccctggcg gcccttacag actgggcaca   3060
agcggcagct gtcccaacgc caccagcaag agcggctttt tcgccacaat ggcctgggcc   3120
gtgcccaagg acaacaacaa gaatgccacc aaccctctga ccgtggaagt gcctacatc   3180 tgcgccgagg cgaggatca gatcacagtg tggggcttcc acagcgacga caagacccag   3240
atgaagaacc tgtacggcga cagcaatccc cagaagttca cctccagcgc caatggcgtg   3300
accacccact acgtgtccca gatcggcggc ttccccgatc agacagagga tggcggactg   3360
ccccagtccg gcagaatcgt ggtggactac atgatgcaga agcccggcaa gaccggcacc   3420
atcgtgtacc agagaggcgt gctgctccct cagaaagtgt ggtgcgcctc tggcagaagc   3480
```

```
tccggagaat ctcaagtccg ccagcagttt tctaaggaca tcgaaaagct gctcaatgaa    3540
caggtcaaca aagagatgca gtcctctaac ctgtatatga gtatgagttc ctggtgctat    3600
acccactctc tcgacggtgc agggctgttc ctcttcgacc acgctgcaga ggaatatgaa    3660
catgctaaga aactgattat ctttctcaac gaaaacaacg tgccagtcca gctcaccagt    3720
atctctgccc ctgaacataa gtttgagggg ctcactcaga tctttcagaa agcttacgag    3780
cacgagcagc atatctctga gtctattaac aacatcgtcg accatgctat caaatctaaa    3840
gaccacgcta cttttaactt ctccaatgg tacgtcgcag agcagcatga ggaagaggtc    3900
ctcttcaagg acattctcga caaaattgaa ctcatcggaa acgaaaacca tgggctctac    3960
ctggctgatc agtacgtcaa gggaatcgca aaaagccgga agtcttgatg a             4011
```

<210> SEQ ID NO 178
<211> LENGTH: 1335
<212> TYPE: PRT
<213> ORGANISM: Artificial Sequence
<220> FEATURE:
<223> OTHER INFORMATION: Synthetic

<400> SEQUENCE: 178

```
Met Asp Ser Lys Gly Ser Ser Gln Lys Gly Ser Arg Leu Leu Leu Leu
1               5                   10                  15

Leu Val Val Ser Asn Leu Leu Pro Gln Gly Val Leu Ala Val Ala
            20                  25                  30

Pro Leu His Leu Gly Lys Cys Asn Ile Ala Gly Trp Ile Leu Gly Asn
        35                  40                  45

Pro Glu Cys Glu Ser Leu Ser Thr Ala Ser Ser Trp Ser Tyr Ile Val
    50                  55                  60

Glu Thr Pro Ser Ser Asp Asn Gly Thr Cys Phe Pro Gly Asp Phe Ile
65                  70                  75                  80

Asp Tyr Glu Glu Leu Arg Glu Gln Leu Ser Ser Val Ser Ser Phe Glu
                85                  90                  95

Arg Phe Glu Ile Phe Pro Lys Thr Ser Ser Trp Pro Asn His Asp Ser
            100                 105                 110

Asn Lys Gly Val Thr Ala Ala Cys Pro His Ala Gly Ala Lys Ser Phe
        115                 120                 125

Tyr Lys Asn Leu Ile Trp Leu Val Lys Lys Gly Asn Ser Tyr Pro Lys
    130                 135                 140

Leu Ser Lys Ser Tyr Ile Asn Asp Lys Gly Lys Glu Val Leu Val Leu
145                 150                 155                 160

Trp Gly Ile His His Pro Ser Thr Ser Ala Asp Gln Gln Ser Leu Tyr
                165                 170                 175

Gln Asn Ala Asp Ala Tyr Val Phe Val Gly Ser Ser Arg Tyr Ser Lys
            180                 185                 190

Lys Phe Lys Pro Glu Ile Ala Ile Arg Pro Lys Val Arg Asp Gln Glu
        195                 200                 205

Gly Arg Met Asn Tyr Tyr Trp Thr Leu Val Glu Pro Gly Asp Lys Ile
    210                 215                 220

Thr Phe Glu Ala Thr Gly Asn Leu Val Val Pro Arg Tyr Ala Phe Ala
225                 230                 235                 240

Met Glu Arg Asn Ala Ser Gly Glu Ser Gln Val Arg Gln Gln Phe Ser
                245                 250                 255

Lys Asp Ile Glu Lys Leu Leu Asn Glu Gln Val Asn Lys Glu Met Gln
            260                 265                 270
```

```
Ser Ser Asn Leu Tyr Met Ser Met Ser Ser Trp Cys Tyr Thr His Ser
        275                 280                 285

Leu Asp Gly Ala Gly Leu Phe Leu Phe Asp His Ala Ala Glu Glu Tyr
    290                 295                 300

Glu His Ala Lys Lys Leu Ile Ile Phe Leu Asn Glu Asn Asn Val Pro
305                 310                 315                 320

Val Gln Leu Thr Ser Ile Ser Ala Pro Glu His Lys Phe Glu Gly Leu
                325                 330                 335

Thr Gln Ile Phe Gln Lys Ala Tyr Glu His Glu Gln His Ile Ser Glu
                340                 345                 350

Ser Ile Asn Asn Ile Val Asp His Ala Ile Lys Ser Lys Asp His Ala
        355                 360                 365

Thr Phe Asn Phe Leu Gln Trp Tyr Val Ala Glu Gln His Glu Glu Glu
    370                 375                 380

Val Leu Phe Lys Asp Ile Leu Asp Lys Ile Glu Leu Ile Gly Asn Glu
385                 390                 395                 400

Asn His Gly Leu Tyr Leu Ala Asp Gln Tyr Val Lys Gly Ile Ala Lys
                405                 410                 415

Ser Arg Lys Ser Arg Lys Arg Ser Gly Ser Gly Ala Pro Val Lys
                420                 425                 430

Gln Thr Leu Asn Phe Asp Leu Leu Lys Leu Ala Gly Asp Val Glu Ser
                435                 440                 445

Asn Pro Gly Pro Met Asp Ser Lys Gly Ser Ser Gln Lys Gly Ser Arg
            450                 455                 460

Leu Leu Leu Leu Leu Val Val Ser Asn Leu Leu Leu Pro Gln Gly Val
465                 470                 475                 480

Leu Ala His Gln Ile Leu Asp Gly Glu Asn Cys Thr Leu Ile Asp Ala
                485                 490                 495

Leu Leu Gly Asp Pro Gln Cys Asp Gly Phe Gln Asn Lys Lys Trp Asp
            500                 505                 510

Leu Phe Val Glu Arg Ser Lys Ala Tyr Ser Asn Cys Phe Pro Tyr Asp
            515                 520                 525

Val Pro Asp Tyr Ala Ser Leu Arg Ser Leu Val Ala Ser Ser Gly Thr
            530                 535                 540

Leu Glu Phe Asn Asn Glu Ser Phe Asn Trp Asn Gly Val Thr Gln Asn
545                 550                 555                 560

Gly Thr Ser Ser Ala Cys Ile Arg Arg Ser Asn Asn Ser Phe Phe Ser
                565                 570                 575

Arg Leu Asn Trp Leu Thr His Leu Asn Phe Lys Tyr Pro Ala Leu Asn
            580                 585                 590

Val Thr Met Pro Asn Asn Glu Gln Phe Asp Lys Leu Tyr Ile Trp Gly
            595                 600                 605

Val His His Pro Val Thr Asp Lys Asp Gln Ile Phe Leu Tyr Ala Gln
            610                 615                 620

Pro Ser Gly Arg Ile Thr Val Ser Thr Lys Arg Ser Gln Gln Ala Val
625                 630                 635                 640

Ile Pro Asn Ile Gly Phe Arg Pro Arg Ile Arg Asn Ile Pro Ser Arg
                645                 650                 655

Ile Ser Ile Tyr Trp Thr Ile Val Lys Pro Gly Asp Ile Leu Leu Ile
                660                 665                 670

Asn Ser Thr Gly Asn Leu Ile Ala Pro Arg Gly Tyr Phe Lys Ile Arg
                675                 680                 685

Ser Gly Ala Ser Gly Glu Ser Gln Val Arg Gln Gln Phe Ser Lys Asp
```

```
                690             695              700
Ile Glu Lys Leu Leu Asn Glu Gln Val Asn Lys Glu Met Gln Ser Ser
705              710             715              720

Asn Leu Tyr Met Ser Met Ser Ser Trp Cys Tyr Thr His Ser Leu Asp
                725             730              735

Gly Ala Gly Leu Phe Leu Phe Asp His Ala Ala Glu Tyr Glu His
                740             745              750

Ala Lys Lys Leu Ile Ile Phe Leu Asn Glu Asn Asn Val Pro Val Gln
                755             760              765

Leu Thr Ser Ile Ser Ala Pro Glu His Lys Phe Glu Gly Leu Thr Gln
770              775             780

Ile Phe Gln Lys Ala Tyr Glu His Glu Gln His Ile Ser Glu Ser Ile
785              790             795              800

Asn Asn Ile Val Asp His Ala Ile Lys Ser Lys Asp His Ala Thr Phe
                805             810             815

Asn Phe Leu Gln Trp Tyr Val Ala Glu Gln His Glu Glu Val Leu
                820             825             830

Phe Lys Asp Ile Leu Asp Lys Ile Glu Leu Ile Gly Asn Glu Asn His
                835             840             845

Gly Leu Tyr Leu Ala Asp Gln Tyr Val Lys Gly Ile Ala Lys Ser Arg
850              855             860

Lys Ser Arg Lys Arg Ser Gly Ser Gly Ala Pro Val Lys Gln Thr
865              870             875             880

Leu Asn Phe Asp Leu Leu Lys Leu Ala Gly Asp Val Glu Ser Asn Pro
                885             890             895

Gly Pro Met Asp Ser Lys Gly Ser Ser Gln Lys Gly Ser Arg Leu Leu
                900             905             910

Leu Leu Leu Val Val Ser Asn Leu Leu Pro Gln Gly Val Leu Ala
                915             920             925

Lys Thr Arg Gly Lys Leu Cys Pro Asp Cys Leu Asn Cys Thr Asp Leu
930              935             940

Asp Val Ala Leu Gly Arg Pro Met Cys Val Gly Thr Thr Pro Ser Ala
945              950             955             960

Lys Ala Ser Ile Leu His Glu Val Arg Pro Val Thr Ser Gly Cys Phe
                965             970             975

Pro Ile Met His Asp Arg Thr Lys Ile Arg Gln Leu Ala Asn Leu Leu
                980             985             990

Arg Gly Tyr Glu Asn Ile Arg Leu Ser Thr Gln Asn Val Ile Asp Ala
                995             1000            1005

Glu Lys Ala Pro Gly Gly Pro Tyr Arg Leu Gly Thr Ser Gly Ser
1010             1015            1020

Cys Pro Asn Ala Thr Ser Lys Ser Gly Phe Phe Ala Thr Met Ala
1025             1030            1035

Trp Ala Val Pro Lys Asp Asn Asn Lys Asn Ala Thr Asn Pro Leu
1040             1045            1050

Thr Val Glu Val Pro Tyr Ile Cys Ala Glu Gly Glu Asp Gln Ile
1055             1060            1065

Thr Val Trp Gly Phe His Ser Asp Asp Lys Thr Gln Met Lys Asn
1070             1075            1080

Leu Tyr Gly Asp Ser Asn Pro Gln Lys Phe Thr Ser Ser Ala Asn
1085             1090            1095

Gly Val Thr Thr His Tyr Val Ser Gln Ile Gly Gly Phe Pro Asp
1100             1105            1110
```

```
Gln Thr Glu Asp Gly Gly Leu Pro Gln Ser Gly Arg Ile Val Val
     1115                1120                1125

Asp Tyr Met Met Gln Lys Pro Gly Lys Thr Gly Thr Ile Val Tyr
     1130                1135                1140

Gln Arg Gly Val Leu Leu Pro Gln Lys Val Trp Cys Ala Ser Gly
     1145                1150                1155

Arg Ser Ser Gly Glu Ser Gln Val Arg Gln Gln Phe Ser Lys Asp
     1160                1165                1170

Ile Glu Lys Leu Leu Asn Glu Gln Val Asn Lys Glu Met Gln Ser
     1175                1180                1185

Ser Asn Leu Tyr Met Ser Met Ser Ser Trp Cys Tyr Thr His Ser
     1190                1195                1200

Leu Asp Gly Ala Gly Leu Phe Leu Phe Asp His Ala Ala Glu Glu
     1205                1210                1215

Tyr Glu His Ala Lys Lys Leu Ile Ile Phe Leu Asn Glu Asn Asn
     1220                1225                1230

Val Pro Val Gln Leu Thr Ser Ile Ser Ala Pro Glu His Lys Phe
     1235                1240                1245

Glu Gly Leu Thr Gln Ile Phe Gln Lys Ala Tyr Glu His Glu Gln
     1250                1255                1260

His Ile Ser Glu Ser Ile Asn Asn Ile Val Asp His Ala Ile Lys
     1265                1270                1275

Ser Lys Asp His Ala Thr Phe Asn Phe Leu Gln Trp Tyr Val Ala
     1280                1285                1290

Glu Gln His Glu Glu Val Leu Phe Lys Asp Ile Leu Asp Lys
     1295                1300                1305

Ile Glu Leu Ile Gly Asn Glu Asn His Gly Leu Tyr Leu Ala Asp
     1310                1315                1320

Gln Tyr Val Lys Gly Ile Ala Lys Ser Arg Lys Ser
     1325                1330                1335

<210> SEQ ID NO 179
<211> LENGTH: 4011
<212> TYPE: DNA
<213> ORGANISM: Artificial Sequence
<220> FEATURE:
<223> OTHER INFORMATION: Synthetic

<400> SEQUENCE: 179
tcatcaagac ttccggcttt ttgcgattcc cttgacgtac tgatcagcca ggtagagccc      60
atggttttcg tttccgatga gttcaatttt gtcgagaatg tccttgaaga ggacctcttc     120
ctcatgctgc tctgcgacgt accattggag aaagttaaaa gtagcgtggt ctttagattt     180
gatagcatgg tcgacgatgt tgttaataga ctcagagata tgctgctcgt gctcgtaagc     240
tttctgaaag atctgagtga gcccctcaaa cttatgttca gggcagagaa tactggtgag     300
ctggactggc acgttgtttt cgttgagaaa gataatcagt ttcttagcat gttcatattc     360
ctctgcagcg tggtcgaaga ggaacagccc tgcaccgtcg agagagtggg tatagcacca     420
ggaactcata tcatataca ggttagagga ctgcatctct ttgttgacct gttcattgag     480
cagcttttcg atgtccttag aaaactgctg gcggacttga gattctccgg agcttctgcc     540
agaggcgcac cacactttct gagggagcag cacgcctctc tggtacacga tggtgccggt     600
cttgccgggc ttctgcatca tgtagtccac cacgattctg ccggactggg gcagtccgcc     660
atcctctgtc tgatcgggga agccgccgat ctgggacacg tagtgggtgg tcacgccatt     720
```

-continued

```
ggcgctggag gtgaacttct ggggattgct gtcgccgtac aggttcttca tctgggtctt      780
gtcgtcgctg tggaagcccc acactgtgat ctgatcctcg ccctcggcgc agatgtaggg      840
cacttccacg gtcagagggt tggtggcatt cttgttgttg tccttgggca cggcccaggc      900
cattgtggcg aaaaagccgc tcttgctggt ggcgttggga cagctgccgc ttgtgcccag      960
tctgtaaggg ccgccagggg ccttctcggc atcgatcaca ttctgggtgc tcagccggat     1020
gttctcgtag cctctcagca gattggccag ctgcctgatc ttggtccggt cgtgcatgat     1080
agggaagcag ccgctggtca caggccgcac ttcgtgcagg atgctggcct ggcgctagg      1140 tgttgtgccc acgcacatag gtctgcccag ggccacatcc aggtcggtgc aattcaggca     1200
gtcggggcac agcttgcctc ttgtcttggc gaggacgccc tggggcagca gcaggttact     1260
gacgaccagc aggagcagga gtcggctgcc tttctggcta gagcctttgc tatccatggg     1320
ccctggattg gactcgacgt ccccagcgag cttgagcaga tcaaaattca gtgtctgttt     1380
gactggggcg ccagagccgc ttctccgctt tctggacttc cgggacttag cgatcccttt     1440
cacatactga tcggcgagat agagcccgtg attctcattc caatgagtt cgatcttatc      1500 gaggatatct ttgaacagga cttcctcttc atgctgctca gcgacatacc attggaggaa     1560
attgaatgta gcatggtcct tggacttaat ggcatgatcg acaatgttgt tgatggactc     1620
ggaaatgtgc tgttcatgct cataggcttt ctgaaaaatc tgtgtgagtc cttcaaattt     1680
gtgctcggga gcggagatgg aggtgagctg acagggaca ttgttctcat tgagaaaaat      1740
gatgagtttt ttggcgtgtt catactcttc agcggcatgg tcgaacagaa acagtccggc     1800
cccatccagg gagtgtgtgt agcaccaaga ggacatagac atgtagaggt tggaggactg     1860
catttccttg ttgacctgtt cattgaggag tttctcaata tccttggaaa actgctggcg     1920
cacttgggac tctccggagg cgccgcttct gatcttgaag tagccccgag gggcgatcag     1980
gttgccggtg ctgttgatca gcaggatgtc gccaggcttc acgattgtcc agtagatgct     2040
gatccggctg gggatgtttc tgatcctggg ccggaagccg atgttgggga tcacggcctg     2100
ctggcttctc ttggtagaca cggtgatccg gccgctgggc tgggcgtaca gaaagatctg     2160
gtccttgtcg gtcacggggt ggtgcactcc ccagatgtac agcttgtcga actgctcatt     2220
gttgggcatg gtcacgttca gggcggggta cttgaaattc aggtgggtca gccagttcag     2280
ccgggagaag aagctgttgt tgcttcttct gatgcaggcg gagctggtgc cgttctgggt     2340
cacgccgttc cagttgaagc tctcgttgtt gaattccagg gtgccgctgc tggccaccag     2400
gcttctcagg ctggcgtagt cgggcacgtc gtaggggaag cagttgctgt aggcctttgct    2460 ccgctcgacg aacaggtccc acttcttgtt ctggaagccg tcgcactgag gtcgcccag      2520 cagggcgtca atcagggtgc agttctcgcc atccaggatc tggtgggcca ggacaccctg     2580
tggcagcagc agattagaca ccacgagcag gaggagcagc cgagatcctt tctggggagga   2640 gcccttggag tccatgggcc cagggttgct ttccacgtcg ccggccagct tcagcaggtc     2700
gaagttcagg gtctgcttca caggagcgcc gctgccagat ctccgcttcc ggctcttttct   2760 gctcttggca atgcccttca cgtactggtc ggccaggtac aggccgtggt tctcgttgcc     2820
gatcagctcg atcttgtcca ggatgtcctt aaacagcact tcttcctcgt gctgttcggc     2880
cacgtaccat tgcagaaagt tgaaggtggc gtgatccttg tcttgatgg cgtggtccac      2940 gatattgttg atgctctcgc tgatgtgctg ctcgtgttcg taggccttct ggaagatctg     3000
ggtcaggccc tcgaacttgt gctctggggc gctgatgctg tcagctgca cgggcacgtt      3060
```

| | |
|---|---|
| gttctcgttc aggaagatga tcagcttctt ggcgtgctcg tattcctcgg cggcgtgatc | 3120 |
| aaacaggaac aggccagcgc cgtccaggct gtgggtgtaa caccagctgg acatgctcat | 3180 |
| gtacaggttg ctgctctgca tctctttgtt gacctgctcg ttcagcagct tctcgatgtc | 3240 |
| cttgctgaac tgctgtcgga cttggctctc gccgctggcg tttctttcca tggcgaaggc | 3300 |
| gtatctgggc accaccagat tgccggtggc ctcgaaggtg atcttgtcgc cgggttccac | 3360 |
| cagggtccag tagtagttca tccggccttc ctggtcccgc actttgggcc ggatggcgat | 3420 |
| ctcgggcttg aacttcttgc tgtaccggga gctgcccacg aacacgtagg cgtcggcgtt | 3480 |
| ctggtacagg ctctgctggt cggcgcttgt gctagggtgg tggatgcccc agaggaccag | 3540 |
| cacctctttg cccttgtcgt tgatgtagct cttgctcagc ttggggtagc tgttgccctt | 3600 |
| cttgaccagc cagatcaggt tcttgtagaa gctcttggcg ccagcgtgag gacaggcggc | 3660 |
| ggtcacgcct ttgttgctgt cgtggttggg ccagctggag gtcttgggga agatctcgaa | 3720 |
| tctctcgaag ctggacacgc tgctcagctg ctcgcgcagt tcctcgtagt cgatgaagtc | 3780 |
| gccggggaaa caggtgccgt tgtcgctgct aggggtttcc acgatgtagg accagctgct | 3840 |
| ggctgtgctc aggctctcgc actcggggtt gcccagaatc cagccggcga tattgcactt | 3900 |
| gcccaggtgc agaggagcca cggctagcac gccctgaggc agcaggaggt tggacaccac | 3960 |
| caggagcagc agcagtctgg agcccttctg gctgctgccc ttgctgtcca t | 4011 |

<210> SEQ ID NO 180
<211> LENGTH: 1518
<212> TYPE: DNA
<213> ORGANISM: Artificial Sequence
<220> FEATURE:
<223> OTHER INFORMATION: Synthetic

<400> SEQUENCE: 180

| | |
|---|---|
| atgcccatgg gcagcctgca gcccctggcc accctgtacc tgctgggcat gctggtggct | 60 |
| agcgtgctgg ccatggagtt cctgaagagg agcttcgccc tctgaccga aagcagtgg | 120 |
| caggagatcg acaacagggc cagggagatc ttcaagaccc agctgtacgg caggaagttc | 180 |
| gtggacgtga gggccccta cggctgggag tacgccgccc accccctggg cgaggtggag | 240 |
| gtgctgagcg acgagaacga ggtggtgaag tggggcctga ggaagagcct gcccctgatc | 300 |
| gagctgaggg ccaccttcac cctggacctg tgggagctgg acaacctgga gggggcaag | 360 |
| cccaacgtgg acctgagcag cctggaggag accgtgagga aggtggccga gttcgaggac | 420 |
| gaggtgatct tcaggggctg cgagaagagc ggcgtgaagg gcctgctgag cttcgaggag | 480 |
| aggaagatcg agtgcggcag cacccccaag gacctgctgg aggccatcgt gagggccctg | 540 |
| agcatcttca gcaaggacgg catcgagggc ccctacaccc tggtgatcaa caccgacagg | 600 |
| tggatcaact tcctgaagga ggaggccggc cactaccccc tggagaagag ggtggaggag | 660 |
| tgcctgaggg gcggcaagat catcaccacc cccaggatcg aggacgccct ggtggtgagc | 720 |
| gagaggggcg gcgacttcaa gctgatcctg gccaggacc tgagcatcgg ctacgaggac | 780 |
| agggagaagg acgccgtgag gctgttcatc accgagacct tcaccttcca ggtggtgaac | 840 |
| cccgaggccc tgatcctgct gaagtccgga attgccctc tgcagctggg caattgttct | 900 |
| gtggccggat ggattctggg caaccccgag tgtgagctgc tgatttctaa ggagagctgg | 960 |
| agctacatcg tggagacccc caatcctgag aatggcacct gctaccctgg ctacttcgcc | 1020 |
| gattacgagg agctgcgcga gcagctgtct agcgtgtcca gcttcgagag attcgagatc | 1080 |
| ttccccaagg agtccagctg gcctaatcac acagtgacag gcgtgtctgc cagctgtagc | 1140 |

```
cacaacggca aaagcagctt ctaccggaac ctgctgtggc tgacaggcaa gaatggcctg    1200
taccccaacc tgagcaagag ctacgtgaac aacaaggaaa aggaagtgct ggtgctgtgg    1260
ggagtgcacc accctcccaa catcggaaat cagcgggccc tgtaccacac agagaacgcc    1320
tatgtgagcg tggtgtccag ccactacagc agaagattca cccccgagat cgccaagaga    1380
cccaaagtga gagaccagga gggccggatc aattactact ggaccctgct ggagcctggc    1440
gataccatca tcttcgaggc caacggcaat ctgatcgccc ttggtatgc ctttgccctg      1500 agcagaggcg cctgatga                                                  1518
```

<210> SEQ ID NO 181
<211> LENGTH: 504
<212> TYPE: PRT
<213> ORGANISM: Artificial Sequence
<220> FEATURE:
<223> OTHER INFORMATION: Synthetic

<400> SEQUENCE: 181

```
Met Pro Met Gly Ser Leu Gln Pro Leu Ala Thr Leu Tyr Leu Leu Gly
1               5                   10                  15

Met Leu Val Ala Ser Val Leu Ala Met Glu Phe Leu Lys Arg Ser Phe
            20                  25                  30

Ala Pro Leu Thr Glu Lys Gln Trp Gln Glu Ile Asp Asn Arg Ala Arg
        35                  40                  45

Glu Ile Phe Lys Thr Gln Leu Tyr Gly Arg Lys Phe Val Asp Val Glu
    50                  55                  60

Gly Pro Tyr Gly Trp Glu Tyr Ala Ala His Pro Leu Gly Glu Val Glu
65                  70                  75                  80

Val Leu Ser Asp Glu Asn Glu Val Val Lys Trp Gly Leu Arg Lys Ser
                85                  90                  95

Leu Pro Leu Ile Glu Leu Arg Ala Thr Phe Thr Leu Asp Leu Trp Glu
            100                 105                 110

Leu Asp Asn Leu Glu Arg Gly Lys Pro Asn Val Asp Leu Ser Ser Leu
        115                 120                 125

Glu Glu Thr Val Arg Lys Val Ala Glu Phe Glu Asp Glu Val Ile Phe
    130                 135                 140

Arg Gly Cys Glu Lys Ser Gly Val Lys Gly Leu Leu Ser Phe Glu Glu
145                 150                 155                 160

Arg Lys Ile Glu Cys Gly Ser Thr Pro Lys Asp Leu Leu Glu Ala Ile
                165                 170                 175

Val Arg Ala Leu Ser Ile Phe Ser Lys Asp Gly Ile Glu Gly Pro Tyr
            180                 185                 190

Thr Leu Val Ile Asn Thr Asp Arg Trp Ile Asn Phe Leu Lys Glu Glu
        195                 200                 205

Ala Gly His Tyr Pro Leu Glu Lys Arg Val Glu Glu Cys Leu Arg Gly
    210                 215                 220

Gly Lys Ile Ile Thr Thr Pro Arg Ile Glu Asp Ala Leu Val Val Ser
225                 230                 235                 240

Glu Arg Gly Gly Asp Phe Lys Leu Ile Leu Gly Gln Asp Leu Ser Ile
                245                 250                 255

Gly Tyr Glu Asp Arg Glu Lys Asp Ala Val Arg Leu Phe Ile Thr Glu
            260                 265                 270

Thr Phe Thr Phe Gln Val Val Asn Pro Glu Ala Leu Ile Leu Leu Lys
        275                 280                 285
```

```
Ser Gly Ile Ala Pro Leu Gln Leu Gly Asn Cys Ser Val Ala Gly Trp
    290                 295                 300

Ile Leu Gly Asn Pro Glu Cys Glu Leu Leu Ile Ser Lys Glu Ser Trp
305                 310                 315                 320

Ser Tyr Ile Val Glu Thr Pro Asn Pro Glu Asn Gly Thr Cys Tyr Pro
                325                 330                 335

Gly Tyr Phe Ala Asp Tyr Glu Glu Leu Arg Glu Gln Leu Ser Ser Val
            340                 345                 350

Ser Ser Phe Glu Arg Phe Glu Ile Phe Pro Lys Glu Ser Ser Trp Pro
        355                 360                 365

Asn His Thr Val Thr Gly Val Ser Ala Ser Cys Ser His Asn Gly Lys
    370                 375                 380

Ser Ser Phe Tyr Arg Asn Leu Leu Trp Leu Thr Gly Lys Asn Gly Leu
385                 390                 395                 400

Tyr Pro Asn Leu Ser Lys Ser Tyr Val Asn Asn Lys Glu Lys Glu Val
                405                 410                 415

Leu Val Leu Trp Gly Val His His Pro Pro Asn Ile Gly Asn Gln Arg
            420                 425                 430

Ala Leu Tyr His Thr Glu Asn Ala Tyr Val Ser Val Val Ser Ser His
        435                 440                 445

Tyr Ser Arg Arg Phe Thr Pro Glu Ile Ala Lys Arg Pro Lys Val Arg
    450                 455                 460

Asp Gln Glu Gly Arg Ile Asn Tyr Tyr Trp Thr Leu Leu Glu Pro Gly
465                 470                 475                 480

Asp Thr Ile Ile Phe Glu Ala Asn Gly Asn Leu Ile Ala Pro Trp Tyr
                485                 490                 495

Ala Phe Ala Leu Ser Arg Gly Ala
            500

<210> SEQ ID NO 182
<211> LENGTH: 1518
<212> TYPE: DNA
<213> ORGANISM: Artificial Sequence
<220> FEATURE:
<223> OTHER INFORMATION: Synthetic

<400> SEQUENCE: 182
tcatcaggcg cctctgctca gggcaaaggc ataccaaggg gcgatcagat tgccgttggc      60
ctcgaagatg atggtatcgc caggctccag cagggtccag tagtaattga tccggccctc     120
ctggtctctc actttgggtc tcttggcgat ctcggggtg aatcttctgc tgtagtggct      180
ggacaccacg ctcacatagg cgttctctgt gtggtacagg gcccgctgat ttccgatgtt     240
gggagggtgg tgcactcccc acagcaccag cacttccttt tccttgttgt tcacgtagct     300
cttgctcagg ttggggtaca ggccattctt gcctgtcagc cacagcaggt tccggtagaa     360
gctgcttttg ccgttgtggc tacagctgga gacacgcct gtcactgtgt gattaggcca      420
gctggactcc ttggggaaga tctcgaatct ctcgaagctg acacgctag acagctgctc      480 gcgcagctcc tcgtaatcgg cgaagtagcc agggtagcag gtgccattct caggattggg     540
ggtctccacg atgtagctcc agctctcctt agaaatcagc agctcacact cggggttgcc     600
cagaatccat ccggccacag aacaattgcc cagctgcaga gggcaattc cggacttcag      660 caggatcagg gctcggggt tcaccacctg gaaggtgaag gtctcggtga tgaacagcct      720 cacgcgtcc ttctccctgt cctcgtagcc gatgctcagg tcctggccca ggatcagctt      780
gaagtcgccg ccctctcgc tcaccaccag ggcgtcctcg atcctggggg tggtgatgat      840
```

| | | |
|---|---|---|
| cttgccgccc ctcaggcact cctccaccct cttctccagg gggtagtggc cggcctcctc | 900 | |
| cttcaggaag ttgatccacc tgtcggtgtt gatcaccagg gtgtagggc cctcgatgcc | 960 | |
| gtccttgctg aagatgctca gggccctcac gatggcctcc agcaggtcct tgggggtgct | 1020 | |
| gccgcactcg atcttcctct cctcgaagct cagcaggccc ttcacgccgc tcttctcgca | 1080 | |
| gcccctgaag atcacctcgt cctcgaactc ggccaccttc ctcacggtct cctccaggct | 1140 | |
| gctcaggtcc acgttgggct tgcccctctc caggttgtcc agctcccaca ggtccagggt | 1200 | |
| gaaggtggcc ctcagctcga tcaggggcag gctcttcctc aggccccact tcaccacctc | 1260 | |
| gttctcgtcg ctcagcacct ccacctcgcc caggggtgg gcggcgtact cccagccgta | 1320 | |
| ggggccctcc acgtccacga acttcctgcc gtacagctgg gtcttgaaga tctccctggc | 1380 | |
| cctgttgtcg atctcctgcc actgcttctc ggtcagaggg gcgaagctcc tcttcaggaa | 1440 | |
| ctccatggcc agcacgctag ccaccagcat gcccagcagg tacagggtgg ccaggggctg | 1500 | |
| caggctgccc atgggcat | 1518 | |

```
<210> SEQ ID NO 183
<211> LENGTH: 1521
<212> TYPE: DNA
<213> ORGANISM: Artificial Sequence
<220> FEATURE:
<223> OTHER INFORMATION: Synthetic

<400> SEQUENCE: 183
```

| | | |
|---|---|---|
| atgcccatgg gcagcctgca gcccctggcc accctgtacc tgctgggcat gctggtggct | 60 | |
| agcgtgctgg ccatggagtt cctgaagagg agcttcgccc tctgaccga gaagcagtgg | 120 | |
| caggagatcg acaacagggc cagggagatc ttcaagaccc agctgtacgg caggaagttc | 180 | |
| gtggacgtgg agggccccta cggctgggag tacgccgccc accccctggg cgaggtggag | 240 | |
| gtgctgagcg acgagaacga ggtggtgaag tggggcctga ggaagagcct gcccctgatc | 300 | |
| gagctgaggg ccaccttcac cctggacctg tgggagctgg acaacctgga gagggcaag | 360 | |
| cccaacgtgg acctgagcag cctggaggag accgtgagga aggtggccga gttcgaggac | 420 | |
| gaggtgatct tcaggggctg cgagaagagc ggcgtgaagg gcctgctgag cttcgaggag | 480 | |
| aggaagatcg agtgcggcag cacccccaag gacctgctgg aggccatcgt gagggccctg | 540 | |
| agcatcttca gcaaggacgg catcgagggc ccctacaccc tggtgatcaa caccgacagg | 600 | |
| tggatcaact tcctgaagga ggaggccggc cactacccc tggagaagag ggtggaggag | 660 | |
| tgcctgaggg gcggcaagat catcaccacc cccaggatcg aggacgccct ggtggtgagc | 720 | |
| gagaggggcg gcgacttcaa gctgatcctg gccaggacc tgagcatcgg ctacgaggac | 780 | |
| agggagaagg acgccgtgag gctgttcatc accgagacct tcaccttcca ggtggtgaac | 840 | |
| cccgaggccc tgatcctgct gaagtccgga gtggccccc tgcacctggg caagtgcaac | 900 | |
| atcgccggct ggattctggg caaccccgag tgcgagagcc tgagcaccgc cagcagctgg | 960 | |
| agctacatcg tggagacccc cagcagcgac aacggcacct gctaccccgg cgacttcatc | 1020 | |
| gactacgagg agctgcggga gcagctgagc agcgtgagca gcttcgagcg gttcgagatc | 1080 | |
| ttccccaaga ccagcagctg gcccaaccac gacagcaaca agggcgtgac cgccgcctgc | 1140 | |
| ccccacgccg cgccaagag cttctacaag aacctgatct ggctggtgaa gagggcaac | 1200 | |
| agctacccca gctgagcaa gagctacatc aacgacaagg gcaaggaggt gctggtgctg | 1260 | |
| tggggcatcc accaccccag caccagcgcc gaccagcaga gcctgtacca gaacgccgac | 1320 | |

-continued

```
acctacgtgt tcgtgggcag cagccggtac agcaagaagt tcaagcccga gatcgccatc    1380
cggcccaagg tgcgggacca ggagggccgg atgaactact actggaccct ggtggagccc    1440
ggcgacaaga tcaccttcga ggccaccggc aacctggtgg tgccccggta cgccttcgcc    1500
atggagcgga acgcctgatg a                                              1521
```

<210> SEQ ID NO 184
<211> LENGTH: 505
<212> TYPE: PRT
<213> ORGANISM: Artificial Sequence
<220> FEATURE:
<223> OTHER INFORMATION: Synthetic

<400> SEQUENCE: 184

```
Met Pro Met Gly Ser Leu Gln Pro Leu Ala Thr Leu Tyr Leu Leu Gly
1               5                   10                  15

Met Leu Val Ala Ser Val Leu Ala Met Glu Phe Leu Lys Arg Ser Phe
            20                  25                  30

Ala Pro Leu Thr Glu Lys Gln Trp Gln Glu Ile Asp Asn Arg Ala Arg
        35                  40                  45

Glu Ile Phe Lys Thr Gln Leu Tyr Gly Arg Lys Phe Val Asp Val Glu
    50                  55                  60

Gly Pro Tyr Gly Trp Glu Tyr Ala Ala His Pro Leu Gly Glu Val Glu
65                  70                  75                  80

Val Leu Ser Asp Glu Asn Glu Val Val Lys Trp Gly Leu Arg Lys Ser
                85                  90                  95

Leu Pro Leu Ile Glu Leu Arg Ala Thr Phe Thr Leu Asp Leu Trp Glu
            100                 105                 110

Leu Asp Asn Leu Glu Arg Gly Lys Pro Asn Val Asp Leu Ser Ser Leu
        115                 120                 125

Glu Glu Thr Val Arg Lys Val Ala Glu Phe Glu Asp Glu Val Ile Phe
    130                 135                 140

Arg Gly Cys Glu Lys Ser Gly Val Lys Gly Leu Leu Ser Phe Glu Glu
145                 150                 155                 160

Arg Lys Ile Glu Cys Gly Ser Thr Pro Lys Asp Leu Leu Glu Ala Ile
                165                 170                 175

Val Arg Ala Leu Ser Ile Phe Ser Lys Asp Gly Ile Glu Gly Pro Tyr
            180                 185                 190

Thr Leu Val Ile Asn Thr Asp Arg Trp Ile Asn Phe Leu Lys Glu Glu
        195                 200                 205

Ala Gly His Tyr Pro Leu Glu Lys Arg Val Glu Glu Cys Leu Arg Gly
    210                 215                 220

Gly Lys Ile Ile Thr Thr Pro Arg Ile Glu Asp Ala Leu Val Val Ser
225                 230                 235                 240

Glu Arg Gly Gly Asp Phe Lys Leu Ile Leu Gly Gln Asp Leu Ser Ile
                245                 250                 255

Gly Tyr Glu Asp Arg Glu Lys Asp Ala Val Arg Leu Phe Ile Thr Glu
            260                 265                 270

Thr Phe Thr Phe Gln Val Val Asn Pro Glu Ala Leu Ile Leu Leu Lys
        275                 280                 285

Ser Gly Val Ala Pro Leu His Leu Gly Lys Cys Asn Ile Ala Gly Trp
    290                 295                 300

Ile Leu Gly Asn Pro Glu Cys Glu Ser Leu Ser Thr Ala Ser Ser Trp
305                 310                 315                 320

Ser Tyr Ile Val Glu Thr Pro Ser Ser Asp Asn Gly Thr Cys Tyr Pro
```

```
                        325                 330                 335
Gly Asp Phe Ile Asp Tyr Glu Glu Leu Arg Glu Gln Leu Ser Ser Val
                340                 345                 350
Ser Ser Phe Glu Arg Phe Glu Ile Phe Pro Lys Thr Ser Ser Trp Pro
                355                 360                 365
Asn His Asp Ser Asn Lys Gly Val Thr Ala Ala Cys Pro His Ala Gly
        370                 375                 380
Ala Lys Ser Phe Tyr Lys Asn Leu Ile Trp Leu Val Lys Lys Gly Asn
385                 390                 395                 400
Ser Tyr Pro Lys Leu Ser Lys Ser Tyr Ile Asn Asp Lys Gly Lys Glu
                405                 410                 415
Val Leu Val Leu Trp Gly Ile His His Pro Ser Thr Ser Ala Asp Gln
                420                 425                 430
Gln Ser Leu Tyr Gln Asn Ala Asp Thr Tyr Val Phe Val Gly Ser Ser
                435                 440                 445
Arg Tyr Ser Lys Lys Phe Lys Pro Glu Ile Ala Ile Arg Pro Lys Val
        450                 455                 460
Arg Asp Gln Glu Gly Arg Met Asn Tyr Tyr Trp Thr Leu Val Glu Pro
465                 470                 475                 480
Gly Asp Lys Ile Thr Phe Glu Ala Thr Gly Asn Leu Val Val Pro Arg
                485                 490                 495
Tyr Ala Phe Ala Met Glu Arg Asn Ala
                500                 505

<210> SEQ ID NO 185
<211> LENGTH: 1521
<212> TYPE: DNA
<213> ORGANISM: Artificial Sequence
<220> FEATURE:
<223> OTHER INFORMATION: Synthetic

<400> SEQUENCE: 185
tcatcaggcg ttccgctcca tggcgaaggc gtaccggggc accaccaggt tgccggtggc      60
ctcgaaggtg atcttgtcgc cgggctccac cagggtccag tagtagttca tccggccctc     120
ctggtcccgc accttgggcc ggatggcgat ctcgggcttg aacttcttgc tgtaccggct     180
gctgcccacg aacacgtagg tgtcggcgtt ctggtacagg ctctgctggt cggcgctggt     240
gctggggtgg tggatgcccc acagcaccag cacctccttg cccttgtcgt tgatgtagct     300
cttgctcagc ttggggtagc tgttgcccct cttcaccagc cagatcaggt tcttgtagaa     360
gctcttggcg ccggcgtggg ggcaggcggc ggtcacgccc ttgttgctgt cgtggttggg     420
ccagctgctg gtcttgggga agatctcgaa ccgctcgaag ctgctcacgc tgctcagctg     480
ctcccgcagc tcctcgtagt cgatgaagtc gccggggtag caggtgccgt tgtcgctgct     540
gggggtctcc acgatgtagc tccagctgct ggcggtgctc aggctctcgc actcggggtt     600
gcccagaatc cagccggcga tgttgcactt gcccaggtgc agggggggcca ctccggactt     660 cagcaggatc agggcctcgg ggttcaccac ctggaaggtg aaggtctcgg tgatgaacag     720
cctcacggcg tccttctccc tgtcctcgta gccgatgctc aggtcctggc ccaggatcag     780
cttgaagtcg ccgccctct cgctcaccac cagggcgtcc tcgatcctgg gggtggtgat     840
gatcttgccg cccctcaggc actcctccac cctcttctcc aggggtagt ggccggcctc     900 ctccttcagg aagttgatcc acctgtcggt gttgatcacc agggtgtagg ggccctcgat     960
gccgtccttg ctgaagatgc tcagggccct cacgatggcc tccagcaggt ccttggggt    1020
```

| | |
|---|---|
| gctgccgcac tcgatcttcc tctcctcgaa gctcagcagg cccttcacgc cgctcttctc | 1080 |
| gcagcccctg aagatcacct cgtcctcgaa ctcggccacc ttcctcacgg tctcctccag | 1140 |
| gctgctcagg tccacgttgg gcttgcccct ctccaggttg tccagctccc acaggtccag | 1200 |
| ggtgaaggtg gccctcagct cgatcagggg caggctcttc ctcaggcccc acttcaccac | 1260 |
| ctcgttctcg tcgctcagca cctccacctc gcccaggggg tgggcggcgt actcccagcc | 1320 |
| gtaggggccc tccacgtcca cgaacttcct gccgtacagc tgggtcttga agatctccct | 1380 |
| ggccctgttg tcgatctcct gccactgctt ctcggtcaga ggggcgaagc tcctcttcag | 1440 |
| gaactccatg ccagcacgc tagccaccag catgcccagc aggtacaggg tggccagggg | 1500 |
| ctgcaggctg cccatgggca t | 1521 |

<210> SEQ ID NO 186
<211> LENGTH: 4359
<212> TYPE: DNA
<213> ORGANISM: Artificial Sequence
<220> FEATURE:
<223> OTHER INFORMATION: Synthetic

<400> SEQUENCE: 186

| | |
|---|---|
| atggagttca tcccgacgca aactttctat aacagaaggt accaaccccg accctgggcc | 60 |
| ccacgcccta caattcaagt aattagacct agaccacgtc cacagaggca ggctgggcaa | 120 |
| ctcgcccagc tgatctccgc agtcaacaaa ttgaccatgc gcgcggtacc tcaacgaaag | 180 |
| cctcgcagaa atcggaaaaa caagaagcaa aggcagaaga agcaggcgcc gcaaaacgac | 240 |
| ccaaagcaaa agaagcaacc accacaaaag aagccggctc aaaagaagaa gaaaccaggc | 300 |
| cgtagggaga gaatgtgcat gaaaattgaa aatgattgca tcttcgaagt caagcatgaa | 360 |
| ggcaaagtga tgggctacgc atgcctggtg ggggataaag taatgaaacc agcacatgtg | 420 |
| aagggaacta tcgacaatgc cgatctggct aaactggcct ttaagcggtc gtctaaatac | 480 |
| gatcttgaat gtgcacagat accggtgcac atgaagtctg atgcctcgaa gtttacccac | 540 |
| gagaaacccg agggtactaa taactggcat cacggagcag tgcagtattc aggaggccgg | 600 |
| ttcactatcc cgacgggtgc aggcaagccg ggagacagcg gcagaccgat cttcgacaac | 660 |
| aaaggacggg tggtggccat cgtcctagga ggggccaacg aaggtgcccg cacggccctc | 720 |
| tccgtggtga cgtggaacaa agacatcgtc acaaaaatta cccctgaggg agccgaagag | 780 |
| tggagcctcg ccctcccggt cttgtgcctg ttggcaaaca ctacattccc ctgctctcag | 840 |
| ccgcccttgca caccctgctg ctacgaaaag gaaccggaaa gcaccttgcg catgcttgag | 900 |
| gacaacgtga tgagacccgg atactaccag ctactaaaag catcgctgac ttgccgccaa | 960 |
| agacgcctgc agctggggaa ttgttctgtg gccggatgga ttctgggcaa ccccgagtgt | 1020 |
| gagctgctga tttctaagga gagctggagc tacatcgtgg agaccccaa tcctgagaat | 1080 |
| ggcacctgct tccctggcta cttcgccgat tacgaggagc tgcgcgagca gctgtctagc | 1140 |
| gtgtccagct tcgagagatt cgagatcttc cccaaggagt ccagctggcc taatcacaca | 1200 |
| gtgacaggcg tgtctgccag ctgtagccac aacggcaaaa gcagcttcta ccggaacctg | 1260 |
| ctgtggctga caggcaagaa tggcctgtac cccaacctga gcaagagcta cgtgaacaac | 1320 |
| aaggaaaagg aagtgctggt gctgtgggga gtgcaccacc ctccaacat cggaaatcag | 1380 |
| cgggccctgt accacacaga gaacgcctat gtgagcgtgg tgtccagcca ctacagcaga | 1440 |
| agattcaccc ccgagatcgc caagagaccc aaagtgagag accaggaggg ccggatcaat | 1500 |
| tactactgga ccctgctgga gcctggcgat accatcatct tcgaggccaa cggcaatctg | 1560 |

```
atcgcccctt ggtatgcctt tgccctgagc agaggcgcca attttaatgt ctataaagcc    1620
acaagaccat atctagctca ttgtcctgac tgcggagaag ggcattcgtg ccacagccct    1680
atcgcattgg agcgcatcag aaatgaagca acggacggaa cgctgaaaat ccaggtctct    1740
ttgcagatcg ggataaagac agatgacagc cacgattgga ccaagctgcg ctatatggat    1800
agccatacgc cagcggacgc ggagcgagcc ggattgcttg taaggacttc agcaccgtgc    1860
acgatcaccg ggaccatggg acactttatt ctcgcccgat gcccgaaagg agagacgctg    1920
acagtgggat ttacggacag cagaaagatc agccacacat gcacacaccc gttccatcat    1980
gaaccacctg tgataggtag ggagaggttc cactctcgac cacaacatgg taaagagtta    2040
ccttgcagca cgtacgtgca gagcaccgct gccactgctg aggagataga ggtgcatatg    2100
cccccagata ctcctgaccg cacgctgatg acgcagcagt ctggcaacgt gaagatcaca    2160
gttaatgggc agacggtgcg gtacaagtgc aactgcggtg gctcaaacga gggactgaca    2220
accacagaca aagtgatcaa taactgcaaa attgatcagt gccatgctgc agtcactaat    2280
cacaagaatt ggcaatacaa ctccccttta gtcccgcgca acgctgaact cggggaccgt    2340
aaaggaaaga tccacatccc attcccattg gcaaacgtga cttgcagagt gccaaaagca    2400
agaaacccta cagtaactta cggaaaaaac caagtcacca tgctgctgta tcctgaccat    2460
ccgacactct tgtcttaccg taacatggga caggaaccaa attaccacga ggagtgggtg    2520
acacacaaga aggaggttac cttgaccgtg cctactgagg gtctggaggt cacttggggc    2580
aacaacgaac catacaagta ctggccgcag atgtctacga acggtactgc tcatggtcac    2640
ccacatgaga taatcttgta ctattatgag ctgtacccca ctatgactgt agtcattgtg    2700
tcggtggcct cgttcgtgct tctgtcgatg gtgggcacag cagtgggaat gtgtgtgtgc    2760
gcacggcgca gatgcattac accatatgaa ttaacaccag gagccactgt tcccttcctg    2820
ctcagcctgc tatgctgcgt cagaacgacc aaggcggcca catattacga ggctgcggca    2880
tatctatgga cgaacagca gcccctgttc tggttgcagg ctcttatccc gctggccgcc    2940
ttgatcgtcc tgtgcaactg tctgaaactc ttgccatgct gctgtaagac cctggctttt    3000
ttagccgtaa tgagcatcgg tgcccacact gtgagcgcgt acgaacacgt aacagtgatc    3060
ccgaacacgg tgggagtacc gtataagact cttgtcaaca gaccgggtta cagccccatg    3120
gtgttggaga tggagctaca atcagtcacc ttggaaccaa cactgtcact tgactacatc    3180
acgtgcgagt acaaaactgt catcccctcc ccgtacgtga agtgctgtgg tacagcagag    3240
tgcaaggaca agagcctacc agactacagc tgcaaggtct ttactggagt ctacccattt    3300
atgtggggcg gcgcctactg cttttgcgac gccgaaaata cgcaattgag cgaggcacat    3360
gtagagaaat ctgaatcttg caaaacagag tttgcatcgg cctacagagc ccacaccgca    3420
tcggcgtcgg cgaagctccg cgtcctttac caaggaaaca acattaccgt agctgcctac    3480
gctaacggtg accatgccgt cacagtaaag gacgccaagt ttgtcgtggg cccaatgtcc    3540
tccgcctgga cccttttga caacaaaatc gtggtgtaca aaggcgacgt ctacaacatg    3600
gactacccac ttttggcgc aggaagacca ggacaatttg gtgacattca aagtcgtaca    3660
ccggaaagta aagacgttta tgccaacact cagttggtac tacagaggcc agcagcaggc    3720
acggtacatg taccatactc tcaggcacca tctggcttca gtattggct gaaggaacga    3780 ggagcatcgc tacagcacac ggcaccgttc ggttgccaga ttgcgacaaa cccggtaaga    3840
gctgtaaatt gcgctgtggg gaacatacca atttccatcg atacccgga tgcggccttt    3900
```

```
actagggttg tcgatgcacc ctctgtaacg acatgtcat gcgaagtacc agcctgcact    3960
cactcctccg actttggggg cgtcgccatc atcaaataca cagctagcaa gaaaggtaaa    4020
tgtgcagtac attcgatgac caacgccgtt accattcgag aagccgacgt agaagtagag    4080
gggaactccc agctgcaaat atccttctca cagccctgg caagcgccga gtttcgcgtg     4140
caagtgtgct ccacacaagt acactgcgca gccgcatgcc accctccaaa ggaccacata    4200
gtcaattacc cagcatcaca caccacccctt ggggtccagg atatatccac aacggcaatg   4260
tcttgggtgc agaagattac gggaggagta ggattaattg ttgctgttgc tgccttaatt    4320
ttaattgtgg tgctatgcgt gtcgtttagc aggcactaa                           4359
```

<210> SEQ ID NO 187
<211> LENGTH: 1452
<212> TYPE: PRT
<213> ORGANISM: Artificial Sequence
<220> FEATURE:
<223> OTHER INFORMATION: Synthetic

<400> SEQUENCE: 187

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
                20                  25                  30

Arg Pro Gln Arg Gln Ala Gly Gln Leu Ala Gln Leu Ile Ser Ala Val
            35                  40                  45

Asn Lys Leu Thr Met Arg Ala Val Pro Gln Gln Lys Pro Arg Arg Asn
50                  55                  60

Arg Lys Asn Lys Lys Gln Arg Gln Lys Lys Gln Ala Pro Gln Asn Asp
65                  70                  75                  80

Pro Lys Gln Lys Lys Gln Pro Pro Gln Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285
```

```
Glu Lys Glu Pro Glu Ser Thr Leu Arg Met Leu Glu Asp Asn Val Met
    290                 295                 300

Arg Pro Gly Tyr Tyr Gln Leu Leu Lys Ala Ser Leu Thr Cys Arg Gln
305                 310                 315                 320

Arg Arg Leu Gln Leu Gly Asn Cys Ser Val Ala Gly Trp Ile Leu Gly
                325                 330                 335

Asn Pro Glu Cys Glu Leu Leu Ile Ser Lys Glu Ser Trp Ser Tyr Ile
                340                 345                 350

Val Glu Thr Pro Asn Pro Glu Asn Gly Thr Cys Phe Pro Gly Tyr Phe
            355                 360                 365

Ala Asp Tyr Glu Glu Leu Arg Glu Gln Leu Ser Ser Val Ser Ser Phe
370                 375                 380

Glu Arg Phe Glu Ile Phe Pro Lys Glu Ser Ser Trp Pro Asn His Thr
385                 390                 395                 400

Val Thr Gly Val Ser Ala Ser Cys Ser His Asn Gly Lys Ser Ser Phe
                405                 410                 415

Tyr Arg Asn Leu Leu Trp Leu Thr Gly Lys Asn Gly Leu Tyr Pro Asn
                420                 425                 430

Leu Ser Lys Ser Tyr Val Asn Asn Lys Glu Lys Glu Val Leu Val Leu
            435                 440                 445

Trp Gly Val His His Pro Pro Asn Ile Gly Asn Gln Arg Ala Leu Tyr
    450                 455                 460

His Thr Glu Asn Ala Tyr Val Ser Val Val Ser Ser His Tyr Ser Arg
465                 470                 475                 480

Arg Phe Thr Pro Glu Ile Ala Lys Arg Pro Lys Val Arg Asp Gln Glu
                485                 490                 495

Gly Arg Ile Asn Tyr Tyr Trp Thr Leu Leu Glu Pro Gly Asp Thr Ile
                500                 505                 510

Ile Phe Glu Ala Asn Gly Asn Leu Ile Ala Pro Trp Tyr Ala Phe Ala
            515                 520                 525

Leu Ser Arg Gly Ala Asn Phe Asn Val Tyr Lys Ala Thr Arg Pro Tyr
            530                 535                 540

Leu Ala His Cys Pro Asp Cys Gly Glu Gly His Ser Cys His Ser Pro
545                 550                 555                 560

Ile Ala Leu Glu Arg Ile Arg Asn Glu Ala Thr Asp Gly Thr Leu Lys
                565                 570                 575

Ile Gln Val Ser Leu Gln Ile Gly Ile Lys Thr Asp Ser His Asp
                580                 585                 590

Trp Thr Lys Leu Arg Tyr Met Asp Ser His Thr Pro Ala Asp Ala Glu
                595                 600                 605

Arg Ala Gly Leu Leu Val Arg Thr Ser Ala Pro Cys Thr Ile Thr Gly
610                 615                 620

Thr Met Gly His Phe Ile Leu Ala Arg Cys Pro Lys Gly Glu Thr Leu
625                 630                 635                 640

Thr Val Gly Phe Thr Asp Ser Arg Lys Ile Ser His Thr Cys Thr His
                645                 650                 655

Pro Phe His His Glu Pro Pro Val Ile Gly Arg Glu Arg Phe His Ser
                660                 665                 670

Arg Pro Gln His Gly Lys Glu Leu Pro Cys Ser Thr Tyr Val Gln Ser
            675                 680                 685

Thr Ala Ala Thr Ala Glu Glu Ile Glu Val His Met Pro Pro Asp Thr
            690                 695                 700
```

```
Pro Asp Arg Thr Leu Met Thr Gln Gln Ser Gly Asn Val Lys Ile Thr
705                 710                 715                 720

Val Asn Gly Gln Thr Val Arg Tyr Lys Cys Asn Cys Gly Gly Ser Asn
                725                 730                 735

Glu Gly Leu Thr Thr Thr Asp Lys Val Ile Asn Asn Cys Lys Ile Asp
                740                 745                 750

Gln Cys His Ala Ala Val Thr Asn His Lys Asn Trp Gln Tyr Asn Ser
            755                 760                 765

Pro Leu Val Pro Arg Asn Ala Glu Leu Gly Asp Arg Lys Gly Lys Ile
        770                 775                 780

His Ile Pro Phe Pro Leu Ala Asn Val Thr Cys Arg Val Pro Lys Ala
785                 790                 795                 800

Arg Asn Pro Thr Val Thr Tyr Gly Lys Asn Gln Val Thr Met Leu Leu
                805                 810                 815

Tyr Pro Asp His Pro Thr Leu Leu Ser Tyr Arg Asn Met Gly Gln Glu
                820                 825                 830

Pro Asn Tyr His Glu Glu Trp Val Thr His Lys Lys Glu Val Thr Leu
            835                 840                 845

Thr Val Pro Thr Glu Gly Leu Glu Val Thr Trp Gly Asn Asn Glu Pro
850                 855                 860

Tyr Lys Tyr Trp Pro Gln Met Ser Thr Asn Gly Thr Ala His Gly His
865                 870                 875                 880

Pro His Glu Ile Ile Leu Tyr Tyr Tyr Glu Leu Tyr Pro Thr Met Thr
                885                 890                 895

Val Val Ile Val Ser Val Ala Ser Phe Val Leu Leu Ser Met Val Gly
                900                 905                 910

Thr Ala Val Gly Met Cys Val Cys Ala Arg Arg Cys Ile Thr Pro
                915                 920                 925

Tyr Glu Leu Thr Pro Gly Ala Thr Val Pro Phe Leu Leu Ser Leu Leu
                930                 935                 940

Cys Cys Val Arg Thr Thr Lys Ala Ala Thr Tyr Tyr Glu Ala Ala Ala
945                 950                 955                 960

Tyr Leu Trp Asn Glu Gln Gln Pro Leu Phe Trp Leu Gln Ala Leu Ile
                965                 970                 975

Pro Leu Ala Ala Leu Ile Val Leu Cys Asn Cys Leu Lys Leu Leu Pro
            980                 985                 990

Cys Cys Cys Lys Thr Leu Ala Phe Leu Ala Val Met Ser Ile Gly Ala
            995                 1000                1005

His Thr Val Ser Ala Tyr Glu His Val Thr Val Ile Pro Asn Thr
    1010                1015                1020

Val Gly Val Pro Tyr Lys Thr Leu Val Asn Arg Pro Gly Tyr Ser
    1025                1030                1035

Pro Met Val Leu Glu Met Glu Leu Gln Ser Val Thr Leu Glu Pro
    1040                1045                1050

Thr Leu Ser Leu Asp Tyr Ile Thr Cys Glu Tyr Lys Thr Val Ile
    1055                1060                1065

Pro Ser Pro Tyr Val Lys Cys Cys Gly Thr Ala Glu Cys Lys Asp
    1070                1075                1080

Lys Ser Leu Pro Asp Tyr Ser Cys Lys Val Phe Thr Gly Val Tyr
    1085                1090                1095

Pro Phe Met Trp Gly Gly Ala Tyr Cys Phe Cys Asp Ala Glu Asn
    1100                1105                1110

Thr Gln Leu Ser Glu Ala His Val Glu Lys Ser Glu Ser Cys Lys
```

Thr Glu Phe Ala Ser Ala Tyr Arg Ala His Thr Ala Ser Ala Ser
    1130                1135                1140

Ala Lys Leu Arg Val Leu Tyr Gln Gly Asn Asn Ile Thr Val Ala
    1145                1150                1155

Ala Tyr Ala Asn Gly Asp His Ala Val Thr Val Lys Asp Ala Lys
    1160                1165                1170

Phe Val Val Gly Pro Met Ser Ser Ala Trp Thr Pro Phe Asp Asn
    1175                1180                1185

Lys Ile Val Val Tyr Lys Gly Asp Val Tyr Asn Met Asp Tyr Pro
    1190                1195                1200

Pro Phe Gly Ala Gly Arg Pro Gly Gln Phe Gly Asp Ile Gln Ser
    1205                1210                1215

Arg Thr Pro Glu Ser Lys Asp Val Tyr Ala Asn Thr Gln Leu Val
    1220                1225                1230

Leu Gln Arg Pro Ala Ala Gly Thr Val His Val Pro Tyr Ser Gln
    1235                1240                1245

Ala Pro Ser Gly Phe Lys Tyr Trp Leu Lys Glu Arg Gly Ala Ser
    1250                1255                1260

Leu Gln His Thr Ala Pro Phe Gly Cys Gln Ile Ala Thr Asn Pro
    1265                1270                1275

Val Arg Ala Val Asn Cys Ala Val Gly Asn Ile Pro Ile Ser Ile
    1280                1285                1290

Asp Ile Pro Asp Ala Ala Phe Thr Arg Val Val Asp Ala Pro Ser
    1295                1300                1305

Val Thr Asp Met Ser Cys Glu Val Pro Ala Cys Thr His Ser Ser
    1310                1315                1320

Asp Phe Gly Gly Val Ala Ile Ile Lys Tyr Thr Ala Ser Lys Lys
    1325                1330                1335

Gly Lys Cys Ala Val His Ser Met Thr Asn Ala Val Thr Ile Arg
    1340                1345                1350

Glu Ala Asp Val Glu Val Glu Gly Asn Ser Gln Leu Gln Ile Ser
    1355                1360                1365

Phe Ser Thr Ala Leu Ala Ser Ala Glu Phe Arg Val Gln Val Cys
    1370                1375                1380

Ser Thr Gln Val His Cys Ala Ala Ala Cys His Pro Pro Lys Asp
    1385                1390                1395

His Ile Val Asn Tyr Pro Ala Ser His Thr Thr Leu Gly Val Gln
    1400                1405                1410

Asp Ile Ser Thr Thr Ala Met Ser Trp Val Gln Lys Ile Thr Gly
    1415                1420                1425

Gly Val Gly Leu Ile Val Ala Val Ala Ala Leu Ile Leu Ile Val
    1430                1435                1440

Val Leu Cys Val Ser Phe Ser Arg His
    1445                1450

<210> SEQ ID NO 188
<211> LENGTH: 4359
<212> TYPE: DNA
<213> ORGANISM: Artificial Sequence
<220> FEATURE:
<223> OTHER INFORMATION: Synthetic

<400> SEQUENCE: 188
ttagtgcctg ctaaacgaca cgcatagcac cacaattaaa attaaggcag caacagcaac    60

-continued

```
aattaatcct actcctcccg taatcttctg cacccaagac attgccgttg tggatatatc      120
ctggacccca agggtggtgt gtgatgctgg gtaattgact atgtggtcct ttggagggtg      180
gcatgcggct gcgcagtgta cttgtgtgga gcacacttgc acgcgaaact cggcgcttgc      240
cagggctgtt gagaaggata tttgcagctg ggagttcccc tctacttcta cgtcggcttc      300
tcgaatggta acggcgttgg tcatcgaatg tactgcacat ttacctttct gctagctgt       360 gtatttgatg atggcgacgc ccccaaagtc ggaggagtga gtgcaggctg gtacttcgca      420
tgacatgtcc gttacagagg gtgcatcgac aaccctagta aaggccgcat ccggtatgtc      480
gatggaaatt ggtatgttcc ccacagcgca atttacagct cttaccgggt tgtcgcaat      540 ctggcaaccg aacggtgccg tgtgctgtag cgatgctcct cgttccttca gccaatactt      600
gaagccagat ggtgcctgag agtatggtac atgtaccgtg cctgctgctg gcctctgtag      660
taccaactga gtgttggcat aaacgtcttt actttccggt gtacgacttt gaatgtcacc      720
aaattgtcct ggtcttcctg cgccaaaagg tgggtagtcc atgttgtaga cgtcgccttt      780
gtacaccacg attttgttgt caaaaggtgt ccaggcggag acattgggc ccacgacaaa       840 cttggcgtcc tttactgtga cggcatggtc accgttagcg taggcagcta cggtaatgtt      900
gtttccttgg taaaggacgc ggagcttcgc cgacgccgat gcggtgtggg ctctgtaggc      960
cgatgcaaac tctgttttgc aagattcaga tttctctaca tgtgcctcgc tcaattgcgt     1020
attttcggcg tcgcaaaagc agtaggcgcc gccccacata aatgggtaga ctccagtaaa     1080
gaccttgcag ctgtagtctg gtaggctctt gtccttgcac tctgctgtac cacagcactt     1140
cacgtacggg gaggggatga cagttttgta ctcgcacgtg atgtagtcaa gtgacagtgt     1200
tggttccaag gtgactgatt gtagctccat ctccaacacc atggggctgt aacccggtct     1260
gttgacaaga gtcttatacg gtactcccac cgtgttcggg atcactgtta cgtgttcgta     1320
cgcgctcaca gtgtgggcac cgatgctcat tacggctaaa aaagccaggg tcttacagca     1380
gcatggcaag agtttcagac agttgcacag gacgatcaag gcggccagcg ggataagagc     1440
ctgcaaccag aacaggggct gctgttcgtt ccatagatat gccgcagcct cgtaatatgt     1500
ggccgccttg gtcgttctga cgcagcatag caggctgagc aggaagggaa cagtggctcc     1560
tggtgttaat tcatatggtg taatgcatct gcgccgtgcg cacacacaca ttcccactgc     1620
tgtgcccacc atcgacagaa gcacgaacga ggccaccgac acaatgacta cagtcatagt     1680
ggggtacagc tcataatagt acaagattat ctcatgtggg tgaccatgag cagtaccgtt     1740
cgtagacatc tgcggccagt acttgtatgg ttcgttgttg ccccaagtga cctccagacc     1800
ctcagtaggc acggtcaagg taacctcctt cttgtgtgtc acccactcct cgtggtaatt     1860
tggttcctgt cccatgttac ggtaagacaa gagtgtcgga tggtcaggat acagcagcat     1920
ggtgacttgg ttttttccgt aagttactgt agggtttctt gcttttggca ctctgcaagt     1980
cacgtttgcc aatgggaatg ggatgtggat ctttcctta cggtcccga gttcagcgtt       2040 gcgcgggact aaagggagt tgtattgcca attcttgtga ttagtgactg cagcatggca      2100
ctgatcaatt ttgcagttat tgatcacttt gtctgtggtt gtcagtccct cgtttgagcc     2160
accgcagttg cacttgtacc gcaccgtctg cccattaact gtgatcttca cgttgccaga     2220
ctgctgcgtc atcagcgtgc ggtcaggagt atctgggggc atatgcacct ctatctcctc     2280
agcagtggca gcggtgctct gcacgtacgt gctgcaaggt aactctttac catgttgtgg    2340
tcgagagtgg aacctctccc tacctatcac aggtggttca tgatggaacg ggtgtgtgca    2400
```

```
tgtgtggctg atctttctgc tgtccgtaaa tcccactgtc agcgtctctc ctttcgggca   2460
tcgggcgaga ataaagtgtc ccatggtccc ggtgatcgtg cacggtgctg aagtccttac   2520
aagcaatccg gctcgctccg cgtccgctgg cgtatggcta tccatatagc gcagcttggt   2580
ccaatcgtgg ctgtcatctg tctttatccc gatctgcaaa gagacctgga ttttcagcgt   2640
tccgtccgtt gcttcatttc tgatgcgctc caatgcgata gggctgtggc acgaatgccc   2700
ttctccgcag tcaggacaat gagctagata tggtcttgtg gctttataga cattaaaatt   2760
ggcgcctctg ctcagggcaa aggcatacca aggggcgatc agattgccgt tggcctcgaa   2820
gatgatggta tcgccaggct ccagcagggt ccagtagtaa ttgatccggc cctcctggtc   2880
tctcactttg ggtctcttgg cgatctcggg ggtgaatctt ctgctgtagt ggctggacac   2940
cacgctcaca taggcgttct ctgtgtggta cagggcccgc tgatttccga tgttgggagg   3000
gtggtgcact ccccacagca ccagcacttc cttttccttg ttgttcacgt agctcttgct   3060
caggttgggg tacaggccat tcttgcctgt cagccacagc aggttccggt agaagctgct   3120
tttgccgttg tggctacagc tggcagacac gcctgtcact gtgtgattag gccagctgga   3180
ctccttgggg aagatctcga atctctcgaa gctggacacg ctagacagct gctcgcgcag   3240
ctcctcgtaa tcggcgaagt agccagggaa gcaggtgcca ttctcaggat tgggggtctc   3300
cacgatgtag ctccagctct ccttagaaat cagcagctca cactcggggt tgcccagaat   3360
ccatccggcc acagaacaat tccccagctg caggcgtctt tggcggcaag tcagcgatgc   3420
ttttagtagc tggtagtatc cgggtctcat cacgttgtcc tcaagcatgc gcaaggtgct   3480
ttccggttcc ttttcgtagc agcagggtgt gcaaggcggc tgagagcagg gaatgtagt   3540 gtttgccaac aggcacaaga ccgggagggc gaggctccac tcttcggctc cctcaggggt   3600
aatttttgtg acgatgtctt tgttccacgt caccacggag agggccgtgc gggcaccttc   3660
gttggcccct cctaggacga tggccaccac ccgtcctttg ttgtcgaaga tcggtctgcc   3720
gctgtctccc ggcttgcctg cacccgtcgg gatagtgaac cggcctcctg aatactgcac   3780
tgctccgtga tgccagttat agtacccctc gggtttctcg tgggtaaact tcgaggcatc   3840
agacttcatg tgcaccggta tctgtgcaca ttcaagatcg tatttagacg accgcttaaa   3900
ggccagttta gccagatcgg cattgtcgat agttcccttc acatgtgctg gtttcattac   3960
tttatccccc accaggcatg cgtagcccat cactttgcct tcatgcttga cttcgaagat   4020
gcaatcattt tcaattttca tgcacattct ctccctacgg cctggtttct tcttcttttg   4080
agccggcttc ttttgtggtg gttgcttctt ttgcttggg tcgttttgcg gcgcctgctt   4140
cttctgcctt tgcttcttgt ttttccgatt tctgcgaggc ttctgttgag gtaccgcgcg   4200
catggtcaat ttgttgactg cggagatcag ctgggcgagt tgcccagcct gcctctgtgg   4260
acgtggtcta ggtctaatta cttgaattgt agggcgtggg gcccagggtc ggggttggta   4320
ccttctgtta tagaaagttt gcgtcgggat gaactccat                          4359
```

<210> SEQ ID NO 189
<211> LENGTH: 4362
<212> TYPE: DNA
<213> ORGANISM: Artificial Sequence
<220> FEATURE:
<223> OTHER INFORMATION: Synthetic

<400> SEQUENCE: 189

```
atggagttca tcccgacgca aactttctat aacagaaggt accaaccccg accctgggcc     60
ccacgcccta caattcaagt aattagacct agaccacgtc cacagaggca ggctgggcaa    120
```

-continued

```
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa aatgattgca tcttcgaagt caagcatgaa    360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
gatcttgaat gtgcacagat accggtgcac atgaagtctg atgcctcgaa gtttacccac    540
gagaaacccg agggggtacta taactggcat cacggagcag tgcagtattc aggaggccgg    600
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagacccgg atactaccag ctactaaaag catcgctgac ttgccgccaa    960
agacgcctgc acctgggcaa gtgcaacatc gccggctgga ttctgggcaa ccccgagtgc   1020
gagagcctga gcaccgccag cagctggagc tacatcgtgg agaccccccag cagcgacaac   1080 ggcacctgct tccccggcga cttcatcgac tacgaggagc tgcgggagca gctgagcagc   1140
gtgagcagct cgagcggtt cgagatcttc cccaagacca gcagctggcc caaccacgac   1200
agcaacaagg gcgtgaccgc cgcctgcccc cacgccggcg ccaagagctt ctacaagaac   1260
ctgatctggc tggtgaagaa gggcaacagc tacccccaagc tgagcaagag ctacatcaac   1320
gacaagggca aggaggtgct ggtgctgtgg ggcatccacc accccagcac cagcgccgac   1380
cagcagagcc tgtaccagaa cgccgacacc tacgtgttcg tgggcagcag ccggtacagc   1440
aagaagttca gcccgagat cgccatccgg cccaaggtgc gggaccagga gggccggatg   1500
aactactact ggaccctggt ggagcccggc gacaagatca ccttcgaggc caccggcaac   1560
ctggtggtgc cccggtacgc cttcgccatg gagcggaacg ccaatttaa tgtctataaa   1620 gccacaagac catatctagc tcattgtcct gactgcggag aagggcattc gtgccacagc   1680
cctatcgcat tggagcgcat cagaaatgaa gcaacgacg gaacgctgaa atccaggtc   1740 tctttgcaga tcgggataaa gacagatgac agccacgatt ggaccaagct gcgctatatg   1800
gatagccata cgccagcgga cgcggagcga gccggattgc ttgtaaggac ttcagcaccg   1860
tgcacgatca ccgggaccat gggacacttt attctcgccc gatgcccgaa aggagagacg   1920
ctgacagtgg gatttacgga cagcagaaag atcagccaca catgcacaca cccgttccat   1980
catgaaccac ctgtgatagg tagggagagg ttccactctc gaccacaaca tggtaaagag   2040
ttaccttgca gcacgtacgt gcagagcacc gctgccactg ctgaggagat agaggtgcat   2100
atgcccccag atactcctga ccgcacgctg atgacgcagc agtctggcaa cgtgaagatc   2160
acagttaatg gcagacggt gcggtacaag tgcaactgcg gtggctcaaa cgagggactg   2220
acaaccacag acaaagtgat caataactgc aaaattgatc agtgccatgc tgcagtcact   2280
aatcacaaga attggcaata caactcccct ttagtcccgc gcaacgctga actcggggac   2340
cgtaaaggaa agatccacat cccattccca ttggcaaacg tgacttgcag agtgccaaaa   2400
gcaagaaacc ctacagtaac ttacggaaaa aaccaagtca ccatgctgct gtatcctgac   2460
```

| | |
|---|---|
| catccgacac tcttgtctta ccgtaacatg ggacaggaac caaattacca cgaggagtgg | 2520 |
| gtgacacaca agaaggaggt taccttgacc gtgcctactg agggtctgga ggtcacttgg | 2580 |
| ggcaacaacg aaccatacaa gtactggccg cagatgtcta cgaacggtac tgctcatggt | 2640 |
| cacccacatg agataatctt gtactattat gagctgtacc ccactatgac tgtagtcatt | 2700 |
| gtgtcggtgg cctcgttcgt gcttctgtcg atggtgggca cagcagtggg aatgtgtgtg | 2760 |
| tgcgcacggc gcagatgcat tacaccatat gaattaacac caggagccac tgttcccttc | 2820 |
| ctgctcagcc tgctatgctg cgtcagaacg accaaggcgg ccacatatta cgaggctgcg | 2880 |
| gcatatctat ggaacgaaca gcagcccctg ttctggttgc aggctcttat cccgctggcc | 2940 |
| gccttgatcg tcctgtgcaa ctgtctgaaa ctcttgccat gctgctgtaa gaccctggct | 3000 |
| tttttagccg taatgagcat cggtgcccac actgtgagcg cgtacgaaca cgtaacagtg | 3060 |
| atcccgaaca cggtgggagt accgtataag actcttgtca acagaccggg ttacagcccc | 3120 |
| atggtgttgg agatggagct acaatcagtc accttggaac caacactgtc acttgactac | 3180 |
| atcacgtgcg agtacaaaac tgtcatcccc tccccgtacg tgaagtgctg tggtacagca | 3240 |
| gagtgcaagg acaagagcct accagactac agctgcaagg tctttactgg agtctaccca | 3300 |
| tttatgtggg gcggcgccta ctgcttttgc gacgccgaaa atacgcaatt gagcgaggca | 3360 |
| catgtagaga aatctgaatc ttgcaaaaca gagtttgcat cggcctacag agcccacacc | 3420 |
| gcatcggcgt cggcgaagct ccgcgtcctt taccaaggaa acaacattac cgtagctgcc | 3480 |
| tacgctaacg gtgaccatgc cgtcacagta aaggacgcca gtttgtcgt gggcccaatg | 3540 |
| tcctccgcct ggacaccttt tgacaacaaa atcgtggtgt acaaaggcga cgtctacaac | 3600 |
| atggactacc caccttttgg cgcaggaaga ccaggacaat ttggtgacat tcaaagtcgt | 3660 |
| acaccggaaa gtaaagacgt ttatgccaac actcagttgg tactacagag gccagcagca | 3720 |
| ggcacggtac atgtaccata ctctcaggca ccatctggct tcaagtattg gctgaaggaa | 3780 |
| cgaggagcat cgctacagca cacggcaccg ttcggttgcc agattgcgac aaacccggta | 3840 |
| agagctgtaa attgcgctgt ggggaacata ccaatttcca tcgacatacc ggatgcggcc | 3900 |
| tttactaggg ttgtcgatgc accctctgta acggacatgt catgcgaagt accagcctgc | 3960 |
| actcactcct ccgactttgg gggcgtcgcc atcatcaaat acacagctag caagaaaggt | 4020 |
| aaatgtgcag tacattcgat gaccaacgcc gttaccattc gagaagccga cgtagaagta | 4080 |
| gaggggaact cccagctgca aatatccttc tcaacagccc tggcaagcgc cgagtttcgc | 4140 |
| gtgcaagtgt gctccacaca agtacactgc gcagccgcat gccacccctcc aaaggaccac | 4200 |
| atagtcaatt acccagcatc acacaccacc cttggggtcc aggatatatc cacaacggca | 4260 |
| atgtcttggg tgcagaagat tacgggagga gtaggattaa ttgttgctgt tgctgcctta | 4320 |
| atttttaattg tggtgctatg cgtgtcgttt agcaggcact aa | 4362 |

<210> SEQ ID NO 190
<211> LENGTH: 1453
<212> TYPE: PRT
<213> ORGANISM: Artificial Sequence
<220> FEATURE:
<223> OTHER INFORMATION: Synthetic

<400> SEQUENCE: 190

Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

```
Arg Pro Gln Arg Gln Ala Gly Gln Leu Ala Gln Leu Ile Ser Ala Val
         35                  40                  45
Asn Lys Leu Thr Met Arg Ala Val Pro Gln Gln Lys Pro Arg Arg Asn
 50                  55                  60
Arg Lys Asn Lys Lys Gln Arg Gln Lys Gln Ala Pro Gln Asn Asp
 65                  70                  75                  80
Pro Lys Gln Lys Gln Pro Pro Gln Lys Lys Pro Ala Gln Lys Lys
                 85                  90                  95
Lys Lys Pro Gly Arg Arg Glu Arg Met Cys Met Lys Ile Glu Asn Asp
                100                 105                 110
Cys Ile Phe Glu Val Lys His Glu Gly Lys Val Met Gly Tyr Ala Cys
        115                 120                 125
Leu Val Gly Asp Lys Val Met Lys Pro Ala His Val Lys Gly Thr Ile
        130                 135                 140
Asp Asn Ala Asp Leu Ala Lys Leu Ala Phe Lys Arg Ser Ser Lys Tyr
145                 150                 155                 160
Asp Leu Glu Cys Ala Gln Ile Pro Val His Met Lys Ser Asp Ala Ser
                165                 170                 175
Lys Phe Thr His Glu Lys Pro Glu Gly Tyr Tyr Asn Trp His His Gly
                180                 185                 190
Ala Val Gln Tyr Ser Gly Gly Arg Phe Thr Ile Pro Thr Gly Ala Gly
        195                 200                 205
Lys Pro Gly Asp Ser Gly Arg Pro Ile Phe Asp Asn Lys Gly Arg Val
        210                 215                 220
Val Ala Ile Val Leu Gly Gly Ala Asn Glu Gly Ala Arg Thr Ala Leu
225                 230                 235                 240
Ser Val Val Thr Trp Asn Lys Asp Ile Val Thr Lys Ile Thr Pro Glu
                245                 250                 255
Gly Ala Glu Glu Trp Ser Leu Ala Leu Pro Val Leu Cys Leu Leu Ala
                260                 265                 270
Asn Thr Thr Phe Pro Cys Ser Gln Pro Pro Cys Thr Pro Cys Cys Tyr
        275                 280                 285
Glu Lys Glu Pro Glu Ser Thr Leu Arg Met Leu Glu Asp Asn Val Met
        290                 295                 300
Arg Pro Gly Tyr Tyr Gln Leu Leu Lys Ala Ser Leu Thr Cys Arg Gln
305                 310                 315                 320
Arg Arg Leu His Leu Gly Lys Cys Asn Ile Ala Gly Trp Ile Leu Gly
                325                 330                 335
Asn Pro Glu Cys Glu Ser Leu Ser Thr Ala Ser Ser Trp Ser Tyr Ile
                340                 345                 350
Val Glu Thr Pro Ser Ser Asp Asn Gly Thr Cys Phe Pro Gly Asp Phe
        355                 360                 365
Ile Asp Tyr Glu Glu Leu Arg Glu Gln Leu Ser Ser Val Ser Ser Phe
        370                 375                 380
Glu Arg Phe Glu Ile Phe Pro Lys Thr Ser Ser Trp Pro Asn His Asp
385                 390                 395                 400
Ser Asn Lys Gly Val Thr Ala Ala Cys Pro His Ala Gly Ala Lys Ser
                405                 410                 415
Phe Tyr Lys Asn Leu Ile Trp Leu Val Lys Lys Gly Asn Ser Tyr Pro
                420                 425                 430
Lys Leu Ser Lys Ser Tyr Ile Asn Asp Lys Gly Lys Glu Val Leu Val
        435                 440                 445
```

-continued

Leu Trp Gly Ile His His Pro Ser Thr Ser Ala Asp Gln Gln Ser Leu
450                 455                 460

Tyr Gln Asn Ala Asp Thr Tyr Val Phe Val Gly Ser Ser Arg Tyr Ser
465                 470                 475                 480

Lys Lys Phe Lys Pro Glu Ile Ala Ile Arg Pro Lys Val Arg Asp Gln
            485                 490                 495

Glu Gly Arg Met Asn Tyr Tyr Trp Thr Leu Val Glu Pro Gly Asp Lys
                500                 505                 510

Ile Thr Phe Glu Ala Thr Gly Asn Leu Val Val Pro Arg Tyr Ala Phe
            515                 520                 525

Ala Met Glu Arg Asn Ala Asn Phe Asn Val Tyr Lys Ala Thr Arg Pro
530                 535                 540

Tyr Leu Ala His Cys Pro Asp Cys Gly Glu Gly His Ser Cys His Ser
545                 550                 555                 560

Pro Ile Ala Leu Glu Arg Ile Arg Asn Glu Ala Thr Asp Gly Thr Leu
                565                 570                 575

Lys Ile Gln Val Ser Leu Gln Ile Gly Ile Lys Thr Asp Asp Ser His
            580                 585                 590

Asp Trp Thr Lys Leu Arg Tyr Met Asp Ser His Thr Pro Ala Asp Ala
            595                 600                 605

Glu Arg Ala Gly Leu Leu Val Arg Thr Ser Ala Pro Cys Thr Ile Thr
610                 615                 620

Gly Thr Met Gly His Phe Ile Leu Ala Arg Cys Pro Lys Gly Glu Thr
625                 630                 635                 640

Leu Thr Val Gly Phe Thr Asp Ser Arg Lys Ile Ser His Thr Cys Thr
                645                 650                 655

His Pro Phe His His Glu Pro Pro Val Ile Gly Arg Glu Arg Phe His
            660                 665                 670

Ser Arg Pro Gln His Gly Lys Glu Leu Pro Cys Ser Thr Tyr Val Gln
    675                 680                 685

Ser Thr Ala Ala Thr Ala Glu Glu Ile Glu Val His Met Pro Pro Asp
690                 695                 700

Thr Pro Asp Arg Thr Leu Met Thr Gln Gln Ser Gly Asn Val Lys Ile
705                 710                 715                 720

Thr Val Asn Gly Gln Thr Val Arg Tyr Lys Cys Asn Cys Gly Gly Ser
                725                 730                 735

Asn Glu Gly Leu Thr Thr Thr Asp Lys Val Ile Asn Asn Cys Lys Ile
            740                 745                 750

Asp Gln Cys His Ala Ala Val Thr Asn His Lys Asn Trp Gln Tyr Asn
            755                 760                 765

Ser Pro Leu Val Pro Arg Asn Ala Glu Leu Gly Asp Arg Lys Gly Lys
770                 775                 780

Ile His Ile Pro Phe Pro Leu Ala Asn Val Thr Cys Arg Val Pro Lys
785                 790                 795                 800

Ala Arg Asn Pro Thr Val Thr Tyr Gly Lys Asn Gln Val Thr Met Leu
                805                 810                 815

Leu Tyr Pro Asp His Pro Thr Leu Leu Ser Tyr Arg Asn Met Gly Gln
            820                 825                 830

Glu Pro Asn Tyr His Glu Glu Trp Val Thr His Lys Lys Glu Val Thr
            835                 840                 845

Leu Thr Val Pro Thr Glu Gly Leu Glu Val Thr Trp Gly Asn Asn Glu
850                 855                 860

Pro Tyr Lys Tyr Trp Pro Gln Met Ser Thr Asn Gly Thr Ala His Gly

```
                865                 870                 875                 880
His Pro His Glu Ile Ile Leu Tyr Tyr Glu Leu Tyr Pro Thr Met
                        885                 890                 895
Thr Val Val Ile Val Ser Val Ala Ser Phe Val Leu Leu Ser Met Val
                900                 905                 910
Gly Thr Ala Val Gly Met Cys Val Cys Ala Arg Arg Arg Cys Ile Thr
                915                 920                 925
Pro Tyr Glu Leu Thr Pro Gly Ala Thr Val Pro Phe Leu Leu Ser Leu
            930                 935                 940
Leu Cys Cys Val Arg Thr Thr Lys Ala Ala Thr Tyr Tyr Glu Ala Ala
945                 950                 955                 960
Ala Tyr Leu Trp Asn Glu Gln Gln Pro Leu Phe Trp Leu Gln Ala Leu
                    965                 970                 975
Ile Pro Leu Ala Ala Leu Ile Val Leu Cys Asn Cys Leu Lys Leu Leu
                980                 985                 990
Pro Cys Cys Cys Lys Thr Leu Ala Phe Leu Ala Val Met Ser Ile Gly
            995                 1000                1005
Ala His Thr Val Ser Ala Tyr Glu His Val Thr Val Ile Pro Asn
    1010                1015                1020
Thr Val Gly Val Pro Tyr Lys Thr Leu Val Asn Arg Pro Gly Tyr
    1025                1030                1035
Ser Pro Met Val Leu Glu Met Glu Leu Gln Ser Val Thr Leu Glu
    1040                1045                1050
Pro Thr Leu Ser Leu Asp Tyr Ile Thr Cys Glu Tyr Lys Thr Val
    1055                1060                1065
Ile Pro Ser Pro Tyr Val Lys Cys Cys Gly Thr Ala Glu Cys Lys
    1070                1075                1080
Asp Lys Ser Leu Pro Asp Tyr Ser Cys Lys Val Phe Thr Gly Val
    1085                1090                1095
Tyr Pro Phe Met Trp Gly Gly Ala Tyr Cys Phe Cys Asp Ala Glu
    1100                1105                1110
Asn Thr Gln Leu Ser Glu Ala His Val Glu Lys Ser Glu Ser Cys
    1115                1120                1125
Lys Thr Glu Phe Ala Ser Ala Tyr Arg Ala His Thr Ala Ser Ala
    1130                1135                1140
Ser Ala Lys Leu Arg Val Leu Tyr Gln Gly Asn Asn Ile Thr Val
    1145                1150                1155
Ala Ala Tyr Ala Asn Gly Asp His Ala Val Thr Val Lys Asp Ala
    1160                1165                1170
Lys Phe Val Val Gly Pro Met Ser Ser Ala Trp Thr Pro Phe Asp
    1175                1180                1185
Asn Lys Ile Val Val Tyr Lys Gly Asp Val Tyr Asn Met Asp Tyr
    1190                1195                1200
Pro Pro Phe Gly Ala Gly Arg Pro Gly Gln Phe Gly Asp Ile Gln
    1205                1210                1215
Ser Arg Thr Pro Glu Ser Lys Asp Val Tyr Ala Asn Thr Gln Leu
    1220                1225                1230
Val Leu Gln Arg Pro Ala Ala Gly Thr Val His Val Pro Tyr Ser
    1235                1240                1245
Gln Ala Pro Ser Gly Phe Lys Tyr Trp Leu Lys Glu Arg Gly Ala
    1250                1255                1260
Ser Leu Gln His Thr Ala Pro Phe Gly Cys Gln Ile Ala Thr Asn
    1265                1270                1275
```

```
Pro Val Arg Ala Val Asn Cys Ala Val Gly Asn Ile Pro Ile Ser
        1280                1285                1290

Ile Asp Ile Pro Asp Ala Ala Phe Thr Arg Val Asp Ala Pro
1295                1300                1305

Ser Val Thr Asp Met Ser Cys Glu Val Pro Ala Cys Thr His Ser
1310                1315                1320

Ser Asp Phe Gly Gly Val Ala Ile Ile Lys Tyr Thr Ala Ser Lys
    1325                1330                1335

Lys Gly Lys Cys Ala Val His Ser Met Thr Asn Ala Val Thr Ile
1340                1345                1350

Arg Glu Ala Asp Val Glu Val Glu Gly Asn Ser Gln Leu Gln Ile
    1355                1360                1365

Ser Phe Ser Thr Ala Leu Ala Ser Ala Glu Phe Arg Val Gln Val
    1370                1375                1380

Cys Ser Thr Gln Val His Cys Ala Ala Ala Cys His Pro Pro Lys
1385                1390                1395

Asp His Ile Val Asn Tyr Pro Ala Ser His Thr Thr Leu Gly Val
    1400                1405                1410

Gln Asp Ile Ser Thr Thr Ala Met Ser Trp Val Gln Lys Ile Thr
    1415                1420                1425

Gly Gly Val Gly Leu Ile Val Ala Val Ala Ala Leu Ile Leu Ile
    1430                1435                1440

Val Val Leu Cys Val Ser Phe Ser Arg His
    1445                1450

<210> SEQ ID NO 191
<211> LENGTH: 4362
<212> TYPE: DNA
<213> ORGANISM: Artificial Sequence
<220> FEATURE:
<223> OTHER INFORMATION: Synthetic

<400> SEQUENCE: 191
ttagtgcctg ctaaacgaca cgcatagcac cacaattaaa attaaggcag caacagcaac      60
aattaatcct actcctcccg taatcttctg cacccaagac attgccgttg tggatatatc     120
ctggacccca agggtggtgt gtgatgctgg gtaattgact atgtggtcct ttggagggtg     180
gcatgcggct gcgcagtgta cttgtgtgga gcacacttgc acgcgaaact cggcgcttgc     240
cagggctgtt gagaaggata tttgcagctg ggagttcccc tctacttcta cgtcggcttc     300
tcgaatggta acggcgttgg tcatcgaatg tactgcacat ttacctttct tgctagctgt     360
gtatttgatg atggcgacgc ccccaaagtc ggaggagtga gtgcaggctg gtacttcgca     420
tgacatgtcc gttacagagg gtgcatcgac aaccctagta aaggccgcat ccggtatgtc     480
gatggaaatt ggtatgttcc ccacagcgca atttacagct cttaccgggt tgtcgcaat      540 ctggcaaccg aacggtgccg tgtgctgtag cgatgctcct cgttccttca gccaatactt     600
gaagccagat ggtgcctgag agtatggtac atgtaccgtg cctgctgctg gcctctgtag     660
taccaactga gtgttggcat aaacgtcttt actttccggt gtacgacttt gaatgtcacc     720
aaattgtcct ggtcttcctg cgccaaaagg tgggtagtcc atgttgtaga cgtcgccttt     780
gtacaccacg attttgttgt caaaaggtgt ccaggcggag acattgggc ccacgacaaa      840 cttggcgtcc tttactgtga cggcatggtc accgttagcg taggcagcta cggtaatgtt     900
gtttccttgg taaggacgc ggagcttcgc cgacgccgat gcggtgtggg ctctgtaggc      960
```

-continued

```
cgatgcaaac tctgttttgc aagattcaga tttctctaca tgtgcctcgc tcaattgcgt    1020
attttcggcg tcgcaaaagc agtaggcgcc gccccacata aatgggtaga ctccagtaaa    1080
gaccttgcag ctgtagtctg gtaggctctt gtccttgcac tctgctgtac cacagcactt    1140
cacgtacggg gaggggatga cagttttgta ctcgcacgtg atgtagtcaa gtgacagtgt    1200
tggttccaag gtgactgatt gtagctccat ctccaacacc atgggctgt aacccggtct     1260 gttgacaaga gtcttatacg gtactcccac cgtgttcggg atcactgtta cgtgttcgta    1320
cgcgctcaca gtgtgggcac cgatgctcat tacggctaaa aaagccaggg tcttacagca    1380
gcatggcaag agtttcagac agttgcacag gacgatcaag gcggccagcg ggataagagc     1440
ctgcaaccag aacaggggct gctgttcgtt ccatagatat gccgcagcct cgtaatatgt    1500
ggccgccttg gtcgttctga cgcagcatag caggctgagc aggaagggaa cagtggctcc    1560
tggtgttaat tcatatggtg taatgcatct gcgccgtgcg cacacacaca ttcccactgc    1620
tgtgcccacc atcgacagaa gcacgaacga ggccaccgac acaatgacta cagtcatagt    1680
ggggtacagc tcataatagt acaagattat ctcatgtggg tgaccatgag cagtaccgtt    1740
cgtagacatc tgcggccagt acttgtatgg ttcgttgttg ccccaagtga cctccagacc    1800
ctcagtaggc acggtcaagg taacctcctt cttgtgtgtc acccactcct cgtggtaatt    1860
tggttcctgt cccatgttac ggtaagacaa gagtgtcgga tggtcaggat acagcagcat    1920
ggtgacttgg ttttttccgt aagttactgt agggtttctt gcttttggca ctctgcaagt    1980
cacgtttgcc aatgggaatg ggatgtggat cttcccttta cggtcccga gttcagcgtt     2040 gcgcgggact aaaggggagt tgtattgcca attcttgtga ttagtgactg cagcatggca    2100
ctgatcaatt ttgcagttat tgatcactt gtctgtggtt gtcagtccct cgtttgagcc     2160
accgcagttg cacttgtacc gcaccgtctg cccattaact gtgatcttca cgttgccaga    2220
ctgctgcgtc atcagcgtgc ggtcaggagt atctggggc atatgcacct ctatctcctc     2280
agcagtggca gcggtgctct gcacgtacgt gctgcaaggt aactctttac catgttgtgg    2340
tcgagagtgg aacctctccc tacctatcac aggtggttca tgatggaacg ggtgtgtgca    2400
tgtgtggctg atctttctgc tgtccgtaaa tcccactgtc agcgtctctc ctttcgggca    2460
tcgggcgaga ataaagtgtc ccatggtccc ggtgatcgtg cacggtgctg aagtccttac    2520
aagcaatccg gctcgctccg cgtccgctgg cgtatggcta tccatatagc gcagcttggt    2580
ccaatcgtgg ctgtcatctg tctttatccc gatctgcaaa gagacctgga ttttcagcgt    2640
tccgtccgtt gcttcatttc tgatgcgctc caatgcgata gggctgtggc acgaatgccc    2700
ttctccgcag tcaggacaat gagctagata tggtcttgtg gctttataga cattaaaatt    2760
ggcgttccgc tccatggcga aggcgtaccg gggcaccacc aggttgccgg tggcctcgaa    2820
ggtgatcttg tcgccgggct ccaccagggt ccagtagtag ttcatccggc cctcctggtc    2880
ccgcaccttg gccggatgg cgatctcggg cttgaacttc ttgctgtacc ggctgctgcc     2940
cacgaacacg taggtgtcgg cgttctgta caggctctgc tggtcggcgc tggtgctggg    3000
gtggtggatg ccccacagca ccagcacctc cttgcccttg tcgttgatgt agctcttgct    3060
cagcttgggg tagctgttgc ccttcttcac cagccgatc aggttcttgt agaagctctt     3120
ggcgccggcg tggggcagg cggcggtcac gcccttgttg ctgtcgtggt tgggccagct    3180
gctggtcttg gggaagatct cgaaccgctc gaagctgctc acgctgctca gctgctcccg    3240
cagctcctcg tagtcgatga agtcgccggg gaagcaggtg ccgttgtcgc tgctggggt    3300 ctccacgatg tagctccagc tgctggcggt gctcaggctc tcgcactcgg ggttgcccag    3360
```

```
aatccagccg gcgatgttgc acttgcccag gtgcaggcgt ctttggcggc aagtcagcga    3420
tgcttttagt agctggtagt atccgggtct catcacgttg tcctcaagca tgcgcaaggt    3480
gctttccggt tccttttcgt agcagcaggg tgtgcaaggc ggctgagagc aggggaatgt    3540
agtgtttgcc aacaggcaca agaccgggag ggcgaggctc cactcttcgg ctccctcagg    3600
ggtaattttt gtgacgatgt ctttgttcca cgtcaccacg gagagggccg tgcgggcacc    3660
ttcgttggcc cctcctagga cgatggccac cacccgtcct ttgttgtcga agatcggtct    3720
gccgctgtct cccggcttgc ctgcacccgt cgggatagtg aaccggcctc ctgaatactg    3780
cactgctccg tgatgccagt tatagtaccc ctcgggtttc tcgtgggtaa acttcgaggc    3840
atcagacttc atgtgcaccg gtatctgtgc acattcaaga tcgtatttag acgaccgctt    3900
aaaggccagt ttagccagat cggcattgtc gatagttccc ttcacatgtg ctggtttcat    3960
tactttatcc cccaccaggc atgcgtagcc catcactttg ccttcatgct tgacttcgaa    4020
gatgcaatca ttttcaattt tcatgcacat tctctcccta cggcctggtt tcttcttctt    4080
ttgagccggc ttcttttgtg gtggttgctt cttttgcttt gggtcgtttt gcggcgcctg    4140
cttcttctgc ctttgcttct tgttttccg atttctgcga ggcttctgtt gaggtaccgc    4200
gcgcatggtc aatttgttga ctgcggagat cagctgggcg agttgcccag cctgcctctg    4260
tggacgtggt ctaggtctaa ttacttgaat tgtagggcgt ggggcccagg gtcggggttg    4320
gtaccttctg ttatagaaag tttgcgtcgg gatgaactcc at                      4362
```

<210> SEQ ID NO 192
<211> LENGTH: 5
<212> TYPE: PRT
<213> ORGANISM: Artificial Sequence
<220> FEATURE:
<223> OTHER INFORMATION: Linker

<400> SEQUENCE: 192

Gly Gly Ser Gly Gly
1               5

MULTIVALENT NANOPARTICLE-BASED VACCINES

CROSS-REFERENCE TO RELATED APPLICATIONS

This is a divisional of U.S. Non-Provisional patent application Ser. No. 15/540,898, filed on Jun. 29, 2017, which is the U.S. National Stage of International Application No. PCT/US2015/068272, filed on Dec. 31, 2015, which was published in English under PCT Article 21(2), which in turn claims the benefit of U.S. Provisional Application No. 62/098,755, filed on Dec. 31, 2014. Each of the above-listed applications is incorporated by reference herein in its entirety.

SUMMARY OF THE INVENTION

The present invention provides novel, nanoparticle-based vaccines that are easily manufactured, potent, and which elicit broadly neutralizing antibodies against infectious agents, such as influenza virus, HIV and human papilloma virus. In particular, the present invention provides novel nanoparticles (nps), the surfaces of which display a heterogeneous population of immunogenic portions of proteins from infectious agents. Such nanoparticles comprise fusion proteins, each of which comprises a monomeric subunit of ferritin joined to one or more immunogenic portions of proteins from infectious agents. When such nanoparticles are administered to an individual, they elicit an immune response to proteins from a broad range of infectious agents.

In one embodiment, the invention is a nanoparticle comprising fusion proteins, wherein the surface of the nanoparticle displays immunogenic portions of corresponding proteins from at least two infectious agents, wherein the at least two infectious agents are from different corresponding taxonomic groups within the same taxonomic family. In certain aspects of the invention, the fusion proteins comprise at least a portion of a self-assembling, monomeric subunit joined to at least one immunogenic portion of a protein from an infectious agent.

In one embodiment, the invention is a nanoparticle comprising at least a first fusion protein and a second fusion protein, each fusion protein comprising at least a portion of a self-assembling, monomeric subunit joined to at least one immunogenic portion of a protein from an infectious agent, wherein the immunogenic portion of the first fusion protein is from a protein from a first infectious agent; wherein the immunogenic portion of the second fusion protein is from a protein from a second infectious agent; wherein the proteins from the first and second infectious agents are corresponding proteins; and wherein the first and second infectious agents are from different corresponding taxonomic groups within the same taxonomic family.

In the above embodiments, the corresponding taxonomic groups can be genera, types, subtypes, species or strains. In certain aspects, the monomeric subunit can be a monomeric ferritin subunit protein, a monomeric encapsulin protein, a monomeric 03-33 protein, a monomeric SOR protein, a monomeric LS protein, a monomeric PDC protein or a Chikungunya virus structural polyprotein. In certain aspects the infectious agents are viruses. In certain aspects, the infectious agents can be, for example, influenza viruses, human immunodeficiency viruses (HIV), flaviviruses (e.g., hepatitis virus, dengue virus, etc.), human papillomaviruses (HPV), rhinoviruses, coronaviruses, enteroviruses, polyomaviruses, respiratory synctial viruses (RSV), human metapneumoviruses, ebola viruses, Marburg viruses, alphaviruses (e.g., Chikungunya virus, Ross River virus, Semliki Forest virus, Sindbis virus, Mayaro virus, etc), Porcine Epidemic Diarrhea, Porcine reproductive and respiratory syndrome virus and foot and mouth disease virus.

In one embodiment, nanoparticles of the above embodiments can be produced by introducing into a cell one or more nucleic acid molecules encoding fusion proteins comprising at least a portion of a self-assembling, monomeric subunit joined to at least one immunogenic portion of a protein from an infectious agent, and incubating the cell under conditions suitable for expression of the encoded proteins to form nanoparticles. In certain embodiments, such a method can comprise further purification and/or isolation of the nanoparticles.

In one embodiment of the invention, nanoparticles of the embodiments listed above are used to prepare a medicament for protecting an individual from an infectious agent. In such embodiments, the nanoparticles comprise immunogenic portions of proteins from infectious agents in the same taxonomic family as the infectious agent against which the individual is being protected. In certain embodiments, the medicament is used to vaccinate the individual.

One embodiment of the invention is a method to elicit a protective immune response against an infectious agent, the method comprising administering to an individual a nanoparticle of the embodiments of the invention, or a composition or medicament comprising embodiments of the invention, wherein the nanoparticles comprise immunogenic portions of proteins from infectious agents in the same taxonomic family as the infectious agent against which the protective immune response is being elicited.

One embodiment of the invention is a method to elicit neutralizing antibodies against an infectious agent, the method comprising administering to an individual a nanoparticle of the embodiments of the invention, or a composition or medicament comprising embodiments of the invention, wherein the nanoparticles comprise immunogenic portions of proteins from infectious agents in the same taxonomic family as the infectious agent against which the neutralizing antibodies are desired.

In one embodiment, the invention is a nanoparticle that comprises self-assembling fusion proteins, and in this embodiment the nanoparticle displays on its surface a heterogeneous population of immunogenic portions from HA proteins from one or more Type, Group, subtype and/or strain of influenza virus.

In another embodiment, the invention is a nanoparticle that comprises a heterogeneous population of fusion proteins, and in this embodiment each fusion protein comprises at least a portion of a monomeric subunit protein capable of self-assembling into a nanoparticle joined to at least one immunogenic portion from an influenza virus hemagglutinin protein, such that the heterogeneous population comprises at least two different species of fusion proteins, and such that the difference between two species of fusion proteins is due, at least in part, to sequence differences in the immunogenic portion from an influenza virus HA protein.

In yet another embodiment, the invention is a nanoparticle that comprises at least two species of fusion proteins, and in this embodiment each fusion protein comprises at least a portion of a monomeric subunit protein capable of self-assembling into a nanoparticle joined to at least one immunogenic portion from an influenza virus HA protein, such that the species of fusion protein differ from one another due, at least in part, to differences in the sequences of the immunogenic portion from an influenza virus hemagglutinin protein.

In still another embodiment, the invention is a nanoparticle that comprises at least a first species of fusion protein and a second species of fusion protein, and in this embodiment the fusion proteins comprise at least a portion of a monomeric subunit protein capable of self-assembling into a nanoparticle joined to at least one immunogenic portion from an influenza virus hemagglutinin protein, such that the species of fusion proteins differ from one another due, at least in part, to differences in the sequences of the immunogenic portion from an influenza virus hemagglutinin protein.

In the above embodiments, the different species of fusion proteins contain immunogenic portions from HA proteins of influenza viruses in different taxonomic groups within the orthomyxoviridae family.

In the above embodiments, ferritin-based nanoparticle can form an octahedron, which can consist of 24 subunits. Further, the immunogenic portions of the influenza HA proteins can be displayed on the surface of the nanoparticle with a spacing range in the range of about 50 Å to about 100 Å. Additionally, the monomeric subunit protein can be selected from a monomeric ferritin subunit protein, a monomeric encapsulin protein, a monomeric O3-33 protein, a monomeric SOR protein, a monomeric LS protein, a monomeric PDC protein and Chikungunya virus envelope protein. The monomeric ferritin subunit protein can be selected from the a bacterial ferritin, a plant ferritin, an algal ferritin, an insect ferritin, a fungal ferritin and a mammalian ferritin and in preferred embodiments, is selected from a monomeric subunit of a *Helicobacter pylori* ferritin protein, a monomeric subunit of a *Escherichia coli* ferritin protein and a monomeric subunit of a bullfrog ferritin protein. In still another preferred embodiment, the monomeric ferritin subunit protein can be a hybrid protein that comprises at least a portion of a bullfrog ferritin protein joined to at least a portion of a ferritin protein selected from a *Helicobacter pylori* ferritin protein and an *Escherichia coli* ferritin protein.

In one aspect of the embodiments of the invention, the monomeric subunit protein can comprise at least 25 contiguous amino acids from a protein selected from a monomeric ferritin subunit protein, a monomeric encapsulin protein, a monomeric O3-33 protein, a monomeric SOR protein, a monomeric LS protein, a monomeric PDC protein and Chikungunya virus envelope protein.

In still another aspect of the embodiments of the invention, the monomeric subunit protein can comprise at least 25 contiguous amino acids from an amino acid sequence selected from a sequence selected from SEQ ID NO:64, SEQ ID NO:67, SEQ ID NO:70, SEQ ID NO:73, SEQ ID NO:76, SEQ ID NO:79, SEQ ID NO:82, SEQ ID NO:85, SEQ ID NO:88, SEQ ID NO:91 and SEQ ID NO:94. Alternatively, the monomeric subunit protein can comprise an amino acid sequence at least about 80% identical to an amino acid sequence selected from SEQ ID NO:64, SEQ ID NO:67, SEQ ID NO:70, SEQ ID NO:73, SEQ ID NO:76, SEQ ID NO:79, SEQ ID NO:82, SEQ ID NO:85, SEQ ID NO:88, SEQ ID NO:91 and SEQ ID NO:94. Also, the monomeric subunit protein can comprise an amino acid sequence selected from SEQ ID NO:64, SEQ ID NO:67, SEQ ID NO:70, SEQ ID NO:73, SEQ ID NO:76, SEQ ID NO:79, SEQ ID NO:82, SEQ ID NO:85, SEQ ID NO:88, SEQ ID NO:91 and SEQ ID NO:94.

In one aspect of the embodiments of the invention, the HA protein can be from a virus selected from A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2).

In yet another aspect of the embodiments of the invention, the HA protein can comprise at least 25 contiguous amino acids from the hemagglutinin protein of an influenza virus selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2).

In yet another aspect of the embodiments of the invention, the HA protein can comprise at least 25 contiguous amino acids from a sequence selected from SEQ ID NOs: 1-62. The HA protein can comprise an amino acid sequence at least about 80% identical to an amino acid sequence selected from SEQ ID NOs: 1-62. Also, the hemagglutinin protein can comprise an amino acid sequence selected from SEQ ID NOs: 1-62.

In still another aspect of the embodiments of the invention, the HA protein can be capable of eliciting an immune response to a protein comprising an amino acid sequence selected from SEQ ID NOs: 1-62.

In another aspect of the embodiments of the invention, the immunogenic portion can comprise the receptor-binding domain of an influenza HA protein. Further, the immunogenic portion can be selected from amino acid residues 56-264 of a sequence selected from SEQ ID NOs: 1-62.

In yet another aspect of the embodiments of the invention, the at least two species of fusion proteins can comprise immunogenic portions obtained from HA proteins from two different strains of influenza virus. Also, the at least two species of fusion proteins can comprise immunogenic portions obtained from HA protein from two different subtypes of influenza virus.

In still another aspect of the embodiments of the invention, at least one species of fusion protein can comprise a linker sequence.

In another aspect of the embodiments of the invention, the nanoparticle can elicit an immune response against the RBD region of an influenza HA protein. In one aspect, the nanoparticle can elicit an immune response to an influenza virus strain that is heterologous to the strains of influenza viruses from which the HA immunogenic portions were obtained. In still another aspect, the nanoparticle can elicit an immune response to an influenza virus that is antigenically divergent from the influenza virus from which the hemagglutinin proteins were obtained.

In still another aspect of the embodiments of the invention, the heterogeneous population can comprise between 2 and 60 species of fusion proteins. In still another aspect of the embodiments of the invention, the heterogeneous population can comprise between 2 and 240 species of fusion proteins.

Another embodiment of the present invention is a fusion protein comprising an amino acid sequence at least 80% identical to a sequence selected from SEQ ID NO:97, SEQ ID NO:100, SEQ ID NO:103, SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:133, SEQ ID NO:136, SEQ ID NO:139, SEQ ID NO:142, SEQ ID NO:145, SEQ ID NO:148, SEQ ID NO:151, SEQ ID NO:154, SEQ ID NO:157, SEQ ID NO:160, SEQ ID NO:163, SEQ ID NO:166, SEQ ID NO:169, SEQ ID NO:172, SEQ ID NO:175, SEQ ID NO:178, SEQ ID NO:181, SEQ ID NO:184, SEQ ID NO:187 and SEQ ID NO:190. The fusion protein can also comprise an amino acid sequence selected from SEQ ID NO:97, SEQ ID NO:100, SEQ ID NO:103, SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:133, SEQ ID NO:136, SEQ ID NO:139, SEQ ID NO:142, SEQ ID NO:145, SEQ ID NO:148, SEQ ID NO:151, SEQ ID NO:154, SEQ ID NO:157, SEQ ID NO:160, SEQ ID NO:163, SEQ ID NO:166, SEQ ID NO:169, SEQ ID NO:172, SEQ ID NO:175, SEQ ID NO:178, SEQ ID NO:181, SEQ ID NO:184, SEQ ID NO:187 and SEQ ID NO:190.

A further embodiment is a nucleic acid molecule encoding any of the fusion proteins described above. In this embodiment, the nucleic acid sequence can be at least 80% identical to a sequence selected from SEQ ID NO:96, SEQ ID NO:99, SEQ ID NO:102, SEQ ID NO:105, SEQ ID NO:108, SEQ ID NO:111, SEQ ID NO:114, SEQ ID NO:117, SEQ ID NO:120, SEQ ID NO:123, SEQ ID NO:126, SEQ ID NO:129, SEQ ID NO:132, SEQ ID NO:135, SEQ ID NO:138, SEQ ID NO:141, SEQ ID NO:144, SEQ ID NO:147, SEQ ID NO:150, SEQ ID NO:153, SEQ ID NO:156, SEQ ID NO:159, SEQ ID NO:162, SEQ ID NO:165, SEQ ID NO:168, SEQ ID NO:171, SEQ ID NO:174, SEQ ID NO:177, SEQ ID NO:180, SEQ ID NO:183, SEQ ID NO:186 and SEQ ID NO:189. In still another aspect, the nucleic acid sequence can comprise a sequence selected from SEQ ID NO:96, SEQ ID NO:99, SEQ ID NO:102, SEQ ID NO:105, SEQ ID NO:108, SEQ ID NO:111, SEQ ID NO:114, SEQ ID NO:117, SEQ ID NO:120, SEQ ID NO:123, SEQ ID NO:126, SEQ ID NO:129, SEQ ID NO:132, SEQ ID NO:135, SEQ ID NO:138, SEQ ID NO:141, SEQ ID NO:144, SEQ ID NO:147, SEQ ID NO:150, SEQ ID NO:153, SEQ ID NO:156, SEQ ID NO:159, SEQ ID NO:162, SEQ ID NO:165, SEQ ID NO:168, SEQ ID NO:171, SEQ ID NO:174, SEQ ID NO:177, SEQ ID NO:180, SEQ ID NO:183, SEQ ID NO:186 and SEQ ID NO:189. Further in this embodiment, a plasmid can comprise the nucleic acid molecule of any of the nucleic acid molecules described above.

Another embodiment of the present invention is a method for producing a nanoparticle of any of the nanoparticles described above, the method comprising introducing one or more nucleic acid molecules encoding fusion proteins, wherein each fusion protein can comprise at least a portion of a monomeric subunit protein capable of self-assembling into a nanoparticle joined to at least one immunogenic portion from an influenza virus hemagglutinin protein; and incubating the cell under conditions suitable for expressing the encoded proteins and forming nanoparticles. A further aspect of this embodiment can comprise isolating the nanoparticles from the cell.

Another embodiment of the present invention is a method of eliciting an immune response against influenza virus, the method comprising administering to an individual a nanoparticle as described above.

Another embodiment of the present invention is a method of vaccinating an individual against influenza virus, such that the method can comprise administering to the individual a nanoparticle as described above. Accordingly, another embodiment of the present invention is an immunogenic composition comprising a nanoparticle of the invention. Another embodiment of the invention is a medicament for use in vaccinating an individual, or electing an immune response, against influenza virus, the medicament comprising a nanoparticle of the present invention.

A further embodiment of the present invention is a kit. The kit can comprise a nanoparticle as described above, compositions and medicaments comprising such nanoparticles, a fusion protein and/or a nucleic acid molecule as described above.

BACKGROUND

Protective immune responses induced by vaccination against influenza virus are primarily directed to the viral hemagglutinin (HA) protein, which is a glycoprotein on the surface of the virus responsible for interaction of the virus with host cell receptors. HA proteins on the virus surface are trimers of hemagglutinin protein monomers that are enzymatically cleaved to yield amino-terminal HA1 and carboxy-terminal HA2 polypeptides. The globular head consists exclusively of the major portion of the HA1 polypeptide, whereas the stem that anchors the hemagglutinin protein into the viral lipid envelope is comprised of HA2 and part of HA1. The globular head of a hemagglutinin protein includes two domains: the receptor binding domain (RBD), an ~148-amino acid residue domain that includes the sialic acid-binding site, and the vestigial esterase domain, a smaller ~75-amino acid residue region just below the RBD. The top part of the RBD adjacent to the 2,6-sialic acid recognition sites includes a large region (amino acids 131-143, 170-182, 205-215 and 257-262, 1918 numbering) (referred to herein as the RBD-A region) of over 6000 Å$^2$ per trimer that is 95% conserved between A/South Carolina/l/1918 (1918 SC) and A/California/04/2009 (2009 CA) pandemic strains. The globular head includes several antigenic sites that include immunodominant epitopes. Examples include the Sa, Sb, Ca$_1$, Ca$_2$ and Cb antigenic sites (see, for example, Caton A J et al, 1982, Cell 31, 417-427). The RBD-A region includes the Sa antigenic site and part of the Sb antigenic site.

Antibodies against influenza often target variable antigenic sites in the globular head of HA, which surround a conserved sialic acid binding site, and thus, neutralize only antigenically closely related viruses. The variability of the HA head is due to the constant antigenic drift of influenza viruses and is responsible for seasonal endemics of influenza. In contrast, gene segments of the viral genome can undergo reassortment (antigenic shift) in host species, creating new viruses with altered antigenicity that are capable of becoming pandemics [Salomon, R. et al. Cell 136, 402-410 (2009)]. Until now, each year, influenza vaccine is updated to reflect the predicted HA and neuraminidase (NA) for upcoming circulating viruses.

Current vaccine strategies for influenza use either a chemically inactivated or a live attenuated influenza virus. Both vaccines are generally produced in embryonated eggs which present major manufacturing limitations due to the time consuming process and limited production capacity. Another more critical limitation of current vaccines is its highly strain-specific efficacy. These challenges became glaring obvious during emergence of the 2009 H1N1 pandemic, thus validating the necessity for new vaccine platforms capable of overcoming these limitations. Virus-like particles represent one of such alternative approaches and are currently being evaluated in clinical trials [Roldao, A. et al. *Expert Rev Vaccines* 9, 1149-1176 (2010); Sheridan, C. *Nat Biotechnol* 27, 489-491 (2009)]. Instead of embryonated eggs, VLPs comprising HA, NA and matrix protein 1 (M1) can be mass-produced in mammalian or insect cell expression systems [Haynes, J. R. *Expert Rev Vaccines* 8, 435-445 (2009)]. The advantages of this approach are its particulate, multivalent nature and the authentic display of properly folded HA proteins that faithfully mimic the infectious virion. In contrast, by the nature of its assembly, the enveloped VLPs contain a small but finite host cell component that may present potential safety, immunogenicity challenges following repeated use of this platform [Wu, C. Y. et al. *PLoS One* 5, e9784 (2010)]. Moreover, the immunity induced by the VLPs is essentially the same as the immunity induced by current vaccines, and thus, does not likely improve both potency and breadth of vaccine-induced protective immunity. In addition to VLPs, a recombinant HA protein has also been evaluated in humans [Treanor, J. J. et al. *Vaccine* 19, 1732-1737 (2001); Treanor, J. J. *JAMA* 297, 1577-1582 (2007)], though the ability to induce protective neutralizing antibody titers are limited. The recombinant HA proteins used in those trials were produced in insect cells and might not form native trimer preferentially [Stevens, J. *Science* 303, 1866-1870 (2004)].

Recently, entirely new classes of broadly neutralizing antibodies against influenza viruses were isolated. One class of antibodies recognizes the highly conserved HA stem [Corti, D. et al. *J Clin Invest* 120, 1663-1673 (2010); Ekiert, D. C. et al. *Science* 324, 246-251 (2009); Kashyap, A. K. et al. *Proc Natl Acad Sci USA* 105, 5986-5991 (2008); Okuno, Y. et al. *J Virol* 67, 2552-2558 (1993); Sui, J. et al. *Nat Struct Mol Biol* 16, 265-273 (2009); Ekiert, D. C. et al. *Science* 333, 843-850 (2011); Corti, D. et al. *Science* 333, 850-856 (2011)], and another class of antibodies precisely recognizes the sialic acid binding site of the RBD on the variable HA head [Whittle, J. R. et al. *Proc Natl Acad Sci USA* 108, 14216-14221 (2011); Krause, J. C. et al. *J Virol* 85, 10905-10908 (2011)]. Unlike strain-specific antibodies, those antibodies are capable of neutralizing multiple antigenically distinct viruses, and hence inducing such antibodies has been a focus of next generation universal vaccine [Nabel, G. J. et al. *Nat Med* 16, 1389-1391 (2010)]. However, robustly eliciting these antibodies with such heterologous neutralizing profile by vaccination has been difficult [Steel, J. et al. *MBio* 1, e0018 (2010); Wang, T. T. et al. *PLoS Pathog* 6, e1000796 (2010); Wei, C. J. et al. *Science* 329, 1060-1064 (2010)].

Despite several alternatives to conventional influenza vaccines, advances in biotechnology in past decades have allowed engineering of biological materials to be exploited for the generation of novel vaccine platforms. Ferritin, an iron storage protein found in almost all living organisms, is an example which has been extensively studied and engineered for a number of potential biochemical/biomedical purposes [Iwahori, K. U.S. Patent 2009/0233377 (2009); Meldrum, F. C. et al. Science 257, 522-523 (1992); Naitou, M. et al. U.S. Patent Publication No. 2011/0038025 (2011); Yamashita, I. Biochim Biophys Acta 1800, 846-857 (2010)], including a potential vaccine platform for displaying exogenous epitope peptides [Carter, D. C. et al. U.S. Patent Publication No. 2006/0251679 (2006); Li, C. Q. et al. Industrial Biotechnol 2, 143-147 (2006)]. Its use as a vaccine platform is particularly interesting because of its self-assembly and multivalent presentation of antigen which induces stronger B cell responses than monovalent form as well as induce T-cell independent antibody responses [Bachmann, M. F. et al. *Annu Rev Immunol* 15, 235-270 (1997); Dintzis, H. M. et al. *Proc Natl Acad Sci USA* 73, 3671-3675 (1976)]. Further, the molecular architecture of ferritin, which consists of 24 subunits assembling into an octahedral cage with 432 symmetry has the potential to display multimeric antigens on its surface.

There remains a need for an efficacious influenza vaccine that provides robust protection against influenza virus. There particularly remains a need for an influenza vaccine that elicits broadly a neutralizing immune response, thereby protecting individuals from heterologous strains of influenza virus, including evolving seasonal and pandemic influenza virus strains of the future. The present invention meets this need by providing a novel, multivalent nanoparticle-based, influenza vaccine that is easily manufactured, potent, and elicits broadly neutralizing influenza antibodies.

Before the present invention is further described, it is to be understood that this invention is not limited to particular embodiments described herein, as such may, of course, vary. It is also to be understood that the terminology used herein is for the purpose of describing particular embodiments only, and is not intended to be limiting on the finally claimed invention, since the scope of the invention will be limited only by the claims. It should also be understood that while elements of the invention appear in specific locations in the application, the present invention encompasses any combination of the elements disclosed herein.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like, in connection with the recitation of claim elements, or use of a "negative" limitation.

Figure 1:
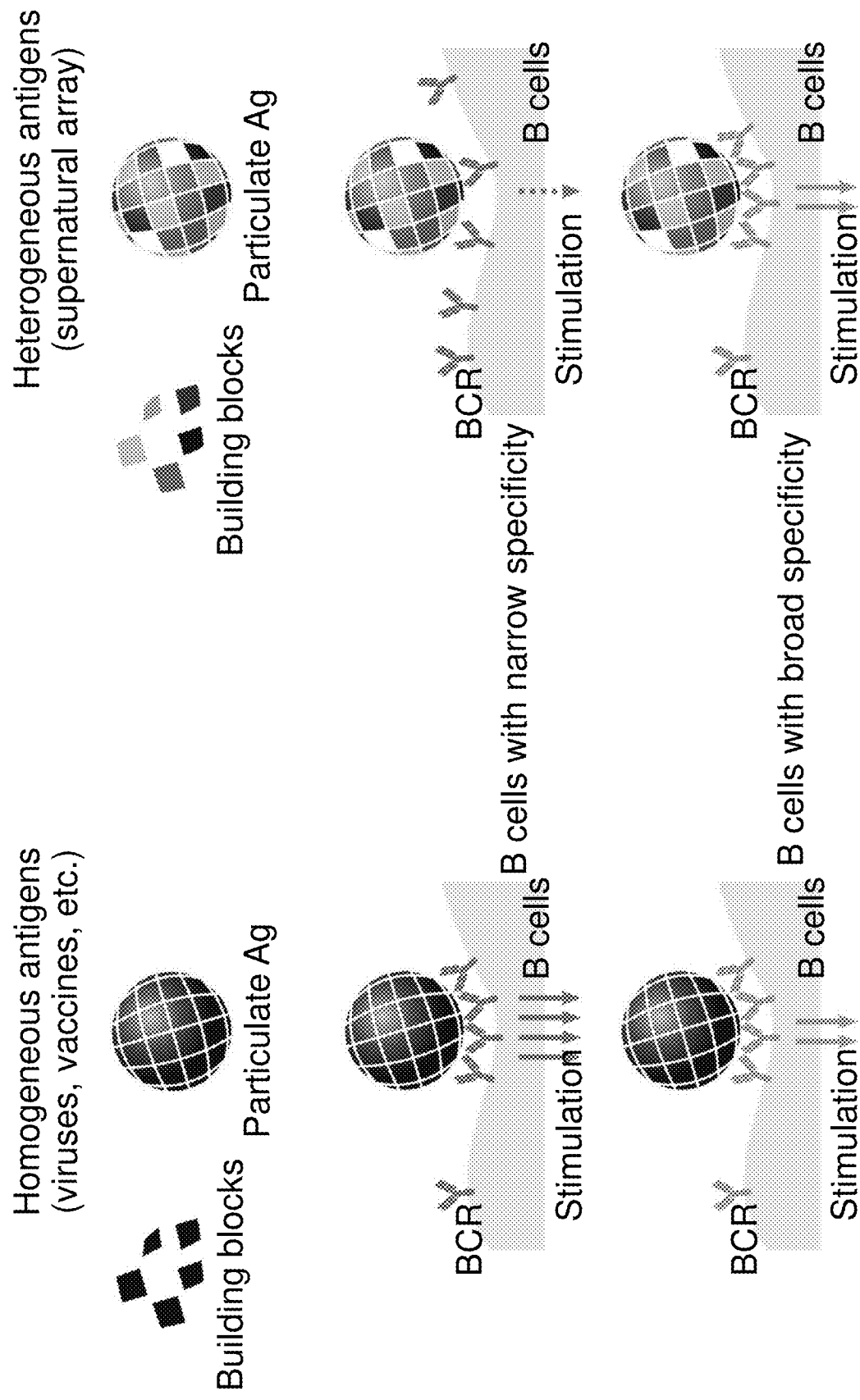
FIG. 1. Theoretical model of immune triggering by a supernatural heterogeneous antigen array on particulate immunogen. (Left Images) Immune triggering upon natural homogeneous antigen array. Particulate homogeneous antigens are built by an antigenically identical subunit and thereby displaying antigenically homogeneous antigens to immune system. B cells harboring B cell receptor (BCR) specific to an antigen displayed on the homogeneous array are stimulated strongly upon encountering the "matched" antigenic stimulation (left middle). B cells harboring more BCR with broader specificity are also stimulated by the homogeneous antigen array but lesser extent presumably the binding affinity of broader specific BCR to the antigen is not as tight as narrower specific BCR to the "matched" antigen (left bottom). The weaker affinity of broader specific BCR to antigen may partly be due to its cross-reactivity because the BCR recognizes other antigenically distinct antigens and thus avoids contacting antigenically heterogeneous parts on antigens (smaller antibody footprint on antigens). (Right Images) Immune triggering upon supernatural heterogeneous antigen array. Particulate heterogeneous antigens are synthetically built using antigenically heterogeneous subunits, which display antigenically heterogeneous antigens to immune system. Upon stimulation with the heterogeneous antigen array, BCRs having narrow specificity only recognize a subset of antigens on the particulate antigen and thus are not stimulated by this antigen (middle right); BCRs having broader specificity recognize larger numbers of antigens on the particulate antigen and thus are stimulated by this antigen (bottom right). In this situation, the B cells harboring BCR with broader specificity have a better chance to outcompete B cells harboring BCR with narrower specificity, therefore selecting cross-reactive B cells otherwise being overcast by others.

As used herein, a nanoparticle refers to a particle formed from self-assembling, monomeric subunit proteins. For example, ferritin subunit proteins self-assemble into ferritin nanoparticles. Nanoparticles of the present invention are generally spherical, or spheroid, in shape, although other shapes, for example, rod, cube, sheet, oblong, ovoid, and the like, are also useful for practicing the present invention. While nanoparticles of the present invention can vary in size, preferred nanoparticles are those in which the distance between the displayed immunogenic portions of the HA protein globular head region is such that two adjacent immunogenic portions displayed on the nanoparticle can fit the distance of the two antigenic-binding sites of a single B-cell receptor, or about 50-100 Å apart. Such spacing allows each of the two adjacent immunogenic portions to interact with one of the two, identical antigen-binding sites in the same B-cell receptor. Binding of a single B-cell receptor to heterologous immunogenic portions that are adjacent on the surface of the nanoparticle is desirable since it allows for the selection of cross-reactive immune responses. While not intending to be bound by theory, the inventors believe that this is due to the fact that high affinity binding of one antigenic site to an immunogenic portion allows stabilization of low-affinity binding of the other antigenic binding site to a heterologous immunogenic portion. Thus, B-cells are selected that produce cross-reactive antibodies. This concept is illustrated in FIG. 1. It is understood by those skilled in the art that the antigenic binding sites of a B-cell receptor are approximately 50-100 angstroms (Å) apart. Thus, in certain embodiments, the immunogenic portions displayed on the surface of the nanoparticle are separated by about 50-100 Å. In specific embodiment, the immunogenic portions displayed on the surface of the nanoparticle are separated by about 50 Å, by about 60 Å, by about 70 Å, by about 80 Å, by about 90 Å, by about 100 Å. With respect to the spacing of immunogenic portions on the surface of a nanoparticle, the term about refers to a variation of no more than 20%.

According to the present invention, a self-assembling monomeric subunit protein, monomeric subunit protein, self-assembly (SA) protein, self-assembling subunit protein, and the like, of the present invention is a full length, monomeric polypeptide, or any portion or variant thereof, which, is capable of directing self-assembly of monomeric self-assembling subunit proteins into a nanoparticle. Such proteins are known to those skilled in the art. Examples of self-assembly proteins useful for producing nanoparticles of the present invention include, but are not limited to, ferritin, encapsulin, sulfur oxygenase reductase (SOR), lumazine synthase (LS), pyruvate dehydrogenase complex (PDC) dihydrolipoamide acetyltransferase (E2) and the envelope (Env) proteins of alphaviruses such as Chikungunya virus. Representative examples of such proteins are listed below in Table 1.

As used herein, a fusion protein is a recombinant protein containing amino acid sequences from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment (e.g., inside a cell). For example, the amino acid sequences of monomeric subunits of ferritin, and the amino acid sequences of influenza hemagglutinin proteins are not normally found joined together via a peptide bond and thus, these two proteins would be considered unrelated. Similarly, the amino acid sequences of monomeric subunits of encapsulin and the amino acid sequences of influenza hemagglutinin proteins or HIV envelope proteins are not normally found joined together via a peptide bond and thus, encapsulin and influenza HA, or encapsulin and HIV envelope protein, would be considered unrelated.

As used herein, a heterogeneous population of immunogenic portions refers a nanoparticle that displays more than one species of immunogenic portion of a protein on its surface. A species of immunogenic portion of a protein of the invention is defined by the specific amino acid sequence of the immunogenic portion. Accordingly, two immunogenic portions having identical amino acid sequences would be considered the same species of immunogenic portion. It should be noted that two fusion proteins comprising the same species of immunogenic portions may or may not vary in regions of amino acid sequences other than the immunogenic portion. If such fusion proteins are identical throughout their entire sequence, they would be considered the same species of fusion protein. Thus, it should be apparent that species of immunogenic portions are defined by variations in their immunogenic portions. Such variation can be due to natural or man-made changes in the amino acid sequence of the immunogenic portion. For example, a new species of immunogenic portion can be made by altering (mutating) the sequence of an existing immunogenic portion through means such as recombinant DNA technology. Methods of making such alterations are known to those skilled in the art.

Alternatively, fusion proteins having different species of immunogenic portions can be made using corresponding proteins, or useful portions thereof, (or nucleic acid molecules encoding such proteins or portions) from unique, but related, infectious agents. For example, it is known that viruses often produce progeny virus having mutations in their envelope (or capsid) protein, the result being that some percentage of the progeny virus avoid detection by the host immune system. Similarly repeated cycles of progeny production result in a heterogeneous population of viruses, with various individual viruses in the population differing in the sequence of their envelope (or capsid) proteins. Such a process eventually results in the production of closely related, but genetically divergent viruses. These divergent viruses are referred to strains, species and subtypes. As these strains, species and subtypes become more divergent, they are further classified into types, generas and/or families. Such classifications can be referred to as taxonomic groups. For examples, a taxonomic group can be a family, a genus, a type, a subtype, a strain or a species. Classification of viruses into various taxonomic groups is well understood by those skilled in the art. With regard to the present invention, preferred nanoparticles are those comprising immunogenic portions from two or more infectious agents within the same family.

As used herein, corresponding proteins are proteins having a similar function in two (or more) different organisms. Corresponding proteins may or may not have identical amino acid sequences, but generally share some sequence homology. In the examples above, the envelope (or capsid) proteins from two closely related viruses are corresponding proteins. As a further example, envelope proteins from different strains of HIV would be considered corresponding proteins, as would hemagglutinin (HA) protein from different strains, subtypes, or genera of influenza virus. In certain embodiments, proteins having the same function in two different infectious agents from the same taxonomic family would be considered corresponding proteins. In certain embodiments, such proteins have at least 50% sequence homology. In certain embodiments, such proteins have at least 50% sequence identity, at least 60% sequence identity, at least 70% sequence identity, at least 80% sequence identity, at least 85% sequence identity, at least 95% sequence identity, at least 97% sequence identity, or at least 99% sequence identity.

As used herein, the term infectious agent refers to any microorganism capable of infecting a mammal. Preferred infectious agents are those which cause illness. Examples of infectious agents include, but are not limited to, viruses, bacteria and parasites. Examples of useful viruses for practicing methods of the present invention include, but are not limited to, viruses from a family selected from the group consisting of orthomyxoviridae, retroviridae, flaviviridae, filoviridae, coronoviridae, paramyxoviridae, picornoviridae, retroviridae, papillomaviridae, togaviridae, and polyomaviridae. More specific examples of useful viruses for practicing methods of the present invention include, but are not limited to, influenza viruses, human immunodeficiency viruses (HIV), flaviviruses (e.g., hepatitis virus, dengue virus, etc.), human papillomaviruses (HPV), rhinoviruses, coronaviruses, enteroviruses, polyomaviruses, respiratory synctial viruses (RSV), human metapneumoviruses, ebola viruses, Marburg viruses, alphaviruses (e.g., Chikungunya virus, Ross River virus, Semliki Forest virus, Sindbis virus, Mayaro virus, etc), Porcine Epidemic Diarrhea virus, Porcine reproductive and respiratory syndrome virus, and foot and mouth disease virus.

Proteins from infectious agents can be any protein useful for generating an immune response against an infectious agent comprising the protein. Useful proteins are those that elicit a protective immune response, such as the production of neutralizing antibodies. A particularly desirable protein is one that elicits the production of broadly neutralizing antibodies. One example of a useful protein with which to practice the present invention is the HIV envelope glycoprotein protein (Gp120). The ability of GP120 to elicit an antibody response, as well as useful mutants thereof, as well as other useful HIV proteins are described in U.S. Patent Publication Nos. US20140322269, US 20040052821, US20030064361, US20030158134, all of which are incorporated herein by reference in their entirety. Another example of a useful protein with which to practice the present invention is the flavivirus envelope protein, which is described in U.S. Patent Publication No. 20110059131, U.S. Patent Publication No. 20090311287, and U.S. Patent Publication No. 20040009469, all of which are incorporated herein by reference in their entirety. Another example of a useful protein with which to practice the present invention is the HCV capsid protein, which is described in U.S. Patent Publication No. 20020107360, U.S. Patent Publication No. 20020119495, and U.S. Patent Publication No. 20050233316, all of which are incorporated herein by reference in their entirety. Other useful proteins with which to practice the present invention are human Papillomavirus (HPV) proteins such as E2. The use of such proteins is described in U.S. Patent Publication No. 20100143408 and U.S. Patent Publication No. 20100183648, both of which are incorporated herein by reference in their entirety. Other useful proteins are disclosed in U.S. Patent Publication No. 20140161833, U.S. Patent Publication No. 20090202583, U.S. Patent Publication No. 20060182762, U.S. Patent Publication No. 20050053622, U.S. Patent Publication No. 20040175395, U.S. Patent Publication No. 20090162395, U.S. Patent Publication No. 20030224015, U.S. Patent Publication No. 20050255123, U.S. Patent Publication No. US 2012-0003266 and U.S. Patent Publication No. 20120315270, all of which are incorporated herein by reference in their entirety.

As used herein, broadly neutralizing antibodies are antibodies that neutralize an infectious agent from a taxonomic group that differs from the taxonomic groups of the infectious agents from which the immunogenic portions used to elicit the antibodies (used produce the nanoparticles) were derived. In preferred embodiments, nanoparticles of the invention elicit broadly neutralizing antibodies that neutralize at least one infectious agent from a genera, type, subtype, species and/or strain that differs from the genera, type, subtype, species and/or strain of the infectious agents from which immunogenic portions were derived in order to produce the nanoparticle. For example, if a nanoparticle is constructed using immunogenic portions of HA proteins from influenza A/Hong Kong/1/1968 (H3N2) and influenza A/Indonesia/05/2005 (H5N1), antibodies elicited by such nanoparticle and that that are broadly neutralizing would be able to neutralize one or more influenza viruses of genera, types, subtypes, species and/or strains other than influenza A/Hong Kong/1/1968 (H3N2) and influenza A/Indonesia/05/2005 (H5N1).

One embodiment of the present invention is a nanoparticle comprising fusion proteins, wherein the surface of the nanoparticle displays immunogenic portions of corresponding proteins from at least two infectious agents, wherein the at least two infectious agents are from different corresponding taxonomic groups within the same taxonomic family. In on embodiment, each fusion protein comprises at least a portion of a self-assembling, monomeric subunit joined to at least one portion of an immunogenic portion of a protein from an infectious agent. In one embodiment, the portion of the self-assembling, monomeric subunit comprises at least 25 amino acids, at least 50 amino acids, at least 75 amino acids, at least 100 amino acids or at least 150 amino acids from a monomeric subunit protein selected from the group consisting of a monomeric ferritin subunit protein, a monomeric encapsulin protein, a monomeric 03-33 protein, a monomeric SOR protein, a monomeric LS protein, a monomeric PDC protein and a Chikungunya virus structural polyprotein. In one embodiment, each fusion protein comprises a monomeric subunit protein selected from the group consisting of a monomeric ferritin subunit protein, a monomeric encapsulin protein, a monomeric 03-33 protein, a monomeric SOR protein, a monomeric LS protein, a monomeric PDC protein and a Chikungunya virus structural polyprotein.

In one embodiment, the infectious agents are viruses. Any virus capable of infecting a mammal can be used in constructing nanoparticles of the present invention. Examples of useful viruses for practicing methods of the present invention include, but are not limited to, viruses from a family selected from the group consisting of orthomyxoviridae, retroviridae, flaviviridae, filoviridae, coronoviridae, paramyxoviridae, picornoviridae, retroviridae, papillomaviridae, togaviridae, and polyomaviridae. Examples of useful viruses include, but are not limited to, influenza viruses, human immunodeficiency viruses (HIV), flaviviruses (e.g., hepatitis virus, dengue virus, etc.), human papillomaviruses (HPV), rhinoviruses, coronaviruses, enteroviruses, polyomaviruses, respiratory synctial viruses (RSV), human metapneumoviruses, ebola viruses, Marburg viruses, alphaviruses (e.g., Chikungunya virus, Ross River virus, Semliki Forest virus, Sindbis virus, Mayaro virus, etc), Porcine Epidemic Diarrhea virus, Porcine reproductive and respiratory syndrome virus and foot and mouth disease virus.

In one embodiment, the at least two infectious agents are from different genera within the same family. In one embodiment, the at least two infectious agents are from different species within the same family. In one embodiment, the at least two infectious agents are from different Types within the same family. In one embodiment, the at least two infectious agents are from different subtypes within the same family. In one embodiment, the at least two infectious agents are different strains within the same family.

One embodiment of the present invention is a nanoparticle comprising a first fusion protein and a second fusion protein, each fusion protein comprising at least a portion of a self-assembling, monomeric subunit joined to at least one immunogenic portion of a protein from an infectious agent, wherein the immunogenic portion of the first fusion protein is from a protein from a first infectious agent; wherein the immunogenic portion of the second fusion protein is from a protein from a second infectious agent; wherein the proteins from the first and second infectious agents are corresponding proteins; and wherein the first and second infectious agents are from different corresponding taxonomic groups within the same taxonomic family.

In one embodiment, the infectious agents are viruses. Any virus capable of infecting a mammal can be used in constructing nanoparticles of the present invention. Examples of useful viruses for practicing methods of the present invention include, but are not limited to, viruses from a family selected from the group consisting of orthomyxoviridae, retroviridae, flaviviridae, filoviridae, coronoviridae, paramyxoviridae, picornoviridae, retroviridae, papillomaviridae, togaviridae, and polyomaviridae. Examples of useful viruses include, but are not limited to, influenza viruses, human immunodeficiency viruses (HIV), flaviviruses (e.g., hepatitis virus, dengue virus, etc.), human papillomaviruses (HPV), rhinoviruses, coronaviruses, enteroviruses, polyomaviruses, respiratory synctial viruses (RSV), human metapneumoviruses, ebola viruses, Marburg viruses, alphaviruses (e.g., Chikungunya virus, Ross River virus, Semliki Forest virus, Sindbis virus, Mayaro virus, etc), Porcine Epidemic Diarrhea, Porcine reproductive and respiratory syndrome virus and foot and mouth disease virus.

In one embodiment, the at least two infectious agents are from different genera within the same family. In one embodiment, the at least two infectious agents are from different species within the same family. In one embodiment, the at least two infectious agents are from different Types within the same family. In one embodiment, the at least two infectious agents are from different subtypes within the same family. In one embodiment, the at least two infectious agents are different strains within the same family.

One embodiment of the present invention is a nanoparticle comprising at least two species of fusion protein, each species of fusion protein comprising at least a portion of a self-assembling, monomeric subunit joined to at least one immunogenic portion of a protein from a unique infectious agent, wherein the proteins in the unique infectious agents correspond to one another, and; wherein each unique infectious agent is from a different corresponding taxonomic group within the same taxonomic family.

As used herein, a unique infectious agent refers to infectious agents from the same taxonomic family, such as orthomyoviridae or retroviridae, which are genetically distinct from one another. Thus, infectious agents that are unique from one another would belong to different taxonomic groups. For example, two different strains of influenza virus would be considered unique from one another. Likewise, two different subtypes of influenza virus would be considered unique from one another.

While not intending to be limited to a specific embodiment, the inventors have chosen to utilize influenza virus to demonstrate the general principles and concepts of the present invention. Thus, with regard to certain embodiments of the present invention, all nomenclature used herein to classify influenza virus is that commonly used by those skilled in the art. Thus, a Type of influenza virus refers to influenza Type A, influenza Type B or influenza type C. It is understood by those skilled in the art that the designation of a virus as a specific Type relates to sequence difference in the respective M1 (matrix) protein or NP (nucleoprotein). Type A influenza viruses are further divided into Group1 and Group 2. These Groups are further divided into subtypes, a designation that refers to classification of a virus based on the sequence of its HA protein. Examples of current commonly recognized subtypes are H1, H2, H3, H4, H5, H6, H7, H8, H9, H10, H11, H12, H13, H14, H15, H16, H17 or H18. Group 1 influenza subtypes are H1, H2, H5, H6, H8, H9, H11, H12, H13, H16, H17 and H18. Group 2 influenza subtypes are H3, H4, H7, H10, H14 and H15. Finally, the term strain refers to viruses within a subtype that differ from one another due to small, genetic variations in their genome. Such genetic variations may, or may not, result in amino acid changes in the encoded influenza protein(s).

As used herein, an influenza hemagglutinin protein, or HA protein, refers the hemagglutinin glycoprotein present on the surface of influenza virus. Influenza virus HA proteins are able to bind sialic acid on the surface of cells, an activity responsible for the viruses ability to cause red blood cells to agglutinate. Influenza virus HA proteins are also responsible for fusion of the influenza virus membrane with the endosome membrane following infection of a cell by influenza virus. Such proteins, and their activities, are known to those skilled in the art. With specific regard to the present invention, an HA protein refers to a full-length influenza virus hemagglutinin protein or any portion thereof, that is, at least, capable of eliciting an immune response. Exemplary influenza proteins useful for producing nanoparticles of the present invention are listed below in Table 1.

TABLE 1

| SEQ ID NOs. | ORGANISM | DESCRIPTION |
|---|---|---|
| | | Ectodomains |
| 1 | Influenza Virus | Amino acid sequence of ectodomain from the hemagglutinin protein from A/New Caledonia/20/1999 (H1N1). |
| 2 | Influenza Virus | Amino acid sequence of ectodomain from the hemagglutinin protein from A/California/04/2009 (H1N1) |
| 3 | Influenza Virus | Amino acid sequence of ectodomain from the hemagglutinin protein from A/Singapore/1/1957 (H2N2) |
| 4 | Influenza Virus | Amino acid sequence of ectodomain from the hemagglutinin protein from A/Hong Kong/1/1968 (H3N2) |
| 5 | Influenza Virus | Amino acid sequence of ectodomain from the hemagglutinin protein from A/Brisbane/10/2007 (H3N2) |
| 6 | Influenza Virus | Amino acid sequence of ectodomain from the hemagglutinin protein from A/Indonesia/05/2005 (H5N1) |
| 7 | Influenza Virus | Amino acid sequence of ectodomain from the hemagglutinin protein from B/Florida/4/2006 (influenza B) |
| 8 | Influenza Virus | Amino acid sequence of ectodomain from the hemagglutinin protein from A/Perth/16/2009 (H3N2) |
| 9 | Influenza Virus | Amino acid sequence of ectodomain from the hemagglutinin protein from A/Brisbane/59/2007 (H1N1) |
| 10 | Influenza Virus | Amino acid sequence of ectodomain from the hemagglutinin protein from B/Brisbane/60/2008 (influenza B) |
| 11 | Influenza Virus | Amino acid sequence of ectodomain from the hemagglutinin protein from A/Wilson-Smith/33 (H1N1) |
| 12 | Influenza Virus | Amino acid sequence of ectodomain from the hemagglutinin protein from A/Tientsin/78/77 (H1N1) |
| 13 | Influenza Virus | Amino acid sequence of ectodomain from the hemagglutinin protein from A/Texas/36/91 (H1N1) |
| 14 | Influenza Virus | Amino acid sequence of ectodomain from the hemagglutinin protein from A/Singapore/6/86 (H1N1) |
| 15 | Influenza Virus | Amino acid sequence of ectodomain from the hemagglutinin protein from A/Memphis/39/83 (H1N1) |
| 16 | Influenza Virus | Amino acid sequence of ectodomain from the hemagglutinin protein from A/Malaysia/54 (H1N1) |
| 17 | Influenza Virus | Amino acid sequence of ectodomain from the hemagglutinin protein from A/Iowa/43 (H1N1) |
| 18 | Influenza Virus | Amino acid sequence of ectodomain from the hemagglutinin protein from A/Hong Kong/117/77 (H1N1) |
| 19 | Influenza virus | Amino acid sequence of ectodomain from the hemagglutinin protein from A/Fort Monmouth/1/47 (H1N1) |
| 20 | Influenza virus | Amino acid sequence of ectodomain from the hemagglutinin protein from A/Brisbane/59/07 (H1N1) |
| 21 | Influenza Virus | Amino acid sequence of ectodomain from the hemagglutinin protein from A/Baylor/4052/81 (H1N1) |
| 22 | Influenza Virus | Amino acid sequence of ectodomain from the hemagglutinin protein from A/Albany/4835/48 (H1N1) |
| 23 | Influenza Virus | Amino acid sequence of ectodomain from the hemagglutinin protein from A/Hong Kong/156/97 (H5N1) |
| 24 | Influenza Virus | Amino acid sequence of ectodomain from the hemagglutinin protein from A/common magpie/Hong Kong/5052/07 (H5N1) |
| 25 | Influenza Virus | Amino acid sequence of ectodomain from the hemagglutinin protein from A/chicken/Shanxi/2/06 (H5N1) |

TABLE 1-continued

| SEQ ID NOs. | ORGANISM | DESCRIPTION |
|---|---|---|
| 26 | Influenza Virus | Amino acid sequence of ectodomain from the hemagglutinin protein from A/silky chicken/Hong Kong/SF189/01 (H5N1) |
| 27 | Influenza Virus | Amino acid sequence of ectodomain from the hemagglutinin protein from A/chicken/Henan/16/04 (H5N1) |
| 28 | Influenza Virus | Amino acid sequence of ectodomain from the hemagglutinin protein from A/Victoria/361/11 (H3N2) |
| 29 | Influenza Virus | Amino acid sequence of ectodomain from the hemagglutinin protein from B/Massachusetts/2/12 (Influenza B) |
| 30 | Influenza Virus | Amino acid sequence of ectodomain from the hemagglutinin protein from B/Brisbane/60/08 (Influenza B) |
| 31 | Influenza Virus | Amino acid sequence of ectodomain from the hemagglutinin protein from A/Texas/50/12 (H3N2) |
| | | Receptor Binding Domains |
| 32 | Influenza Virus | Amino acid sequence of RBD from hemagglutinin protein of A/New Caledonia/20/1999 (H1N1); (56-264, F264A) |
| 33 | Influenza Virus | Amino acid sequence of RBD from hemagglutinin protein of A/New Caledonia/20/1999 (H1N1); (56-264, Y98F, F264A) |
| 34 | Influenza Virus | Amino acid sequence of RBD from hemagglutinin protein of A/California/04/2009 (H1N1); (56-264) |
| 35 | Influenza Virus | Amino acid sequence of RBD from hemagglutinin protein of A/California/04/2009 (H1N1); (56-264, Y98F) |
| 36 | Influenza Virus | Amino acid sequence of RBD from hemagglutinin protein of A/Singapore/1/1957 (H2N2) |
| 37 | Influenza Virus | Amino acid sequence of RBD from hemagglutinin protein of A/Hong Kong/1/1968 (H3N2) |
| 38 | Influenza Virus | Amino acid sequence of RBD from hemagglutinin protein of A/Brisbane/10/2007 (H3N2) |
| 39 | Influenza Virus | Amino acid sequence of RBD from hemagglutinin protein of B/Florida/4/2006 (influenza B) |
| 40 | Influenza Virus | Amino acid sequence of RBD from hemagglutinin protein of A/Perth/16/2009 (H3N2) |
| 41 | Influenza Virus | Amino acid sequence of RBD from hemagglutinin protein of A/Wilson-Smith/33 (H1N1) (56-264, Y98F, F264A) |
| 42 | Influenza Virus | Amino acid sequence of RBD from hemagglutinin protein of A/Tientsin/78/77 (H1N1) (56-264, Y98F, F264A) |
| 43 | Influenza Virus | Amino acid sequence of RBD from hemagglutinin protein of A/Texas/36/91 (H1N1) (56-264, Y98F, F264A) |
| 44 | Influenza Virus | Amino acid sequence of RBD from hemagglutinin protein of A/Singapore/6/86 (H1N1) (56-264, Y98F, F264A) |
| 45 | Influenza Virus | Amino acid sequence of RBD from hemagglutinin protein of A/Memphis/39/83 (H1N1) (56-264, Y98F, F264A) |
| 46 | Influenza Virus | Amino acid sequence of RBD from hemagglutinin protein of A/Malaysia/54 (H1N1) (56-264, Y98F) (56-264, Y98F) |
| 47 | Influenza Virus | Amino acid sequence of RBD from hemagglutinin protein of A/Iowa/43 (H1N1) (56-264, Y98F, F264A) |
| 48 | Influenza Virus | Amino acid sequence of RBD from hemagglutinin protein of A/Hong Kong/117/77 (H1N1) (56-264, Y98F, F264A) |
| 49 | Influenza Virus | Amino acid sequence of RBD from hemagglutinin protein of Fort Monmouth/1/47 (H1N1) (56-264, Y98F, F264A) |
| 50 | Influenza virus | Amino acid sequence of RBD from hemagglutinin protein of Brisbane/59/07 (H1N1) (56-264, Y98F, F264A) |
| 51 | Influenza Virus | Amino acid sequence of RBD from hemagglutinin protein of A/Baylor/4052/81 (H1N1) (56-264, Y98F, F264A) |
| 52 | Influenza Virus | Amino acid sequence of RBD from hemagglutinin protein of A/Albany/4835/48 (H1N1) (56-264, Y98F, F264A) |
| 53 | Influenza virus | Amino acid sequence of RBD from hemagglutinin protein of Indonesia/05/05 (H5N1) (56-264, Y98F) |
| 54 | Influenza Virus | Amino acid sequence of RBD from hemagglutinin protein of A/Hong Kong/156/97 (H5N1) (56-264, Y98F) |
| 55 | Influenza Virus | Amino acid sequence of RBD from hemagglutinin protein of A/common magpie/Hong Kong/5052/07 (H5N1) (56-264, Y98F) |
| 56 | Influenza Virus | Amino acid sequence of RBD from hemagglutinin protein of A/chicken/Shanxi/2/06 (H5N1) (56-264, Y98F) |
| 57 | Influenza Virus | Amino acid sequence of RBD from hemagglutinin protein of A/silky chicken/Hong Kong/SF189/01 (H5N1) (56-264, Y98F) |
| 58 | Influenza Virus | Amino acid sequence of RBD from hemagglutinin protein of A/chicken/Henan/16/04 (H5N1) (56-264, Y98F) |
| 59 | Influenza Virus | Amino acid sequence of RBD from hemagglutinin protein of A/Victoria/361/11 (H3N2) (56-264, Y98F, K264A)) |
| 60 | Influenza Virus | Amino acid sequence of RBD from hemagglutinin protein of B/Massachusetts/2/12 (Influenza B) (63-294) |
| 61 | Influenza Virus | Amino acid sequence of RBD from hemagglutinin protein of B/Brisbane/60/08 (Influenza B) (63-294) |
| 62 | Influenza Virus | Amino acid sequence of RBD from hemagglutinin protein of A/Texas/50/12 (H3N2) |

TABLE 1-continued

| SEQ ID NOs. | ORGANISM | DESCRIPTION |
|---|---|---|
| | | Self-Assembly Proteins |
| | | Ferritin Proteins |
| 63 | Helicobacter pylori | Coding sequence for ferritin monomeric subunit protein from H. pylori |
| 64 | Helicobacter pylori | Amino acid sequence encoded by SEQ ID NO: 63 |
| 65 | Helicobacter pylori | Complement of SEQ ID NO: 63 |
| 66 | Escherichia coli | Coding sequence for ferritin monomeric subunit protein from E. coli (gi 446839951_WP_000917207.1) |
| 67 | Escherichia coli | Amino acid sequence encoded by SEQ ID NO: 66 |
| 68 | Escherichia coli | Complement of SEQ ID NO: 66 |
| 69 | Rana catesbeiana | Coding sequence for bullfrog ferritin monomeric subunit protein (gi 13675 gb AAA49524.1) |
| 70 | Rana catesbeiana | Amino acid sequence encoded by SEQ ID NO: 69 SEQ ID NO: 8 from 6137NIAID-34-PCT |
| 71 | Rana catesbeiana | Complement of SEQ ID NO: 69 |
| | | Hybrid Ferritin Proteins |
| 72 | Artificial Sequence | Coding sequence for H. pylori-ferritin/bullfrog-ferritin fusion protein |
| 73 | Artificial Sequence | Amino acid sequence encoded by SEQ ID NO: 72 |
| 74 | Artificial Sequence | Complement of SEQ ID NO: 72 |
| 75 | Artificial Sequence | Coding sequence for E. coli-ferritin/bullfrog-ferritin fusion protein |
| 76 | Artificial Sequence | Amino acid sequence encoded by SEQ ID NO: 75 |
| 77 | Artificial Sequence | Complement of SEQ ID NO: 75 |
| | | Other Self-Assembling Monomeric Subunits |
| 78 | Thermotoga maritima | Coding sequence for encapsulin protein |
| 79 | Thermotoga maritime | Amino acid sequence encoded by SEQ ID NO: 78 |
| 80 | Thermotoga maritime | Complement of SEQ ID NO: 78 |
| 81 | Artificial Sequence | Coding sequence for Salmonella enteritis 03-33 protein (gi 390136278 pdb 3VCD) |
| 82 | Artificial Sequence | Amino acid sequence encoded by SEQ ID NO: 81 |
| 83 | Artificial Sequence | Complement of SEQ ID NO: 81 |
| 84 | Acidianus ambivalens | Coding sequence for sulfur oxygenase reductase protein from Acidianus ambivalens (gi 93279016 pdb 2CB2) |
| 85 | Acidianus ambivalens | Amino acid sequence encoded by SEQ ID NO: 84 |
| 86 | Acidianus ambivalens | Complement of SEQ ID NO: 84 |
| 87 | Aquifex aeolicus | Coding sequence for lumazine synthase protein from Aquifex aeolicus (gi 18159011 pdb1HQK) |
| 88 | Aquifex aeolicus | Amino acid sequence encoded by SEQ ID NO: 87 |
| 89 | Aquifex aeolicus | Complement of SEQ ID NO: 87 |
| 90 | Bacillus stearothermophilus | Coding sequence for dihydrolipoamide acetyltransferase (E2p) protein from Bacillus stearothermophilus (gi 4558102 pdb1B5S) |
| 91 | Bacillus stearothermophilus | Amino acid sequence encoded by SEQ ID NO: 90 |
| 92 | Bacillus stearothermophilus | Complement of SEQ ID NO: 90 |
| 93 | Chikungunya virus | Coding sequence for Chikungunya virus capsid, envelope E3, E2, 6K, and E1 polyprotein |
| 94 | Chikungunya virus | Amino acid sequence encoded by SEQ ID NO: 93 |
| 95 | Chikungunya virus | Complement of SEQ ID NO: 93 |
| | | Ferritin Fusion Proteins |
| 96 | Artificial Sequence | Nucleic acid sequence of H1 NC99 RBD-Ferritin (56-264, F264A) |
| 97 | Artificial Sequence | Amino acid sequence of H1 NC99 RBD-Ferritin (56-264, F264A) |
| 98 | Artificial Sequence | Complement of SEQ ID NO: 96 |
| 99 | Artificial Sequence | Nucleic acid sequence of H1 NC99 RBD-Ferritin (56-264, Y98F, F264A) |
| 100 | Artificial Sequence | Amino acid sequence of H1 NC99 RBD-Ferritin (56-264, F264A) |
| 101 | Artificial Sequence | Complement of SEQ ID NO: 99 |
| 102 | Artificial Sequence | Nucleic acid sequence of H1 CA09 RBD-Ferritin (56-264) |
| 103 | Artificial Sequence | Amino acid sequence of H1 CA09 RBD-Ferritin (56-264) |
| 104 | Artificial Sequence | Complement of SEQ ID NO: 102 |
| 105 | Artificial Sequence | Nucleic acid sequence of H1 CA09 RBD-Ferritin (56-264, Y98F) |
| 106 | Artificial Sequence | Amino acid sequence of H1 CA09 RBD-Ferritin (56-264, Y98F) |
| 107 | Artificial Sequence | Complement of SEQ ID NO: 105 |
| 108 | Artificial Sequence | Nucleic acid sequence of H1 WS33 RBD-Ferritin (56-264, Y98F, F264A) |

TABLE 1-continued

| SEQ ID NOs. | ORGANISM | DESCRIPTION |
|---|---|---|
| 109 | Artificial Sequence | Amino acid sequence of H1 WS33 RBD-Ferritin (56-264, Y98F, F264A) |
| 110 | Artificial Sequence | Complement of SEQ ID NO: 108 |
| 111 | Artificial Sequence | Nucleic acid sequence of H1 Tien 77 RBD-Ferritin (56-264, Y98F, F264A) |
| 112 | Artificial Sequence | Amino acid sequence of H1 Tien 77 RBD-Ferritin (56-264, Y98F, F264A) |
| 113 | Artificial Sequence | Complement of SEQ ID NO: 111 |
| 114 | Artificial Sequence | Nucleic acid sequence of H1 TX91 RBD-Ferritin (56-264, Y98F, F264A) |
| 115 | Artificial Sequence | Amino acid sequence of H1 TX91 RBD-Ferritin (56-264, Y98F, F264A) |
| 116 | Artificial Sequence | Complement of SEQ ID NO: 114 |
| 117 | Artificial Sequence | Nucleic acid sequence of H1 SG86 RBD-Ferritin (56-264, Y98F, F264A) |
| 118 | Artificial Sequence | Amino acid sequence of H1 SG86 RBD-Ferritin (56-264, Y98F, F264A) |
| 119 | Artificial Sequence | Complement of SEQ ID NO: 117 |
| 120 | Artificial Sequence | Nucleic acid sequence of H1 Mem83 RBD-Ferritin (56-264, Y98F, F264A) |
| 121 | Artificial Sequence | Amino acid sequence of H1 Mem83 RBD-Ferritin (56-264, Y98F, F264A) |
| 122 | Artificial Sequence | Complement of SEQ ID NO: 120 |
| 123 | Artificial Sequence | Nucleic acid sequence of H1 Mal54 RBD-Ferritin (56-264, Y98F) |
| 124 | Artificial Sequence | Amino acid sequence of H1 Mal54 RBD-Ferritin (56-264, Y98F) |
| 125 | Artificial Sequence | Complement of SEQ ID NO: 123 |
| 126 | Artificial Sequence | Nucleic acid sequence of H1 IA43 RBD-Ferritin (56-264, Y98F, F264A) |
| 127 | Artificial Sequence | Amino acid sequence of H1 IA43 RBD-Ferritin (56-264, Y98F, F264A) |
| 128 | Artificial Sequence | Complement of SEQ ID NO: 126 |
| 129 | Artificial Sequence | Nucleic acid sequence of H1 HK77 RBD-Ferritin (56-264, Y98F, F264A) |
| 130 | Artificial Sequence | Amino acid sequence of H1 HK77 RBD-Ferritin (56-264, Y98F, F264A) |
| 131 | Artificial Sequence | Complement of SEQ ID NO: 129 |
| 132 | Artificial Sequence | Nucleic acid sequence of H1 FM47 RBD-Ferritin (56-264, Y98F, F264A) |
| 133 | Artificial Sequence | Amino acid sequence of H1 FM47 RBD-Ferritin (56-264, Y98F, F264A) |
| 134 | Artificial Sequence | Complement of SEQ ID NO: 132 |
| 135 | Artificial Sequence | Nucleic acid sequence of H1 BRO7 RBD-Ferritin (56-264, Y98F, F264A) |
| 136 | Artificial Sequence | Amino acid sequence of H1 BRO7 RBD-Ferritin (56-264, Y98F, F264A) |
| 137 | Artificial Sequence | Complement of SEQ ID NO: 135 |
| 138 | Artificial Sequence | Nucleic acid sequence of H1 Bay81 RBD-Ferritin (56-264, Y98F, F264A) |
| 139 | Artificial Sequence | Amino acid sequence of H1 Bay81 RBD-Ferritin (56-264, Y98F, F264A) |
| 140 | Artificial Sequence | Complement of SEQ ID NO: 138 |
| 141 | Artificial Sequence | Nucleic acid sequence of H1 Alb48 RBD-Ferritin (56-264, Y98F, F264A) |
| 142 | Artificial Sequence | Amino acid sequence of H1 Alb48 RBD-Ferritin (56-264, Y98F, F264A) |
| 143 | Artificial Sequence | Complement of SEQ ID NO: 141 |
| 144 | Artificial Sequence | Nucleic acid sequence of H5 IN05 RBD-Ferritin (56-264, Y98F) |
| 145 | Artificial Sequence | Amino acid sequence of H5 IN05 RBD-Ferritin (56-264, Y98F) |
| 146 | Artificial Sequence | Complement of SEQ ID NO: 144 |
| 147 | Artificial Sequence | Nucleic acid sequence of H5 HK97(c0) RBD-Ferritin (56-264, Y98F) |
| 148 | Artificial Sequence | Amino acid sequence of H5 HK97(c0) RBD-Ferritin (56-264, Y98F) |
| 149 | Artificial Sequence | Complement of SEQ ID NO: 147 |
| 150 | Artificial Sequence | Nucleic acid sequence of H5 HK07(c2.3.2.1) RBD-Ferritin (56-264, Y98F) |
| 151 | Artificial Sequence | Amino acid sequence of H5 HK07(c2.3.2.1) RBD-Ferritin (56-264, Y98F) |
| 152 | Artificial Sequence | Complement of SEQ ID NO: 150 |
| 153 | Artificial Sequence | Nucleic acid sequence of H5 SX06(c7.2) RBD-Ferritin (56-264, Y98F) |
| 154 | Artificial Sequence | Amino acid sequence of H5 SX06(c7.2) RBD-Ferritin (56-264, Y98F) |
| 155 | Artificial Sequence | Complement of SEQ ID NO: 153 |
| 156 | Artificial Sequence | Nucleic acid sequence of H5 HK01(c3) RBD-Ferritin (56-264, Y98F) |

TABLE 1-continued

| SEQ ID NOs. | ORGANISM | DESCRIPTION |
|---|---|---|
| 157 | Artificial Sequence | Amino acid sequence of H5 HK01(c3) RBD-Ferritin (56-264, Y98F) |
| 158 | Artificial Sequence | Complement of SEQ ID NO: 156 |
| 159 | Artificial Sequence | Nucleic acid sequence of H5 HN04(c8) RBD-Ferritin (56-264, Y98F) |
| 160 | Artificial Sequence | Amino acid sequence of H5 HN04(c8) RBD-Ferritin (56-264, Y98F) |
| 161 | Artificial Sequence | Complement of SEQ ID NO: 159 |
| 162 | Artificial Sequence | Nucleic acid sequence of H3 Vic11 RBD-Ferritin (56-264, Y98F, K264A) |
| 163 | Artificial Sequence | Amino acid sequence of H3 Vic11 RBD-Ferritin (56-264, Y98F, K264A) |
| 164 | Artificial Sequence | Complement of SEQ ID NO: 162 |
| 165 | Artificial Sequence | Nucleic acid sequence of B MA12 RBD-Ferritin (63-294) |
| 166 | Artificial Sequence | Amino acid sequence of B MA12 RBD-Ferritin (63-294) |
| 167 | Artificial Sequence | Complement of SEQ ID NO: 165 |
| 168 | Artificial Sequence | Nucleic acid sequence of B BRO8 RBD-Ferritin (63-295) |
| 169 | Artificial Sequence | Amino acid sequence of B BRO8 RBD-Ferritin (63-295) |
| 170 | Artificial Sequence | Complement of SEQ ID NO: 168 |
| | | Ferritin Single Polypeptide Design Fusion Proteins |
| 171 | Artificial Sequence | Nucleic acid sequence H1/H3 CA09 TX12 F2A RBD-Ferritin |
| 172 | Artificial Sequence | Amino acid sequence of H1/H3 CA09 TX12 F2A RBD-Ferritin |
| 173 | Artificial Sequence | Complement of SEQ ID NO: 171 |
| 174 | Artificial Sequence | Nucleic acid sequence of B/B BRO8 MA12 F2A RBD-Ferritin |
| 175 | Artificial Sequence | Amino acid sequence of B/B BRO8 MA12 F2A RBD-Ferritin |
| 176 | Artificial Sequence | Complement of SEQ ID NO: 174 |
| 177 | Artificial Sequence | Nucleic acid sequence H1/H3/B CA09 TX12 MA12 F2A RBD-Ferritin |
| 178 | Artificial Sequence | Amino acid sequence of H1/H3 CA09 TX12 MA12 F2A RBD-Ferritin |
| 179 | Artificial Sequence | Complement of SEQ ID NO: 177 |
| | | Encapsulin Fusion Proteins |
| 180 | Artificial Sequence | Nucleic acid sequence of H1 NC99 RBD-Encapsulin (56-264, F264A) |
| 181 | Artificial Sequence | Amino acid sequence of H1 NC99 RBD-Encapsulin (56-264, F264A) |
| 182 | Artificial Sequence | Complement of SEQ ID NO: 180 |
| 183 | Artificial Sequence | Nucleic acid sequence of H1 CA09 RBD-Encapsulin (56-264) |
| 184 | Artificial Sequence | Amino acid sequence of H1 CA09 RBD-Encapsulin (56-264) |
| 185 | Artificial Sequence | Complement of SEQ ID NO: 183 |
| | | CHIK VLP Fusion Proteins |
| 186 | Artificial Sequence | Nucleic acid sequence of H1 NC99 RBD-CHIKVLP (59-264, Y98F, F264A) |
| 187 | Artificial Sequence | Amino acid sequence of NC99 RBD-CHIKVLP (59-264, Y98F, F264A) |
| 188 | Artificial Sequence | Complement of SEQ ID NO: 186 |
| 189 | Artificial Sequence | Nucleic acid sequence of H1 CA09 RBD-CHIKVLP (59-264, Y98F) |
| 190 | Artificial Sequence | Amino acid sequence of H1 CA09 RBD-CHIKVLP (59-264, Y98F) |
| 191 | Artificial Sequence | Complement of SEQ ID NO: 189 |

It is understood by those skilled in the art that HA proteins from different influenza viruses may have different lengths, due to insertions and/or deletions of amino acid residue in one or both of the HA proteins. Thus, reference to a corresponding region refers to a region of another proteins that is identical, or nearly so (e.g., at least 95%, identical, at least 98% identical or at least 99% identical), in sequence, structure and/or function to the region being compared. For example, with regard to the globular head region or RBD of a hemagglutinin protein, the corresponding region in another hemagglutinin protein may not have the same residue numbers, but will have a very similar sequence and will perform the same function. To improve sequence comparisons between viruses, numbering systems are used by those in the field, which relate amino acid positions to a reference sequence. Thus, corresponding amino acid residues in hemagglutinin proteins from different strains of influenza may not have the same residue number with respect to their distance from the N-terminal amino acid of the mature protein. For example, using the H3 numbering system, reference to residue 100 in A/New Caledonia/20/1999 (1999 NC, H1) does not mean it is the $100^{th}$ residue from the N-terminal amino acid of the mature protein. Instead, residue 100 of A/New Caledonia/20/1999 (1999 NC, H1) HA protein aligns with residue 100 of the HA protein from influenza H3N2 strain. The use of such numbering systems is understood by those skilled in the art. Unless otherwise noted, reference to amino acid positions in hemagglutinin proteins herein is made using the H3 numbering system.

As used herein, the term immunogenic refers to the ability of a specific protein, or a specific region thereof (i.e., a specific amino acid sequence), to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 94% identical, at least 96% identical, at least 98% identical or at least 99% identical. Preferred immunogenic proteins, or portions thereof, are those that elicit neutralizing antibodies to influenza virus.

As used herein, a heterogeneous population refers to a population of molecules in which at least one molecule in the population differs in sequence from at least one other molecule in the population. For example, with particular regard to the present invention, in a heterogeneous population of immunogenic portions from influenza HA proteins, the population is heterologous due to the fact that the amino acid sequence of at least one immunogenic portion in the population differs from the amino acid sequence of at least one other immunogenic portion in the population. With regard to the present invention, each unique sequence is referred to as a species of molecule (e.g., a species of immunogenic portion, a species of fusion protein, etc.). The difference in sequence between two species of molecule can involve a single amino acid difference or it can involve more than one amino acid difference. Moreover, such differences may, or may not, result in different species having different epitopes.

As used herein, epitopes are clusters of amino acid residues that are recognized by (e.g., bound by) components of the immune system, such as B-cell receptors, T-cell receptors, antibodies, and the like, thus forming an immune complex and eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the linear protein) but which are in close spatial proximity in three-dimensional space in the finally folded protein. Thus, in one embodiment the immunogenic portion comprises at least one epitope from an influenza virus HA protein.

As used herein, a monovalent nanoparticle refers to a nanoparticle that displays a single species of immunogenic portion from an HA protein on its surface. That is, all of the immunogenic portions have the same sequence. As used herein, Admixed nanoparticles refers to a population of nanoparticles that contains a mixture of monovalent nanoparticle species. In such a population, each monovalent nanoparticle is produced separately from other monovalent nanoparticles, and the monovalent nanoparticles are then mixed together to produce Admixed nanoparticles. It will be understood by those skilled in the art that while a population of Admixed nanoparticles comprises more than one species of immunogenic portion, each monovalent nanoparticle in the Admixed population comprises a single species of immunogenic portion. As used herein, a multivalent co-assembled nanoparticle, co-assembled nanoparticle, and the like, refers to a nanoparticle made by combining more than one species of fusion protein, wherein at least two fusion proteins differ in the sequence of their immunogenic portions. The result is a nanoparticle comprising a heterogeneous population of self-assembling fusion proteins, wherein the nanoparticle displays on its surface a heterogeneous population of immunogenic portions from HA proteins. Such multivalent nanoparticles can also be referred to as mosaic nanoparticles.

One embodiment of the present invention is a nanoparticle comprising a heterologous population of fusion proteins, wherein each fusion protein comprises at least one immunogenic portion from an influenza HA protein joined to at least 25 contiguous amino acids from a monomeric subunit protein capable of assembling into a nanoparticle (i.e., a self-assembly (SA) protein), wherein the heterologous population of fusion proteins comprises at least two different species of fusion proteins. Nanoparticles of the present invention can be made from fusion proteins comprising immunogenic portions of HA proteins from any Type, sub-type, strain, or combinations thereof, of influenza virus. In certain embodiments, the immunogenic portions are from HA proteins from one or more influenza viruses selected from the group consisting of Type A influenza viruses, Type B influenza viruses and Type C influenza viruses. In one embodiment, the immunogenic portions are from HA proteins from one or more virus selected from the group consisting of Group I influenza viruses and Group II influenza virus. In one embodiment, the immunogenic portions are from HA proteins from one or more virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, an H18 influenza virus and an influenza B lineage virus. In certain embodiments, the immunogenic portions are from HA proteins from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In certain embodiments, the immunogenic portions are from one or more HA proteins Listed in Table 1. In certain embodiments, the immunogenic portions are from one or more HA proteins selected from the group consisting of HA proteins comprising SEQ ID NO:1-SEQ ID NO:62. In certain embodiments, the immunogenic portions are from one or more HA proteins selected from the group consisting of HA proteins consisting of SEQ ID NO:1-SEQ ID NO:62.

Immunogenic portions useful for constructing nanoparticles of the present invention can also be obtained from variants of influenza virus HA proteins disclosed herein. As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as such alterations do not significantly affect the activity of the variant protein and the variant protein retains the desired activity. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

As noted, variant proteins of the present invention can contain amino acid substitutions relative to the influenza HA proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:
1) hydrophobic: Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the HA protein, or to increase or decrease the immunogenicity, solubility or stability of the HA proteins described herein. Exemplary amino acid substitutions are shown below in Table 2.

TABLE 2

Amino Acid Substitutions

| Original Amino Acid | Exemplary Substitutions |
| --- | --- |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30%, at least 40% or at least 50%. With regard to the present invention, such activity may be ability to elicit antibodies, including neutralizing antibodies, against an influenza virus. The determination of antibody production may be measured by measuring the titer of such antibodies against influenza virus, or by measuring the number of types, subtypes or strains bound by the elicited antibodies. Methods of determining antibody titers and methods of performing virus neutralization assays are known to those skilled in the art. In addition to the activities described above, examples of other activities that may be measured include the ability to agglutinate red blood cells, the ability to bind sialic acid or the binding affinity of the protein for a cell. Methods of measuring such activities are known to those skilled in the art.

Thus, in one embodiment, nanoparticles of the present invention comprise fusion proteins comprising immunogenic portions from HA proteins comprising amino acid sequences at least 80%, at least 85%, at least 90%, at least 92%, at least 94%, at least 96%, at least 98% or at least 99% identical to amino acid sequences from one or more HA proteins from any Type, sub-type, strain, or combinations thereof, of influenza virus. In certain embodiments, the immunogenic portions are from HA proteins from one or more influenza viruses selected from the group consisting of Type A influenza virus, Type B influenza virus and Type C influenza viruses. In certain embodiments, the immunogenic portions are from HA proteins from one or more influenza viruses selected from the group consisting of Group 1 influenza virus and Group 2 influenza viruses. In one embodiment, the immunogenic portions are from one or more HA proteins comprising amino acid sequences at least 80%, at least 85%, at least 90%, at least 92%, at least 94%, at least 96%, at least 98% or at least 99% identical to amino acid sequences of HA proteins from one or more viruses selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, an H18 influenza virus and an influenza lineage B virus. In certain embodiments, the immunogenic portions are from HA proteins comprising amino acid sequence at least 80%, at least 85%, at least 90%, at least 92%, at least 94%, at least 96%, at least 98% or at least 99% identical to amino acid sequences of HA proteins from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In certain embodiments, the immunogenic portions are from HA proteins comprising amino acid sequences at least 80%, at least 85%, at least 90%, at least 92%, at least 94%, at least 96%, at least 98% or at least 99% identical to amino acid sequences of one or more HA proteins Listed in Table 1. In certain embodiments, the immunogenic portions are from HA proteins comprising amino acid sequences at least 80%, at least 85%, at least 90%, at least 92%, at least 94%, at least 96%, at least 98% or at least 99% identical to amino acid sequences of one or more HA proteins selected from the group consisting of HA proteins comprising SEQ ID NO:1-SEQ ID NO:62. In certain embodiments, the immunogenic portions are from HA proteins comprising amino acid sequences at least 80%, at least 85%, at least 90%, at least 92%, at least 94%, at least 96%, at least 98% or at least 99% identical to amino acid sequences of one or more HA proteins selected from the group consisting of HA proteins consisting of SEQ ID NO:1-SEQ ID NO:62.

It is understood by those skilled in the art that the influenza HA protein contains different regions or domains. Examples of such regions include the stem region and the globular head region. Thus, while nanoparticle-based influenza vaccines can be made using immunogenic portions from any influenza HA proteins, in preferred embodiments the immunogenic portions are from a specific region or domain of the selected HA proteins. One embodiment of the present invention is a nanoparticle comprising a heterologous population of fusion proteins, wherein each fusion protein comprises at least one immunogenic portion from the globular head region of an influenza HA protein joined to at least 25 contiguous amino acids from a monomeric subunit protein capable of assembling into a nanoparticle (i.e., a self-assembly (SA) protein), wherein the heterologous population of fusion proteins comprises at least two different species of fusion proteins. The globular head region, which comprises (approximately) amino acid residues 52-277 of influenza A HA protein (H3 numbering system), consists exclusively of the major portion of the HA1 polypeptide and includes two domains: the receptor binding domain (RBD and the vestigial esterase sub-domain. One example of a globular head region is represented by amino acids 52-277 from an HA protein comprising a region corresponding to an amino acid sequence selected from the group consisting of SEQ ID NO:1-62. In one embodiment, the immunogenic portions are from the globular head regions of HA proteins comprising amino acid sequences at least 80%, at least 85%, at least 90%, at least 92%, at least 94%, at least 96%, at least 98% at least 99%, or which are, identical to the amino acid sequences of HA proteins from one or more influenza viruses selected from the group consisting of Type A influenza viruses, Type B influenza viruses and Type C influenza viruses. In one embodiment, the immunogenic portions are from the globular head regions of HA proteins comprising amino acid sequences at least 80%, at least 85%, at least 90%, at least 92%, at least 94%, at least 96%, at least 98% at least 99%, or which are, identical to the amino acid sequences of HA proteins from one or more influenza viruses selected from the group consisting of Group I influenza viruses and Group II influenza viruses. In one embodiment, the immunogenic portions are from globular head regions of HA proteins comprising amino acid sequences at least 80%, at least 85%, at least 90%, at least 92%, at least 94%, at least 96%, at least 98%, at least 99%, or which are, identical to the amino acid sequences of HA proteins from one or more viruses selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, a H17 influenza virus, an H18 influenza virus and an influenza linage B virus. In one embodiment, the immunogenic portions are from the globular head regions of HA proteins comprising amino acid sequences at least 80%, at least 85%, at least 90%, at least 92%, at least 94%, at least 96%, at least 98% at least 99%, or which are, identical to the amino acid sequences of HA proteins from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In one embodiment, the immunogenic portions are from the globular head regions of HA proteins comprising amino acid sequences at least 80%, at least 85%, at least 90%, at least 92%, at least 94%, at least 96%, at least 98% at least 99%, or which are, identical to the amino acid sequences of one or more HA proteins Listed in Table 1.

As has been discussed, the globular head region comprises several other regions or domains. Thus, it will be appreciated by those skilled in the art that the immunogenic portions of the self-assembling fusion proteins can be fragments from the globular head regions from one or more influenza virus HA proteins. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from globular head regions of influenza virus HA proteins. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the globular head regions of HA proteins, or variant, thereof, from one or more influenza viruses selected form the group consisting of Type A influenza viruses, Type B influenza viruses and Type C influenza viruses. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the globular head regions of HA proteins, or variants, thereof, from one or more influenza viruses selected from the group consisting of Group I influenza viruses and Group II influenza viruses. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the globular head regions of HA proteins, or variant thereof, from one or more viruses selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, an H18 influenza virus and an influenza lineage B virus. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the region corresponding to the globular head regions of HA proteins, or variant thereof, from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In one embodiment, the immunogenic portions comprises at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the regions corresponding to the globular head regions of one or more HA proteins, or variant thereof, listed in Table 1. In one embodiment, the immunogenic portions comprises at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from regions corresponding to the globular head regions of one or more HA proteins, or variant thereof, comprising sequences selected from the group consisting of SEQ ID NO:1-SEQ ID NO:31.

A particularly useful portion of the globular head region is the receptor-binding domain (RBD). The receptor-binding domain comprises (approximately) amino acid residues 56-264 of influenza A HA protein (H3 numbering system). One embodiment of the present invention is a nanoparticle comprising a heterologous population of fusion proteins, wherein each fusion protein comprises at least one immunogenic portion from the RBD of an influenza HA protein joined to at least 25 contiguous amino acids from a monomeric subunit protein capable of assembling into a nanoparticle (i.e., a self-assembly (SA) protein), wherein the heterologous population of fusion proteins comprises at least two different species of fusion proteins. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the receptor-binding domains (RBDs) of one or more influenza virus HA proteins. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of HA proteins, or variants thereof, from one or more influenza viruses selected from the group consisting of Type A influenza viruses, Type B influenza viruses and Type C influenza viruses. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of HA proteins, or variants thereof, from one or more influenza viruses selected from the group consisting of Group 1 influenza viruses and Group 2 influenza viruses. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of HA proteins, or variants thereof, from one or more viruses selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, an H18 influenza virus and an influenza lineage B virus. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of HA proteins, or variants thereof, from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of one or more HA proteins, or variants thereof, Listed in Table 1. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from an amino acid sequence at least 80%, at least 85%, at least 90%, at least 92%, at least 94%, at least 96%, at least 98% or at least 99% identical to a sequence selected from the group consisting of SEQ ID NO:32-SEQ ID NO:62. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from one or more amino acid sequences selected from the group consisting of SEQ ID NO:32-SEQ ID NO:62. In one embodiment, the immunogenic portions comprise one or more amino acid sequence selected from the group consisting of SEQ ID NO:32-SEQ ID NO:62.

As described herein, in order to form nanoparticles expressing immunogenic portions of influenza HA proteins on theirs surfaces, each immunogenic portion is joined to a self-assembly (SA) subunit protein, or a functional portion or variant thereof, thereby forming a hemagglutinin-self-assembly (HA-SA) fusion protein. Upon expression, the HA-SA fusion proteins assemble into a nanoparticle that displays the immunogenic portion of the HA protein on its surface. Any self-assembly subunit protein, or variant thereof, can be used to produce a fusion protein of the present invention, as long as the resulting fusion protein is capable of self-assembling into a nanoparticle. Examples of self-assembly subunit proteins useful for constructing fusion proteins of the present invention include, but are not limited to, ferritin, encapsulin, sulfur oxygenase reductase, lumazine synthase, dihydrolipoamide acetyltransferase (E2), Chikungunya virus envelope proteins, and fragments and/or variants thereof.

In one embodiment, the self-assembly protein is ferritin. Ferritin, which is found in all animals, bacteria and plants, forms a spherical protein complex that acts primarily to control the rate and location of polynuclear $Fe(III)_2O_3$ formation through the transportation of hydrated iron ions and protons to and from a mineralized core. The spherical form of ferritin is made up of monomeric subunit proteins (also referred to as monomeric ferritin subunits), which are polypeptides having a molecule weight of approximately 17-20 kDa.

Examples of the sequences of monomeric ferritin subunits are represented by SEQ ID NO:64, SEQ ID NO:67 and SEQ ID NO:69. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, and D & E' from the N-terminus respectively. The N-terminal sequence lies adjacent to the capsid three-fold axis and extends to the surface, while the E helices pack together at the four-fold axis with the C-terminus extending into the particle core. The consequence of this packing creates two pores on the capsid surface. While not intended to be bound by theory, it is expected that one or both of these pores represent the point by which the hydrated iron diffuses into and out of the capsid. Following production, these monomeric ferritin subunit proteins self-assemble into the spherical ferritin protein. Thus, the spherical form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the spherical form of the protein.

Amino acid sequences from monomeric ferritin subunits of any known ferritin protein can be used to produce fusion proteins of the present invention, so long as the monomeric ferritin subunit is capable of directing self-assembly of the fusion protein into a nanoparticle displaying immunogenic portions from influenza virus HA proteins on its surface. In one embodiment, the monomeric ferritin subunit is selected from the group consisting of a bacterial ferritin protein, a plant ferritin protein, an algal ferritin protein, an insect ferritin protein, a fungal ferritin protein and a mammalian ferritin protein. In one embodiment, the monomeric ferritin subunit is from *Helicobacter pylori*. In one embodiment, the monomeric ferritin subunit is from *E. coli*. In one embodiment, the monomeric ferritin subunit is bullfrog ferritin. In one embodiment, the monomeric ferritin subunit is a hybrid ferritin protein made by joining amino acid sequences from more than one ferritin proteins selected from the group consisting of *H. pylori* ferritin, *E. coli* ferritin and bullfrog ferritin. Amino acid sequences from representative ferritin proteins of the present invention are disclosed herein as SEQ ID NO:64 (*H. pylori* ferritin), SEQ ID NO:66 (*E. coli* ferritin), SEQ ID NO:70 (bullfrog ferritin). Examples of representative hybrid ferritin proteins of the present invention include SEQ ID NO:73 (*H. pylori* ferritin-bullfrog ferritin fusion) and SEQ ID NO:76 (*E. coli* ferritin-bullfrog ferritin fusion. In one embodiment, nanoparticles of the present invention contain fusion proteins comprising an amino acid sequence selected from the group consisting of SEQ ID NO:64, SEQ ID NO:67, SEQ ID NO:70, SEQ ID NO:73 and SEQ ID NO:76.

In one embodiment, the self-assembly protein is encapsulin. According to the present invention, a monomeric encapsulin subunit of the present invention is a full length, single polypeptide of an encapsulin protein, or any portion thereof, which is capable of directing self-assembly of monomeric encapsulin subunits into a nanoparticle. Amino acid sequences from monomeric encapsulin subunits of any known encapsulin protein can be used to produce fusion proteins of the present invention, so long as the monomeric encapsulin subunit is capable of directing self-assembly of the fusion protein into a nanoparticle displaying immunogenic portions from influenza virus HA proteins on its surface. The amino acid sequence of a representative encapsulin protein is disclosed herein as SEQ ID NO:79. The spherical form of encapsulin comprises 60 monomeric encapsulin subunit proteins.

In one embodiment, the self-assembly protein is artificially designed *Salmonella enteritis* 03-33 subunit protein. According to the present invention, a monomeric 03-33 subunit of the present invention is a full length, single polypeptide of an 03-33 protein, or any portion thereof, which is capable of directing self-assembly of monomeric 03-33 subunits into a nanoparticle. Amino acid sequences from monomeric 03-33 subunits of any known 03-33 protein can be used to produce fusion proteins of the present invention, so long as the monomeric 03-33 subunit is capable of directing self-assembly of the fusion protein into a nanoparticle displaying immunogenic portions from influenza virus HA proteins on its surface. The amino acid sequence of a representative 03-33 protein is disclosed herein as SEQ ID NO:82.

In one embodiment, the self-assembly protein is sulfur oxygenase reductase (SOR). According to the present invention, a monomeric SOR subunit of the present invention is a full length, single polypeptide of an SOR protein, or any portion thereof, which is capable of directing self-assembly of monomeric SOR subunits into a nanoparticle. Amino acid sequences from monomeric SOR subunits of any known SOR protein can be used to produce fusion proteins of the present invention, so long as the monomeric SOR subunit is capable of directing self-assembly of the fusion protein into a nanoparticle displaying immunogenic portions from influenza virus HA proteins on its surface. The amino acid sequence of a representative SOR protein is disclosed herein as SEQ ID NO:85. The spherical form of SOR comprises 24 monomeric SOR subunit proteins.

In one embodiment, the self-assembly protein is lumazine synthase (LS). According to the present invention, a monomeric LS subunit of the present invention is a full length, single polypeptide of an LS protein, or any portion thereof, which is capable of directing self-assembly of monomeric LS subunits into a nanoparticle. Amino acid sequences from monomeric LS subunits of any known LS protein can be used to produce fusion proteins of the present invention, so long as the monomeric LS subunit is capable of directing self-assembly of the fusion protein into a nanoparticle displaying immunogenic portions from influenza virus HA proteins on its surface. The amino acid sequence of a representative LS protein is disclosed herein as SEQ ID NO:88. The spherical form of LS comprises a 60 monomeric subunit capsid comprising 12 pentameric units.

In one embodiment, the self-assembly protein is pyruvate dehydrogenase complex (PDC) dihydrolipoamide acetyltransferase (E2p). According to the present invention, a monomeric E2p subunit of the present invention is a full length, single polypeptide of an E2p protein, or any portion thereof, which is capable of directing self-assembly of monomeric E2p subunits into a nanoparticle. Amino acid sequences from monomeric E2p subunits of any known E2p protein can be used to produce fusion proteins of the present invention, so long as the monomeric E2p subunit is capable of directing self-assembly of the fusion protein into a nanoparticle displaying immunogenic portions from influenza virus HA proteins on its surface. The amino acid sequence of a representative E2p protein is disclosed herein as SEQ ID NO:91.

In one embodiment, the nanoparticles comprise self-assembly proteins from Chikungunya virus. In particular, the nanoparticles comprises one or more structural proteins (e.g., capsid, E1, E2 an E3) from Chikungunya virus (CHKV). Methods of forming nanoparticles from CHKV are disclosed herein and are also taught in U.S. patent application Ser. No. 13/131,287, which is incorporated herein in its entirety by reference. According to the present invention, CHKV structural proteins are full length, single polypeptides of CHKV envelope proteins, or any portion thereof, which are capable of directing self-assembly of monomeric structural proteins into a nanoparticle. Amino acid sequences of structural proteins from any known CHKV virus can be used to produce fusion proteins of the present invention, so long as the amino acid sequences are capable of directing self-assembly of the fusion protein into a nanoparticle displaying immunogenic portions from an influenza virus HA protein on its surface. It is understood by those skilled in the art that CHKV proteins are expressed as a polyprotein, which is subsequently cleaved into individual proteins. The amino acid sequence of a representative CHKV polyprotein is disclosed herein as SEQ ID NO:94. It should be further understood that the amino acid sequences of immunogenic portions can be inserted into the polyprotein such upon cleavage of the polyprotein and formation of the virus-like particle, the immunogenic portions are properly folded and displayed on the surface of the nanoparticle.

HA-SA fusion proteins of the present invention need not comprise the full-length sequence of a monomeric subunit polypeptide of a self-assembly protein. Portions, or regions, of the monomeric SA subunit protein can be utilized so long as the portion comprises an amino acid sequence that directs self-assembly of the HA-SA fusion protein into a nanoparticle. One example of such a portion is located between amino acids 5 and 167 of the *Helicobacter pylori* ferritin protein (SEQ ID NO:64). More specific regions of the ferritin protein are described in Zhang, Y. Self-Assembly in the Ferritin Nano-Cage Protein Super Family. 2011, Int. J. Mol. Sci., 12, 5406-5421, which is incorporated herein by reference in its entirety.

One embodiment of the present invention is a nanoparticle comprising a heterogeneous population of HA-SA fusion proteins, wherein each HA-SA fusion protein comprises at least one immunogenic portion an influenza virus HA protein, joined to at least 25 contiguous amino acids, at least 50 contiguous amino acids, at least 75 contiguous amino acids, at least 100 contiguous amino acids, or at least 150 contiguous amino acids from a protein selected from the group consisting of ferritin, encapsulin, sulfur oxygenase reductase, lumazine synthase and pyruvate dehydrogenase complex (PDC) dihydrolipoamide acetyltransferase (E2), wherein the HA-SA fusion protein is capable of being assembled into a nanoparticle. One embodiment of the present invention is a nanoparticle comprising a heterogeneous population of HA-SA fusion proteins, wherein each HA-SA fusion protein comprises at least one immunogenic portion of an influenza virus HA protein joined to at least 25 contiguous amino acids, at least 50 contiguous amino acids, at least 75 contiguous amino acids, at least 100 contiguous amino acids, or at least 150 contiguous amino acids from an amino acid sequence selected from the group consisting of SEQ ID NO:64, SEQ ID NO:67, SEQ ID NO:70, SEQ ID NO:73, SEQ ID NO:76, SEQ ID NO:79, SEQ ID NO:82, SEQ ID NO:85, SEQ ID NO:88, SEQ ID NO:91 and SEQ ID NO:94, wherein the HA-SA fusion protein is capable of being assembled into a nanoparticle. One embodiment of the present invention is nanoparticle comprising a heterogeneous population of HA-SA fusion proteins, wherein each fusion protein comprises at least one immunogenic portion of an influenza virus HA protein joined to at least 25 contiguous amino acids, at least 50 contiguous amino acids, at least 75 contiguous amino acids, at least 100 contiguous amino acids, or at least 150 contiguous amino acids from a region of a ferritin protein comprising amino acid residues 5-167 of SEQ ID NO:64, wherein the HA-SA fusion protein is capable of being assembled into a nanoparticle.

As has been previously discussed, it is well-known in the art that some variations can be made in the amino acid sequence of a protein without affecting the activity of that protein. Such variations include insertion of amino acid residues, deletions of amino acid residues, and substitutions of amino acid residues. Thus, in one embodiment, the sequence of a SA protein subunit is divergent enough from the sequence of a SA protein subunit found in nature, such that when the variant SA protein subunit is introduced into an animal, such as a mouse, it does not result in the production of antibodies that react with the natural SA protein. According to the present invention, such a monomeric subunit is referred to as immunogenically neutral. One embodiment of the present invention is a nanoparticle comprising a heterogeneous population of HA-SA fusion proteins, wherein each fusion protein comprises at least one immunogenic portion from an influenza virus HA protein joined to an amino acid sequence at least 80%, at least 85%, at least 90%, at least 95%, or at least 97% identical to the amino acid sequence of a monomeric SA protein subunit protein capable of self-assembling into a nanoparticle, wherein the HA-SA fusion protein is capable of self-assembling into nanoparticles. In one embodiment, the HA-SA fusion protein comprises a polypeptide sequence identical in sequence to a monomeric SA protein subunit selected from the group consisting of ferritin, encapsulin, sulfur oxygenase reductase, lumazine synthase, pyruvate dehydrogenase complex (PDC) dihydrolipoamide acetyltransferase (E2) and the structural proteins of CHKV. One embodiment of the present invention is a nanoparticle comprising a heterogeneous population of HA-SA fusion proteins, wherein each fusion protein comprises at least one influenza virus HA protein immunogenic portion of the present invention joined to an amino acid sequence at least 80%, at least 85%, at least 90%, at least 95%, or at least 97% identical to the amino acid sequence of a monomeric SA protein subunit selected from the group consisting of ferritin, encapsulin, sulfur oxygenase reductase, lumazine synthase, pyruvate dehydrogenase complex (PDC) dihydrolipoamide acetyltransferase (E2) and the envelope proteins of CHKV, wherein the HA-SA fusion protein is capable of self-assembling into nanoparticles. One embodiment of the present invention is a nanoparticle comprising a heterogeneous population of HA-SA fusion proteins, wherein each fusion protein comprises at least one immunogenic portion of an influenza HA protein of the present invention joined to an amino acid sequence at least 80%, at least 85%, at least 90%, at least 95%, and at least 97% identical to a sequence selected from the group consisting of SEQ ID NO:64, SEQ ID NO:67, SEQ ID NO:70, SEQ ID NO:73, SEQ ID NO:76, SEQ ID NO:79, SEQ ID NO:82, SEQ ID NO:85, SEQ ID NO:88, SEQ ID NO:91 and SEQ ID NO:94, wherein the HA-SA fusion protein is capable of self-assembling into nanoparticles.

In some embodiments of the present invention, the immunogenic portion of an influenza virus HA protein and the amino acid sequence of the SA protein may be joined directly to one another. In other embodiments, it may be necessary to employ linkers (also referred to as a spacer sequences) so that the various domains are in the proper special orientation. The linker sequence is designed to position the immunogenic portion of the influenza virus HA protein in such a way to that it maintains the ability to elicit an immune response to the influenza virus. Linker sequences of the present invention comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. Examples of such linker sequences include, but are not limited to, SG, SGG, GSG, GG and GGSGG (SEQ ID NO: 192). Amino acids can be added, subtracted or rearranged as needed. Those skilled in the art are capable of determining appropriate linker sequences for proteins of the present invention.

In addition to linker sequences, fusion proteins of the present invention can also comprise other heterologous amino acid sequences. For example, fusion proteins may comprise signal sequences that direct the fusion protein into the proper cellular pathway. For example, a signal sequence may direct the protein into the ER-golgi complex so that it is properly glycosylated and secreted. Any signal sequence can be used as long as it directs the fusion protein in the desired manner. Examples of signal sequences useful for preparing fusion proteins of the present invention include, but are not limited to, the signal sequence from bovine prolactin, the human CD5 signal sequence and the CHIKV signal sequence.

Figure 2:
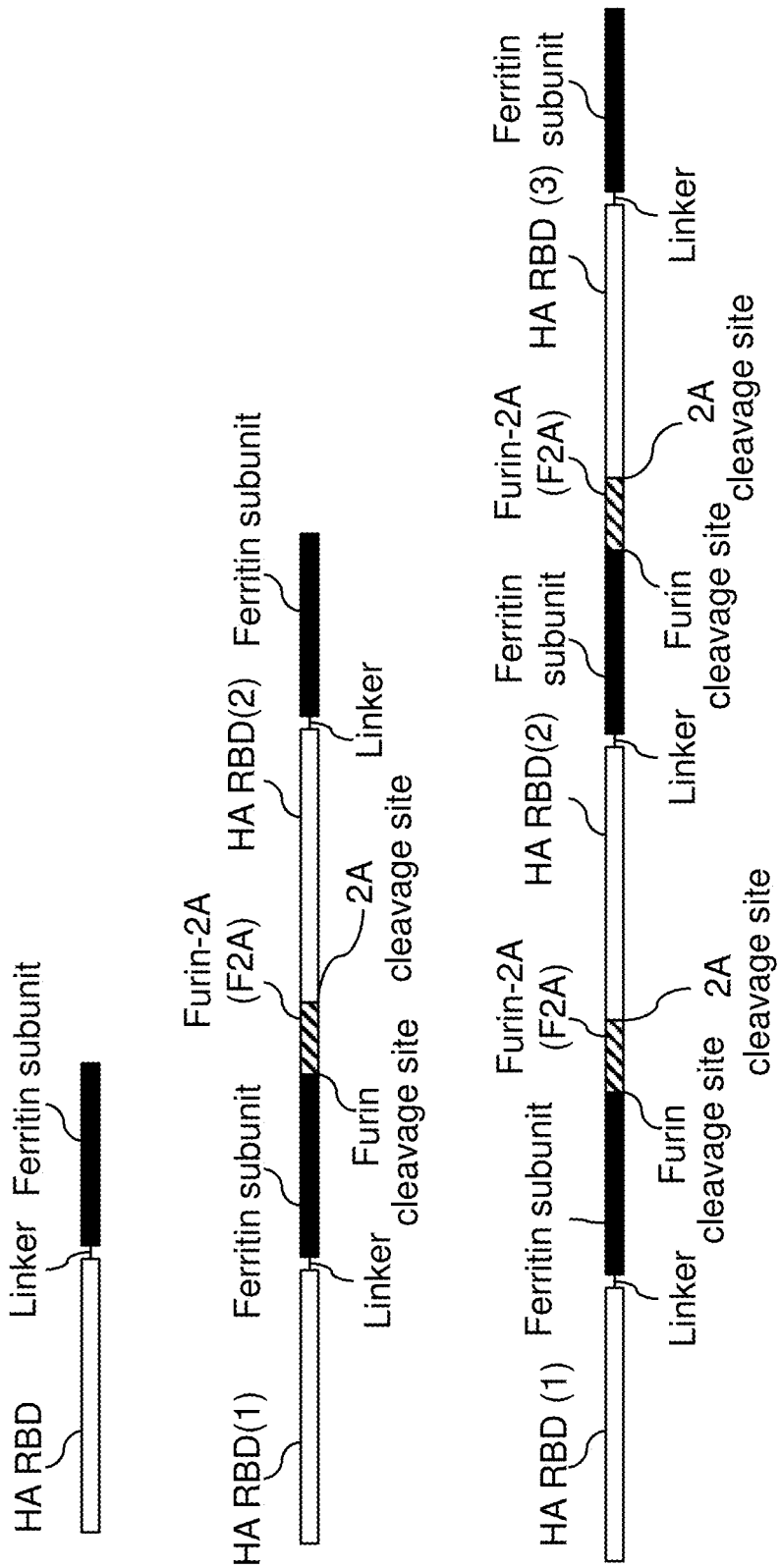
FIG. 2. Schematic representation of HA RBD-ferritin single polypeptide design. HA RBD-ferritin construct without Furin-2A (F2A) self cleavage module (top). Two or three HA RBD-ferritin constructs are connected with F2A self cleavage module (middle or bottom, respectively). As the fusion proteins are produced in producer cells, the cellular protease furin cleaves its cleavage site at the N-terminus of F2A module, and 2A protease cleaves the second (and third) HA RBD-ferritin from the F2A module. As the result, equimolar amount of each HA-RBD-ferritin is produced.

Fusion proteins of the present invention can also contain cleavage sequences. For example, in embodiments in which more than one immunogenic portion from influenza HA proteins are linked together in the fusion protein, enzyme cleavage sites can be included between segments of the fusion protein (e.g., immunogenic portions, SA proteins, linker sequences, etc.) such that upon expression of the protein, the various domains are cleaved from one another. Any cleavage sequence can be used to prepare fusion proteins of the present invention. Examples of such cleavage sequences are furin and 2A cleavage sequences. An exemplary embodiment is illustrated in FIG. 2.

In some embodiments, it may be useful to engineer mutations into the amino acid sequences of fusion proteins of the present invention. For example, it may be useful to alter sites such as enzyme recognition sites or glycosylation sites in the monomeric SA protein, the linker sequence or the immunogenic portions of the influenza HA proteins, in order to give the fusion protein beneficial properties (e.g., stability, solubility, half-life, mask portions of the protein from immune surveillance, avoid steric hinderance, etc). For example, it is known that the monomeric subunit of ferritin is not glycosylated naturally. However, it can be glycosylated if it is expressed as a secreted protein in mammalian or yeast cells. Thus, in one embodiment, potential N-linked glycosylation sites in the amino acid sequences from the monomeric ferritin subunit are mutated so that the mutated ferritin subunit sequences are no longer glycosylated at the mutated site. Examples of useful sites at which to introduce mutations include, but are not limited to, amino acid residues 98 and 264 of influenza virus HA proteins.

One embodiment of the present invention is a fusion protein encoded by a nucleic acid molecule of the present invention. One embodiment of the present invention is a fusion protein encoded by a nucleic acid molecule comprising a nucleic acid sequence at least 80%, at least 85%, at least 90%, at least 95% at least 97%, or which is, identical to a sequence selected from the group consisting of SEQ ID NO:96, SEQ ID NO:99, SEQ ID NO:102, SEQ ID NO:105, SEQ ID NO:108, SEQ ID NO:111, SEQ ID NO:114, SEQ ID NO:117, SEQ ID NO:120, SEQ ID NO:123, SEQ ID NO:126, SEQ ID NO:129, SEQ ID NO:132, SEQ ID NO:135, SEQ ID NO:138, SEQ ID NO:141, SEQ ID NO:144, SEQ ID NO:147, SEQ ID NO:150, SEQ ID NO:153, SEQ ID NO:156, SEQ ID NO:159, SEQ ID NO:162, SEQ ID NO:165, SEQ ID NO:168, SEQ ID NO:171, SEQ ID NO:174, SEQ ID NO:177, SEQ ID NO:180, SEQ ID NO:183, SEQ ID NO:186 and SEQ ID NO:189. One embodiment of the present invention is a fusion protein encoded by a nucleic acid molecule comprising a nucleic acid sequence selected from the group consisting of SEQ ID NO:96, SEQ ID NO:99, SEQ ID NO:102, SEQ ID NO:105, SEQ ID NO:108, SEQ ID NO:111, SEQ ID NO:114, SEQ ID NO:117, SEQ ID NO:120, SEQ ID NO:123, SEQ ID NO:126, SEQ ID NO:129, SEQ ID NO:132, SEQ ID NO:135, SEQ ID NO:138, SEQ ID NO:141, SEQ ID NO:144, SEQ ID NO:147, SEQ ID NO:150, SEQ ID NO:153, SEQ ID NO:156, SEQ ID NO:159, SEQ ID NO:162, SEQ ID NO:165, SEQ ID NO:168, SEQ ID NO:171, SEQ ID NO:174, SEQ ID NO:177, SEQ ID NO:180, SEQ ID NO:183, SEQ ID NO:186 and SEQ ID NO:189. One embodiment of the present invention is a fusion protein encoded by a nucleic acid molecule consisting of a nucleic acid sequence selected from the group consisting of SEQ ID NO:96, SEQ ID NO:99, SEQ ID NO:102, SEQ ID NO:105, SEQ ID NO:108, SEQ ID NO:111, SEQ ID NO:114, SEQ ID NO:117, SEQ ID NO:120, SEQ ID NO:123, SEQ ID NO:126, SEQ ID NO:129, SEQ ID NO:132, SEQ ID NO:135, SEQ ID NO:138, SEQ ID NO:141, SEQ ID NO:144, SEQ ID NO:147, SEQ ID NO:150, SEQ ID NO:153, SEQ ID NO:156, SEQ ID NO:159, SEQ ID NO:162, SEQ ID NO:165, SEQ ID NO:168, SEQ ID NO:171, SEQ ID NO:174, SEQ ID NO:177, SEQ ID NO:180, SEQ ID NO:183, SEQ ID NO:186 and SEQ ID NO:189.

One embodiment of the present invention is a fusion protein comprising an amino acid sequence at least 80%, at least 85%, at least 90%, at least 95% at least 97%, or which is, identical to an amino acid sequence selected form the group consisting of SEQ ID NO:97, SEQ ID NO:100, SEQ ID NO:103, SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:133, SEQ ID NO:136, SEQ ID NO:139, SEQ ID NO:142, SEQ ID NO:145, SEQ ID NO:148, SEQ ID NO:151, SEQ ID NO:154, SEQ ID NO:157, SEQ ID NO:160, SEQ ID NO:163, SEQ ID NO:166, SEQ ID NO:169, SEQ ID NO:172, SEQ ID NO:175, SEQ ID NO:178, SEQ ID NO:181, SEQ ID NO:184, SEQ ID NO:187 and SEQ ID NO:190. One embodiment of the present invention is a fusion protein consisting of an amino acid sequence selected form the group consisting of SEQ ID NO:97, SEQ ID NO:100, SEQ ID NO:103, SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:133, SEQ ID NO:136, SEQ ID NO:139, SEQ ID NO:142, SEQ ID NO:145, SEQ ID NO:148, SEQ ID NO:151, SEQ ID NO:154, SEQ ID NO:157, SEQ ID NO:160, SEQ ID NO:163, SEQ ID NO:166, SEQ ID NO:169, SEQ ID NO:172, SEQ ID NO:175, SEQ ID NO:178, SEQ ID NO:181, SEQ ID NO:184, SEQ ID NO:187 and SEQ ID NO:190.

Fusion proteins of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can effect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, an mRNA, a viral vector, or other vector. In one embodiment, a vector can be a cytomegalovirus (CMV), retrovirus, adenovirus, adeno-associated virus, herpes virus, vaccinia virus, poliovirus, sindbis virus, or any other DNA or RNA virus vector. In one embodiment, a vector can be a pseudotyped lentiviral or retroviral vector. In one embodiment, a vector can be a DNA plasmid. In one embodiment, a vector can be a DNA plasmid comprising viral components and plasmid components to enable nucleic acid molecule delivery and expression. Methods for the construction of nucleic acid constructs of the present disclosure are well known. See, for example, *Molecular Cloning: a Laboratory Manual,* 3$^{rd}$ edition, Sambrook et al. 2001 Cold Spring Harbor Laboratory Press, and *Current Protocols in Molecular Biology*, Ausubel et al. eds., John Wiley & Sons, 1994. In one embodiment, the vector is a DNA plasmid, such as a CMV/R plasmid such as CMV/R or CMV/R 8κB (also referred to herein as CMV/R 8κb). Examples of CMV/R and CMV/R 8 κb are provided herein. CMV/R is also described in U.S. Pat. No. 7,094,598 B2, issued Aug. 22, 2006.

As used herein, a nucleic acid molecule comprises a nucleic acid sequence that encodes an HA-SA fusion protein of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is know. It is to be appreciated that a nucleic acid construct can comprise one nucleic acid molecule or more than one nucleic acid molecule. It is also to be appreciated that a nucleic acid molecule can encode one protein or more than one protein.

One embodiment of the present invention is a nucleic acid molecule comprising a nucleic acid sequence encoding a fusion protein of the present invention. One embodiment of the present invention is a nucleic acid molecule comprising a nucleic acid sequence encoding a fusion protein that comprises a monomeric self-assembly subunit protein joined to one or more immunogenic portions of one or more influenza hemagglutinin proteins. One embodiment of the present invention is a nucleic acid molecule comprising a nucleic acid sequence encoding a fusion protein comprising one or more amino acid sequence at least 80%, at least 85%, at least 90%, at least 95% at least 97%, or which are, identical to one or more immunogenic portions from one or more influenza hemagglutinin proteins of the present invention, wherein the fusion protein is capable of forming a nanoparticle displaying the immunogenic portions on its surface. In a further embodiment, a nucleic acid molecule of the present invention comprises a nucleic acid sequence encoding a fusion protein comprising an amino acid sequence at least 80%, at least 85%, at least 90%, at least 95% at least 97%, or which is, identical to the amino acid sequence of a monomeric self-assembly subunit protein of the present invention, wherein the fusion protein is capable of forming a nanoparticle displaying the immunogenic portions on its surface. In one embodiment, a nucleic acid molecule of the present invention comprises a nucleic acid sequence encoding a fusion protein comprising i) one or more amino acid sequence at least 80%, at least 85%, at least 90%, at least 95% at least 97%, or which are, identical to one or more immunogenic portions from one or more influenza hemagglutinin proteins of the present invention; and, ii) an amino acid sequence at least 80%, at least 85%, at least 90%, at least 95% at least 97%, or which is, identical to the amino acid sequence of a monomeric self-assembly subunit protein of the present invention, wherein the fusion protein is capable of forming a nanoparticle displaying the immunogenic portions on its surface. One embodiment of the present invention is a nucleic acid molecule comprising a nucleic acid sequence encoding a fusion protein comprising an amino acid sequence at least 80%, at least 85%, at least 90%, at least 95% at least 97%, or which is, identical to an amino acid sequence selected form the group consisting of SEQ ID NO:97, SEQ ID NO:100, SEQ ID NO:103, SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:133, SEQ ID NO:136, SEQ ID NO:139, SEQ ID NO:142, SEQ ID NO:145, SEQ ID NO:148, SEQ ID NO:151, SEQ ID NO:154, SEQ ID NO:157, SEQ ID NO:160, SEQ ID NO:163, SEQ ID NO:166, SEQ ID NO:169, SEQ ID NO:172, SEQ ID NO:175, SEQ ID NO:178, SEQ ID NO:181, SEQ ID NO:184, SEQ ID NO:187 and SEQ ID NO:190. One embodiment of the present invention is a nucleic acid molecule comprising a nucleic acid sequence encoding a fusion protein comprising an amino acid sequence selected form the group consisting of SEQ ID NO:97, SEQ ID NO:100, SEQ ID NO:103, SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:133, SEQ ID NO:136, SEQ ID NO:139, SEQ ID NO:142, SEQ ID NO:145, SEQ ID NO:148, SEQ ID NO:151, SEQ ID NO:154, SEQ ID NO:157, SEQ ID NO:160, SEQ ID NO:163, SEQ ID NO:166, SEQ ID NO:169, SEQ ID NO:172, SEQ ID NO:175, SEQ ID NO:178, SEQ ID NO:181, SEQ ID NO:184, SEQ ID NO:187 and SEQ ID NO:190. One embodiment of the present invention is a nucleic acid molecule comprising a nucleic acid sequence at least 80%, at least 85%, at least 90%, at least 95% at least 97%, or which is, identical to a sequence selected form the group consisting of SEQ ID NO:96, SEQ ID NO:98, SEQ ID NO:99, SEQ ID NO:101, SEQ ID NO:102, SEQ ID NO:104, SEQ ID NO:105, SEQ ID NO:107, SEQ ID NO:108, SEQ ID NO:110, SEQ ID NO:111, SEQ ID NO:113, SEQ ID NO:114, SEQ ID NO:116, SEQ ID NO:117, SEQ ID NO:119, SEQ ID NO:120, SEQ ID NO:122, SEQ ID NO:123, SEQ ID NO:125, SEQ ID NO:126, SEQ ID NO:128, SEQ ID NO:129, SEQ ID NO:131, SEQ ID NO:132, SEQ ID NO:134, SEQ ID NO:135, SEQ ID NO:137, SEQ ID NO:138, SEQ ID NO:140, SEQ ID NO:141, SEQ ID NO:143, SEQ ID NO:144, SEQ ID NO:146, SEQ ID NO:147, SEQ ID NO:149, SEQ ID NO:150, SEQ ID NO:152, SEQ ID NO:153, SEQ ID NO:155, SEQ ID NO:156, SEQ ID NO:158, SEQ ID NO:159, SEQ ID NO:161, SEQ ID NO:162, SEQ ID NO:164, SEQ ID NO:165, SEQ ID NO:167, SEQ ID NO:168, SEQ ID NO:170, SEQ ID NO:171, SEQ ID NO:173, SEQ ID NO:174, SEQ ID NO:176, SEQ ID NO:177, SEQ ID NO:179, SEQ ID NO:180, SEQ ID NO:182, SEQ ID NO:183, SEQ ID NO:185, SEQ ID NO:186, SEQ ID NO:188, SEQ ID NO:189 and SEQ ID NO:191. One embodiment of the present invention is a nucleic acid molecule comprising a nucleic acid sequence selected from the group consisting of SEQ ID NO:96, SEQ ID NO:98, SEQ ID NO:99, SEQ ID NO:101, SEQ ID NO:102, SEQ ID NO:104, SEQ ID NO:105, SEQ ID NO:107, SEQ ID NO:108, SEQ ID NO:110, SEQ ID NO:111, SEQ ID NO:113, SEQ ID NO:114, SEQ ID NO:116, SEQ ID NO:117, SEQ ID NO:119, SEQ ID NO:120, SEQ ID NO:122, SEQ ID NO:123, SEQ ID NO:125, SEQ ID NO:126, SEQ ID NO:128, SEQ ID NO:129, SEQ ID NO:131, SEQ ID NO:132, SEQ ID NO:134, SEQ ID NO:135, SEQ ID NO:137, SEQ ID NO:138, SEQ ID NO:140, SEQ ID NO:141, SEQ ID NO:143, SEQ ID NO:144, SEQ ID NO:146, SEQ ID NO:147, SEQ ID NO:149, SEQ ID NO:150, SEQ ID NO:152, SEQ ID NO:153, SEQ ID NO:155, SEQ ID NO:156, SEQ ID NO:158, SEQ ID NO:159, SEQ ID NO:161, SEQ ID NO:162, SEQ ID NO:164, SEQ ID NO:165, SEQ ID NO:167, SEQ ID NO:168, SEQ ID NO:170, SEQ ID NO:171, SEQ ID NO:173, SEQ ID NO:174, SEQ ID NO:176, SEQ ID NO:177, SEQ ID NO:179, SEQ ID NO:180, SEQ ID NO:182, SEQ ID NO:183, SEQ ID NO:185, SEQ ID NO:186, SEQ ID NO:188, SEQ ID NO:189 and SEQ ID NO:191. One embodiment of the present invention is a nucleic acid molecule consisting of a nucleic acid sequence selected from the group consisting of SEQ ID NO:96, SEQ ID NO:98, SEQ ID NO:99, SEQ ID NO:101, SEQ ID NO:102, SEQ ID NO:104, SEQ ID NO:105, SEQ ID NO:107, SEQ ID NO:108, SEQ ID NO:110, SEQ ID NO:111, SEQ ID NO:113, SEQ ID NO:114, SEQ ID NO:116, SEQ ID NO:117, SEQ ID NO:119, SEQ ID NO:120, SEQ ID NO:122, SEQ ID NO:123, SEQ ID NO:125, SEQ ID NO:126, SEQ ID NO:128, SEQ ID NO:129, SEQ ID NO:131, SEQ ID NO:132, SEQ ID NO:134, SEQ ID NO:135, SEQ ID NO:137, SEQ ID NO:138, SEQ ID NO:140, SEQ ID NO:141, SEQ ID NO:143, SEQ ID NO:144, SEQ ID NO:146, SEQ ID NO:147, SEQ ID NO:149, SEQ ID NO:150, SEQ ID NO:152, SEQ ID NO:153, SEQ ID NO:155, SEQ ID NO:156, SEQ ID NO:158, SEQ ID NO:159, SEQ ID NO:161, SEQ ID NO:162, SEQ ID NO:164, SEQ ID NO:165, SEQ ID NO:167, SEQ ID NO:168, SEQ ID NO:170, SEQ ID NO:171, SEQ ID NO:173, SEQ ID NO:174, SEQ ID NO:176, SEQ ID NO:177, SEQ ID NO:179, SEQ ID NO:180, SEQ ID NO:182, SEQ ID NO:183, SEQ ID NO:185, SEQ ID NO:186, SEQ ID NO:188, SEQ ID NO:189 and SEQ ID NO:191.

As has been discussed, nanoparticles of the present invention comprise populations of fusion proteins which are heterogeneous due to at least two fusion proteins in the population differing in their amino acid sequences by at least one amino acid. It will be appreciated by those skilled in the art that, as described hereto, a heterogeneous population of fusion proteins can be due to the aforementioned amino acid difference being at any location in the fusion protein, including in the SA portion of the protein. However, preferred nanoparticles of the present invention are those in which a single nanoparticle is capable of eliciting an immune response to more than one Type, sub-type or strain of influenza virus. Consequently, preferred nanoparticles are those comprising a heterogeneous population of fusion proteins, wherein at least two fusion proteins in the heterogeneous population differ in the sequences of their immunogenic portions by at least one amino acid. It should be understood that fusion proteins of preferred nanoparticles are not excluded from having sequences differences in regions other than the immunogenic portion. However, in order to elicit an immune response against more than one Type, Group, sub-type or strain of influenza virus, preferred nanoparticles comprise at least two fusion proteins that differ by at least one amino acid residue in the their immunogenic portions. It will be understood by those skilled in the art that differences in the amino acid sequences of the immunogenic portion of two fusion proteins may or may not cause the two different immunogenic portions (i.e., the two species of immunogenic portions) to be recognized by two different receptors (e.g., B-cell, T-cell, etc). Such differences, or lack thereof, in recognition depend on such things as, for example, the differences in properties between the corresponding amino acid residues in the immunogenic portions and whether or not the locations at which the sequences differ (i.e., the amino acid residue) are part of the recognized epitope. In preferred embodiments, the heterogeneous population comprises at least two species of fusion proteins, wherein the immunogenic portions of each of the species is recognized by the same B-cell receptor, T-cell receptor and/or antibody. Thus, in one embodiment, a nanoparticle of the present invention elicits a cross-reactive immune response (an immune response against more than one Type, subtype or strain of influenza virus).

It should be understood that the number of immunogenic regions displayed by nanoparticles of the present invention is only limited by the number of fusion proteins that make up the nanoparticle, which itself is determined by the SA protein used to construct the fusion proteins. For example, ferritin forms a nanoparticle consisting of 24 monomeric, ferritin subunit proteins. Thus, ferritin-based nanoparticle of the present invention can comprise a maximum of 24 fusion proteins and thus, can display a maximum of 24 different immunogenic portions. Similarly, encapsulin proteins from *Thermotoga maritima* form nanoparticles having 60 subunits. Thus, encapsulin-based nanoparticle of the present invention can display a maximum of 60 different immunogenic portions. Likewise, structural proteins from CHIKV form virus-like particles having 240 envelope E2 subunits. Thus CHIKV-based virus-like particle of the present invention can display a maximum of 240 different immunogenic portions. Those skilled in the art will understand that such calculations assume each fusion protein comprises a single immunogenic portion. Nanoparticles displaying higher numbers of immunogenic portions could of course be constructed using fusion proteins comprising two or more immunogenic portions. An example of a fusion protein comprising multiple epitopes is illustrated in FIG. 2. In one embodiment, the nanoparticles comprises a heterogeneous population of fusion proteins, wherein each fusion protein comprises a single immunogenic portion of an influenza HA protein. In one embodiment, the nanoparticles comprises a heterogeneous population of fusion proteins, wherein each fusion protein comprises multiple immunogenic portions from one or more influenza HA proteins. In one embodiment, the nanoparticles comprises a heterogeneous population of fusion proteins, wherein each fusion protein comprises at least 2, at least 3, at least 4 or at least 5 immunogenic portions from one or more influenza HA proteins.

In one embodiment, a nanoparticle of the present invention comprises between 2 and 240 species of fusion proteins, wherein each species differs from every other species, at least in part, by at least one amino acid in change in the sequence of its immunogenic portion. In certain embodiments, a nanoparticle of the present invention comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 3, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230 or at least 240 species of fusion proteins, wherein the species differ from one another, at least in part, by at least one amino acid in their immunogenic portions. In certain embodiments, a nanoparticle of the present invention display at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 3, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59 or at least 60 unique immunogenic portions.

One embodiment of the present invention is a method of producing nanoparticles of the present invention, the method comprising introducing one or more nucleic acid molecules encoding fusion proteins of the present invention into a cell, and incubating the cell under conditions suitable for expressing the encoded proteins and forming nanoparticles. In a further embodiment, the nanoparticles are isolated from the cell into which the nucleic acid molecule was introduced. Methods of isolating nanoparticles are known to those skilled in the art and are also described in U.S. patent application Ser. No. 13/131,287 and International Application No. PCT/US14/60142, both of which are incorporated herein by reference in their entirety. It should be realized by those skilled in the art nanoparticles displaying a heterogeneous population of immunogenic portions on its surface can be produced by either i) introducing more than one nucleic acid molecule into the cell, wherein each nucleic acid molecule encodes a different species of fusion protein; and/or ii) introducing one or more nucleic acid molecule into a cell, wherein at least one nucleic acid molecule encode at least one of the one or more nucleic acid molecules encode a species of fusion protein that differs from a fusion protein encoded by a nucleic acid molecule introduced into the cell. Thus, for example, a nanoparticle comprising a heterogeneous population of fusion proteins can be produced by introducing into a cell a nucleic acid molecule encoding two different species of fusion proteins.

Nanoparticles of the present invention can also be produced by combining expressed and isolated recombinant proteins. Thus, one embodiment of the present invention is a method of producing nanoparticles of the present invention, the method comprising introducing into a cell a nucleic acid molecule encoding a fusion protein of the present invention, incubating the cell under conditions suitable for expressing the protein encoded by the nucleic acid molecule, and isolating the expressed protein. The isolated proteins are then disassembled and combined with one or more heterogeneous species of isolated, disassembled fusion protein (i.e., fusion proteins having a different sequence, especially in their immunogenic portion) such that the mixture of heterogeneous species of fusion proteins reassembles in a nanoparticle comprising a heterogeneous population of fusion proteins, wherein each nanoparticle comprises at least two different species of fusion proteins.

Because nanoparticles of the present invention elicit an immune response to an infectious agent, such as influenza virus, they can be used as vaccines to protect individuals against infection by one or more Types, sub-types, strains and/or species of infectious agent (e.g., influenza virus). Thus, one embodiment of the present invention is a vaccine comprising a nanoparticle of the present invention. Vaccines of the present invention can also contain other components such as adjuvants, buffers and the like. Although any adjuvant can be used, preferred embodiments can contain: chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C-C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C-C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the present invention is a method to vaccinate an individual against an infectious agent, the method comprising administering to the individual a nanoparticle of the present invention. One embodiment of the present invention is a method to vaccinate an individual against influenza virus, the method comprising administering to the individual a nanoparticle vaccine of the present invention. In one embodiment, the nanoparticle comprises self-assembling fusion proteins of the present invention, and the nanoparticle displays on its surface a heterogeneous population of immunogenic portions from HA proteins from one or more types, subtypes or strains of influenza virus.

One embodiment of the present invention is a method to vaccinate an individual against infection with influenza virus, the method comprising:

a) obtaining a nanoparticle of the present invention; and,
b) administering the nanoparticle to an individual such that an immune response against an influenza virus is produced. As used herein, an immune response to a vaccine, or nanoparticle, of the present invention is the development in a subject of a humoral and/or a cellular immune response to a hemagglutinin protein present in the vaccine. For purposes of the present invention, a "humoral immune response" refers to an immune response mediated by antibody molecules, including secretory IgA or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to a protein (e.g., hemagglutinin) present in the vaccine. These responses may serve to neutralize infectivity, and/or mediate antibody-complement, or antibody dependent cell cytotoxicity (ADCC) to provide protection to an immunized individual. Such responses can be determined using standard immunoassays and neutralization assays, well known in the art.

As used herein, neutralizing antibodies are antibodies that prevent in infectious agent from replicating and spreading within a host. With regard to influenza virus, neutralizing antibodies prevent influenza virus from completing one round of replication. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, cleavage and rearrangement of the HA protein, fusion of the viral membrane with the endosomal membrane, release of viral ribonucleoproteins into the cytoplasm, formation of new viral particles and budding of viral particles from the host cell membrane.

In one embodiment, a vaccine or nanoparticle of the present invention elicits broadly neutralizing antibodies. As used herein, broadly neutralizing antibodies are antibodies that neutralize more than one genera, type, subtype, species and/or strain of infectious agent within a taxonomic family. With specific regard to influenza viruses used herein, broadly neutralizing antibodies are antibodies that neutralize more than one type, subtype and/or strain of influenza virus. For example, broadly neutralizing antibodies elicited against an HA protein from a Type A influenza virus may neutralize a Type B or Type C virus. As a further example, broadly neutralizing antibodies elicited against an HA protein from Group 1 influenza virus may neutralize a Group 2 virus. As an additional example, broadly neutralizing antibodies elicited against an HA protein from one sub-type or strain of virus, may neutralize another sub-type or strain of virus. For example, broadly neutralizing antibodies elicited against an HA protein from an H1 influenza virus may neutralize viruses from one or more sub-types selected from the group consisting of H2, H3, H4, H5, H6, H7, H8, H8, H10, H11, H12, H13, H14, H15, H16, H17 or H18.

The terms individual, subject, and patient are well-recognized in the art, and are herein used interchangeably to refer to any human or other animal susceptible to influenza infection. Examples include, but are not limited to, humans and other primates, including non-human primates such as chimpanzees and other apes and monkey species; farm animals such as cattle, sheep, pigs, seals, goats and horses; domestic mammals such as seals, dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have influenza virus in their body.

Methods of the present invention can be used to vaccinate any individual. Such individual can, but need not, be suspected of having been exposed to an infectious agent, such as influenza virus. Similarly, methods of the present invention can be used to vaccinate an individual known to have been exposed to and infectious agent, such as influenza virus, or a person suspected of, or known to have, having been exposed to an infectious agent, such as influenza virus. As such, methods of the present invention can be used to contain a known, or potential, out break of an infectious agent, such as influenza (e.g., epidemic, pandemic).

One embodiment of the present invention is a method to vaccinate an individual against influenza virus, the method comprising administering a vaccine of the embodiments to an individual in need of such a vaccine, such that an immune response against influenza virus is produced in the individual, wherein the vaccine comprises a nanoparticle comprising self-assembling fusion proteins, wherein the nanoparticle displays on its surface a heterogeneous population of immunogenic portions from HA proteins from one or more Type, Group, sub-type or strain of influenza virus. In one embodiment, the immunogenic portions are from the globular head regions of HA proteins from one or more Type, Group, sub-type or strain of influenza virus. In one embodiment, the immunogenic portions are from the RBDs of HA proteins from one or more Type, group, sub-type or strain of influenza virus.

Another embodiment of the present invention is a method to vaccinate an individual against infection with influenza virus, the method comprising:
 a) obtaining a vaccine comprising at least one nanoparticle comprising HA-SA fusion proteins, wherein the fusion proteins comprise an SA protein joined to an immunogenic portion of an influenza HA protein, and wherein the nanoparticle displays on its surface a heterogeneous population of immunogenic portions from HA proteins from one or more Type, Group, sub-type or strain of influenza virus; and,
 b) administering the vaccine to an individual such that an immune response against an influenza virus is produced. In one embodiment, the immunogenic portions are from the globular head regions of HA proteins from one or more Types, sub-types or strains of influenza virus. In one embodiment, the immunogenic portions are from the RBDs of HA proteins from one or more Types, sub-types or strains of influenza virus.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. In one embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition. As used herein, a vaccinated subject is a subject that has been administered a vaccine that is intended to provide a protective effect against an influenza virus.

The first and second vaccine compositions can be, but need not be, the same composition. Thus, in one embodiment of the present invention, the step of administering the vaccine comprises administering a first vaccine composition, and then at a later time, administering a second vaccine composition. In one embodiment, the first vaccine composition comprises a nanoparticle of the present invention.

In one embodiment, the individual has been exposed to influenza virus. As used herein, the terms exposed, exposure, and the like, indicate the subject has come in contact with a person of animal that is known to be infected with an influenza virus. Vaccines of the present invention may be administered using techniques well known to those in the art. Techniques for formulation and administration may be found, for example, in "Remington's Pharmaceutical Sciences", 18$^{th}$ ed., 1990, Mack Publishing Co., Easton, PA. Vaccines may be administered by means including, but not limited to, traditional syringes, needleless injection devices, or microprojectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

In one embodiment, vaccines, or nanoparticles, of the present invention can be used to protect an individual against infection by heterologous influenza virus. That is, a vaccine made using hemagglutinin protein from one strain of influenza virus is capable of protecting an individual against infection by different strains of influenza. For example, a vaccine made using hemagglutinin protein from influenza A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2).

In one embodiment, vaccines, or nanoparticles, of the present invention can be used to protect an individual against infection by an antigenically divergent influenza virus. In this regard, the term antigenically divergent refers to the tendency of a strain of influenza virus to mutate over time, thereby changing the amino acids that are displayed to the immune system. Such mutation over time is also referred to as antigenic drift. Thus, for example, a vaccine made using hemagglutinin protein from an A/New Caledonia/20/1999 (H1N1) strain of influenza virus is capable of protecting an individual against infection by earlier, antigenically divergent New Caledonia strains of influenza, and by evolving (or diverging) influenza strains of the future.

One embodiment of the present invention is a kit for practicing methods of the present invention. Kits can include nanoparticles or vaccines of the present invention as well components for making such nanoparticles and vaccines. As such, kits can include, for example, primers, nucleic acid molecules, expression vectors, DNA constructs encoding proteins of the present invention, cells, buffers, reagents, syringes, and directions for using any of said components. It should be appreciated that a kit may comprise more than one container comprising any of the aforementioned, or related, components. For example, certain parts of the kit may require refrigeration, whereas other parts can be stored at room temperature. Thus, as used herein, a kit comprises components sold in separate containers by one or more entity, with the intention that the components contained therein be used together.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

The inventors have discovered that specific fusion proteins comprising portions of hemagglutinin protein are useful for eliciting a broad immune response against influenza viruses. Each of these embodiments will now be disclosed in detail below.

EXAMPLES

Example 1. Production of Heterogeneous Nanoparticles

A. Gene Synthesis and Vector Construction

All genes used in the study were human codon optimized. The gene encoding *Helicobacter pylori*-bullfrog hybrid ferritin was constructed by fusing residues 2-9 of bullfrog (*Rana catesbeiana*) ferritin lower subunit (UniProt: P07797 with a point mutation at residue 8 (N8Q) to abolish a potential N-glycosylation site) to *H. pylori* nonheme ferritin (UniProt: Q9ZLI1, residues 3-167) with mutations at residue 7 (I7E) and residue 19 (N19Q) to make a salt bridge with 6R of bullfrog ferritin and abolish a potential N-glycosylation site, respectively. In some cases, there were extra GS residues at the carboxyl terminus of *H. pylori* ferritin. The secreted encapsulin gene was constructed by fusing a human CD5 signal to *Termotoga maritima* encapsulin (UniProt: Q9WZP2, residues 1-264). The genes encoding HA RBD (residues 56-264, H3 numbering system) were synthesized or amplified from appropriate plasmids. In some cases, the Y98F mutation was introduced to abolish sialic acid binding property of HA, and the F/K264A mutation to avoid potential steric crash at the junction between HA RBD and nanoparticle scaffolds. These fragments were fused to downstream of a modified bovine prolactin signal sequence (bPRL: MDSKGSSQKG SRLLLLLVVS NLLLPQGVLA, residues 1-30 of SEQ ID NO: 97) and upstream of the hybrid ferritin with a SG linker to give rise to the HA RBD-ferritin genes. To construct the HA RBD-encapsulin genes, gp350 fragments were fused to downstream of encapsulin with a SG linker. To construct HA RBD-Chikungunya virus-like particle (CHIKVLP), the HA RBD gene fragments (residues 59-264, H3 numbering system) were amplified and inserted in the furin cleavage loop between envelope E3 and E2. To accommodate HA RBD insertion and furin cleavage, there were 3 amino acid deletions in E3 (E3 residues 58-60, SPH) and 4 amino acid deletions in E2 (E2 residues 1-4, STKD). All genes were then cloned into the CMV/R or CMV/R 8кb mammalian expression vector for protein production.

B. Biosynthesis of Recombinant Proteins and Purification

The expression vectors were transiently transfected into FreeStyle 293F or Expi293F cells (Life Technologies) using 293fectin or ExpiFectamine 293 transfection reagents, respectively (Life Technologies). For co-transfection, equimolar amount of 2-8 different plasmids were mixed (a total DNA amount was constant for all transfections). Four days after transfection, culture supernatants were harvested and cleared. The HA RBD-ferritin and HA RBD-encapsulin nanoparticles were purified by ion exchange chromatography using Q Sepharose HP (GE Healthcare) followed by size exclusion chromatography with a Superose 6 10/300 GL column (GE Healthcare) in PBS. The HA RBD-CHIKVLP were purified by ultracentrifugation using Opriprep (Sigma-Aldrich). Briefly, the cleared culture supernatants were overlaid on 1 ml of Optiprep and spun at 50,000 rcf in an SW 32 Ti rotor for 90 min. After the spin, bottom 2 ml was collected, mixed thoroughly to make 1:1 Optiprep/concentrated supernatant mixture, and spun again at 360,000 rcf in an NVT 100 rotor for 3 hours. The band corresponding HA RBD-CHIKVLP was collected and further purified by a Sephacryl S-500 16/60 HR column (GE Healthcare) in PBS.

C. Electron Microscopy (EM) of Purified Nanoparticles

Figure 3B:
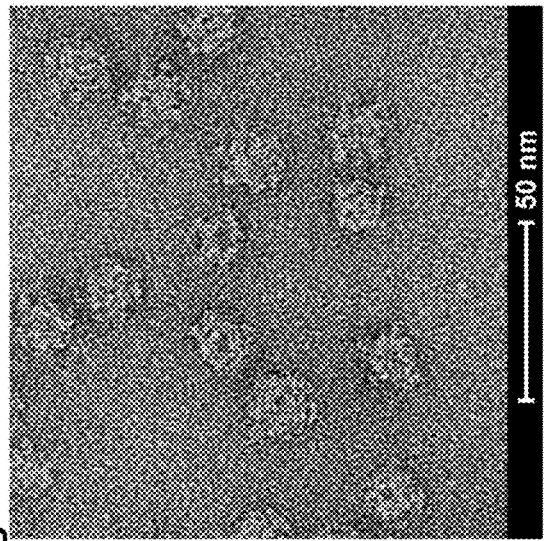
FIGS. 3A-3C. Electron microscopic analysis of HA RBD-nanoparticles. (A) Negative stain electron micrographs of NC99 RBD-nanoparticles; (B) Negative stain electron micrographs of CA09 RBD-nanoparticles; (C) Negative stain electron micrographs of co-assembled (CoAsmbl 2) RBD-nanoparticles. Purified particles were adsorbed to freshly glow-discharged carbon-coated grids and stained with uranyl formate.
Figure 3C:
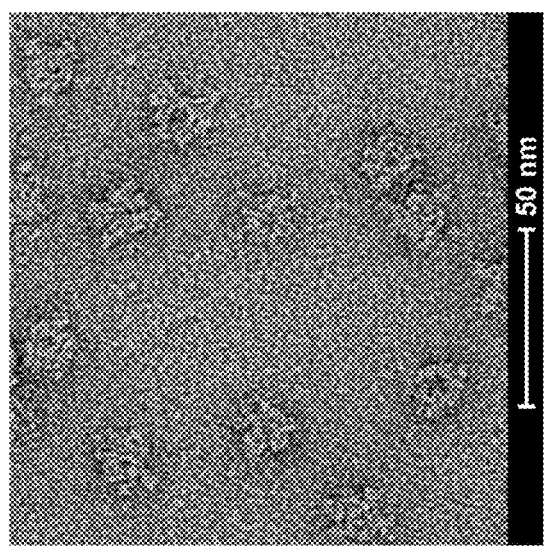
Figure 3A:
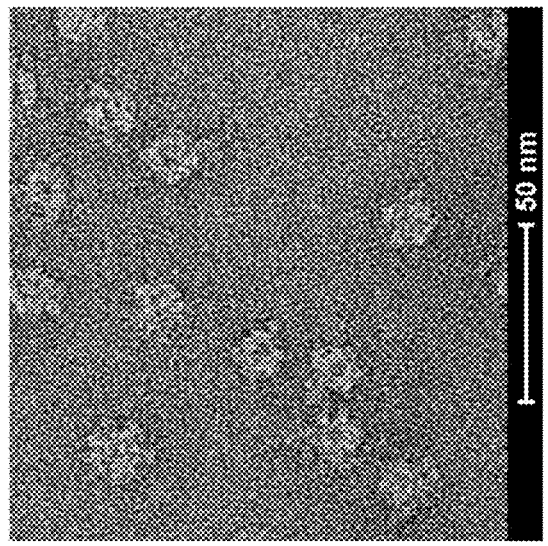
Figure 4:
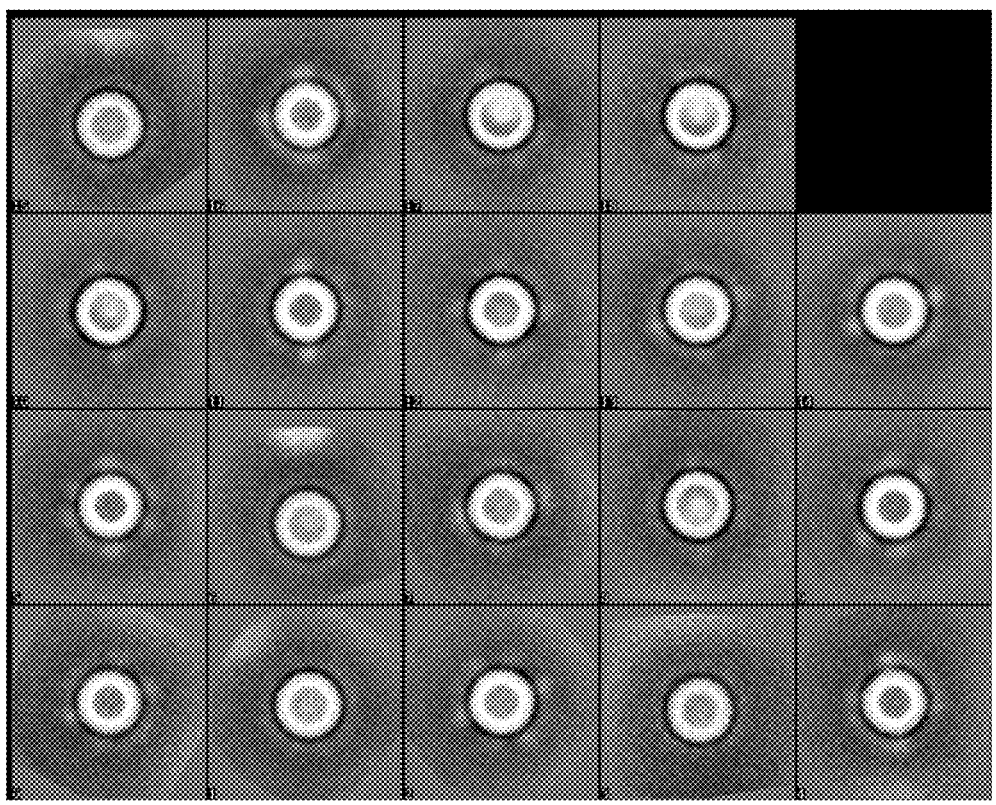
FIG. 4. Two-dimension classifications of NC99 RBD-nanoparticles were calculated using images stained with ammonium molybdate instead of uranyl formate.

The nanoparticles purified in part (B) were analyzed by negative stain EM. Briefly, samples of about 50 µg ml$^{-1}$ were adsorbed to freshly glow-discharged carbon-coated grids, rinsed with PBS, and stained with 0.75% uranyl formate solution. Images were recorded on an FEI T20 microscope with an Eagle CCD camera. The results of these analyses are shown in FIGS. 3 and 4.

Figure 5:
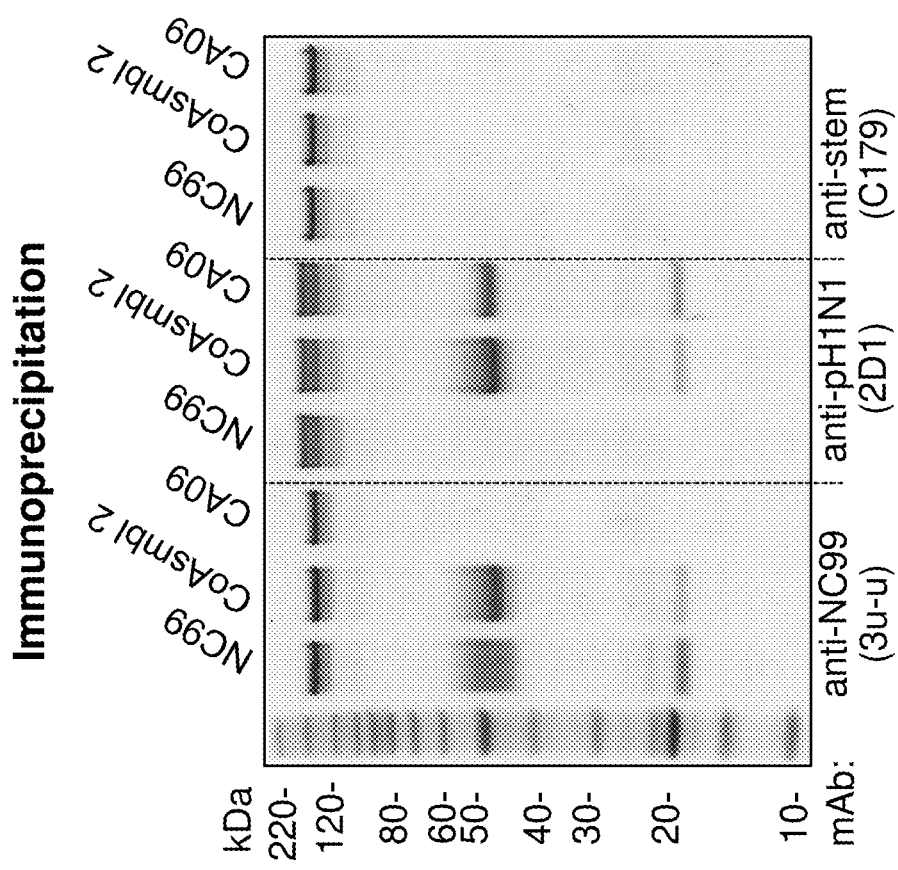
FIG. 5. Characterization of HA RBD-nanoparticles. Monovalent (N example, previous work in the field of influenza vaccines demonstrated that fusion proteins comprising an immunogenic portion of an influenza virus hemagglutinin (HA) protein joined to a self-assembly (SA) protein, to produce an HA-SA fusion protein, will self-assemble into nanoparticles displaying the immunogenic portion of the influenza HA protein on their surface. Moreover, when such nanoparticles are administered to an individual, they elicit a robust, neutralizing immune response to influenza virus. The construction and use of such nanoparticles has been described in U.S. Patent Publication No. 2014-0302079A1, which is incorporated herein by reference in its entirety. Similarly, nanoparticle-based vaccines for Epstein-Barr Virus have been described in International Patent Application No. PCT/US14/60142, which is incorporated herein by reference in its entirety. The present inventors have now discovered that nanoparticles displaying immunogenic portions of proteins from more than one genera, Type, Group, subtype or strain of infectious agent (e.g., influenza virus) can be used as a vaccine to elicit an immune response that neutralizes a variety, including a heterogeneous population, of different, but related, infectious agents. Moreover, the inventors have found that, surprisingly, such multivalent nanoparticles elicit a greater immune response than do vaccines comprising a single species of monovalent nanoparticles, or a mixture of two or more species of monovalent nanoparticles. Thus, a general embodiment of the invention is a nanoparticle made from self-assembling fusion proteins, wherein the surface of the nanoparticle displays a heterogeneous population of immunogenic portions of proteins from two or more infectious agents of the same taxonomic family. In specific embodiments, the two or more infectious agents are divergent enough such that the amino acid sequence of the immunogenic portions of corresponding proteins from the two or more infectious agents differ by at least one amino acid. In certain embodiments, the infectious agents are from different taxonomic groups within the same taxonomic family.
Figure 6:
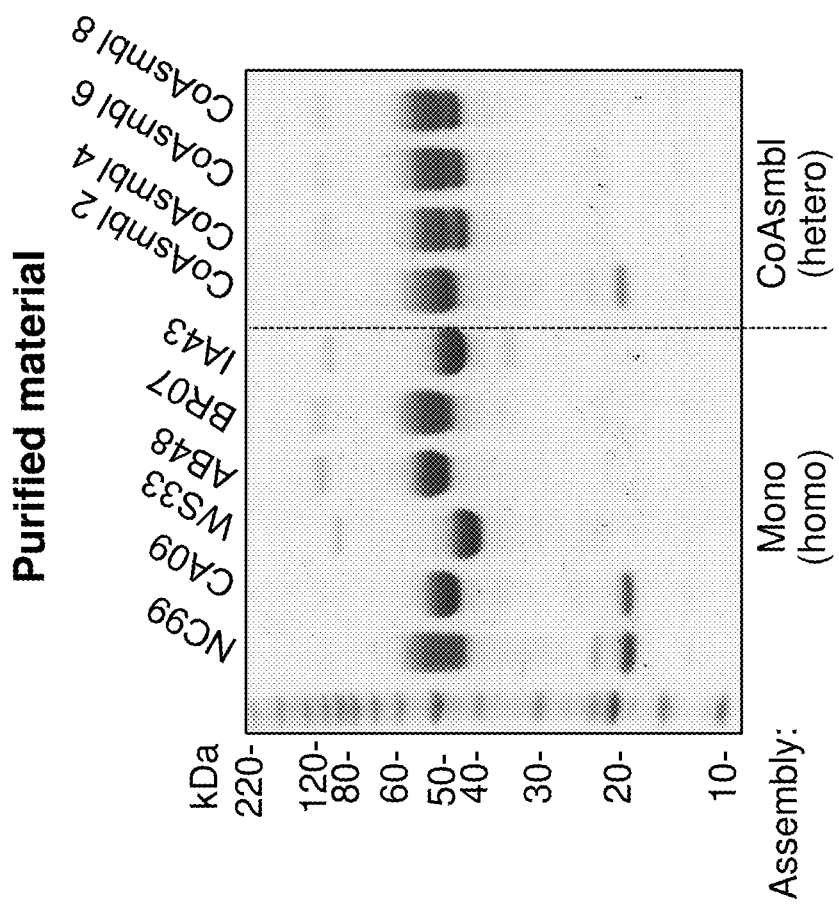

Example 2. Immunoprecipitation Analysis of Purified Nanoparticles Expressing Influenza HA Protein RBDs HA RBD-nanoparticles expressing RBDs from NC99, CA09 or both (CoAsmbl 2) were prepared and purified as described in Example 1. Four micrograms of purified RBD-nanoparticles were incubated with 4 µg of either anti-NC99 (3u-u), anti-pandemic H1N1 HA (2D1) or anti-HA stem (C179) monoclonal antibodies for 30 min at room temperature. Immune complexes were then captured using protein G-conjugated magnetic beads, and the complexes washed thoroughly with PBS containing 0.01% Tween 20. The washed pellets were resuspended in 20 µl of Laemmli buffer without reducing agent and analyzed on SDS-PAGE. Five micrograms of each protein were loaded. NC99, A/New Caledonia/20/1999; CA09, A/California/04/2009; WS33, A/Wilson-Smith/1933; AB48, A/Albany/4835/1948; BR07, A/Brisbane/59/2007; IA43, A/Iowa/1943; HK77, A/Hong Kong/117/1977; FM47, A/Fort Monmouth/1/1947. The results of these analyses are shown in FIGS. 5 and 6

Example 3. Immunization of Mice Using Purified Nanoparticles

The ability of compositions comprising purified monovalent, admixed, or heterogeneous nanoparticles to elicit a neutralizing immune response was tested in mice. Six to eight week old BALB/c mice were divided into 9 groups (N=5). To each group was administered a composition comprising 2 µg of either a) a monovalent (i.e., expresses single HA RBD) nanoparticle, b) a mixture of various monovalent nanoparticle, or c) the indicated, co-assembled nanoparticles, in the presence of Sigma Adjuvant System (SAS) at weeks 0 and 3. The immunogens administered and the dosing schedule is shown below in Table 3.

TABLE 3

| Group[1] | HA RBD[2] | Dose[3] | Adjuvant[4] | Immunization |
|---|---|---|---|---|
| Mono (NC99) | NC99 | 2 µg | SAS | Week 0, 3 (20) |
| Mono (CA09) | CA09 | 2 µg | SAS | Week 0, 3 (20) |
| Admixed 2 | NC99/CA09 | 2 µg total | SAS | Week 0, 3 (20) |
| Admixed 4 | 2 + WS33/AB48 | 2 µg total | SAS | Week 0, 3 (20) |
| Admixed 6 | 4 + BR07/IA43 | 2 µg total | SAS | Week 0, 3 (20) |
| CoAsmbl 2 | NC99/CA09 | 2 µg | SAS | Week 0, 3 (20) |
| CoAsmbl 4 | 2 + WS33/AB48 | 2 µg | SAS | Week 0, 3 (20) |
| CoAsmbl 6 | 4 + BR07/IA43 | 2 µg | SAS | Week 0, 3 (20) |
| CoAsmbl 8 | 6 + HK77/FM47 | 2 µg | SAS | Week 0, 3 (20) |

[1]Balb/c mice (N = 5)
[2]A/New Caledonia/20/99 (NC99); A/California/04/09 (CA09); A/Wilson-Smith/33 (WS33); A/Albany/4835/48 (AB48); A/Brisbane/59/07 (BR07); A/Iowa/43 (IA43); A/Hong Kong/117/77 (HK77); A/Fort Monmouth/1/47 (FM47)
[3]Total protein amount per dose
[4]Sigma Adjuvant System (SAS)

Figure 7:
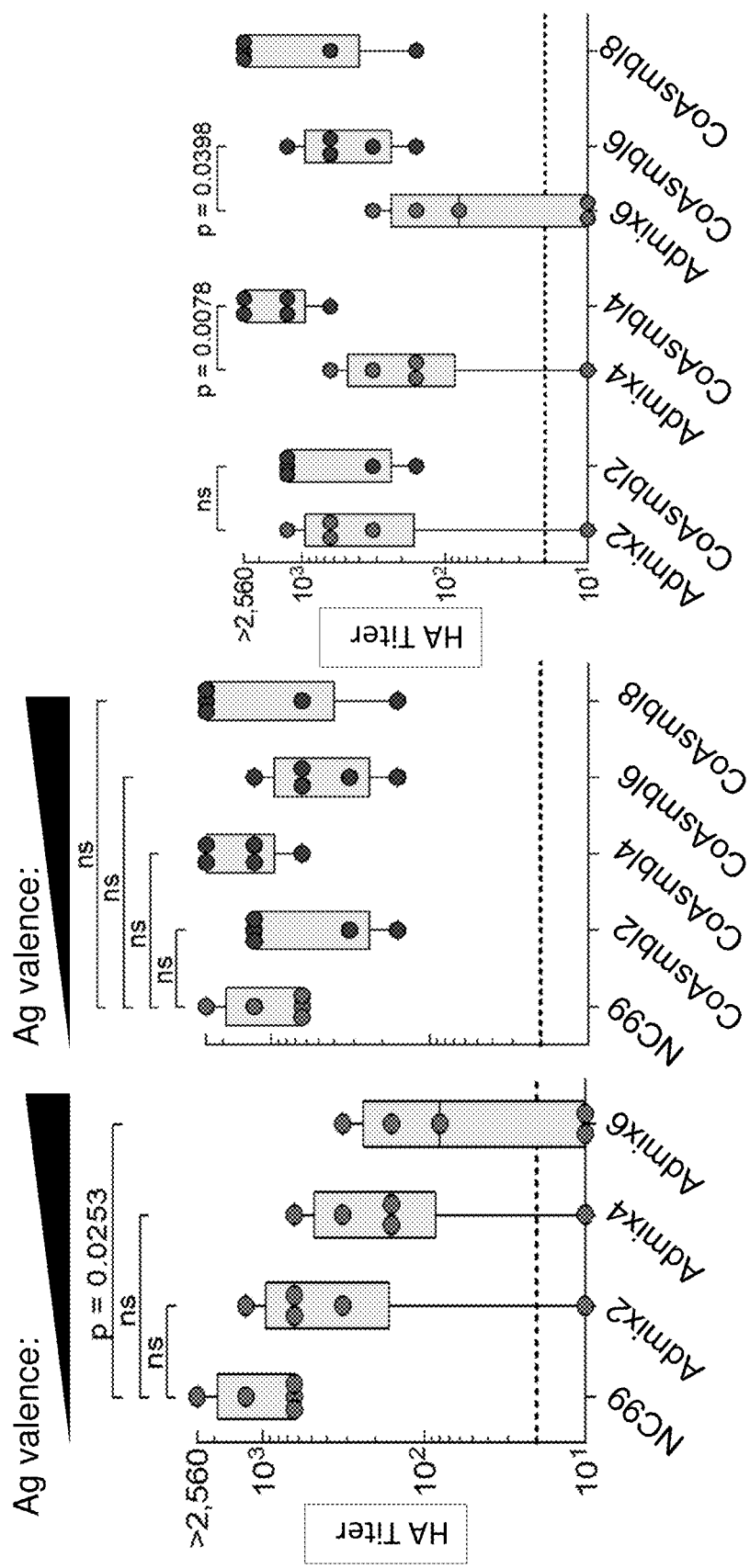
Figure 8:
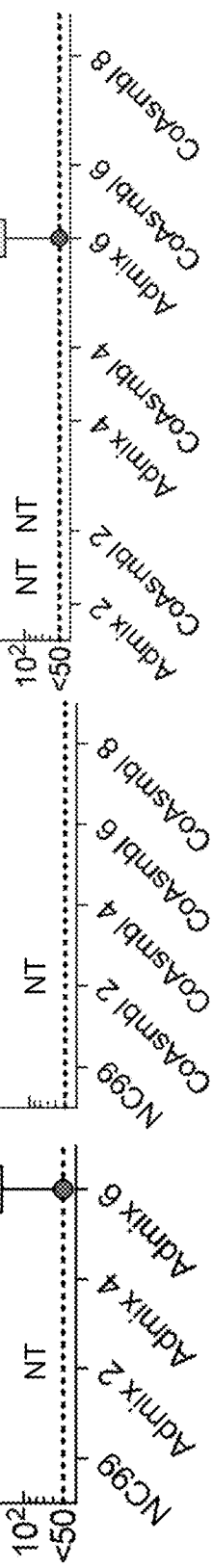

Serum samples were collected prior to the first immunization and at two and three weeks after the second immunization for serological analyses. More specifically the immune sera were tested for their ability to inhibit hemagglutination mediated by NC99 virus and neutralize NC99 pseudotyped lentivirus The results of these analyses are shown in FIGS. 7 and 8.

Figure 9:
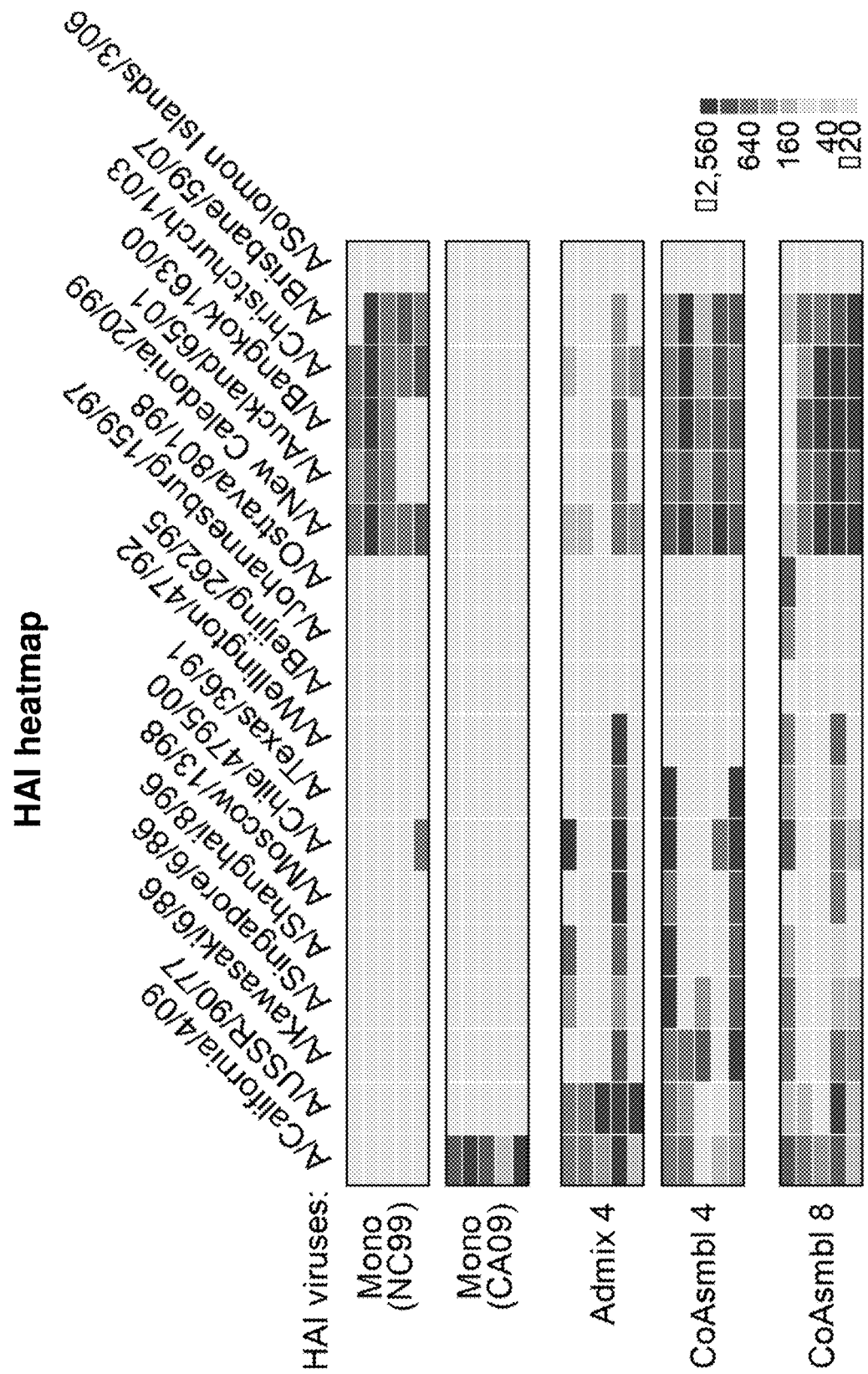

Example 4. Analysis of Breadth of Immune Response Using Monovalent Nanoparticles, Admixed Monovalent Nanoparticles or Multivalent, Co-Assembled Nanoparticles Mice (N=5) were immunized with either monovalent nanoparticles against NC99 or CA09, admixed nanoparticles (Admix 4), or multivalent nanoparticles (CoAsmbl 4 or CoAsmbl 8) (N=5) at week 0 and again at week 3. At 2-3 weeks following the second immunization, sera was collected from each mouse and the sera analyzed by HAI assays using a panel of 18 H1N1 viruses. The resulting titers are shown as a heatmap in FIG. 9.

The results of this analysis demonstrate that immunization with multivalent co-assembled particles produces a broader immune response (i.e., an immune response against a wider range of influenza viruses) than does immunization with either monovalent nanoparticles or admixed monovalent nanoparticles.

Figure 10:
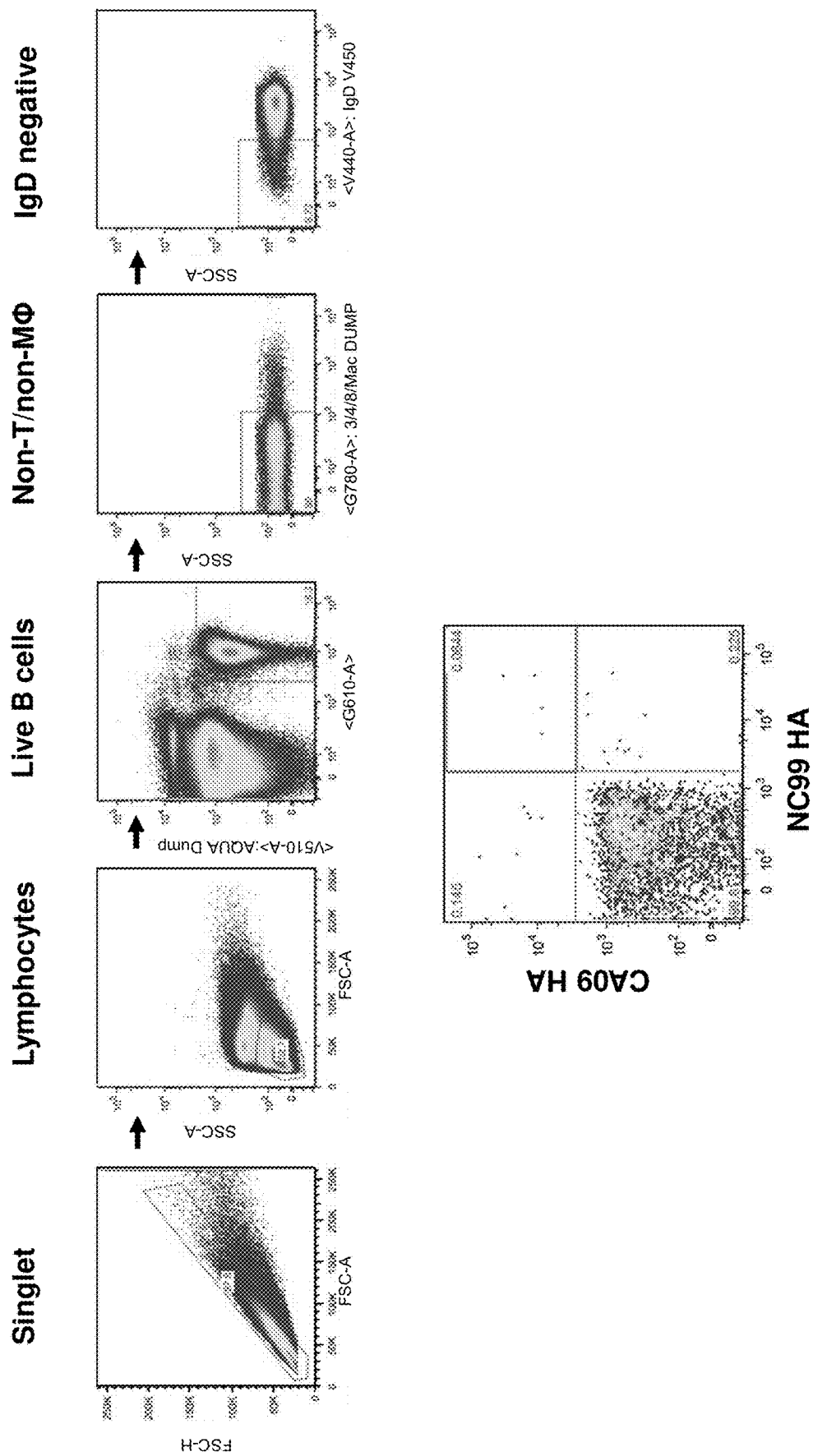
Figure 11:
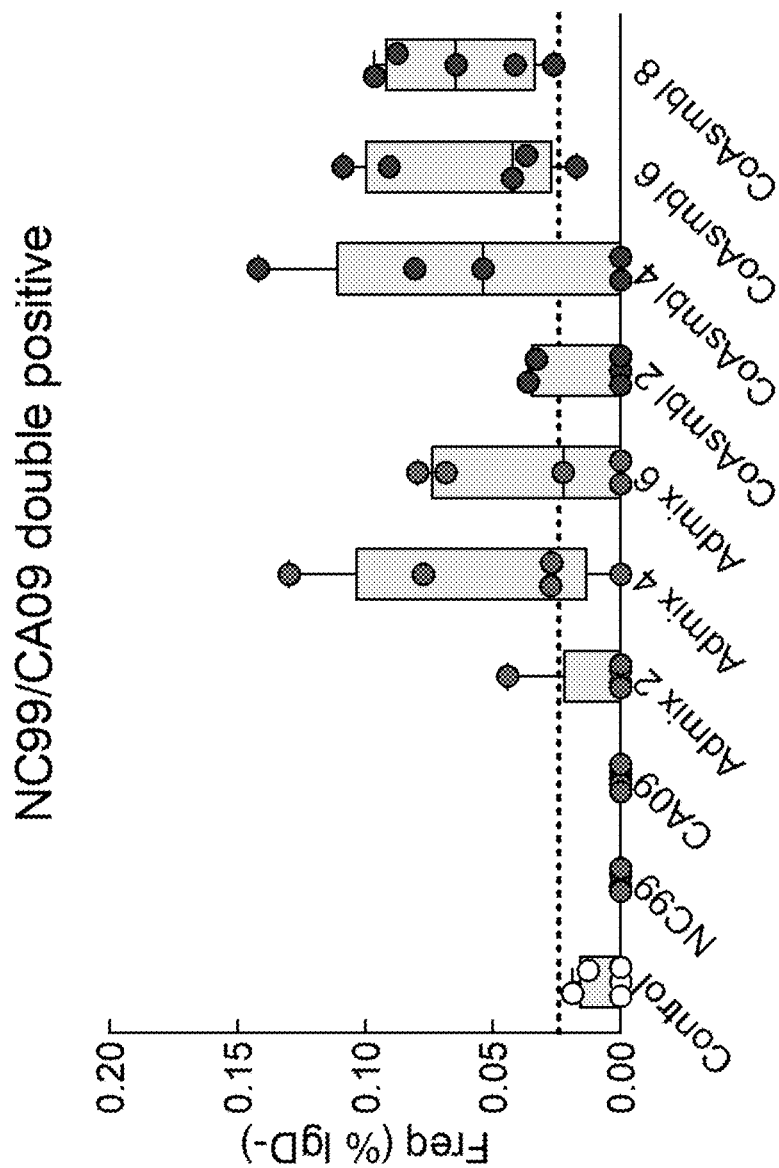

Example 5. Detection of HA-Specific, Cross-Reactive B-Cells in Peripheral Cells in HA RBD-Nanoparticle Immunized Mice Mice (N=5) were immunized with either monovalent nanoparticles against NC99 or CA09, admixed nanoparticles (Admix 2, Admix 4, or Admix 6), or multivalent nanoparticles (CoAsmbl 2, CoAsmbl 4, CoAsmbl 6 or CoAsmbl 8) at week 0, 3 and 20. At 10 days following the third immunization, peripheral blood was collected from each mouse and the white blood cells were isolated and analyzed by flow cytometer using NC99 and CA09 HA probes. Live, non-T, non-macrophage, IgD negative, singlet memory B cells were gated and the cell population (percentage of memory B cells) positive to both NC99 and CA09 HA was quantitated. The gating strategy and the resulting frequency of HA double positive cells across different immunization groups are shown in FIGS. 10 and 11.

The results of this analysis demonstrate that immunization with multivalent co-assembled particles induces an increased frequency of cross-reactive HA-specific memory B cells in immunized animals (i.e., B cells specific for both NC99 and CA09 HA) than does immunization with either monovalent nanoparticles or admixed monovalent nanoparticles.

Figure 12:
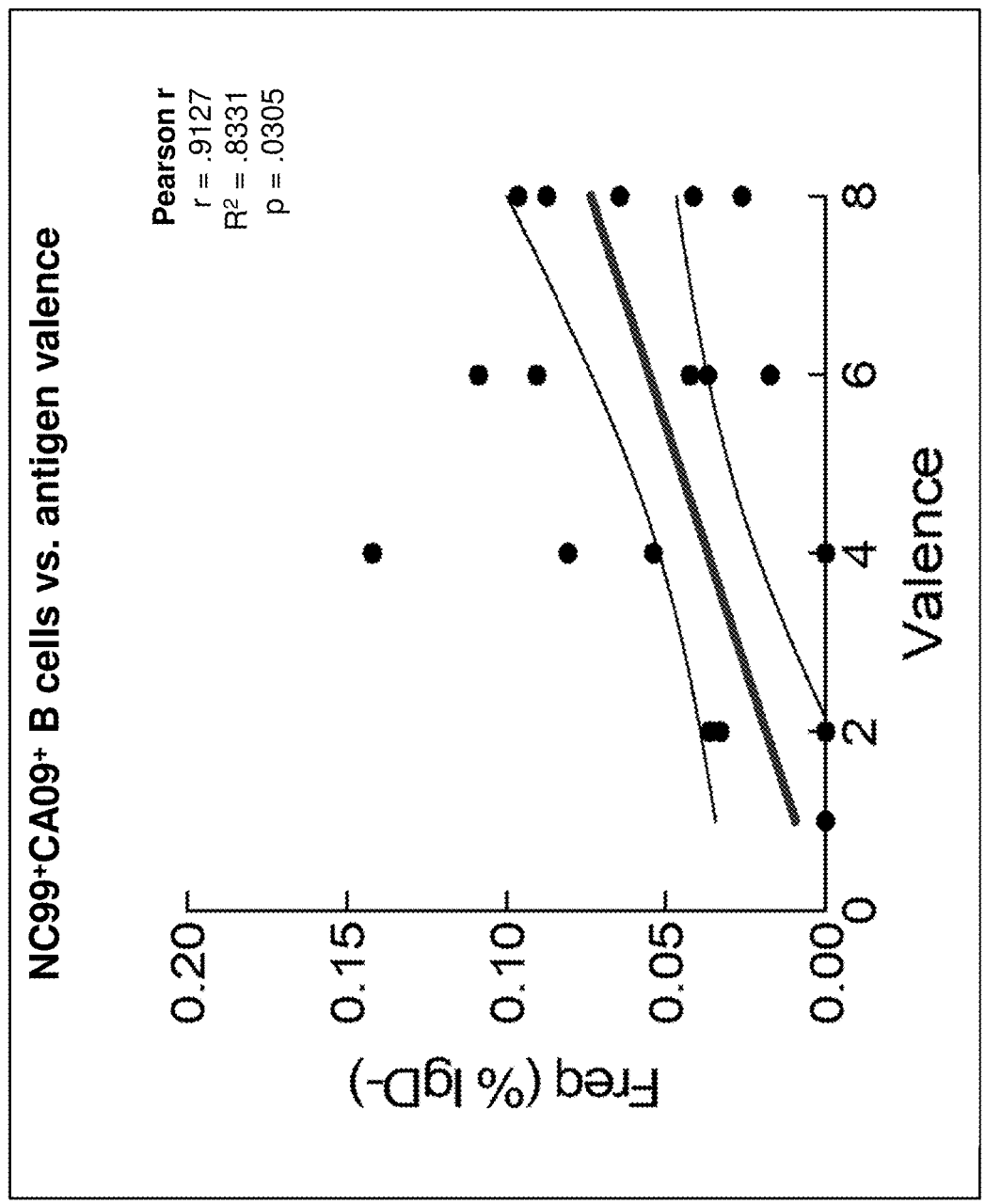

Example 6. Correlation of NC99/CA09 Cross-Reactive B-Cell Frequency and Antigenic Heterogeneity of Co-Assembled RDP-Nanoparticle Relationship between frequency of HA double positive cells in immunized animals and antigen valence of co-assembled immunogens was examined by Pearson product moment correlation analysis. This relationship is illustrated by the graph in FIG. 12.

The result of this analysis show that the degree of heterogeneity on the co-assembled immunogens positively correlates with frequency of cross-reactive HA-specific memory B cells in immunized animal.

Example 7. Neutralization Breadth Elicited by Vaccination with Co-Assembled HA RBD-Nanoparticles Mice were vaccinated with co-assembled nanoparticles, according to the schedule shown above in Table 3. Ten days after the final immunization, sera were collected and tested for its ability to neutralize pseudotyped lentiviruses expressing HA and NA from various H1N1 virus strains. The serum neutralization titers obtained from these assays are shown below in Table 4.

TABLE 4

Serum neutralization titers from mice immunized with co-assembled nanoparticles

| H1N1 pseudovirus | $IC_{50}$ (serum dilution) | | | | |
|---|---|---|---|---|---|
| | #8441 | #8442 | #8443 | #8444 | #8445 |
| A/California/4/09 | NT | NT | NT | NT | NT |
| A/New Jersey/76 | 2528 | 947 | 27580 | 11222 | 7463 |
| A/South Carolina/1/18 | 1146 | 242 | 1354 | 11129 | 217 |
| A/Wilson-Smith/33 | NT | NT | NT | NT | NT |
| A/Puerto Rico/8/34 | 5439 | <40 | 3440 | 9822 | 2817 |
| A/Iowa/43 | 3062 | 1709 | 12821 | 12095 | 2466 |
| A/Fort Monmouth/1/47 | 31302 | 85350 | 77846 | 126781 | 719 |
| A/Malaysia/54 | NT | NT | NT | NT | NT |
| A/Albany/4835/48 | NT | NT | NT | NT | NT |
| A/Hong Kong/117/77 | 2636 | 7525 | 16876 | 37845 | 1724 |
| A/Singapore/6/86 | 8888 | 4064 | 9822 | 3469 | 24751 |
| A/New York/146/00 | 13366 | 7780 | 6866 | 3113 | 15399 |
| A/New York/653/96 | 17302 | 158 | 9190 | 5349 | 22212 |
| A/Beijing/262/95 | 5960 | <40 | 1905 | 9422 | 96 |
| A/New Caledonia/20/99 | 5217 | 15788 | 18649 | 42171 | 46992 |
| A/New York/8/06 | 1695 | 423 | 947 | 620 | 2317 |
| A/Solomon Islands/3/06 | 1072 | 604 | 226 | 1072 | 1858 |
| A/Brisbane/59/07 | NT | NT | NT | NT | NT |

NT, not tested.

Example 8. Neutralization Breadth of an Isolated, Anti-HA Monoclonal Antibody B cells obtained from mouse #8441 in Example 7 were sorted using fluorescently labeled HA probe as bait. Genes encoding variable regions of the antibody heavy and light chains were then amplified from single B cells, sequenced, and cloned into appropriate backbone vectors (mouse IgG2a heavy and kappa light chain backbone) to express the encoded proteins as an antibody. Reconstructed antibody vectors were used for transient transfection in 293-Freestyle expression system (Life technologies) and the IgG was purified by affinity column purification using protein A resin. The resulting antibody was referred to as 441D6. Neutralization $IC_{50}$ titers of 441D6 were determined by lentivirus pseudotype neutralization assays in which pseudoviruses express HA and NA from various H1N1 viral strains. Monoclonal antibodies CH65 (anti-receptor binding site of HA) and FI6v3 (anti-HA stem region) were used as controls. NT=not tested. The neutralization titers obtained from these assays are shown below in Table 5.

TABLE 5

Neutralization titers of monoclonal antibody 441D6

| H1N1 pseudovirus | $IC_{50}$ (μg/ml) | | |
|---|---|---|---|
| | CH65 | 441D6 | FI6v3 |
| A/California/4/09 | 6.25 | 0.16 | 0.13 |
| A/New Jersey/76 | >25 | 0.03 | 0.36 |
| A/South Carolina/1/18 | 0.57 | 0.04 | 4.40 |
| A/Wilson-Smith/33 | NT | NT | NT |
| A/Puerto Rico/8/34 | 0.44 | 0.08 | 0.97 |
| A/Iowa/43 | >50 | 11.08 | 3.40 |
| A/Fort Monmouth/1/47 | 5.86 | 0.02 | 22.17 |
| A/Malaysia/54 | NT | NT | NT |
| A/Albany/4835/48 | NT | NT | NT |
| A/Hong Kong/117/77 | 0.97 | 0.04 | 0.09 |
| A/Singapore/6/86 | <0.005 | 0.01 | 0.01 |
| A/New York/146/00 | 0.03 | 0.01 | 0.08 |
| A/New York/653/96 | <0.005 | 0.02 | 0.15 |
| A/Beijing/262/95 | 0.01 | 0.07 | 1.01 |
| A/New Caledonia/20/99 | 0.01 | 0.04 | 0.09 |

TABLE 5-continued

Neutralization titers of monoclonal antibody 441D6

| H1N1 pseudovirus | IC$_{50}$ (μg/ml) | | |
|---|---|---|---|
| | CH65 | 441D6 | FI6v3 |
| A/New York/8/06 | 0.02 | 0.14 | >25 |
| A/Solomon Islands/3/06 | 1.30 | 0.29 | 0.94 |
| A/Brisbane/59/07 | NT | NT | NT |

NT, not tested.

The results demonstrate the ability of the monoclonal antibody 441D6 to neutralize broader range of H1N1 viruses than CH65 and more potently neutralize viruses than FI6v3, documenting a novel broad and potent neutralizing monoclonal antibody 441D6 against H1N1 viruses.

Figure 13:
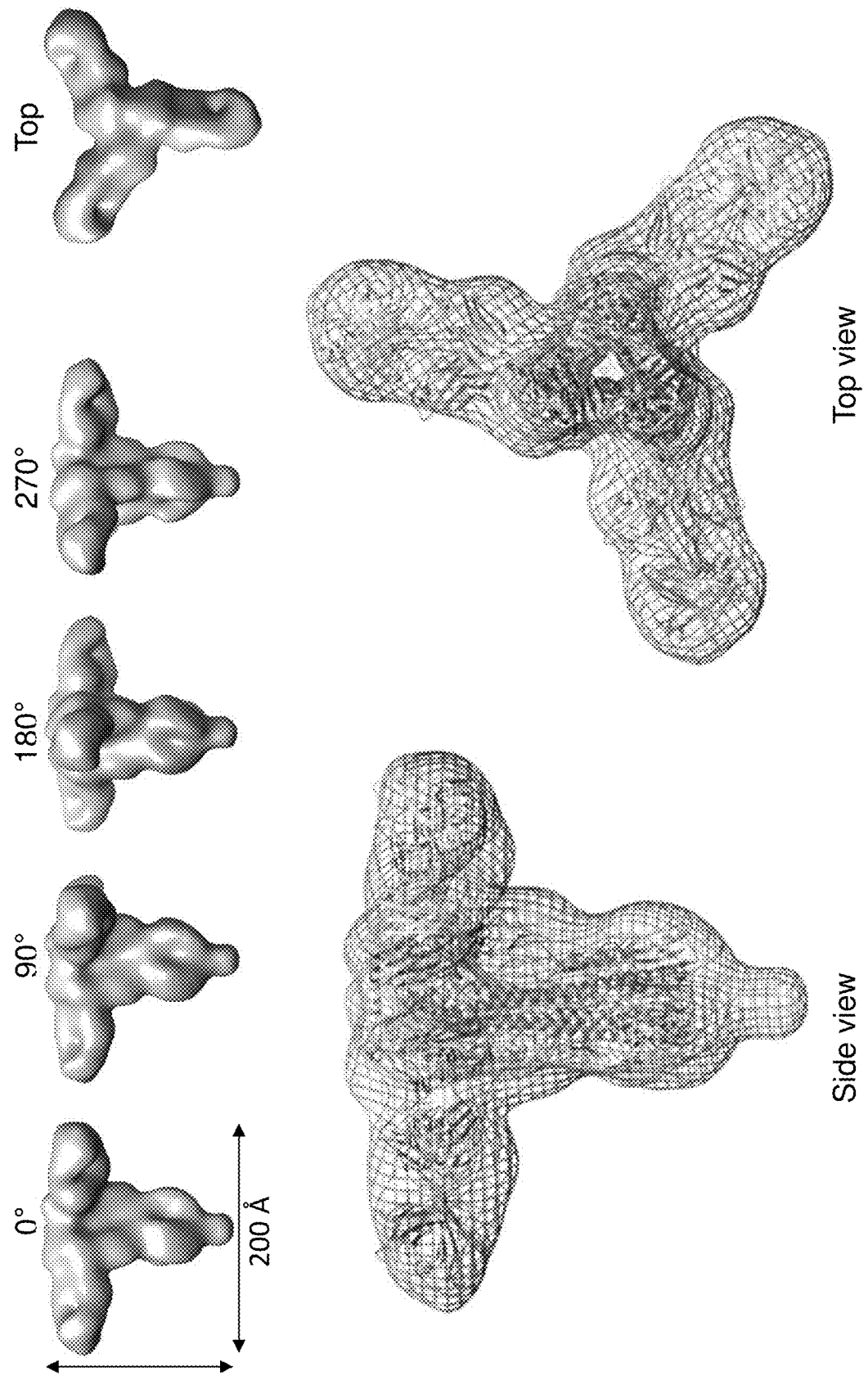

To better understand the interaction of monoclonal antibody 441D6 with influenza HA protein, a three-dimensional reconstruction model of an HA trimer complexed with Fab 441D6 was produced. Briefly, HA trimer (A/New York/653/1996 (H1N1)) was incubated with 1.5 times excess amount of Fab 441D6 and the complex purified by size exclusion column chromatography. The purified HA-Fab complex was then used in negative stain electron microscopy experiments. Approximately 9,000 particles were used for three dimensional reconstruction and the calculated resolution of the final model was ~18.5 Å. HA and Fab models were docked in the EM density (bottom). The resulting three-dimensional model is shown in FIG. 13.

What is claimed:

1. A method of eliciting in an individual, a broadly neutralizing immune response against influenza virus, comprising administering to the individual a nanoparticle comprising:
at least two species of self-assembling fusion proteins, each fusion protein comprising a self-assembling, monomeric subunit protein joined to an immunogenic portion of an influenza virus hemagglutinin (HA) protein, wherein the immunogenic portion of the influenza virus HA protein is a receptor binding domain (RBD);
wherein the immunogenic portion in each species of self-assembling fusion protein differs from the immunogenic portion in the other species of self-assembling fusion proteins by at least one amino acid;
wherein the nanoparticle displays on its surface, the immunogenic portions of the at least two species of self-assembling fusion proteins; and
wherein at least one of the species of self-assembling fusion proteins comprises an amino acid sequence at least 80% identical to SEQ ID NO: 97.

2. The method of claim 1, comprising at least four species of the self-assembling fusion proteins, wherein the immunogenic portion in each species of self-assembling fusion protein differs from the immunogenic portion in the other species of self-assembling fusion proteins by at least one amino acid, and wherein the nanoparticle displays on its surface, the immunogenic portions of the at least four species of self-assembling fusion proteins.

3. The method of claim 1, wherein the at least one species of self-assembling fusion protein comprises an amino acid sequence selected from the group consisting of SEQ ID NO:97, SEQ ID NO:100, SEQ ID NO:103, SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:133, SEQ ID NO:136, SEQ ID NO:139, and SEQ ID NO:142.

4. A method of vaccinating an individual against influenza virus infection, comprising administering to the individual a nanoparticle comprising:
at least two species of self-assembling fusion proteins, each fusion protein comprising a self-assembling, monomeric subunit protein joined to an immunogenic portion of an influenza virus hemagglutinin (HA) protein, wherein the immunogenic portion of the influenza virus HA protein is a receptor binding domain (RBD);
wherein the immunogenic portion in each species of self-assembling fusion protein differs from the immunogenic portion in the other species of self-assembling fusion proteins by at least one amino acid;

wherein the nanoparticle displays on its surface, the immunogenic portions of the at least two species of self-assembling fusion proteins; and wherein at least one of the species of self-assembling fusion proteins comprises an amino acid sequence at least 80% identical to SEQ ID NO: 97.

5. The method of claim 4, comprising at least four species of the self-assembling fusion proteins, wherein the immunogenic portion in each species of self-assembling fusion protein differs from the immunogenic portion in the other species of self-assembling fusion proteins by at least one amino acid, and wherein the nanoparticle displays on its surface, the immunogenic portions of the at least four species of self-assembling fusion proteins.

6. The method of claim 4, wherein the at least one species of self-assembling fusion protein comprises an amino acid sequence selected from the group consisting of SEQ ID NO:97, SEQ ID NO:100, SEQ ID NO:103, SEQ ID NO:106, SEQ ID NO:109, SEQ ID NO:112, SEQ ID NO:115, SEQ ID NO:118, SEQ ID NO:121, SEQ ID NO:124, SEQ ID NO:127, SEQ ID NO:130, SEQ ID NO:133, SEQ ID NO:136, SEQ ID NO: 139, and SEQ ID NO: 142.

7. The method of claim 3, wherein the at least one species of self-assembling fusion protein comprises an amino acid sequence set forth as SEQ ID NO: 97.

8. The method of claim 6, wherein the at least one species of self-assembling fusion protein comprises an amino acid sequence set forth as SEQ ID NO: 97.

* * * * *

UNITED STATES PATENT AND TRADEMARK OFFICE
CERTIFICATE OF CORRECTION

PATENT NO. : 11,938,221 B2
APPLICATION NO. : 17/519142
DATED : March 26, 2024
INVENTOR(S) : Graham et al.

Page 1 of 1

It is certified that error appears in the above-identified patent and that said Letters Patent is hereby corrected as shown below:

On the Title Page

Item (57) Abstract
Lines 10-13 "When administered to an individual, such nanoparticles elicit an immune response to different strains, types, subtypes and species with in the same taxonomic family" should read -- When administered to an individual, such nanoparticles elicit an immune response to different strains, types, subtypes and species within the same taxonomic family --

Signed and Sealed this
Eleventh Day of February, 2025

Coke Morgan Stewart
*Acting Director of the United States Patent and Trademark Office*